United States Patent
Maring et al.

(10) Patent No.: US 6,518,305 B1
(45) Date of Patent: *Feb. 11, 2003

(54) FIVE-MEMBERED CARBOCYCLIC AND HETEROCYCLIC INHIBITORS OF NEURAMINIDASES

(75) Inventors: Clarence J. Maring, Palatine, IL (US); Yuanwei Chen, North Haven, CT (US); David A. Degoey, Kenosha, WI (US); Vincent L. Giranda, Gurnee, IL (US); David J. Grampovnik, Waukegan, IL (US); Yu Gui Gu, Grayslake, IL (US); Warren M. Kati, Gurnee, IL (US); Dale J. Kempf, Libertyville, IL (US); April Kennedy, Grayslake, CO (US); Allan C. Krueger, Gurnee, IL (US); Zhen Lin, Gurnee, IL (US); Darold L. Madigan, Elk Grove Village, IL (US); Steven W. Muchmore, Libertyville, IL (US); Hing L. Sham, Mundelein, IL (US); Kent D. Stewart, Gurnee, IL (US); Vincent S. Stoll, Libertyville, IL (US); Minghua Sun, Libertyville, IL (US); Gary T. Wang, Niles, IL (US); Sheldon Wang, Grayslake, IL (US); Ming C. Yeung, Grayslake, IL (US); Chen Zhao, Libertyville, IL (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/422,093

(22) Filed: Oct. 19, 1999

Related U.S. Application Data

(63) Continuation-in-part of application No. 09/282,138, filed on Mar. 31, 1999, now abandoned
(60) Provisional application No. 60/082,843, filed on Apr. 23, 1998.

(51) Int. Cl.[7] .................. A61K 31/195; C07C 233/48
(52) U.S. Cl. .................. 514/530; 514/573; 548/236; 548/315; 548/345.1; 560/122; 562/504
(58) Field of Search .................. 562/504; 560/122; 514/530, 573

(56) References Cited

U.S. PATENT DOCUMENTS

| | | | |
|---|---|---|---|
| 5,360,817 A | 11/1994 | von Itzstein et al. | 514/424 |
| 5,453,533 A | 9/1995 | Luo et al. | 560/142 |
| 5,512,596 A | 4/1996 | Kim et al. | 514/568 |
| 5,541,343 A | 7/1996 | Himmelsbach et al. | 514/424 |
| 5,591,769 A | 1/1997 | Himmelsbach et al. | 514/423 |
| 5,602,277 A | 2/1997 | Babu et al. | 562/439 |
| 5,648,379 A | 7/1997 | von Itzstein et al. | 514/459 |
| 5,763,483 A | 6/1998 | Birchofberger et al. | 514/529 |
| 5,919,819 A | 7/1999 | Andrews et al. | 514/529 |

FOREIGN PATENT DOCUMENTS

| | | |
|---|---|---|
| EP | 0483667 | 5/1992 |
| EP | 0539204 | 4/1993 |
| EP | 0823428 | 2/1998 |
| GB | 229081 | 2/1996 |
| WO | 9116320 | 10/1991 |
| WO | 9206691 | 4/1992 |

(List continued on next page.)

OTHER PUBLICATIONS

B. Glanzer, et al., Helvetica Chimica Acta 74 343–369 (1991).
L. Czollner, et al., Helvetica Chimica Acta 73 1338–1358 (1990).
Y. Nishimura, et al., Natural Product Letters 1 39–44 (1992).
Y. Nishimura, et al., Natural Product Letters 1 33–38 (1992).
G. Kok, et al., J. Chem. Soc. Perkin Trans. I 905–908 (1998).
Petersen, et al., J. Am. Chem. Soc. 106 4539–4547 (1984).
Skibic, et al., J. Pharm. Sci. 82 (10) 1010–1017 (1993).
Atigadda, et al., J. Med. Chem. 42 2332–2343 (1999).

Primary Examiner—Fiona T. Powers
(74) Attorney, Agent, or Firm—B. Gregory Donner

(57) ABSTRACT

Disclosed are compounds of the formula:

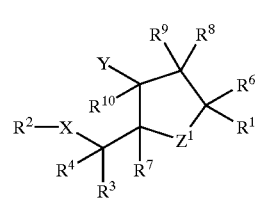

I

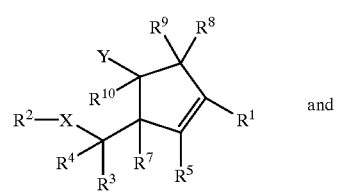

II and

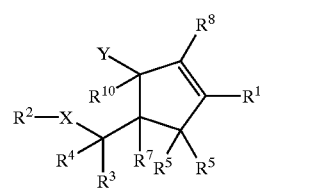

III which are useful for inhibiting neuraminidases from disease-causing microorganisms, especially, influenza neuraminidase. Also disclosed are compositions and methods for preventing and treating diseases caused by microorganisms having a neuraminidase, processes for preparing the compounds and synthetic intermediates used in these processes.

110 Claims, No Drawings

FOREIGN PATENT DOCUMENTS

| | | |
|---|---|---|
| WO | 9518800 | 7/1995 |
| WO | 9520583 | 8/1995 |
| WO | 9626933 | 9/1996 |
| WO | 9630329 | 10/1996 |
| WO | 9636628 | 11/1996 |
| WO | 9706157 | 2/1997 |
| WO | 9732214 | 9/1997 |
| WO | 9747194 | 12/1997 |
| WO | 9803487 | 1/1998 |
| WO | 9806712 | 2/1998 |
| WO | 9807685 | 2/1998 |
| WO | 9811083 | 3/1998 |
| WO | 9817647 | 4/1998 |
| WO | 9821243 | 5/1998 |
| WO | 0882721 | 12/1998 |
| WO | 9906369 | 2/1999 |
| WO | 9914185 | 3/1999 |
| WO | 9914191 | 3/1999 |
| WO | 9931047 | 6/1999 |
| WO | 9933781 | 7/1999 |
| WO | 9954290 | 10/1999 |

FIVE-MEMBERED CARBOCYCLIC AND HETEROCYCLIC INHIBITORS OF NEURAMINIDASES

This application is a continuation-in-part of U.S. application Ser. No. 09/282,138, filed Mar. 31, 1999, now abandoned which claims the benefit of U.S. Provisional Application No. 60/082,843, filed Apr. 23, 1998, both of which are incorporated herein by reference.

TECHNICAL FIELD

The present invention relates to novel compounds, compositions and methods for inhibiting neuraminidase, especially influenza neuraminidase. The invention also contemplates a composition and methods for preventing and treating an influenza infection and processes for making such compounds and synthetic intermediates employed in these processes.

BACKGROUND OF THE INVENTION

Many disease-causing microorganisms possess a neuraminidase (also known as sialidase) which is involved in the replication process of the microorganism. In particular, viruses of the orthomyxovirus and paramyxovirus groups possess a neuraminidase. Diseases associated with paramyxoviruses include RSV (respiratory syncytial virus-related diseases), pneumonia and bronchiolitis (associated with paramyxovirus type 3) and laryngotracheobronchitis (associated with paramyxovirus type 1). Some of the more important disease-causing microorganisms in man and/or animals which possess a neuraminidase include Vibrio cholerae, Clostridium perfringens, Streptococos pneumonia, Arthobacter sialophilus, influenza virus, parainfluenza virus, mumps virus, Newcastle disease virus, fowl plague virus, equine influenza virus and Sendai virus.

Mortality due to influenza is a serious problem throughout the world. The disease is devastating to man, lower mammals and some birds. Although vaccines containing attenuated influenza virus are available, those vaccines only provide immunological protection toward a few influenza strains and are less effective in otherwise immunologically compromised populations such as the elderly, young children, and in those who suffer from chronic respiratory illness. The productivity loss from absence due to sickness from influenza virus infection has been estimated to be more than $1 billion per year.

There are two major strains of influenza virus (designated A and B). Currently, there are only a few pharmaceutical products approved for treating influenza. These include amantadine and rimantadine, which are active only against the A strain of influenza viruses, and ribavirin, which suffers from dose-limiting toxicity. Mutant virus which is resistant to amantadine and rimantadine emerges quickly during treatment with these agents.

Very recently the first influenza neuraminidase inhibitor, zanamivir, was approved. However, it can only be administered by inhalation. Therefore, there is a continuing need for improved agents for treatment and/or prevention of influenza infection.

Neuraminidase is one of two major viral proteins which protrude from the envelope of influenza virus. During the release of progeny virus from infected cells, neuraminidase cleaves terminal sialic acid residues from glycoproteins, glycolipids and oligosaccharides on the cell surface. Inhibition of neuraminidase enzymatic activity leads to aggregation of progeny virus at the surface. Such virus is incapable of infecting new cells, and viral replication is therefore retarded or blocked. X-ray crystallographic studies and sequence alignments have shown that the residues which directly contact the sialic acid portion of the substrate are strictly conserved in the neuraminidase from all A and B influenza strains. Thus, a compound which binds to the sialic acid binding region of the neuraminidase active site will block the replication of both the A and B strains of influenza virus. Compounds which are influenza neuraminidase inhibitors will be useful for the prevention of influenza infection and will be useful for the treatment of influenza infection.

The following references disclose substituted cyclopentanes that are useful as neuraminidase inhibitors and treatments for influenza:

Y. Babu, et al., International Patent Application No. WO97/47194, published Dec. 18, 1997; and Y. Babu, et al., International Patent Application No. WO99/33781, published Jul. 8, 1999.

The following references disclose neuraminic acid derivatives with the disclosed utility listed after each reference:

L. Von ltzstein, et al., European Patent Application No. EP539204, published Apr. 28, 1993 (antiviral agent);

T. Honda, et al., European Patent Application No. EP823428, published Feb. 11, 1998 (sialidase inhibitor; influenza treatment);

T. Honda, et al., International Patent Application No. WO98/06712, published Feb. 19, 1998 (sialidase inhibitor; influenza remedy);

L. Von Itzstein, et al., International Patent Application No. WO95/20583, published Aug. 3, 1995 (viral neuraminidase inhibitor; influenza treatment);

P. Smith, International Patent Application No. WO95/18800, published Jul. 13, 1995 (viral neuraminidase inhibitor);

P. Colman, et al., International Patent Application No. WO92/06691, published Apr. 30, 1992 (viral neuraminidase inhibitor);

L. Von Itzstein, et al., U.S. Pat. No. 5,648,379, issued Jul. 15, 1997 (influenza treatment);

P. Reece, et al., International Patent Application No. WO97/32214, published Sep. 4, 1997 (bind to influenza virus neuraminidase active site); and P. Reece, et al., International Patent Application No. WO98/21243, published May 23, 1998 (anti-influenza agent).

The following references disclose sialic acid derivatives with the disclosed utility listed after each reference:

Y. Ohira, et al., International Patent Application No. WO98/11083, published Mar. 19, 1998 (antiviral agent);

Y. Ohira, European Patent Application No. EP882721, published Dec. 9, 1998 (antiviral agent); and B. Glanzer, et al., Helvetica Chimica Acta 74 343–369 (1991) (Vibrio cholerae neuraminidase inhibitor).

The following references disclose benzene derivatives, cyclohexane derivatives or cyclohexene derivatives with the disclosed utility listed after each reference:

Y. Babu, et al., U.S. Pat. No. 5,602,277, issued Feb. 11, 1997 (neuraminidase inhibitors);

M. Luo, et al., U.S. Pat. No. 5,453,533, issued Sep. 26, 1995 (influenza neuraminidase inhibitor; influenza treatment);

Y. Babu, et al., International Patent Application No. WO96/30329, published Oct. 3, 1996 (neuraminidase inhibitor; viral infection treatment);

N. Bischofberger, et al., U.S. Pat. No. 5,763,483, issued Jun. 9, 1998 (neuraminidase inhibitor);

C. Kim, et al., International Patent Application No. WO99/31047, published Jun. 24, 1999 (neuraminidase inhibitor; influenza treatment);

V. Atigadda, et al., J. Med. Chem. 42 2332–2343 (1999) (influenza neuraminidase inhibitor); and K. Kent, et al., International Patent Application No. 98/07685, published Feb. 26, 1998 (intermediates for the preparation of neuraminidase inhibitors).

C. Kim, et al., International Patent Application No. WO98/17647, published Apr. 30, 1998 discloses piperidine derivatives that are useful as neuraminidase inhibitors.

N. Bischofberger, et al., International Patent Application No. WO96/26933, published Sep. 6, 1996 and N. Bischofberger, et al., International Patent Application No. WO99/14185, published Mar. 25, 1999 disclose various substituted 6-membered ring compounds that are useful as neuraminidase inhibitors.

The following references disclose dihydropyran derivatives that are useful as viral neuraminidase inhibitors:

D. Andrews, et al., International Patent Application No. WO97/06157, published Feb. 20, 1997 and U.S. Pat. No. 5,919,819, issued Jul. 6, 1999; and P. Cherry, et al., International Patent Application No. WO96/36628, published Nov. 21, 1996.

C. Kim, et al., U.S. Pat. No. 5,512,596, issued Apr. 30, 1996 discloses 6-membered aromatic ring derivatives that are useful as neuraminidase inhibitors.

G. Diana, et al., International Patent Application No. WO98/03487, published Jan. 29, 1998 discloses substituted pyridazines that are useful for treatment of influenza.

B. Horenstein, et al., International Patent Application No. WO99/06369, published Feb. 11, 1999 discloses piperazine derivatives that are useful as neuraminidase inhibitors.

L. Czollner, et al., Helvetica Chimica Acta 73 1338–1358 (1990) discloses pyrrolidine analogs of neuraminic acid that are useful as Vibrio cholerae sialidase inhibitors.

W. Brouillette, et al., International Patent Application No. WO99/14191, published Mar. 25, 1999, discloses substituted pyrrolidin-2-one compounds that are useful as neuraminidase inhibitors and treatments for influenza.

The following references disclose siastatin B analogs that are useful as neuraminidase inhibitors:

Y. Nishimura, et al., Natural Product Letters 1 39–44 (1992); and

Y. Nishimura, et al., Natural Product Letters 1 33–38 (1992).

C. Penn, UK Patent Application No. GB2292081, published Feb. 14, 1996 discloses the use of a neuraminidase inhibitor in combination with an influenza vaccine.

An object of the invention is to provide compounds which inhibit neuraminidase of disease-causing microorganisms; especially, viral neuraminidase; and, most especially, influenza neuraminidase.

An object of the invention is also to provide compounds which inhibit neuraminidase from both A and B strains of influenza.

Another object of the invention is to provide prohylaxis of influenza infection in humans and other mammals.

Another object of the invention is to provide treatment of influenza infection in humans and other mammals.

Another object of the invention is to provide compounds which exhibit activity against influenza A virus and and influenza B virus by virtue of inhibiting influenza neuraminidase when such compounds are administered orally.

Another object of the invention is to provide a compound which can be effectively transported from the plasma into the lung bronchoaveolar fluid of humans and other mammals in order to block the replication of influenza virus in that tissue.

DISCLOSURE OF THE INVENTION

In one embodiment, the present invention discloses compounds having Formula Ia, IIa or IIIa Ia
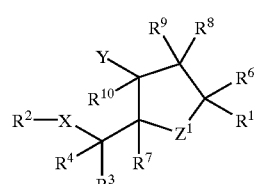

IIa
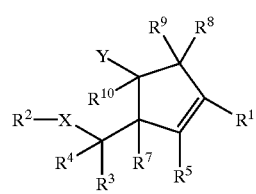

IIIa
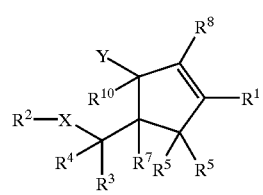

or a pharmaceutically acceptable salt, ester or prodrug thereof, wherein $R^1$ is selected from the group consisting of
(a) —$CO_2H$, (b) —$CH_2CO_2H$, (c) —$SO_3H$, (d) —$CH_2SO_3H$, (e) —$SO_2H$, (f) —$CH_2SO_2H$, (g) —$PO_3H_2$, (h) —$CH_2PO_3H_2$, (i) —$PO_2H$, (j) —$CH_2PO_2H$, (k) tetrazolyl, (l) —$CH_2$-tetrazolyl, (m) —C(=O)—NH—S(O)$_2$—$R^{11}$, (n) —$CH_2C$(=O)—NH—S(O)$_2$—$R^{11}$, (o) —$SO_2N(T$—$R^{11})R^{12}$ and (p) —$CH^2SO_2N(T$—$R^{11})R^{12}$
wherein T is selected from the group consisting of
(i) a bond, (ii) —C(=O)—, (iii) —C(=O)O—, (iv) —C(=O)S—, (v) —C(=O)—$NR^{36}$—, (vi) —C(=S)O—, (vii) —C(=S)S—, and (viii) —C(=S)$NR^{36}$—, $R^{11}$ is selected from the group consisting of
(i) $C_1$–$C_{12}$ alkyl, (ii) $C_2$–$C_{12}$ alkenyl, (iii) cycloalkyl, (iv) (cycloalkyl)alkyl, (v) (cycloalkyl)alkenyl, (vi) cycloalkenyl, (vii) (cycloalkenyl)alkyl, (viii) (cycloalkenyl)alkenyl, (ix) aryl, (x) (aryl)alkyl, (xi) (aryl)alkenyl, (xii) heterocyclic, (xiii) (heterocyclic)alkyl and (xiii) (xiv) (heterocyclic) alkenyl; and $R^{12}$ and $R^{36}$ are independently selected from the group consisting of
(i) hydrogen, (ii) $C_1$–$C_{12}$ alkyl, (iii) $C_2$–$C_{12}$ alkenyl, (iv) cycloalkyl, (v) (cycloalkyl)alkyl, (vi) (cycloalkyl)alkenyl, (vii) cycloalkenyl, (viii) (cycloalkenyl)alkyl, (ix) (cycloalkenyl)alkenyl, (x) aryl, (xi) (aryl)alkyl, (xii) (aryl)alkenyl, (xiii) heterocyclic, (xiv) (heterocyclic)alkyl and (xv) (heterocyclic)alkenyl;

X is selected from the group consisting of
(a) —C(=O)—N(R*)—, (b) —N(R*)—C(=O)—, (c) —C(=S)—N(R*)—, (d) —N(R*)—C(=S)—, (e) —N(R*)—$SO_2$—, and (f)—$SO_2$—N(R*)— wherein R* is hydrogen, $C_1$–$C_3$ loweralkyl or cyclopropyl;

$R^2$ is selected from the group consisting of
(a) hydrogen, (b) $C_1$–$C_6$ alkyl, (c) $C_2$–$C_6$ alkenyl, (d) $C_3$–$C_6$ cycloalkyl, (e) $C_5$–$C_6$ cycloalkenyl, (f) halo $C_1$–$C_6$ alkyl and (g) halo $C_2$–$C_6$ alkenyl;

or R²—X— is

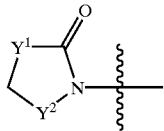

wherein Y¹ is —CH₂—, —O—, —S— or —NH— and Y² is —C(=O)— or —C(R$^{aa}$)(R$^{bb}$)— wherein R$^{aa}$ and R$^{bb}$ are indepedently selected from the group consisting of hydrogen, $C_1$-$C_3$ loweralkyl, hydroxymethyl, 1-hydroxyethyl, 2-hydroxyethyl, aminomethyl, 1-aminoethyl, 2-aminoethyl, thiolmethyl, 1-thiolethyl, 2-thiolethyl, methoxymethyl, N-methylaminomethyl and methylthiomethyl;

$Z^1$ is —O—, —S—, or C($R^5$)₂;

$R^3$ and $R^4$ are independently selected from the group consisting of
(a) hydrogen, (b) cycloalkyl, (c) cycloalkenyl, (d) heterocyclic, (e) aryl and (f) —Z—$R^{14}$
wherein Z is
(i) —C($R^{37a}$)($R^{37b}$)—, (i) C($R^{47}$)=C($R^{48}$)—, (iii) —C≡C—, (iv) —C(=O)—, (v) —C(=S)—, (vi) —C(=N$R^{15}$)—, (vii) —C($R^{37a}$)(O$R^{37c}$)—, (viii) —C($R^{37a}$)(S$R^{37c}$)—, (ix) —C($R^{37a}$)(N($R^{37b}$)($R^{37c}$))—, (x) —C($R^{37a}$)($R^{37b}$)—O—, (xi) —C($R^{37a}$)($R^{37b}$)—N($R^{37c}$)—, (xii) —C($R^{37a}$)($R^{37b}$)—N(O)($R^{37c}$)—, (xiii) —C($R^{37a}$)($R^{37b}$)—N(OH)—, (xiv) —C($R^{37a}$)($R^{37b}$)—S—, (xv) —C($R^{37a}$)($R^{37b}$)—S(O)—, (xvi) —C($R^{37a}$)($R^{37b}$)—S(O)₂—, (xvii) —C($R^{37a}$)($R^{37b}$)—C(=O)—, (xviii) —C($R^{37a}$)($R^{37b}$)—C(=S)S—, (xix) —C($R^{37a}$)($R^{37b}$)—C(=N$R^{15}$)—, (xx) —C($R^{37a}$)(O$R^{37c}$)—C(=O)—, (xxi) —C($R^{37a}$)(S$R^{37c}$)—C(=O)—, (xxii) —C($R^{37a}$)(O$R^{37c}$)—C(=S)—, (xxiii) —C($R^{37a}$)(S$R^{37c}$)—C(=S)—, (xxiv) —C(=O)—C($R^{37a}$)(O$R^{37c}$)—, (xxv) —C(O)—C($R^{37a}$)(S$R^{37c}$)—, (xxvi) —C(=S)—C($R^{37a}$)(O$R^{37c}$)—, (xvii) —C(=S)—C($R^{37a}$)(S$R^{37c}$)—, (xxviii) —C($R^{37a}$)(O$R^{37c}$)—C($R^{37a}$)(O$R^{37c}$)—, (xxix) —C($R^{37a}$)(S$R^{37c}$)—C($R^{37a}$)(O$R^{37c}$)—, (xxx) —C($R^{37a}$)(O$R^{37c}$)—C(=$R^{37a}$)(S$R^{37c}$)—, (xxi) —C($R^{37a}$)(S$R^{37c}$)—C($R^{37a}$)(S$R^{37c}$), (xxxii) —C(=O)—C(=O)—, (xxxiii) —C(=S)—C(=S)—, (xxxiv) —C(=O)—O—, (xxxv) —C(=O)—S—, (xxxvi) —C(=S)—O—, (xxxvii) —C(=S)—S—, (xxxviii) —C(=O)—N($R^{37a}$)—, (xxxix) —C(=S)—N($R^{37a}$)—, (xl) —C($R^{37a}$)($R^{37b}$)—C(=O)—N($R^{37a}$)—, (xli) —C($R^{37a}$)($R^{37b}$)—C(=S)—N($R^{37a}$)—, (Xlii) —C($R^{37a}$)($R^{37b}$)—C(=O)—O—, (Xliii) —C($R^{37a}$)($R^{37b}$)—C(=O)—S—, (xliv) —C($R^{37a}$)($R^{37b}$)—C(=S)—O—, (Xlv) —C($R^{37a}$)($R^{37b}$)—C(=S)—S—, (xlvi) —C($R^{37a}$)($R^{37b}$)—N($R^{37b}$)—C(=O)—, (xlvii) —C($R^{37a}$)($R^{37b}$)—N($R^{37b}$)—C(=S)—, (xlviii) —C($R^{37a}$)($R^{37b}$)—O—C(=O)—, (xlix) —C($R^{37a}$)($R^{37b}$)—S—C(=O)—, (l) —C($R^{37a}$)($R^{37b}$)—O—C(=S)—, (li) —C($R^{37a}$)($R^{37b}$)—S—C(=S)—, (lii) —C($R^{37a}$)($R^{37b}$)—N($R^{37b}$)—C(O)—N($R^{37a}$)—, (liii) —C($R^{37a}$)($R^{37b}$)—N($R^{37b}$)—C(=S)—N($R^{37a}$)—, (liv) —C($R^{37a}$)($R^{37b}$)—N($R^{37b}$)—C(=O)—O—, (lv) —C($R^{37a}$)($R^{37b}$)—N($R^{37b}$)—C(=O)—S—, (lvi) —C($R^{37a}$)($R^{37b}$)—N($R^{37b}$)—C(=S)—O—, (lvii) —C($R^{37a}$)($R^{37b}$)—N($R^{37b}$)—C(=S)—S—, (lviii) —C($R^{37a}$)($R^{37b}$)—O—C(=O)—N($R^{37a}$)—, (lix) —C($R^{37a}$)($R^{37b}$)—S—C(=O)—N($R^{37a}$)—, (lx) —C($R^{37a}$)($R^{37b}$)—O—C(=S)—N($R^{37a}$)—, (lxi) —C($R^{37a}$)($R^{37b}$)—S—C(=S)—N($R^{37a}$)—, (lxii) —C($R^{37a}$)($R^{37b}$)—O—C(=O)—O—, (lxiii) —C($R^{37a}$)($R^{37b}$)—S—C(=O)—O—, (lxiv) —C($R^{37a}$)($R^{37b}$)—O—C(=O)—S—, (lxv) —C($R^{37a}$)($R^{37b}$)—S—C(=O)—S—, (lxvi) —C($R^{37a}$)($R^{37b}$)—O—C(=S)—O—, (lxvii) —C($R^{37a}$)($R^{37b}$)—S—C(=S)—O—, (lxviii) —C($R^{37a}$)($R^{37b}$)—O—C(=S)—S—, (lxix) —C($R^{37a}$)($R^{37b}$)—S—C(=S)—S— or (lxx) —C($R^{37a}$)($R^{37b}$)—C($R^{37a}$)(O$R^{37c}$)—;

$R^{14}$ is
(i) hydrogen, (ii) $C_1$-$C_{12}$ alkyl, (iii) haloalkyl, (iv) hydroxyalkyl, (v) thiol-substituted alkyl, (vi) $R^{37c}$O-substituted alkyl, (vii) $R^{37c}$S-substituted alkyl, (viii) aminoalkyl, (ix) ($R^{37c}$)NH-substituted alkyl, (x) ($R^{37a}$)($R^{37c}$)N-susbstituted alkyl, (xi) $R^{37a}$O—(O=)C-substituted alkyl, (xii) $R^{37a}$S—(O=)C-substituted alkyl, (xiii) $R^{37a}$O—(S=)C-substituted alkyl, (xiv) $R^{37a}$S—(S=)C-substituted alkyl, (xv) ($R^{37a}$O)₂—P(=O)-substituted alkyl, (xvi) cyanoalkyl, (xvi) $C_2$-$C_{12}$ alkenyl, (xviii) haloalkenyl, (xix) $C_2$-$C_{12}$ alkynyl, (xx) cycloalkyl, (xxi) (cycloalkyl)alkyl, (xxii) (cycloalkyl)alkenyl, (xxiii) (cycloalkyl)alkynyl, (xxiv) cycloalkenyl, (xxv) (cycloalkenyl)alkyl, (xxvi) (cycloalkenyl)alkenyl, (xxvii) (cycloalkenyl)alkynyl, (xxviii) aryl, (xxix) (aryl)alkyl, (xxx) (aryl)alkenyl, (xxxi) (aryl)alkynyl, (xxxii) heterocyclic, (xxxiii) (heterocyclic)alkyl, (xxxiv) (heterocyclic)alkenyl or (xxxv) (heterocyclic)alkynyl, with the proviso that $R^{14}$ is other than hydrogen when Z is —C($R^{37a}$)($R^{37b}$)—N($R^{37b}$)—C(=O)—O—, —C($R^{37a}$)($R^{37b}$)—N($R^{37b}$)—C(=S)—O—, —C($R^{37a}$)($R^{37b}$)—N($R^{37b}$)—C(=O)—S—, —C($R^{37a}$)($R^{37b}$)—N($R^{37b}$)—C(=S)—S—, —C($R^{37a}$)($R^{37b}$)—O—C(=O)—O—, —C($R^{37a}$)($R^{37b}$)—O—C(=S)—O—, —C($R^{37a}$)($R^{37b}$)—S—C(=O)—O—, —C($R^{37a}$)($R^{37b}$)—S—C(=S)—O—, —C($R^{37a}$)($R^{37b}$)—O—C(=O)—S—, —C($R^{37a}$)($R^{37b}$)—O—C(=S)—S—, —C($R^{37a}$)($R^{37b}$)—S—C(=O)—S— or —C($R^{37a}$)($R^{37b}$)—S—C(=S)—S—;

$R^{37a}$, $R^{37b}$, $R^{47}$, and $R^{48}$ at each occurrence are independently selected from the group consisting of
(i) hydrogen, (ii) $C_1$-$C_{12}$ alkyl, (iii) haloalkyl, (iv) hydroxyalkyl, (v) alkoxyalkyl, (vi) $C_2$-$C_{12}$ alkenyl, (vii) haloalkenyl, (viii) $C_2$-$C_{12}$ alkynyl, (ix) cycloalkyl, (x) (cycloalkyl)alkyl, (xi) (cycloalkyl)alkenyl, (xii) (cycloalkyl)alkynyl, (xiii) cycloalkenyl, (xiv) (cycloalkenyl)alkyl, (xv) (cycloalkenyl)alkenyl, (xvi) (cycloalkenyl) alkynyl, (xvii) aryl, (xviii) (aryl)alkyl, (xix) (aryl) alkenyl, (xx) (aryl)alkynyl, (xxi) heterocyclic, (xxii) (heterocyclic)alkyl, (xxiii) (heterocyclic) alkenyl and (xxiv) (heterocyclic)alkynyl;

$R^{37c}$ at each occurrence is independently selected from the group consisting of
(i) hydrogen, (ii) $C_1$-$C_{12}$ alkyl, (iii) haloalkyl, (iv) $C_2$-$C_{12}$ alkenyl, (v) haloalkenyl, (vi) $C_2$-$C_{12}$ alkynyl, (vii) cycloalkyl, (viii) (cycloalkyl)alkyl, (ix) (cycloalkyl)alkenyl, (x) (cycloalkyl)alkynyl, (xi) cycloalkenyl, (xii) (cycloalkenyl)alkyl, (xiii)

(cycloalkenyl)alkenyl, (xiv) (cycloalkenyl) alkynyl, (xv) aryl, (xvi) (aryl)alkyl, (xvii) (aryl) alkenyl, (xviii) (aryl)alkynyl, (xix) heterocyclic, (xx) (heterocyclic)alkyl, (xxi) (heterocyclic) alkenyl, (xxii) (heterocyclic)alkynyl, (xxiii) —C(=O)—R$^{14}$, (xxiv) —C(=S)—R$^{14}$, (xxv) —S(O)$_2$—R$^{14}$ and (xxvi) hydroxyalkyl;

or when Z is —C(R$^{37a}$)(R$^{37b}$)—N(R$^{37c}$) then N(R$^{37c}$) and R$^{14}$ when taken together are an azido group;

or when Z is —C(R$^{37a}$)(R$^{37b}$)—N(O)(R$^{37c}$), then N(O)(R$^{37c}$) and R$^{14}$ when taken together are an N-oxidized 3–7 membered heterocyclic ring having at least one N-oxidized ring nitrogen atom;

or when Z is —C(R$^{37a}$)(R$^{37b}$)—, —C(R$^{37a}$) (OR$^{37c}$—, —C(R$^{37a}$)(SR$^{37c}$) or —C(R$^{37a}$)(N(R$^{37b}$) (R$^{37c}$))—, then R$^{37a}$, R$^{14}$ and the carbon atom to which they are bonded when taken together form a cyclopentyl, cyclopentenyl, cyclohexyl or cyclohexenyl ring or then OR$^{37c}$ or SR$^{37c}$ or N(R$^{37c}$) and R$^{14}$ and the carbon atom to which they are bonded when taken together form a heterocyclic ring containing an O, S or N atom, respectively, and having from 4 to 8 ring atoms;

R$^{15}$ is selected from the group consisting of (i) hydrogen, (ii) hydroxy, (iii) amino, (iv) C$_1$–C$_{12}$ alkyl, (v) haloalkyl, (vi) C$_2$–C$_{12}$ alkenyl, (vii) haloalkenyl, (viii) cycloalkyl, (ix) (cycloalkyl)alkyl, (x) (cycloalkyl)alkenyl, (xi) cycloalkenyl, (xii) (cycloalkenyl)alkyl, (xiii) (cycloalkenyl)alkenyl, (xiv) aryl, (xv) (aryl)alkyl, (xvi) (aryl)alkenyl, (xvii) heterocyclic, (xviii) (heterocyclic)alkyl and (xix) (heterocyclic)alkenyl;

or R$^3$ and R$^4$ taken together, with the atom to which they are attached, form a carbocyclic or heterocyclic ring having from 3 to 8 ring atoms;

R$^5$ at each occurrence is independently selected from the group consisting of
(a) hydrogen, (b) —CH(R$^{38}$)$_2$, (c) —(CH$_2$)$_r$—O—R$^{40}$, (d) C$_2$–C$_4$ alkynyl, (e) cyclopropyl, (f) cyclobutyl, (g) —C(=Q$^1$)—R$^{17}$, and (h) —(CH$_2$)$_r$—N(R$^{19}$)$_2$ wherein r is 0, 1 or 2; with the proviso that when one R$^5$ is —O—R$^{40}$ or —N(R$^{19}$)$_2$, then the other R$^5$ is other than —O—R$^{40}$ or —N(R$^{19}$)$_2$;
wherein Q$^1$ is O, S, or N(R$^{18}$);

R$^{17}$ and R$^{18}$ are independently selected, at each occurrence, from the group consisting of hydrogen, methyl, and ethyl;

R$^{19}$, R$^{38}$, and R$^{40}$ are independently selected, at each occurrence, from the group consisting of
(i) hydrogen, (ii) C$_1$–C$_{12}$ alkyl, (iii) haloalkyl, (iv) C$_2$–C$_{12}$ alkenyl, (v) haloalkenyl, (vi) cycloalkyl, (vii) (cycloalkyl)alkyl, (viii) (cycloalkyl)alkenyl, (ix) cycloalkenyl, (x) (cycloalkenyl)alkyl, (xi) (cycloalkenyl)alkenyl, (xii) aryl, (xiii) (aryl)alkyl, (xiv) (aryl)alkenyl, (xv) heterocyclic, (xvi) (heterocyclic)alkyl and (xvii) (heterocyclic) alkenyl;

or one R$_{19}$ is an N-protecting group;

or the two R$^5$ groups taken together with the carbon atom to which they are bonded, form a carbocyclic or heterocyclic ring having from 3 to 6 ring atoms;

Y is selected from the group consisting of
(a) C$_1$–C$_5$ alkyl, (b) C$_1$–C$_5$ haloalkyl, (c) C$_2$–C$_5$ alkenyl, (d) C$_2$–C$_5$ haloalkenyl, (e) C$_2$–C$_5$ alkynyl, (f) C$_3$–C$_5$ cycloalkyl, (g) C$_3$–C$_5$ cycloalkyl-C$_1$-to-C$_3$-alkyl, (h) C$_5$ cycloalkyl, (i) C$_5$ cycloalkenyl-C$_1$- to C$_3$-alkyl, (j) C$_5$ cycloalkenyl C$_2$-to C$_3$-alkenyl, (k) —(CHR$^{39}$)$_n$OR$^{20}$, (l) —CH(OR$^{20}$)—CH$_2$ (OR$^{20}$), (m) —(CHR$^{39}$)$_n$SR$^{21}$ (n) phenyl, (o) halo-substituted phenyl, (p) —(CHR$^{39}$)$_n$C(=Q$^2$)R$^{22}$, (q) ——(CHR$^{39}$)$_n$N(=Q$^3$), (r) —N(O)=CHCH$_3$, (s) —(CHR$^{39}$)$_n$N(CH$_3$)R$^{24}$ and (t) a heterocyclic ring having from 3 to 6 ring atoms;

wherein n is 0, 1, or 2; Q$^2$ is O, S, NR$^{25}$, or CHR$^{26}$; and Q$^3$ is NR$^{41}$, or CHR$^{42}$; R$^{20}$ at each occurrence is independently
(i) methyl, (ii) ethyl, (iii) n-propyl, (iv) isopropyl, (v) C$_1$–C$_3$ haloalkyl, (vi) vinyl, (vii) propenyl, (viii) isopropenyl, (ix) allyl, (x) C$_2$–C$_3$ haloalkenyl, (xi) amino, (xii) —NHCH$_3$, (xiii) —N(CH$_3$)$_2$, (xiv) —NHCH$_2$CH$_3$, (xv) —N(CH$_3$)(CH$_2$CH$_3$), (xvi) —N(CH$_2$CH$_3$)$_2$ or (xvii) —N(=CH$_2$);

R$^{21}$ is (i) hydrogen, (ii) methyl, (iii) ethyl, (iv) n-propyl, (v) isopropyl, (vi) C$_1$–C$_3$ haloalkyl, (vii) vinyl, (viii) propenyl, (ix) isopropenyl, (x) allyl or (xi) C$_2$–C$_3$ haloalkenyl;

R$^{22}$ is
(i) hydrogen, (ii) methyl, (iii) ethyl, (iv) n-propyl, (v) isopropyl, (vi) hydroxy, (vii) thiol, (viii) methoxy, (ix) ethoxy, (x) n-propoxy, (xi) isopropoxy, (xii) cyclopropyloxy, (xiii) methylthio, (xiv) ethylthio, (xv) n-propylthio, (xvi) isopropylthio, (xvii) cyclopropylthio, (xviii) vinyl, (xix) propenyl, (xx) isopropenyl, (xxi) allyl, (xxii) —N(R$^{28a}$)(R$^{28b}$), (xxiii) —CH$_2$R$^{29}$, (xxiv) aminomethyl, (xxv) hydroxymethyl, (xxvi) thiolmethyl, (xxvii) —NHNH$_2$, (xxviii) —N(CH$_3$)NH$_2$ or (xxix) —NHNH(CH$_3$);

R$^{23}$ and R$^{39}$ are independently hydrogen or methyl;

R$^{41}$ and R$^{42}$ are independently hydrogen, methyl, or ethyl;

R$^{24}$ is selected from the group consisting of
(i) hydrogen, (ii) C$_1$–C$_4$ alkyl, (iii) C$_2$–C$_4$ alkenyl, (iv) C$_2$–C$_4$ alkynyl, (v) cyclopropyl, (vi) —C(=Q$^4$)—R$^{30}$, (v) —OR$^{31}$, and (vi) —N(R$^{32}$)$_2$, wherein Q$^4$ is O, S, or N(R$^{33}$);

R$^{25}$ is hydroxy, methyl, ethyl, amino, —CN, or —NO$_2$;

R$^{26}$ group is hydrogen, methyl or ethyl;

R$^{28a}$ hydrogen, hydroxy, methyl, ethyl, amino, —NHCH$_3$, —N(CH$_3$)$_2$, methoxy, ethoxy, or —CN;

R$^{28b}$ is hydrogen, methyl or ethyl;

or R$^{28a}$, R$^{28b}$ and the nitrogen to which they are bonded taken together represent azetidinyl;

R$^{29}$ group is hydrogen, hydroxy, thiol, methyl, ethyl, amino, methoxy, ethoxy, methylthio, ethylthio, methylamino or ethylamino;

R$^{30}$ group is hydrogen, methyl, ethyl, —OR$^{34}$, —SR$^{34}$, —N(R$^{35}$)$_2$, —NHOH, —NHNH$_2$, —N(CH$_3$)NH$_2$, or —N(CH$_2$CH$_3$)NH$_2$;

R$^{31}$ and R$^{32}$ substituents, at each occurrence, are independently hydrogen, methyl or ethyl;

R$^{33}$ group is hydrogen, hydroxy, methyl, ethyl, amino, —CN, or —NO$_2$;

R$^{34}$ group is methyl or ethyl;

R$^{35}$ group is independently hydrogen, methyl or ethyl;

with the proviso that when Q$^2$ is CHR$^{26}$ then R$^{22}$ is selected from the group consisting of hydrogen, —CH$_3$, —C$_2$H$_5$, —C$_3$H$_7$, —OCH$_3$, —SCH$_3$, —O—C$_2$H$_5$, and —S—C$_2$H$_5$;

R$^6$ and R$^7$ are independently selected from the group consisting of (a) hydrogen, (b) $C_1$–$C_{12}$ alkyl, (c) $C_2$–$C_{12}$ alkenyl, (d) cycloalkyl, (e) (cycloalkyl)alkyl, (f) (cycloalkyl) alkenyl, (g) cycloalkenyl, (h) (cycloalkenyl)alkyl, (i) (cycloalkenyl)alkenyl, 0) aryl, (k) (aryl)alkyl, (l) (aryl)alkenyl, (m) heterocyclic, (n) (heterocyclic) alkyl, (o) (heterocyclic)alkenyl, (p) —$OR^{37a}$ and (q) —$N(R^{37a})_2$; and $R^8$, $R^9$, and $R^{10}$ are independently selected from the group consisting of (a) hydrogen, (b) $C_1$–$C_6$ alkyl, (c) $C_2$–$C_6$ alkenyl, (d) $C_3$–$C_6$ cycloalkyl, (e) $C_3$–$C_6$ cycloalkenyl, and (f) fluorine, with the proviso that the total number of atoms, other than hydrogen, in each of $R^8$, $R^9$, and $R^{10}$, is 6 atoms or less.

In another embodiment, the present invention discloses compounds having Formula Ib, IIb or IIIb

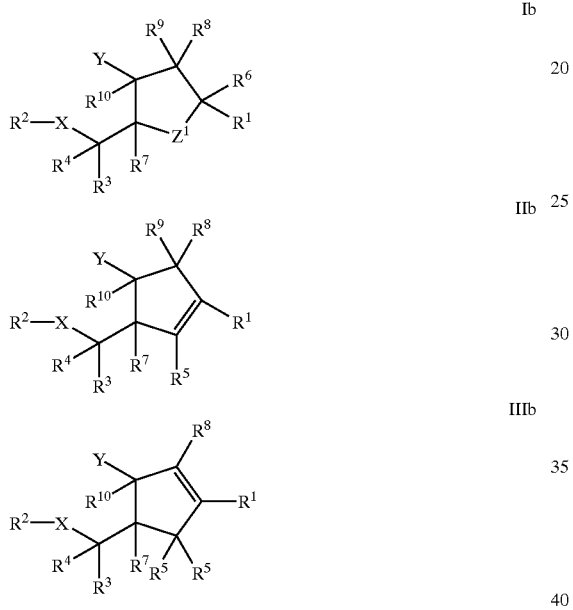

or a pharmaceutically acceptable salt, ester or prodrug thereof, wherein $R^1$, $R^2$, $R^4$, $R^5$, $R^6$, $R^7$, $R^8$, $R^9$, $R^{10}$, X and $Z^1$ are as defined above for the compounds of the Formula Ia, IIa, and IIIa and wherein Y is —$(CHR^{39})_n N(H)R^{24}$ wherein n, $R^{24}$ and $R^{39}$ are as defined above for the compounds of the Formula Ia, IIa, and IIIa and wherein $R^3$ is —Z—$R^{14}$
  wherein Z is
  (i) —$C(R^{37a})(R^{37b})$—, (ii) —$C(R^{37a})(OR^{37c})$—, (iii) —$C(R^{37a})(SR^{37c})$—, (iv) —$C(R^{37a})(N(R^{37b})(R^{37c}))$—, (v) —$C(R^{37a})(R^{37b})$—O—, (vi) —$C(R^{37a})(R^{37b})$—$N(R^{37c})$—, (vii) —$C(R^{37a})(R^{37b})$—$N(O)(R^{37c})$—, (viii) —$C(R^{37a})(R^{37b})$—N(OH)—, (ix) —$C(R^{37a})(R^{37b})$—S—, (x) —$C(R^{37a})(R^{37b})$—S(O)—, (xi) —$C(R^{37a})(R^{37b})$—$S(O)_2$—, (xii) —$C(R^{37a})(R^{37b})$—C(=O)—, (xiii) —$C(R^{37a})(R^{37b})$—C(=S)—, (xiv) —$C(R^{37a})(R^{37b})$—$C(=NR^{15})$, (xv) —$C(R^{37a})(OR^{37c})$—C(=O)—, (xvi) —$C(R^{37a})(SR^{37c})$—C(=O)—, (xvii) —$C(R^{37a})(OR^{37c})$—C(=S)—, (xviii) —$C(R^{37a})(SR^{37c})$—C(=S)—, (xix) —$C(R^{37a})(OR^{37c})$—$C(R^{37a})(OR^{37c})$—, (xx) —$C(R^{37a})(SR^{37c})$—$C(R^{37a})(OR^{37c})$—, (xxi) —$C(R^{37a})(OR^{37c})$—$C(R^{37a})(SR^{37c})$—, (xxii) —$C(R^{37a})(SR^{37c})$—$C(R^{37a})(SR^{37c})$—, (xxiii)

—$C(R^{37a})(R^{37b})$—C(=O)—$N(R^{37a})$—, (xxiv) —$C(R^{37a})(R^{37b})$—C(=S)—$N(R^{37a})$—, (xxv) —$C(R^{37a})(R^{37b})$—C(=O)O—O—, (xxvi) —$C(R^{37a})(R^{37b})$—C(=O)—S—, (xxvii) —$C(R^{37a})(R^{37b})$—C(=S)—O—, (xxviii) —$C(R^{37a})(R^{37b})$—C(=S)—S—, (xxix) —$C(R^{37a})(R^{37b})$—$N(R^{37b})$—C(=O)—, (xxx) —$C(R^{37a})(R^{37b})$—$N(R^{37b})$—C(=S)—, (xxxi) —$C(R^{37a})(R^{37b})$—O—C(=O)—, (xxxii) —$C(R^{37a})(R^{37b})$—S—C(=O)—, (xxxiii) —$C(R^{37a})(R^{37b})$—O—C(=S)—, (xxxiv) —$C(R^{37a})(R^{37b})$—S—C(=S)—, (xxxv) —$C(R^{37a})(R^{37b})$—$N(R^{37b})$—C(=O)—$N(R^{37a})$—, (xxxvi) —$C(R^{37a})(R^{37b})$—$N(R^{37b})$—C(=S)—$N(R^{37a})$—, (xxxvii) —$C(R^{37a})(R^{37b})$—$N(R^{37b})$—C(=O)—O—, (xxxviii) —$C(R^{37a})(R^{37b})$—$N(R^{37b})$—C(=O)—S—, (xxxvix) —$C(R^{37a})(R^{37b})$—$N(R^{37b})$—C(=S)—O—, (xl) —$C(R^{37a})(R^{37b})$—$N(R^{37b})$—C(=S)—S—, (xli) —$C(R^{37a})(R^{37b})$—O—C(=O)—$N(R^{37a})$—, (xlii) —$C(R^{37a})(R^{37b})$—S—C(=O)—$N(R^{37a})$—, (xliii) —$C(R^{37a})(R^{37b})$—O—C(=S)—$N(R^{37a})$—, (xliv) —$C(R^{37a})(R^{37b})$—S—C(=S)—$N(R^{37a})$—, (xlv) —$C(R^{37a})(R^{37b})$—O—C(=O)—O—, (xlvi) —$C(R^{37a})(R^{37b})$—S—C(=O)—O—, (xlvii) —$C(R^{37a})(R^{37b})$—O—C(=O)—S—, (xlviii) —$C(R^{37a})(R^{37b})$—S—C(=O)—S—, (xiix) —$C(R^{37a})(R^{37b})$—O—C(=S)—O—, (l) —$C(R^{37a})(R^{37b})$—S—C(=S)—O—, (li) —$C(R^{37a})(R^{37b})$—O—C(=S)—S—, (lii) —$C(R^{37a})(R^{37b})$—S—C(=S)—S— or (iii) —$C(R^{37a})(R^{37b})$—$C(R^{37a})(OR^{37c})$— wherein $R^{37a}$, $R^{37b}$, $R^{37c}$ and $R^{14}$ are as defined above for the compounds of the Formula Ia, IIa, and IIIa with the proviso that $R^{37a}$ when bonded to the first carbon atom in the Z group is other than hydrogen and with the proviso that $R^{37b}$ when bonded to the first carbon atom in the Z group is other than hydrogen and with the proviso that $R^{14}$ is other than hydrogen when Z is —$C(R^{37a})(R^{37b})$—, —$C(R^{37a})(OR^{37c})$—, —$C(R^{37a})(SR^{37c})$— or —$C(R^{37a})(N(R^{37b})(R^{37c}))$—. To illustrate what is meant by first carbon atom in the Z group, representative Z groups are shown in the following list in which the first carbon atom is asterisked: —C*$(R^{37a})(R^{37b})$—, —C*$(R^{37a})(R^{37b})$—C(=O)—, —C*$(R^{37a})(R^{37b})$—$N(R^{37b})$—C(=O)—O—, —C*$(R^{37a})(OR^{37c})$—C(=O)—, —C*$(R^{37a})(R^{37b})$—$C(R^{37a})(OR^{37c})$—.

Preferred compounds of the invention include compounds wherein $R^3$ and $R^4$ are not the same and which have the relative stereochemistry depicted by Formula IVa, IVb, Va, Vb, VIa, VIb, VIIa, VIIb, VIIIa, VIIIb, IXa or IXb:

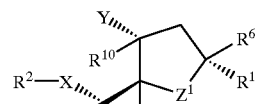

IVa or IVb

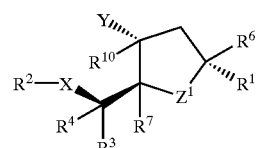

Va or Vb

-continued

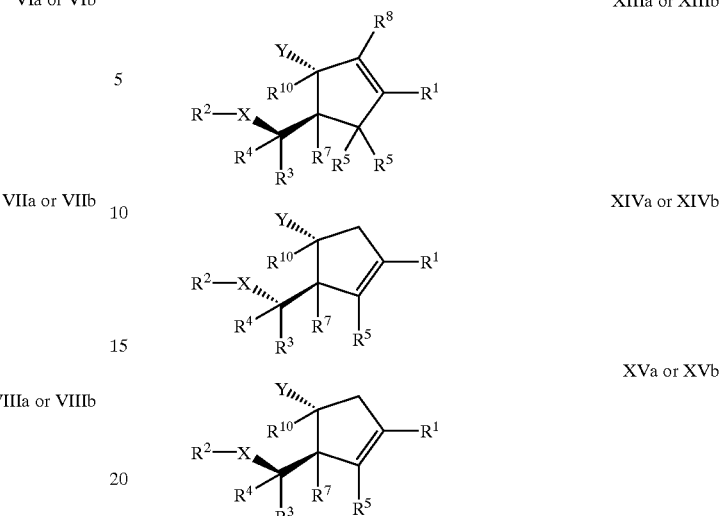

VIa or VIb

VIIa or VIIb

VIIIa or VIIIb

IXa or IXb

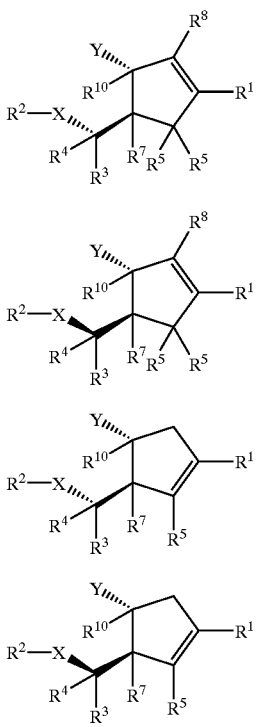

or a pharmaceutically acceptable salt, ester or prodrug thereof, wherein $R^1$, $R^2$, $R^3$, $R^4$, $R^5$, $R^6$, $R^7$, $R^8$, $R^{10}$, X, Y and $Z^1$ are as defined above for Ia, IIa and IIIa for IVa, Va, VIa, VIIa, VIIIa or IXa and wherein $R^1$, $R^2$, $R^3$, $R^4$, $R^5$, $R^6$, $R^7$, $R^8$, $R^{10}$, X, Y and $Z^1$ are as defined above for Ib, IIb and IIIb for IVb, Vb, VIb, VIIb, VIIIb or IXb.

More preferred compounds of the invention include enantiomerically enriched compounds wherein $R^3$ and $R^4$ are not the same and which have the absolute stereochemistry depicted by Formula Xa, Xb, XIa, XIb, XIIa, XIIb, XIIIa, XIIIb, XIVa, XIVb, XVa or XVb:

Xa or Xb

XIa or XIb

XIIa or XIIb

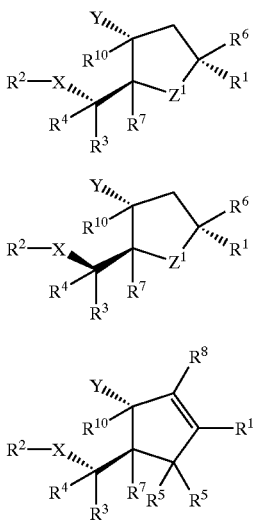

XIIIa or XIIIb

XIVa or XIVb

XVa or XVb or a pharmaceutically acceptable salt, ester or prodrug thereof, wherein $R^1$, $R^2$, $R^3$, $R^4$, $R^5$, $R^6$, $R^7$, $R^8$, $R^{10}$, X, Y and $Z^1$ are as defined above for Ia, IIa and IIIa for Xa, XIa, XIIa, XIIIa, XIVa, XVa or XVb and wherein $R^1$, $R^2$, $R^3$, $R^4$, $R^5$, $R^6$, $R^7$, $R^8$, $R^{10}$, X, Y and $Z^1$ are as defined above for Ib, IIb and IIIb for Xb, XIb, XIIb, XIIIb, XIVb or XVb.

Other preferred compounds of the invention are compounds having Formula Ia, Ib, IIa, IIb, IIIa, IIIb, IVa, IVb, Va, Vb, VIa, VIb, VIIa, VIIb, VIIIa, VIIIb, IXa, IXb, Xa, Xb, XIa, XIb, XIIa, XIIb, XIIIa, XIIIb, XIVa, XIVb, XVa or XVb or a salt, ester or prodrug thereof wherein $R^1$ is defined as above;

—X—$R^2$ is $R^2$—C(=O)—NH—, $R^2$—NH—C(=O)—, $R^2$—NH—$SO_2$— or $R^2$—$SO_2$—NH— wherein $R^2$ is $C_1$-$C_3$ loweralkyl, halo $C_1$-$C_3$ loweralkyl, $C_2$-$C_3$ alkenyl or halo $C_2$-$C_3$ alkenyl or —X—$R^2$ is

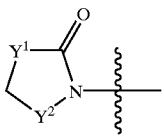

wherein $Y^1$ is —$CH_2$—, —O—, —S— or —NH— and $Y^2$ is —C(=O)— or —C($R^{aa}$)($R^{bb}$)— wherein $R^{aa}$ and $R^{bb}$ are independently selected from the group consisting of hydrogen, $C_1$-$C_3$ loweralkyl, hydroxymethyl, 1-hydroxyethyl, 2-hydroxyethyl, aminomethyl, 1-aminoethyl, 2-aminoethyl, thiolmethyl, 1-thiolethyl, 2-thiolethyl, methoxymethyl, N-methylaminomethyl and methylthiomethyl;

for compounds having Formula Ia, IIa, IIIa, IVa, Va, VIa, VIIa, VIIIa, IXa, Xa, XIa, XIIa, XIIIa, XIVa or XVa, $R^3$ and $R^4$ are independently selected from hydrogen, heterocyclic and —Z—$R^{14}$ wherein Z and $R^{14}$ are defined as above for compounds having Formula Ia, IIa and IIIa and wherein one of $R^3$ and $R^4$ is other than hydrogen;

for compounds having Formula Ib, IIb, IIIb, IVb, Vb, VIb, VIIb, VIIIb, IXb, Xb, XIb, XIIb, XIIIb, XIVb or XVb, $R^4$ is hydrogen or loweralkyl and $R^3$ is defined as above for compounds having Formula Ib, IIb and IIIb and wherein one of $R^3$ and $R^4$ is other than hydrogen;

$Z^1$ is —O—, —S— or —CH($R^5$)— wherein $R^5$ is hydrogen, loweralkyl, —$(CH_2)_rOR^{40}$ or —$(CH_2)_rN(R^{19})_2$ wherein r and $R^{19}$ and $R^{40}$ are defined as above; or $R^5$ is hydrogen, loweralkyl, —$(CH_2)_rOR^{40}$ or —$(CH_2)_rN(R^{19})_2$ wherein r and $R^{19}$ and $R^{40}$ are defined as above;

$R^6$ and $R^7$ are independently hydrogen or loweralkyl;

$R^8$ and $R^9$ are independently hydrogen, fluoro or loweralkyl;

$R^{10}$ is hydrogen, fluoro or loweralkyl; and for compounds having Formula Ia, IIa, IIIa, IVa, Va, VIa, VIIa, VIIIa, IXa, Xa, XIa, XIIa, XIIIa, XIVa or XVa, Y is $C_2$–$C_5$ alkenyl, $C_2$–$C_5$ haloalkenyl, —C(=$Q^2$)$R^{22}$, —N(=$Q^3$), —N(O)=$CHCH_3$, —N($CH_3$)$R^{24}$ or a heterocyclic ring having from 3 to 6 ring atoms, wherein $R^{22}$, $R^{24}$, $Q^2$ and $Q^3$ are defined as above for compounds having Formula Ia, IIa and IIIa;

for compounds having Formula Ib, IIb, IIIb, IVb, Vb, VIb, VIIb, VIIIb, IXb, Xb, XIb, XIIb, XIIIb, XIVb or XVb, Y is —NHR$^{24}$ wherein $R^{24}$ is defined as above for compounds having Formula Ia, IIa and IIIa.

More preferred compounds of the invention are compounds having Formula Ia, Ib, IIa, IIb, IIIa, IIIb, IVa, IVb, Va, Vb, VIa, VIb, VIIa, VIIb, VIIIa, VIIIb, IXa, IXb, Xa, Xb, XIa, XIb, XIIa, XIIb, XIIIa, XIIIb, XIVa, XIVb, XVa or XVb or a salt, ester or prodrug thereof wherein $R^1$ is defined as above;

—X—$R^2$ is $R^2$—C(=O)—NH—, $R^2$—NH—C(=O)—, $R^2$—NH—$SO_2$— or $R^2$—$SO_2$—NH— wherein $R^2$ is $C_1$–$C_3$ loweralkyl, halo $C_1$–$C_3$ loweralkyl, $C_2$–$C_3$ alkenyl or halo $C_2$–$C_3$ alkenyl or —X—$R^2$ is

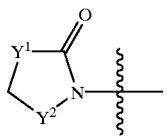

alkenyl or —X—$R^2$ is wherein $Y^1$ is —$CH_2$— and $Y^2$ is —C(=O)— or —C($R^{aa}$)($R^{bb}$)— wherein $R^{aa}$ and $R^{bb}$ are independently selected from the group consisting of hydrogen, $C_1$–$C_3$ loweralkyl, hydroxymethyl, 1-hydroxyethyl and 2-hydroxyethyl;

for compounds having Formula Ia, IIa, IIIa, IVa, Va, VIa, VIIa, VIIIa, IXa, Xa, XIa, XIIa, XIIIa, XIVa or XVa, $R^3$ and $R^4$ are independently selected from hydrogen, heterocyclic and —Z—$R^{14}$ wherein Z and $R^{14}$ are defined as above for compounds having Formula Ia, IIa and IIIa and wherein one of $R^3$ and $R^4$ is other than hydrogen;

for compounds having Formula Ib, IIb, IIIb, IVb, Vb, VIb, VIIb, VIIIb, IXb, Xb, XIb, XIIb, XIIIb, XIVb or XVb, $R^4$ is hydrogen or loweralkyl and $R^3$ is defined as above for compounds having Formula Ib, IIb and IIIb and wherein one of $R^3$ and $R^4$ is other than hydrogen;

$Z^1$ is —O—, —S— or —CH($R^5$)— wherein $R^5$ is hydrogen, loweralkyl, —$(CH_2)_rOR^{40}$ or —$(CH_2)_rN(R^{19})_2$ wherein r and $R^{19}$ and $R^{40}$ are defined as above; or $R^5$ is hydrogen, loweralkyl, —$(CH_2)_rOR^{40}$ or —$(CH_2)_rN(R^{19})_2$ wherein r and $R^{19}$ and $R^{40}$ are defined as above;

$R^6$ and $R^7$ are independently hydrogen or loweralkyl;

$R^8$ and $R^9$ are independently hydrogen or loweralkyl;

$R^{10}$ is hydrogen or loweralkyl; and for compounds having Formula Ia, IIa, IIIa, IVa, Va, VIa, VIIa, VIIIa, IXa, Xa, XIa, XIIa, XIIIa, XIVa or XVa, Y is $C_2$–$C_5$ alkenyl, $C_2$–$C_5$ haloalkenyl, —C(=$Q^2$)$R^{22}$, —N(=$Q^3$), —N(O)=$CHCH_3$ or a heterocyclic ring having 5 ring atoms and also containing one or two double bonds, wherein $R^{22}$, $Q^2$ and $Q^3$ are defined as above for compounds having Formula Ia, IIa and IIIa;

for compounds having Formula Ib, IIb, IIIb, IVb, Vb, VIb, VIIb, VIIIb, IXb, Xb, XIb, XIIb, XIIIb, XIVb or XVb, Y is —NHR$^{24}$ wherein $R^{24}$ is defined as above for compounds having Formula Ia, IIa and IIIa.

Even more preferred compounds of the invention are compounds having Formula Ia, Ib, IIa, IIb, IIIa, IIIb, IVa, IVb, Va, Vb, VIa, VIb, VIIa, VIIb, VIIIa, VIIIb, IXa, IXb, Xa, Xb, XIa, XIb, XIIa, XIIb, XIIIa, XIIIb, XIVa, XIVb, XVa or XVb or a salt, ester or prodrug thereof wherein $R^1$ is defined as above;

—X—$R^2$ is $R^2$—C(=O)—NH—, $R^2$—NH—C(=O)—, $R^2$—NH—$SO_2$— or $R^2$—$SO_2$—NH— wherein $R^2$ is $C_1$–$C_3$ loweralkyl, halo $C_1$–$C_3$ loweralkyl, $C_2$–$C_3$ alkenyl or halo $C_1$–$C_3$ alkenyl or —X—$R^2$ is

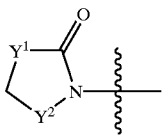

alkenyl or —X—$R^2$ is wherein $Y^1$ is —$CH_2$— and $Y^2$ is —C(=O)— or —C($R^{aa}$)($R^{bb}$)— wherein $R^{aa}$ and $R^{bb}$ are independently selected from the group consisting of hydrogen, $C_1$–$C_3$ loweralkyl, hydroxymethyl, 1-hydroxyethyl and 2-hydroxyethyl;

for compounds having Formula Ia, IIa, IIIa, IVa, Va, VIa, VIIa, VIIIa, IXa, Xa, XIa, XIIa, XIIIa, XIVa or XVa, $R^3$ and $R^4$ are independently selected from hydrogen, heterocyclic and —Z—$R^{14}$ wherein Z and $R^{14}$ are defined as above for compounds having Formula Ia, IIa and IIIa and wherein one of $R^3$ and $R^4$ is other than hydrogen;

for compounds having Formula Ib, IIb, IIIb, IVb, Vb, VIb, VIIb, VIIIb, IXb, Xb, XIb, XIIb, XIIIb, XIVb or XVb, $R^4$ is hydrogen or loweralkyl and $R^3$ is defined as above for compounds having Formula Ib, IIb and IIIb and wherein one of $R^3$ and $R^4$ is other than hydrogen;

$Z^1$ is —O—, —S— or —CH($R^5$)— wherein $R^5$ is hydrogen, loweralkyl, —$(CH_2)_rOR^{40}$ or —$(CH_2)_rN(R^{19})_2$ wherein r and $R^{19}$ and $R^{40}$ are defined as above; or $R^5$ is hydrogen, loweralkyl, —$(CH_2)_rOR^{40}$ or —$(CH_2)_rN(R^{19})_2$ wherein r and $R^{19}$ and $R^{40}$ are defined as above;

$R^6$ and $R^7$ are independently hydrogen or loweralkyl;

$R^8$ and $R^9$ are independently hydrogen or loweralkyl;

$R^{10}$ is hydrogen or loweralkyl; and for compounds having Formula Ia, IIa, IIIa, IVa, Va, VIa, VIIa, VIIIa, IXa, Xa, XIa, XIIa, XIIIa, XIVa or XVa, Y is $C_2$–$C_5$ alkenyl, $C_2$–$C_5$ haloalkenyl or a heterocyclic ring having 5 ring atoms and also containing one or two double bonds;

for compounds having Formula Ib, IIb, IIIb, IVb, Vb, VIb, VIIb, VIIIb, IXb, Xb, XIb, XIIb, XIIIb, XIVb or XVb, Y is —NHR$^{24}$ wherein R$^{24}$ is defined as above for compounds having Formula Ia, IIa and IIIa.

More highly preferred compounds of the invention are compounds having Formula Ia, Ib, IIa, IIb, IIIa, IIIb, IVa, IVb, Va, Vb, VIa, VIb, VIIa, VIIb, VIIIa, VIIIb, IXa, IXb, Xa, Xb, XIa, XIb, XIIa, XIIb, XIIIa, XIIIb, XIVa, XIVb, XVa or XVb or a salt, ester or prodrug thereof wherein R$^1$ is —CO$_2$H;

—X—R$^2$ is R$^2$—C(=O)—NH—, R$^2$—NH—C(=O)—, R$^2$—NH—SO$_2$— or R$^2$—SO$_2$—NH— wherein R$^2$ is C$_1$-C$_3$ loweralkyl or halo-C$_1$-C$_3$ loweralkyl;

for compounds having Formula Ia, IIa, IIIa, IVa, Va, VIa, VIIa, VIIIa, IXa, Xa, XIa, XIIa, XIIIa, XIVa or XVa, R$^3$ and R$^4$ are independently selected from hydrogen, heterocyclic and —Z—R$^{14}$ wherein Z and R$^{14}$ are defined as above for compounds having Formula Ia, IIa and IIIa and wherein one of R$^3$ and R$^4$ is other than hydrogen;

for compounds having Formula Ib, IIb, IIIb, IVb, Vb, VIb, VIIb, VIIIb, IXb, Xb, XIb, XIIb, XIIIb, XIVb or XVb, R$^4$ is hydrogen or loweralkyl and R$^3$ is defined as above for compounds having Formula Ib, IIb and IIIb and wherein one of R$^3$ and R$^4$ is other than hydrogen;

Z$^1$ is —O—, —S—, —CH$_2$—, $$\begin{array}{c}-\overset{\phantom{.}}{\underset{\phantom{.}}{C}}-\\ H\quad NH_2 \end{array}$$ or $$\begin{array}{c}-\overset{\phantom{.}}{\underset{\phantom{.}}{C}}-\\ H\quad OH \end{array}$$;

or R$^5$ is hydrogen;

R$^6$ and R$^7$ are independently hydrogen or loweralkyl;

R$^8$ and R$^9$ are hydrogen independently hydrogen or loweralkyl;

R$^{10}$ is hydrogen or loweralkyl; and for compounds having Formula Ia, IIa, IIIa, IVa, Va, VIa, VIIa, VIIIa, IXa, Xa, XIa, XIIa, XIIIa, XIVa or XVa, Y is C$_2$-C$_5$ alkenyl, C$_2$-C$_5$ haloalkenyl or a heterocyclic ring having 5 ring atoms and also containing one or two double bonds;

for compounds having Formula Ib, IIb, IIIb, IVb, Vb, VIb, VIIb, VIIIb, IXb, Xb, XIb, XIIb, XIIIb, XIVb or XVb, Y is —NHR$^{24}$ wherein R$^{24}$ is defined as above for compounds having Formula Ia, IIa and IIIa.

Even more highly preferred compounds of the invention are compounds having Formula Ia, Ib, IIa, IIb, IIIa, IIIb, IVa, IVb, Va, Vb, VIa, VIb, VIIa, VIIb, VIIIa, VIIIb, IXa, IXb, Xa, Xb, XIa, XIb, XIIa, XIIb, XIIIa, XIIIb, XIVa, XIVb, XVa or XVb or a salt, ester or prodrug thereof wherein R$^1$ is —CO$_2$H;

—X—R$^2$ is R$^2$—C(=O)—NH—, R$^2$—NH—C(=O)—, R$^2$—NH—SO$_2$— or R$^2$—SO$_2$—NH— wherein R$^2$ is C$_1$-C$_3$ loweralkyl or halo-C$_1$-C$_3$ loweralkyl;

for compounds having Formula Ia, IIa, IIIa, IVa, Va, VIa, VIIa, VIIIa, IXa, Xa, XIa, XIIa, XIIIa, XIVa or XVa, R$^4$ is hydrogen or loweralkyl and R$^3$ is heterocyclic or —Z—R$^{14}$ wherein Z and R$^{14}$ are defined as above for compounds having Formula Ia, IIa and IIIa;

for compounds having Formula Ib, IIb, IIIb, IVb, Vb, VIb, VIIb, VIIIb, IXb, Xb, XIb, XIIb, XIIIb, XIVb or XVb, R$^4$ is hydrogen or loweralkyl and R$^3$ is defined as above for compounds having Formula Ib, IIb and IIIb and wherein one of R$^3$ and R$^4$ is other than hydrogen;

Z$^1$ is —O—, —S—, —CH$_2$—, $$\begin{array}{c}-\overset{\phantom{.}}{\underset{\phantom{.}}{C}}-\\ H\quad NH_2 \end{array}$$ or $$\begin{array}{c}-\overset{\phantom{.}}{\underset{\phantom{.}}{C}}-\\ H\quad OH \end{array}$$;

or R$^5$ is hydrogen;

R$^6$ and R$^7$ are hydrogen;

R$^8$ and R$^9$ are hydrogen;

R$^{10}$ is hydrogen; and for compounds having Formula Ia, IIa, IIIa, IVa, Va, VIa, VIIa, VIIIa, IXa, Xa, XIa, XIIa, XIIIa, XIVa or XVa, Y is C$_2$-C$_5$ alkenyl, C$_2$-C$_5$ haloalkenyl or a heterocyclic ring having 5 ring atoms and also containing one or two double bonds;

for compounds having Formula Ib, IIb, IIb, IVb, Vb, VIb, VIIb, VIIIb, IXb, Xb, XIb, XIIb, XIIIb, XIVb or XVb, Y is —NHR$^{24}$ wherein R$^{24}$ is defined as above for compounds having Formula Ia, IIa and IIIa.

Other even more highly preferred compounds of the invention are compounds having Formula Ia, Ib, IIa, IIb, IIIa, IIIb, IVa, IVb, Va, Vb, VIa, VIb, VIIa, VIIb, VIIIa, VIIIb, IXa, IXb, Xa, Xb, XIa, XIb, XIIa, XIIb, XIIIa, XIIIb, XIVa, XIVb, XVa or XVb or a salt, ester or prodrug thereof wherein R$^1$ is —CO$_2$H;

—X—R$^2$ is R$^2$—C(=O)—NH—, R$^2$—NH—C(=O)—, R$^2$—NH—SO$_2$— or R$^2$—SO$_2$—NH— wherein R$^2$ is C$_1$-C$_3$ loweralkyl or halo C$_1$-C$_3$ loweralkyl;

for compounds having Formula Ia, IIa, IIIa, IVa, Va, VIa, VIIa, VIIIa, IXa, Xa, XIa, XIIa, XIIIa, XIVa or XVa, R$^4$ is hydrogen or loweralkyl and R$^3$ is (a) heterocyclic, (b) alkyl, (c) cycloalkyl, (d) cycloalkylalkyl, (e) alkenyl, (f) alkynyl, (g) —C(=O)—R$^{14}$, (h) —C(R$^{37c}$)(OR$^{37c}$)—R$^{14}$ or (i) —C(R$^{37a}$)(R$^{37b}$)—N(O)(R$^{37c}$)R$^{14}$ wherein R$^{14}$ is (i) alkyl, (ii) cycloalkyl, (iii) cycloalkylalkyl, (iv) alkenyl, (v) haloalkyl, (vi) haloalkenyl, (vii) aryl, (viii) arylalkyl, (ix) heterocyclic, (x) (heterocyclic)alkyl, (xi) hydroxyalkyl, (xii) alkoxyalkyl, (xiii) cyanoalkyl, (xiv) (R$^{37a}$O)—(O=)C-substituted alkyl or (xv) (R$^{37a}$O)$_2$—P(=O)-substituted alkyl;

R$^{37a}$ and R$^{37b}$ are independently selected from the group consisting of (i) hydrogen, (ii) loweralkyl and (iii) loweralkenyl; and R$^{37c}$ is (i) hydrogen, (ii) loweralkyl or (iii) loweralkenyl;

for compounds having Formula Ib, IIb, IIIb, IVb, Vb, VIb, VIIb, VIIIb, IXb, Xb, XIb, XIIb, XIIb, XIVb or XVb, R$^4$ is hydrogen or loweralkyl and R$^3$ is —C(R$^{37a}$)(OR$^{37c}$)—R$^{14}$ or —C(R$^{37a}$)(R$^{37b}$)—N(O)(R$^{37c}$)R$^{14}$ wherein R$^{14}$ is (i) alkyl, (ii) cycloalkyl, (iii) cycloalkylalkyl, (iv) alkenyl, (v) haloalkyl, (vi) haloalkenyl, (vii) aryl, (viii) arylalkyl, (ix) heterocyclic, (x) (heterocyclic)alkyl, (xi) hydroxyalkyl, (xii) alkoxyalkyl, (xiii) cyanoalkyl, (xiv) (R$^{37a}$O)—(O=)—C-substituted alkyl or (xv) (R$^{37a}$O)$_2$—P(=O)-substituted alkyl;

R$^{37a}$ and R$^{37b}$ are independently selected from the group consisting of (i) loweralkyl and (ii) loweralkenyl; and R$^{37c}$ is (i) hydrogen, (ii) loweralkyl or (iii) loweralkenyl;

$Z^1$ is —O—, —S—, —CH$_2$—, 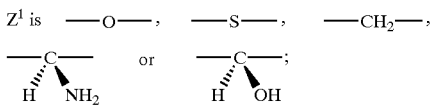 or or $R^5$ is hydrogen;
$R^6$ and $R^7$ are hydrogen;
$R^8$ and $R^9$ are hydrogen;
$R^{10}$ is hydrogen; and for compounds having Formula Ia, IIa, IIIa, IVa, Va, VIa, VIIa, VIIIa, IXa, Xa, XIa, XIIa, XIIIa, XIVa or XVa, Y is $C_2$–$C_5$ alkenyl, $C_2$–$C_5$ haloalkenyl or a heterocyclic ring having 5 ring atoms and also containing one or two double bonds;

for compounds having Formula Ib, IIb, IIIb, IVb, Vb, VIb, VIIb, VIIIb, IXb, Xb, XIb, XIIb, XIIIb, XIVb or XVb, Y is —NHR$^{24}$ wherein R$^{24}$ is defined as above for compounds having Formula Ia, IIa and IIIa.

Most highly preferred compounds of the invention are compounds having Formula Ia, Ib, IIa, IIb, IIIa, IIb, IVa, IVb, Va, Vb, VIa, VIb, VIIa, VIIb, VIIIa, VIIIb, IXa, IXb, Xa, Xb, XIa, XIb, XIIa, XIIIb, XIIIa, XIIIb, XIVa, XIVb, XVa or XVb or a salt, ester or prodrug thereof wherein $R^1$ is —CO$_2$H;

—X—R$^2$ is R$^2$—C(=O)—NH—, R$^2$—NH—C(=O)—, R$^2$—NH—SO$_2$— or R$^2$—SO$_2$—NH— wherein R$^2$ is $C_1$–$C_3$ loweralkyl or halo $C_1$–$C_3$ loweralkyl;

for compounds having Formula Ia, IIa, IIIa, IVa, Va, VIa, VIIa, VIIIa, IXa, Xa, XIa, XIIa, XIIIa, XIVa or XVa, R$^4$ is hydrogen and R$^3$ is (a) heterocyclic, (b) alkyl or (c) —C(R$^{37a}$)(OR$^{37c}$)—R$^{14}$ wherein R$^{14}$ is (i) alkyl, (ii) cycloalkyl, (iii) cycloalkylalkyl, (iv) alkenyl, (v) haloalkyl, (vi) haloalkenyl, (vii) aryl, (viii) arylalkyl, (ix) heterocyclic, (x) (heterocyclic)alkyl, (xi) hydroxyalkyl, (xii) alkoxyalkyl, (xiii) cyanoalkyl, (xiv) (R$^{37a}$O)—(O=)—C-substituted alkyl or (xv) (R$^{37a}$O)$_2$—P(=O)-substituted alkyl;

R$^{37a}$ and R$^{37b}$ are independently selected from the group consisting of (i) hydrogen, (ii) loweralkyl and (iii) loweralkenyl; and R$^{37c}$ is (i) hydrogen, (ii) $C_1$–$C_3$ loweralkyl or (iii) allyl;

for compounds having Formula Ib, IIb, IIIb, IVb, Vb, VIb, VIIb, VIIIb, IXb, Xb, XIb, XIIb, XIIIb, XIVb or XVb, R$^4$ is hydrogen and
R$^3$ is —C(R$^{37a}$)(OR$^{37c}$)—R$^{14}$ wherein R$^{14}$ is (ii) alkyl, (ii) cycloalkyl, (iii) cycloalkylalkyl, (iv) alkenyl, (v) haloalkyl, (vi) haloalkenyl, (vii) aryl, (viii) arylalkyl, (ix) heterocyclic, (x) (heterocyclic)alkyl, (xi) hydroxyalkyl, (xii) alkoxyalkyl, (xiii) cyanoalkyl, (xiv) (R$^{37a}$O)—(O=)—C-substituted alkyl or (xv) (R$^{37a}$O)$_2$—P(=O)-substituted alkyl;

R$^{37a}$ is loweralkyl or loweralkenyl; and
R$^{37c}$ is (i) hydrogen, (ii) $C_1$–$C_3$ loweralkyl or (iii) allyl;

$Z^1$ is —O—, —S—, —CH$_2$—, 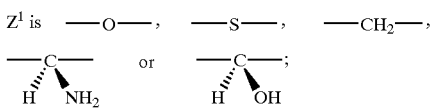 or or $R^5$ is hydrogen;
$R^6$ and $R^7$ are hydrogen;
$R^8$ and $R^9$ are hydrogen;
$R^{10}$ is hydrogen; and for compounds having Formula Ia, IIa, IIIa, IVa, Va, VIa, VIIa, VIIIa, IXa, Xa, XIa, XIIa, XIIIa, XIVa or XVa, Y is $C_2$–$C_5$ alkenyl, $C_2$–$C_5$ haloalkenyl or a heterocyclic ring having 5 ring atoms and also containing one or two double bonds;

for compounds having Formula Ib, IIb, IIIb, IVb, Vb, VIb, VIIb, VIIIb, IXb, Xb, XIb, XIIb, XIIIb, XIVb or XVb, Y is —NHR$^{24}$ wherein R$^{24}$ is defined as above for compounds having Formula Ia, IIa and IIIa.

Other most highly preferred compounds of the invention are compounds having Formula Ia, Ib, IIa, IIb, IIIa, lIIb, IVa, IVb, Va, Vb, VIa, VIb, VIIa, VIIb, VIIIa, VIIIb, IXa, IXb, Xa, Xb, XIa, XIb, XIIa, XIIb, XIIIa, XIIIb, XIVa, XIVb, XVa or XVb or a salt, ester or prodrug thereof wherein R$^1$ is —CO$_2$H;

—X—R$^2$ is R$^2$—C(=O)—NH— or R$^2$—SO$_2$—NH— wherein R$^2$ is $C_1$–$C_3$ loweralkyl or halo $C_1$–$C_3$ loweralkyl;

for compounds having Formula Ia, IIa, IIIa, IVa, Va, VIa, VIIa, VIIIa, IXa, Xa, XIa, XIIa, XIIIa, XIVa or XVa, R$^4$ is hydrogen and R$^3$ is (a) heterocyclic, (b) alkyl or (c) —C(R$^{37a}$)(OR$^{37c}$)—R$^{14}$ wherein R$^{14}$ is (i) loweralkyl, (ii) loweralkenyl, (iii) hydroxy-substituted loweralkyl or (iv) alkoxy-substituted loweralkyl;

R$^{37a}$ is (i) hydrogen, (ii) loweralkyl or (iii) loweralkenyl; and

R$^{37c}$ is (i) hydrogen, (ii) $C_1$–$C_3$ loweralkyl or (iii) allyl;

for compounds having Formula Ib, IIb, IIb, IVb, Vb, VIb, VIIb, VIIIb, IXb, Xb, XIb, XIIb, XIIIb, XIVb or XVb, R$^4$ is hydrogen and R$^3$ is —C(R$^{37a}$)(OR$^{37c}$)—R$^{14}$ wherein R$^{14}$ is (i) loweralkyl, (ii) loweralkenyl, (iii) hydroxy-substituted loweralkyl or (iv) alkoxy-substituted loweralkyl;

R$^{37a}$ is loweralkyl or loweralkenyl; and
R$^{37c}$ is (i) hydrogen, (ii) $C_1$–$C_3$ loweralkyl or (iii) allyl;

$Z^1$ is —O—, —S—, —CH$_2$—, 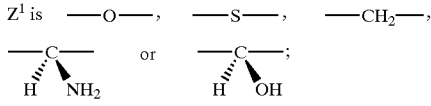 or or $R^5$ is hydrogen;
$R^6$ and $R^7$ are hydrogen;
$R^8$ and $R^9$ are hydrogen;
$R^{10}$ is hydrogen; and for compounds having Formula Ia, IIa, IIIa, IVa, Va, VIa, VIIa, VIIIa, IXa, Xa, XIa, XIIa, XIIIa, XIVa or XVa, Y is $C_2$–$C_5$ alkenyl, $C_2$–$C_5$ haloalkenyl or a heterocyclic ring having 5 ring atoms and also containing one or two double bonds;

for compounds having Formula Ib, IIb, IIIb, IVb, Vb, VIb, VIIb, VIIIb, IXb, Xb, XIb, XIIb, XIIIb, XIVb or XVb, Y is —NHR$^{24}$ wherein R$^{24}$ is defined as above for compounds having Formula Ia, IIa and IIIa.

Other most highly preferred compounds of the invention are compounds having Formula Ia, Ib, IIa, IIb, IIIa, IIIb, IVa, IVb, Va, Vb, VIa, VIb, VIIa, VIIb, VIIIa, VIIIb, IXa, IXb, Xa, Xb, XIa, XIb, XIIa, XIIb, XIIIa, XIIIb, XIVa, XIVb, XVa or XVb or a salt, ester or prodrug thereof wherein R$^1$ is —CO$_2$H;

—X—R$^2$ is R$^2$—C(=O)—NH— or R$^2$—SO$_2$—NH— wherein R$^2$ is C$_1$–C$_3$ loweralkyl or halo C$_1$–C$_3$ loweralkyl;

for compounds having Formula Ia, IIa, IIIa, IVa, Va, VIa, VIIa, VIIIa, IXa, Xa, XIa, XIIa, XIIIa, XIVa or XVa, R$^4$ is hydrogen and R$^3$ is C(R$^{37a}$)(OR$^{37c}$)—R$^{14}$ wherein R$^{14}$ is loweralkyl, loweralkenyl or alkoxy-substituted loweralkyl;

R$^{37a}$ is loweralkyl or loweralkenyl; and

R$^{37c}$ is hydrogen, C$_1$–C$_3$ loweralkyl or allyl;

for compounds having Formula Ib, IIb, IIIb, IVb, Vb, VIb, VIIb, VIIIb, IXb, Xb, XIb, XIIb, XIIIb, XIVb or XVb, R$^4$ is hydrogen and R$^3$ is —C(R$^{37a}$)(OR$^{37c}$)—R$^{14}$ wherein R$^{14}$ is loweralkyl, loweralkenyl or alkoxy-substituted loweralkyl;

R$^{37a}$ is loweralkyl or loweralkenyl; and

R$^{37c}$ is (i) hydrogen, (ii) C$_1$–C$_3$ loweralkyl or (iii) allyl;

Z$^1$ is —O—, —S—, —CH$_2$—, $$\overset{\cdot\cdot\cdot}{-\underset{H}{\overset{NH_2}{C}}-} \quad \text{or} \quad \overset{\cdot\cdot\cdot}{-\underset{H}{\overset{OH}{C}}-};$$

or R$^5$ is hydrogen;

R$^6$ and R$^7$ are hydrogen;

R$^3$ and R$^9$ are hydrogen;

R$^{10}$ is hydrogen; and for compounds having Formula Ia, IIa, IIIa, IVa, Va, VIa, VIIa, VIIIa, IXa, Xa, XIa, XIIa, XIIIa, XIVa or XVa, Y is C$_2$–C$_5$ alkenyl, C$_2$–C$_5$ haloalkenyl or a heterocyclic ring having 5 ring atoms and also containing one or two double bonds;

for compounds having Formula Ib, IIb, IIIb, IVb, Vb, VIb, VIIb, VIIIb, IXb, Xb, XIb, XIIb, XIIIb, XIVb or XVb, Y is —NHR$^{24}$ wherein R$^{24}$ is hydrogen or —C(=Q$^4$)—R$^{30}$ wherein Q$^4$ is O, S or N(R$^{33}$) wherein R$^{33}$ is hydrogen, hydroxy, methyl, ethyl, amino, —CN or —NO$_2$ and R$^{30}$ is —N(R$^{35}$)$_2$, —NHOH, —NHNH$_2$, —N(CH$_3$)NH$_2$ or —N(CH$_2$CH$_3$)NH$_2$ wherein each R$^{35}$ is independently hydrogen, methyl or ethyl.

Other most highly preferred compounds of the invention are compounds having Formula Ia, Ib, IIa, IIb, IIIa, IIIb, IVa, IVb, Va, Vb, VIa, VIb, VIIa, VIIb, VIIIa, VIIIb, IXa, IXb, Xa, Xb, XIa, XIb, XIIa, XIIb, XIIIa, XIIIb, XIVa, XIVb, XVa or XVb or a salt, ester or prodrug thereof wherein R$^1$ is —CO$_2$H;

—X—R$^2$ is R$^2$—C(=O)—NH— or R$^2$—SO$_2$—NH— wherein R$^2$ is C$_1$–C$_3$ loweralkyl or halo C$_1$–C$_3$ loweralkyl;

for compounds having Formula Ia, IIa, IIIa, IVa, Va, VIa, VIIa, VIIIa, IXa, Xa, XIa, XIIa, XIIIa, XIVa or XVa, R$^4$ is hydrogen and R$^3$ is —C(R$^{37a}$)(OR$^{37c}$)—R$^{14}$ wherein R$^{14}$ is loweralkyl, loweralkenyl or alkoxy-substituted loweralkyl;

R$^{37a}$ is loweralkyl or loweralkenyl; and

R$^{37c}$ is hydrogen, C$_1$–C$_3$ loweralkyl or allyl;

for compounds having Formula Ib, IIb, IIIb, IVb, Vb, VIb, VIIb, VIIIb, IXb, Xb, XIb, XIIb, XIIIb, XIVb or XVb, R$^4$ is hydrogen and R$^3$ is —C(R$^{37a}$)(OR$^{37c}$)—R$^{14}$ wherein R$^{14}$ is loweralkyl, loweralkenyl or alkoxy-substituted loweralkyl;

R$^{37a}$ is loweralkyl or loweralkenyl; and

R$^{37c}$ is (i) hydrogen, (ii) C$_1$–C$_3$ loweralkyl or (iii) allyl;

Z$^1$ is —CH$_2$—, $$\overset{\cdot\cdot\cdot}{-\underset{H}{\overset{NH_2}{C}}-} \quad \text{or} \quad \overset{\cdot\cdot\cdot}{-\underset{H}{\overset{OH}{C}}-};$$

or R$^5$ is hydrogen;

R$^5$ is hydrogen;

R$^6$ and R$^7$ are hydrogen;

R$^8$ and R$^9$ are hydrogen;

R$^{10}$ is hydrogen; and for compounds having Formula Ia, IIa, IIIa, IVa, Va, VIa, VIIa, VIIIa, IXa, Xa, XIa, XIIa, XIIIa, XIVa or XVa, Y is C$_2$–C$_5$ alkenyl;

for compounds having Formula Ib, IIb, IIIb, IVb, Vb, VIb, VIIb, VIIIb, IXb, Xb, XIb, XIIb, XIIIb, XIVb or XVb, Y is —NH$_2$ or —N—C(=NH)—NH$_2$.

Preferred substituents R$^1$ include —CO$_2$H or esters or prodrugs thereof. Preferred esters include C$_1$–C$_6$ loweralkyl esters, cycloalkyl esters (for example, cyclopropyl ester, cyclohexyl ester and the like), cycloalkylalkyl esters, aryl esters (for example, phenyl ester, 2-methylphenyl ester and the like), arylalkyl esters (for example, benzyl ester, phenylethyl ester and the like), haloalkyl esters (for example, 2,2,2-trichloroethyl ester and the like), heterocyclic esters (for example, N-methylpiperazin-4-yl ester and the like), (heterocyclic)alkyl esters (for example, pyridyl methyl ester, pyridylethyl ester, N-methylpiperazin-4-ylmethyl ester, piperidin-1-ylmethyl ester, morpholin-4-ylmethyl ester, 2-(piperidin-1-yl)ethyl ester, 2-(morpholin-4-yl)ethyl ester, 2. (-N-methylpiperazin-4-yl)ethyl ester, 1,1-dimethyl-2-(piperidin-1-yl)ethyl ester, 1,1-dimethyl-2-(morpholin-4-yl) ethyl ester, 1,1-dimethyl-2-(N-methylpiperazin-4-yl)ethyl ester, phthalidylmethyl ester and the like), di-loweralkylaminoalkyl esters (for example, 2-N,N-dimethylaminoethyl ester, 2-N,N-diethylaminoethyl ester and the like), acyloxyalkyl esters (for example, t-butylcarbonyloxymethyl ester and the like), alkoxycarbonyloxyalkyl esters (for example, t-butyloxycarbonyloxymethyl ester and the like), di-loweralkylaminocarbonylalkyl esters (for example, N,N-dimethylaminocarbonylmethyl ester, N,N-diethylaminocarbonylmethyl ester and the like), acylalkyl esters (for example, t-butylcarbonylmethyl ester and the like), (heterocyclic)carbonylalkyl esters (for example, piperidin-1-ylcarbonylmethyl ester, morpholin-4-ylcarbonylmethyl ester, N-methylpiperazin-4-ylcarbonylmethyl ester and the like), di-loweralkylaminocarbonyloxyalkyl esters (for example, N,N-dimthylaminocarbonyloxymethyl ester, N,N-diethylaminocarbonyloxymethyl ester, N-t-butyl-N-methyl-aminocarbonyloxymethyl ester and the like), alkoxycarbonylalkyl esters (for example, ethoxycarbonylmethyl ester, isopropoxycarbonylmethyl ester and the like), (heterocyclic) carbonyloxyalkyl esters (for example, pyridylcarbonyloxymethyl ester and the like) and the like. Preferred substituents R$^1$ also include —S(O)$_2$NHC(=O)R$^{11}$ wherein R$^{11}$ is defined as above.

Most highly preferred substituents R$^1$ include —CO$_2$H or esters or prodrugs thereof. Most highly preferred esters include C$_1$–C$_6$ loweralkyl esters, cycloalkyl esters, cycloalkylalkyl esters or substituted or unsubstituted benzyl esters.

Preferred substituents —X—R$^2$ include R$^2$—C(=O)—NH—, R$^2$—NH—C(=O)—, R$^2$—NH—SO$_2$— or $R^2$—$SO_2$—NH— wherein $R^2$ is $C_1$-$C_3$ loweralkyl, halo $C_1$-$C_3$ loweralkyl, $C_2$-$C_3$ alkenyl or halo $C_2$-$C_3$ alkenyl or —X—$R^2$ is

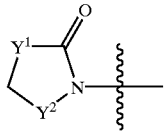

wherein $Y^1$ is —$CH_2$—, —O—, —S— or —NH— and $Y^2$ is —C(=O)— or —C($R^{aa}$)($R^{bb}$)— wherein $R^{aa}$ and $R^{bb}$ are independently selected from the group consisting of hydrogen, $C_1$-$C_3$ loweralkyl, hydroxymethyl, 1-hydroxyethyl, 2-hydroxyethyl, aminomethyl, 1-aminoethyl, 2-aminoethyl, thiolmethyl, 1-thiolethyl, 2-thiolethyl, methoxymethyl, N-methylaminomethyl and methylthiomethyl.

More preferred substituents —X—$R^2$ include $R^2$—C(=O)—NH—, $R^2$—NH—C(=O)—, $R^2$—NH—$SO_2$— or $R^2$—$SO_2$—NH— wherein $R^2$ is $C_1$-$C_3$ loweralkyl, halo $C_1$-$C_3$ loweralkyl, $C_2$-$C_3$ alkenyl or halo $C_2$-$C_3$ alkenyl or —X—$R^2$ is

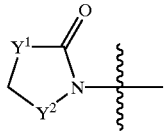

wherein $Y^1$ is —$CH_2$— and $Y^2$ is —C(=O)— or —C($R^{aa}$)($R^{bb}$)— wherein $R^{aa}$ and $R^{bb}$ are independently selected from the group consisting of hydrogen, $C_1$-$C_3$ loweralkyl, hydroxymethyl, 1-hydroxyethyl and 2-hydroxyethyl.

Even more preferred substituents —X—$R^2$ include $R^2$—C(=O)—NH—, $R^2$—NH—C(=O)—, $R^2$—NH—$SO_2$— or $R^2$—$SO_2$—NH— wherein $R^2$ is $C_1$-$C_3$ loweralkyl, halo $C_1$-$C_3$ loweralkyl, $C_2$-$C_3$ alkenyl or halo $C_2$-$C_3$ alkenyl.

More highly preferred substituents —X—$R^2$ include $R^2$—C(=O)—NH—, $R^2$—NH—C(=O)—, $R^2$—NH—$SO_2$— or $R^2$—$SO_2$—NH— wherein $R^2$ is $C_1$-$C_3$ loweralkyl or halo-$C_1$-$C_3$ loweralkyl.

Even more highly preferred substituents —X—$R^2$ include $R^2$—C(=O)—NH—, $R^2$—NH—C(=O)—, $R^2$—NH—$SO_2$— or $R^2$—$SO_2$—NH— wherein $R^2$ is $C_1$-$C_2$ loweralkyl or halo $C_1$-$C_2$ loweralkyl, and especially, $CH_3$—C(=O)—NH—, $CF_3$—C(=O)—NH—, $CH_3$—$SO_2$—NH— or $CF_3$—$SO_2$—NH—.

$Z^1$ is —O—, —S— or —CH($R^5$)— wherein $R^5$ is hydrogen, loweralkyl, —($CH_2$)$_r$$OR^{40}$ or —($CH_2$)$_r$$N(R^{19})_2$ wherein r and $R^{19}$ and $R^{40}$ are defined as above; or $R^5$ is hydrogen, loweralkyl, —($CH_2$)$_r$$OR^{40}$ or —($CH_2$)$_r$$N(R^{19})_2$ wherein r and $R^{19}$ and $R^{40}$ are defined as above.

More preferred substituents $Z^1$ are —O—, —S— or —CH($R^5$)— wherein $R^5$ is hydrogen, loweralkyl, $NH_2$ or —OH.

More highly preferred substituents $Z^1$ are —O—, —S—, —$CH_2$— or

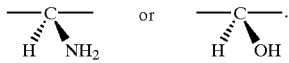

Even more highly preferred substituents $Z^1$ are —O—, —$CH_2$— or

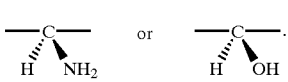

For compounds having Formula Ia, IIa, IIIa, IVa, Va, VIa, VIIa, VIIIa, IXa, Xa, XIa, XIIa, XIIIa, XIVa or XVa:

preferred substituents $R^3$ and $R^4$ are independently selected from the group consisting of hydrogen, heterocyclic and —Z—$R^{14}$ wherein Z and $R^{14}$ are defined as most broadly defined previously herein for Formula Ia, IIa and IIIa and wherein one of $R^3$ and $R^4$ is other than hydrogen;

more highly preferred, substituent $R^4$ is hydrogen or loweralkyl and $R^3$ includes heterocyclic or —Z—$R^{14}$ wherein Z and $R^{14}$ are defined as most broadly defined previously herein;

even more highly preferred, substituent $R^4$ is hydrogen or loweralkyl and $R^3$ includes
(a) heterocyclic, (b) alkyl, (c) cycloalkyl, (d) cycloalkylalkyl, (e) alkenyl, (f) alkynyl, (g) —C(=O)—$R^{14}$, (h) —C($R^{37a}$)($OR^{37c}$)—$R^{14}$ or (i) —C($R^{37a}$)($R^{37b}$)—N(O)($R^{37c}$)$R^{14}$ wherein $R^{14}$ is
(i) alkyl, (ii) cycloalkyl, (iii) cycloalkylalkyl, (iv) alkenyl, (v) haloalkyl, (vi) haloalkenyl, (vii) aryl, (viii) arylalkyl, (ix) heterocyclic, (x) (heterocyclic)alkyl, (xi) hydroxyalkyl, (xii) alkoxyalkyl, (xiii) cyanoalkyl, (xiv) ($R^{37a}$O)—(O=)C-substituted alkyl or (xv) ($R^{37a}$O)$_2$—P(=O)-substituted alkyl;

$R^{37a}$ and $R^{37b}$ are independently selected from the group consisting of (i) hydrogen, (ii) loweralkyl and (iii) loweralkenyl; and $R^{37c}$ is (i) hydrogen, (ii) loweralkyl or (iii) loweralkenyl.

Most highly preferred, substituent $R^4$ is hydrogen and $R^3$ includes (a) heterocyclic, (b) alkyl or (c) —C($R^{37a}$)($OR^{37c}$)—$R^{14}$ wherein $R^{14}$ (i) alkyl, (ii) cycloalkyl, (iii) cycloalkylalkyl, (iv) alkenyl, (v) haloalkyl, (vi) haloalkenyl, (vii) aryl, (viii) arylalkyl, (ix) heterocyclic, (x) (heterocyclic)alkyl, (xi) hydroxyalkyl, (xii) alkoxyalkyl, (xiii) cyanoalkyl, (xiv) ($R^{37a}$O)—(O=)C-substituted alkyl or (xv) ($R^{37a}$O)$_2$—P(=O)-substituted alkyl;

$R^{37a}$ and $R^{37b}$ are independently selected from the group consisting of (i) hydrogen, (ii) loweralkyl and (iii) loweralkenyl; and $R^{37c}$ is (i) hydrogen, (ii) $C_1$-$C_3$ loweralkyl or (iii) allyl;

also most highly preferred, substituent $R^4$ is hydrogen and $R^3$ includes (a) heterocyclic, (b) alkyl or (c) —C($R^{37a}$)($OR^{37c}$)$R^{14}$ wherein $R^{14}$ is (i) loweralkyl, (ii) loweralkenyl, (iii) hydroxy-substituted loweralkyl or (iv) alkoxy-substituted loweralkyl;

$R^{37a}$ is (i) hydrogen, (ii) loweralkyl or (iii) loweralkenyl; and $R^{37c}$ is (i) hydrogen, (ii) $C_1$-$C_3$ loweralkyl or (iii) allyl; and also most highly preferred, substituent $R^4$ is hydrogen and $R^3$ includes —C($R^{37a}$)($OR^{37c}$)—$R^{14}$ wherein $R^{14}$ is loweralkyl, loweralkenyl or alkoxy-substituted loweralkyl;

$R^{37a}$ is loweralkyl or loweralkenyl; and $R^{37c}$ is hydrogen, $C_1$-$C_3$ loweralkyl or allyl, and especially, wherein $R^{37c}$ is hydrogen or methyl.

For compounds having Formula Ib, IIb, IIIb, IVb, Vb, VIb, VIIb, VIIIb, IXb, Xb, XIb, XIIb, XIIb, XIVb or XVb:

preferred $R^4$ is hydrogen or loweralkyl and
$R^3$ is defined as above for compounds having Formula Ib, IIb and IIIb and
wherein one of $R^3$ and $R^4$ is other than hydrogen;
more highly preferred $R^4$ is hydrogen or loweralkyl and $R^3$ is —$C(R^{37a})(OR^{37c})$—$R^{14}$ or —$C(R^{37a})(R^{37b})$—$N(O)(R^{37c})R^{14}$ wherein $R^{14}$ is (iii) alkyl, (ii) cycloalkyl, (iii) cycloalkylalkyl, (iv) alkenyl, (v) haloalkyl, (vi) haloalkenyl, (vii) aryl, (viii) arylalkyl, (ix) heterocyclic, (x) (heterocyclic)alkyl, (xi) hydroxyalkyl, (xii) alkoxyalkyl, (xiii) cyanoalkyl, (xiv) $(R^{37a}O)$—(O=)C-substituted alkyl or (xv) $(R^{37a}O)_2$—P(=O)-substituted alkyl;

$R^{37a}$ and $R^{37b}$ are independently selected from the group consisting of (i) loweralkyl and (ii) loweralkenyl; and $R^{37c}$ is (i) hydrogen, (ii) loweralkyl or (iii) loweralkenyl;
even more highly preferred $R^4$ is hydrogen and $R^3$ is —$C(R^{37a})(OR^{37c})$—$R^{14}$ wherein $R^{14}$ is (iv) alkyl, (ii) cycloalkyl, (iii) cycloalkylalkyl, (iv) alkenyl, (v) haloalkyl, (vi) haloalkenyl, (vii) aryl, (viii) arylalkyl, (ix) heterocyclic, (x) (heterocyclic)alkyl, (xi) hydroxyalkyl, (xii) alkoxyalkyl, (xiii) cyanoalkyl, (xiv) $(R^{37a}O)$—(O=)C-substituted alkyl or (xv) $(R^{37a}O)_2$—P(=O)-substituted alkyl;

$R^{37a}$ is loweralkyl or loweralkenyl; and
$R^{37c}$ is (i) hydrogen, (ii) $C_1$–$C_3$ loweralkyl or (iii) allyl;
most highly preferred $R^4$ is hydrogen and $R^3$ is —$C(R^{37a})(OR^{37c})$—$R^{14}$ wherein $R^{14}$ is (i) loweralkyl, (ii) loweralkenyl, (iii) hydroxy-substituted loweralkyl or (iv) alkoxy-substituted loweralkyl;

$R^{37a}$ is loweralkyl or loweralkenyl; and
$R^{37c}$ is (i) hydrogen, (ii) $C_1$–$C_3$ loweralkyl or (iii) allyl; and
also most highly preferred $R^4$ is hydrogen and $R^3$ is —$C(R^{37a})(OR^{37c})$—$R^{14}$ wherein $R^{14}$ is loweralkyl, loweralkenyl or alkoxy-substituted loweralkyl;

$R^{37a}$ is loweralkyl or loweralkenyl; and
$R^{37c}$ is (i) hydrogen, (ii) $C_1$–$C_3$ loweralkyl or (iii) allyl.

Preferred substituents $R^5$ include those independently selected from hydrogen, loweralkyl, —$(CH_2)_rOR^{40}$ and —$(CH_2)_rN(R^{19})_2$ wherein r and $R^{19}$ and $R^{40}$ are defined as above.

More preferred substituents $R^5$ are independently selected from hydrogen, loweralkyl, —$(CH_2)_rOR^{40}$ and —$(CH_2)_rN(R^{19})_2$ wherein r is 0 or 1 and one $R^{19}$ is hydrogen or loweralkyl and the other $R^{19}$ is hydrogen, loweralkyl or an N-protecting group and $R^{40}$ is hydrogen.

Even more preferred substituents $R^5$ are independently selected from hydrogen, loweralkyl, —$NH_2$ and —OH.

Most highly preferred, $R^5$ is hydrogen, —$NH_2$ or —OH.

Preferred substituents $R^6$ and $R^7$ include independently hydrogen and loweralkyl. Most highly preferred, $R^6$ and $R^7$ are hydrogen.

Preferred substituents $R^8$, $R^9$ and $R^{10}$ include independently hydrogen, fluoro and loweralkyl. Most highly preferred, $R^8$, $R^9$ and $R^{10}$ are hydrogen.

For compounds having Formula Ia, IIa, IIIa, IVa, Va, VIa, VIIa, VIIIa, IXa, Xa, XIa, XIIa, XIIIa, XIVa or XVa:
preferred substituent Y includes $C_2$–$C_5$ alkenyl, $C_2$–$C_5$ haloalkenyl, —$C(=Q^2)R^{22}$, —$N(=Q^3)$, —$N(O)$=$CHCH_3$, —$N(CH_3)R^{24}$ or a heterocyclic ring having from 3 to 6 ring atoms, wherein $R^{22}$, $R^{24}$, $Q^2$ and $Q^3$ are defined as above;
more preferred substituent Y includes $C_2$–$C_5$ alkenyl, $C_2$–$C_5$ haloalkenyl, —$C(=Q^2)R^{22}$, —$N(=Q^3)$, —$N(O)$=$CHCH_3$ or a heterocyclic ring having 5 ring atoms and also containing one or two double bonds, wherein $R^{22}$, $Q^2$ and $Q^3$ are defined as above;
even more preferred substituent Y includes $C_2$–$C_5$ alkenyl, $C_2$–$C_5$ haloalkenyl or a heterocyclic ring having 5 ring atoms and also containing one or two double bonds. Representative alkenyl and haloalkenyl substituents Y include:
—CH=CH$_2$, —CH=CHF, —CH=CH—CH$_3$, —CH=CH—CF$_3$, —CH=CHCl, —CH=CHBr, —CH=CF$_2$, —CH=CF(CH$_3$), —CH=CF(CF$_3$), —CH=CFCl, —CH=CFBr, —CH=C(CH$_3$)$_2$, —CH=C(CH$_3$) (CF$_3$), —CH=CCl(CH$_3$), —CH=CBr(CH$_3$), —CH=C(CF$_3$)$_2$, —CH=CCl (CF$_3$), —CH=CBr(CF$_3$), —CH=CCl$_2$, —CH=CClBr, —CF=CH$_2$, —CF=CHF, —CF=CH—CH$_3$, —CF=CH—CF$_3$, —CF=CHCl, —CF=CHBr, —CF=CF$_2$, —CF=CF(CH$_3$), —CF=CF(CF$_3$), —CF=CFCl, —CF=CFBr, —CF=C(CH$_3$)$_2$, —CF=C(CH$_3$) (CF$_3$), —CF=CCl(CH$_3$), —CF=CBr(CH$_3$), —CF=C(CF$_3$)$_2$, —CF=CCl(CF$_3$), —CF=CBr (CF$_3$), —CF=CCl$_2$, —CF=CClBr, —C(CH$_3$)=CH$_2$, —C(CH$_3$)=CHF, —C(CH$_3$)=CH—CH$_3$, —C(CH$_3$)=CH—CF$_3$, —C(CH$_3$)=CHCl, —C(CH$_3$)=CHBr, —C(CH$_3$)=CF$_2$, —C(CH$_3$)=CF(CH$_3$), —C(CH$_3$)=CF(CF$_3$), —C(CH$_3$)=CFCl, —C(CH$_3$)=CFBr, —C(CH$_3$)=C(CH$_3$)$_2$, —C(CH$_3$)=C(CH$_3$) (CF$_3$), —C(CH$_3$)=CCl(CH$_3$), —C(CH$_3$)=CBr(CH$_3$), —C(CH$_3$)=C(CF$_3$)$_2$, —C(CH$_3$)=CCl(CF$_3$), —C(CH$_3$)=CBr(CF$_3$), —C(CH$_3$)=CCl$_2$, —C(CH$_3$)=CClBr, —C(CF$_3$)=CH$_2$, —C(CF$_3$)=CHF, —C(CF$_3$)=CH—CH$_3$, —C(CF$_3$)=CH—CF$_3$, —C(CF$_3$)=CHCl, —C(CF$_3$)=CHBr, —C(CF$_3$)=CF$_2$, —C(CF$_3$)=CF (CH$_3$), —C(CF$_3$)=CF(CF$_3$), —C(CF$_3$)=CFCl, —C(CF$_3$)=CFBr, —C(CF$_3$)=C(CH$_3$)$_2$, —C(CF$_3$)=C(CH$_3$)(CF$_3$), —C(CF$_3$)=CCl(CH$_3$), —C(CF$_3$)=CBr(CH$_3$), —C(CF$_3$)=C(CF$_3$)$_2$, —C(CF$_3$)=CCl (CF$_3$), —C(CF$_3$)=CBr(CF$_3$), —C(CF$_3$)=CCl$_2$, —C(CF$_3$)=CClBr, —CCl=CH$_2$, —CCl=CHF, —CCl=CH—CH$_3$, —CCl=CH—CF$_3$, —CCl=CHCl, —CCl=CHBr, —CCl=CF$_2$, —CCl=CF(CH$_3$), —CCl=CF(CF$_3$), —CCl=CFCl, —CCl=CFBr, —CCl=C(CH$_3$)$_2$, —CCl=C(CH$_3$) (CF$_3$), —CCl=CCl(CH$_3$), —CCl=CBr(CH$_3$), —CCl=C(CF$_3$)$_2$, —CCl=CCl (CF$_3$), —CCl=CBr(CF$_3$), —CCl=CCl$_2$, —CCl=CClBr, —CH=CH—CH$_2$CH$_3$, —CH=CF—CH$_2$CH$_3$, —CF=CH—CH$_2$CH$_3$, —CF=CF—CH$_2$CH$_3$, —CH=C(CH$_3$)(CH$_2$CH$_3$), —CF=C(CH$_3$)(CH$_2$CH$_3$), —CH=CCl(CH$_2$CH$_3$), —CF=CCl(CH$_2$CH$_3$), —C(CH$_3$)=CH—CH$_2$CH$_3$, —C(CH$_3$)=CF—CH$_2$CH$_3$, —CCl=CH—CH$_2$CH$_3$, —CCl=CF—CH$_2$CH$_3$, —C(CH$_2$CH$_3$)=CH$_2$, —C(CH$_2$CH$_3$)=CHF, —C(CH$_2$CH$_3$)=CF$_2$, —C(CH$_2$CH$_3$)=CH—CH$_3$, —C(CH$_2$CH$_3$)=CF—CH$_3$, —C(CH$_2$CH$_3$)=CH—Cl, —C(CH$_2$CH$_3$)=CFCl;

representative Y substituents which are heterocyclic rings having 5 ring atoms and also containing one or two double bonds include:
furanyl, dihydrofuranyl, didehydrodioxolanyl, dithiolyl, imidazolyl, imidazolinyl, isothiazolyl, isothiazolinyl, isoxazolyl, isoxazolinyl, oxadiazolyl, oxadiazolinyl, oxathiolyl, oxazolyl, oxazolinyl, pyrazolyl, pyrazolinyl, pyrrolyl, dihydropyrrolyl, tetrazolyl, tetrazolinyl, thiadiazolyl, thiadiazolinyl, thiazolyl, thiazolinyl, thienyl, dihydrothienyl, triazolyl, triazolinyl;

more highly preferred substituents Y include cis-propenyl, trans-propenyl, isobutenyl, cis-2-chlorovinyl, vinyl, 2,2-difluorovinyl, imidazolyl, pyrazolyl, oxazolyl, isoxazolyl, thiazolyl, isoxazolyl; and most highly preferred substituents Y include cis-propenyl, cis-2-chlorovinyl, vinyl, imidazolyl, pyrazolyl, oxazolyl, isoxazolyl, thiazolyl, isoxazolyl, especially, cis-propenyl.

For compounds having Formula Ib, IIb, IIIb, IVb, Vb, VIb, VIIb, VIIIb, IXb, Xb, XIb, XIIb, XIIIb, XIVb or XVb:

preferred Y is —NHR$^{24}$ wherein R$^{24}$ is defined as above for compounds having Formula Ia, IIa and IIIa;

more preferred Y is —NHR$^{24}$ wherein R$^{24}$ is hydrogen or —C(=Q$^4$)—R$^{30}$ wherein Q$^4$ is O, S or N(R$^{33}$) wherein R$^{33}$ is hydrogen, hydroxy, methyl, ethyl, amino, —CN or —NO$_2$ and R$^{30}$ is —N(R$^{35}$)$_2$, —NHOH, —NHNH$_2$, —N(CH$_3$)NH$_2$ or —N(CH$_2$CH$_3$)NH$_2$ wherein each R$^{35}$ is independently hydrogen, methyl or ethyl; and even more preferred Y is —NH$_2$ or —N—C(=NH)—NH$_2$.

Preferred definitions for the substituents in the compounds of the invention also apply to the intermediates disclosed herein that are useful in the preparation of the compounds of the invention.

The term "acid protecting group" as used herein refers to groups used to protect acid groups (for example, —CO$_2$H, —SO$_3$H, —SO$_2$H, —PO$_3$H$_2$, —PO$_2$H groups and the like) against undesirable reactions during synthetic procedures. Commonly used acid protecting groups are disclosed in T. H. Greene and P. G. M. Wuts, *Protective Groups in Organic Synthesis*. 2nd edition, John Wiley & Sons, New York (1991), which is incorporated herein by reference. Most frequently, such acid protecting groups are esters.

Such esters include:

alkyl esters, especially loweralkyl esters, including, but not limited to, ethyl, n-propyl, isopropyl, n-butyl, sec-butyl, isobutyl, t-butyl, n-pentyl esters and the like;

arylalkyl esters including, but not limited to, benzyl, phenethyl, 3-phenylpropyl, naphthylmethyl esters and the like, wherein the aryl part of the arylalkyl group is unsubstituted or substituted as previously defined herein;

silylesters, especially, (tri-loweralkyl)silyl esters, (di-loweralkyl) (aryl)silyl esters and (loweralkyl) (di-aryl) silyl esters, including, but not limited to, trimethylsilyl, triethylsilyl, isopropyldimethylsilyl, t-butyldimethylsilyl, methyldiisopropylsilyl, methyldi-t-butylsilyl, triisopropylsilyl, methyldiphenylsilyl, isopropyldiphenylsilyl, butyldiphenylsilyl, phenyldiisopropylsilyl esters and the like; and the like.

Preferred acid protecting groups are loweralkyl esters.

The term "activated carboxylic acid group" as used herein refers to acid halides such as acid chlorides and also refers to activated ester derivatives including, but not limited to, formic and acetic acid derived anhydrides, anhydrides derived from alkoxycarbonyl halides such as isobutyloxycarbonylchloride and the like, anhydrides derived from reaction of the carboxylic acid with N,N'-carbonyldiimidazole and the like, N-hydroxysuccinimide derived esters, N-hydroxyphthalimide derived esters, N-hydroxybenzotriazole derived esters, N-hydroxy-5-norbornene-2,3-dicarboximide derived esters, 2,4,5-trichlorophenol derived esters, p-nitrophenol derived esters, phenol derived esters, pentachlorophenol derived esters, 8-hydroxyquinoline derived esters and the like.

The term "acyl" as used herein, refers to groups having the formula —C(=O)—R$^{95}$ wherein R$^{95}$ is hydrogen or an alkyl group. Preferred alkyl groups as R$^{95}$ are loweralkyl groups. Representative examples of acyl groups include groups such as, for example, formyl, acetyl, propionyl, and the like.

The term "acylalkyl" as used herein refers to an acyl group appended to an alkyl radical. Representative examples of acylalkyl groups include acetylmethyl, acetylethyl, propionylmethyl, propionylethyl and the like.

The term "acyloxyalkyl" as used herein refers to an acyloxy group (i.e., R$^{95}$—C(O)—O— wherein R$^{95}$ is hydrogen or an alkyl group) which is appended to an alkyl radical. Representative examples of acyloxyalkyl include acetyloxymethyl, acetyloxyethyl, propioyloxymethyl, propionyloxyethyl and the like.

The term "acylamino" as used herein, refers to groups having the formula —NHR$^{89}$ wherein R$^{89}$ is an acyl group. Representative examples of acylamino include acetylamino, propionylamino, and the like.

The term "alkenyl" as used herein, refers to a straight or branched chain hydrocarbon radical containing from 2 to 15 carbon atoms and also containing at least one carbon-carbon double bond. The term "lower alkenyl" refers to straight or branched chain alkenyl radicals containing from 2 to 6 carbon atoms. Representative examples of alkenyl groups include groups such as, for example, vinyl, 2-propenyl, 2-methyl-1-propenyl, 3-butenyl, 4-pentenyl, 5-hexenyl and the like.

The term "alkenylene" as used herein, refers to a divalent group derived from a straight or branched chain hydrocarbon containing from 2 to 15 carbon atoms and also containing at least one carbon-carbon double bond. The term "lower alkenylene" refers to a divalent group derived from a straight or branched chain alkene group having from 2 to 6 carbon atoms. Representative examples of alkenylene groups include groups such as, for example, —CH=CH—, —CH$_2$CH=CH—, —C(CH$_3$)=CH—, —CH$_2$CH=CHCH$_2$—, and the like.

The term "alkenyloxy" as used herein, refers to groups having the formula —OR$^{81}$ where R$^{81}$ is an alkenyl group.

The term "alkoxy" as used herein, refers to groups having the formula —OR$^{99}$ wherein R$^{99}$ is an alkyl group. Preferred R$^{99}$ groups are loweralkyl groups. Representative examples of alkoxy groups include groups such as, for example, methoxy, ethoxy, tert-butoxy, and the like.

The term "alkoxyalkoxy" as used herein, refers to groups having the formula —O—R$^{96}$—O—R$^{97}$ wherein R$^{97}$ is loweralkyl, as defined herein, and R$^{96}$ is a lower alkylene group. Representative examples of alkoxyalkoxy groups include groups such as, for example, methoxymethoxy, ethoxymethoxy, t-butoxymethoxy and the like.

The term "alkoxyalkyl" as used herein refers to an alkyl radical to which is appended an alkoxy group, for example, methoxymethyl, methoxypropyl and the like.

The term "alkoxycarbonyl" as used herein, refers to groups having the formula, —C(=O)—R$^{80}$, where R$^{80}$ is an alkoxy group.

The term "alkoxycarbonylalkyl" as used herein, refers to groups having the formula, —C(=O)—R$^{79}$, appended to the parent molecular moiety through an alkylene linkage, where R$^{79}$ is an alkoxy group.

The term "alkoxycarbonyloxyalkyl" as used herein refers to an alkoxycarbonyloxy group (i.e., R$^{80}$—C(O)—O— wherein $R^{80}$ is an alkoxy group) appended to an alkyl radical. Representative examples of alkoxycarbonyloxyalkyl include methoxycarbonyloxymethyl, ethoxycarbonyloxymethyl, methoxycarbonyloxyethyl and the like.

As used herein, the term "alkyl" refers to straight or branched chain hydrocarbon radicals containing from 1 to 12 carbon atoms. The term "loweralkyl" refers to straight or branched chain alkyl radicals containing from 1 to 6 carbon atoms. Representative examples of alkyl groups include groups such as, for example, methyl, ethyl, n-propyl, iso-propyl, n-butyl, iso-butyl, sec-butyl, t-butyl n-pentyl, 1-methylbutyl, 2,2-dimethylbutyl, 2-methylpentyl, 2,2-dimethyl-propyl, n-hexyl, and the like. The hydrocarbon chains in alkyl groups or the alkyl portion of an alkyl-containing substituent can be optionally interrupted by one or two heteroatoms or heterogroups independently selected from the group consisting of oxygen, —N($R^{27}$)— and sulfur wherein $R^{27}$ at each occurrence is independently hydrogen, loweralkyl, cylcoalkyl, cycloalkylalkyl or arylalkyl and wherein two such heteroatoms or heterogroups are separated by at least one carbon atom.

The term "alkylamino" as used herein, refers to groups having the formula —NHR$^{91}$ wherein $R^{91}$ is an alkyl group. Preferred $R^{91}$ groups are loweralkyl groups. Representative examples of alkylamino include methylamino, ethylamino, and the like.

The term "alkylene" as used herein, refers to a divalent group derived from a straight or branched chain saturated hydrocarbon group having from 1 to 15 carbon. The term "lower alkylene" refers to a divalent group derived from a straight or branched chain saturated hydrocarbon group having from 1 to 6 carbon atoms. Representative examples of alkylene groups include groups such as, for example, methylene (—CH$_2$—), 1,2-ethylene (—CH$_2$CH$_2$—), 1,1-ethylene (—CH(CH$_3$)—), 1,3-propylene (—CH$_2$CH$_2$CH$_2$—), 2,2-dimethylpropylene (—CH$_2$C(CH$_3$)$_2$CH$_2$—), and the like. The hydrocarbon chains in alkylene groups or the alkylene portion of an alkylene-containing substituent can be optionally interrupted by one or two heteroatoms or heterogroups independently selected from the group consisting of oxygen, —N($R^{27}$)— and sulfur wherein $R^{27}$ at each occurrence is independently hydrogen, loweralkyl, cylcoalkyl, cycloalkylalkyl or arylalkyl and wherein two such heteroatoms or heterogroups are separated by at least one carbon atom.

The term "alkylsulfonyl" as used herein refers to the group having the formula, —SO$_2$—$R^{78}$, where $R^{78}$ is an alkyl group. Preferred groups $R^{78}$ are loweralkyl groups.

The term "alkylsulfonylamino" as used herein refers to the group having the formula, —SO$_2$—$R^{77}$, appended to the parent molecular moiety through an amino linkage (—NH—), where $R^{77}$ is an alkyl group. Preferred groups $R^{77}$ are loweralkyl groups.

The term "alkynyl" as used herein, refers to a straight or branched chain hydrocarbon radical containing from 2 to 15 carbon atoms and also containing at least one carbon-carbon triple bond. The term "lower alkynyl" refers to straight or branched chain alkynyl radicals containing from 2 to 6 carbon atoms. Representative examples of alkynyl groups include groups such as, for example, acetylenyl, 1-propynyl, 2-propynyl, 3-butynyl, 2-pentynyl, 1-butynyl and the like.

The term "alkynylene" as used herein, refers to a divalent group derived from a straight or branched chain hydrocarbon containing from 2 to 15 carbon atoms and also containing at least one carbon-carbon triple bond. The term "lower alkynylene" refers to a divalent group derived from a straight or branched chain alkynylene group from 2 to 6 carbon atoms. Representative examples of alkynylene groups include groups such as, for example, —C≡C—, —CH$_2$—C≡C—, —C≡C—CH$_2$—, —CH(CH$_3$)—C≡C—, and the like.

The term "aminoalkyl" as used herein refers to an alkyl radical to which is appended an amino (—NH$_2$) group.

The term "aryl" as used herein refers to a carbocyclic ring system having 6–10 ring atoms and one or two aromatic rings. Representative examples of aryl groups include groups such as, for example, phenyl, naphthyl, tetrahydronaphthyl, indanyl, indenyl and the like.

The aryl groups can be unsubstituted or substituted with one, two or three substituents, each independently selected from loweralkyl, halo, haloalkyl, haloalkoxy, hydroxy, oxo (=O), hydroxyalkyl, alkenyloxy, alkoxy, alkoxyalkoxy, alkoxycarbonyl, alkoxycarbonylalkyl, thioalkoxy, amino, alkylamino, alkylsulfonyl, dialkylamino, acylamino, unsubstituted aryl, unsubstituted arylalkyl, unsubstituted arylalkoxy, unsubstituted aryloxy, mercapto, cyano, nitro, carboxy, carboxaldehyde, NH$_2$C(=O)—, cycloalkyl, carboxyalkyl, alkylsulfonylamino, unsubstituted heterocyclic, unsubstituted (heterocyclic)alkyl, unsubstituted (heterocyclic)alkoxy, unsubstituted (heterocyclic)oxy and —SO$_3$H. Preferred aryl substituents are each independently selected from the group consisting of loweralkyl, halo, haloalkyl, hydroxy, hydroxyalkyl, alkenyloxy, alkoxy, alkoxyalkoxy, thioalkoxy, amino, alkylamino, dialkylamino, alkylsulfonyl, acylamino, cyano and nitro. Examples of substituted aryl include 3-chlorophenyl, 3-fluorophenyl, 4-chlorophenyl, 4-fluorophenyl, 3,4-dichlorophenyl, 3-chloro-4-fluoro-phenyl, 4-methylsulfonylphenyl, and the like.

The term "(aryl)alkenyl" refers to a lower alkenyl group having appended thereto an aryl group. Representative examples of (aryl)alkenyl groups include groups such as, for example phenylethylenyl, phenylpropenyl, and the like.

The term "(aryl)alkyl" refers to a loweralkyl group having appended thereto an aryl group. Representative examples of (aryl)alkyl groups include groups such as, for example benzyl and phenylethyl.

The term "arylalkoxy" as used herein refers to the group having the formula, —O—$R^{76}$ where $R^{76}$ is an arylalkyl group.

The term "(aryl)alkynyl" refers to an alkynylene group having appended thereto an aryl group. Representative examples of (aryl)alkynyl groups include groups such as, for example phenylacetylenyl, phenylpropynyl, and the like.

The term "aryloxy" as used herein refers to the group having the formula, —O—$R^{72}$, where $R^{72}$ is an aryl group.

The term "carbamoyl" as used herein refers to the group having the formula, —C(=O)—NH$_2$.

The term "carboxyalkyl" as used herein, refers to the group having the formula, —$R^{64}$—COOH, where $R^{64}$ is a lower alkylene group.

The term "cyanoalkyl" as used herein refers to an alkyl radical to which is appended a cyano group (—CN).

The term "cycloalkenyl" as used herein refers to an aliphatic ring system having 5 to 10 carbon atoms and 1 or 2 rings containing at least one double bond in the ring structure. Representative examples of cycloalkenyl groups include groups such as, for example, cyclohexene, cyclopentene, norbornene and the like.

Cycloalkenyl groups can be unsubstituted or substituted with one, two or three substituents independently selected hydroxy, halo, amino, alkylamino, dialkylamino, alkoxy, alkoxyalkoxy, thioalkoxy, haloalkyl, mercapto, loweralkenyl and loweralkyl. Preferred substitutents are independently selected from loweralkyl, loweralkenyl, haloalkyl, halo, hydroxy and alkoxy.

The term "(cycloalkenyl)alkenyl" as used herein refers to a cycloalkenyl group appended to a lower alkenyl radical. Representative examples of (cycloalkenyl)alkenyl groups include groups such as, for example, cyclohexenylethylene, cyclopentenylethylene, and the like.

The term "(cycloalkenyl)alkyl" as used herein refers to a cycloalkenyl group appended to a lower alkyl radical. Representative examples of (cycloalkenyl)alkyl groups include groups such as, for example, cyclohexenylmethyl, cyclopentenylmethyl, cyclohexenylethyl, cyclopentenylethyl, and the like.

The term "(cycloalkenyl)alkynyl" as used herein refers to a cycloalkenyl group appended to a lower alkynyl radical. Representative examples of (cycloalkenyl)alkynyl groups include groups such as, for example, cyclohexenylacetylenyl, cyclopentenylpropynyl, and the like.

The term "cycloalkyl" as used herein refers to a n aliphatic ring system having 3 to 10 carbon atoms and 1 or 2 rings. Representative cylcoalkyl groups include, for example, cyclopropyl, cyclobutyl, cyclopentyl, cyclohexyl, cycloheptyl, norbornane, bicyclo[2.2.2]octane and the like.

Cycloalkyl groups can be unsubstituted or substituted with one, two or three substituents independently selected hydroxy, halo, amino, alkylamino, dialkylamino, alkoxy, alkoxyalkoxy, thioalkoxy, haloalkyl, mercapto, loweralkenyl and loweralkyl. Preferred substitutents are independently selected from loweralkyl, loweralkenyl, haloalkyl, halo, hydroxy and alkoxy.

The term "(cycloalkyl)alkyl" as used herein refers to a cycloalkyl group appended to a loweralkyl radical. Representative examples of (cycloalkyl)alkyl groups include groups such as, for example, cyclohexylmethyl, cyclopentylmethyl, cyclohexylethyl, cyclopentylethyl, and the like.

The term "(cycloalkyl)alkenyl" as used herein refers to a cycloalkyl group appended to a lower alkenyl radical . Representative examples of (cycloalkyl)-alkenyl groups include groups such as, for example, cyclohexylethylene, cyclopentylethylene, and the like.

The term "(cycloalkyl)alkynyl" as used herein refers to a cycloalkyl group appended to a lower alkynyl radical. Representative examples of (cycloalkyl) alkynyl groups include groups such as, for example, cyclohexylacetylenyl, cyclopentylpropynyl, and the like.

The term "dialkylamino" as used herein, refers to groups having the formula —N($R^{90}$)$_2$ wherein each $R^{90}$ is independently a lower alkyl group. Representative examples of dialkylamino include dimethylamino, diethylamino, N-methyl-N-isopropylamino and the like.

The term "dialkylaminocarbonylalkyl" as used herein refers to a —C(O)—N($R^{90}$)$_2$ group (wherein each $R^{90}$ is independently a lower alkyl group) appended to an alkyl radical. Representative examples of dialkylaminocarbonylalkyl include dimethylaminocarbonylmethyl, diethylaminocarbonylmethyl, N-methyl-N-ethylaminocarbonylethyl and the like.

The term "dialkylaminocarbonyloxyalkyl" as used herein refers to a —O—C(O)—N($R^{90}$)$_2$ group (wherein each $R^{90}$ is independently a lower alkyl group) appended to an alkyl radical. Representative examples of dialkylaminocarbonyloxyalkyl include dimethylaminocarbonyloxymethyl, diethylaminocarbonyloxymethyl, N-methyl-N-ethylaminocarbonyloxyethyl and the like.

The term "enantiomerically enriched" as used herein refers to a compound which comprises unequal amounts of the enantiomers of an enantiomeric pair. In other words, an enantiomerically enriched compound comprises more than 50% of one enantiomer of an enantiomeric pair and less than 50% of the other enantiomer of the enantiomeric pair. Preferably, a compound that is enantiomerically enriched comprises predominantly one enantiomer of an enantiomeric pair. Preferably, an enantiomerically enriched compound comprises greater than 80% of one enantiomer of an enantiomeric pair and less than 20% of the other enantiomer of the enantiomeric pair. More preferably, an enantiomerically enriched compound comprises greater than 90% of one enantiomer of an enantiomeric pair and less than 10% of the other enantiomer of the enantiomeric pair. Even more preferably, an enantiomerically enriched compound comprises greater than 95% of one enantiomer of an enantiomeric pair and less than 5% of the other enantiomer of the enantiomeric pair. Even more highly preferably, an enantiomerically enriched compound comprises greater than 97% of one enantiomer of an enantiomeric pair and less than 3% of the other enantiomer of the enantiomeric pair. Yet even more highly preferably, an enantiomerically enriched compound comprises greater than 98% of one enantiomer of an enantiomeric pair and less than 2% of the other enantiomer of the enantiomeric pair. Most preferably, an enantiomerically enriched compound comprises greater than 99% of one enantiomer of an enantiomeric pair and less than 1% of the other enantiomer of the enantiomeric pair.

The term "halo" as used herein refers to F, Cl, Br or I.

The term "haloalkenyl" as used herein refers to a loweralkenyl group in which one or more hydrogen atoms is replaced with a halogen. Examples of haloalkenyl groups include 2-fluoroethylene, 1-chloroethylene, 1,2-difluoroethylene, trifluoroethylene, 1,1,1-trifluoro-2-propylene and the like.

The term "haloalkoxy" as used herein refers to the group having the formula, —O$R^{69}$, where $R^{69}$ is a haloalkyl group as defined herein. Examples of haloalkoxy include chloromethoxy, fluoromethoxy, dichloromethoxy, trifluoromethoxy and the like.

The term "haloalkyl" as used herein, refers to a loweralkyl group in which one or more hydrogen atoms has been replaced with a halogen including, but not limited to, trifluoromethyl, trichloromethyl, difluoromethyl, dichloromethyl, fluoromethyl, chloromethyl, chloroethyl, 2,2-dichloroethyl, pentafluoroethyl and the like.

The term "heterocyclic ring" or "heterocyclic" or "heterocycle" as used herein, refers to any 3- or 4-membered ring containing a heteroatom selected from oxygen, nitrogen and sulfur; or a 5-, 6- or 7-membered ring containing one, two, three, or four nitrogen atoms; one oxygen atom; one sulfur atom; one nitrogen atom and one sulfur atom; two nitrogen atoms and one sulfur atom; one nitrogen atom and one oxygen atom; two nitrogen atoms and one oxygen atom; two oxygen atoms in non-adjacent positions; one oxygen atom and one sulfur atom in non-adjacent positions; or two sulfur atoms in non-adjacent positions. The 5-membered ring has 0–2 double bonds and the 6- and 7-membered rings have 0–3 double bonds. The nitrogen heteroatoms can be optionally quaternized. The term "heterocyclic" also includes bicyclic groups in which any of the above heterocyclic rings is fused to a benzene ring or a cyclohexane ring or another heterocyclic ring, such as, for example, indolyl, dihydroindolyl, quinolyl, isoquinolyl, tetrahydroquinolyl, tetrahydroisoquinolyl, decahydroquinolyl, decahydroisoquinolyl, benzofuryl, dihydrobenzofuryl or benzothienyl and the like.

Heterocyclic groups include, but are not limited to groups such as, for example, aziridinyl, azetidinyl, epoxide, oxetanyl, thietanyl, pyrrolyl, pyrrolinyl, pyrrolidinyl, pyrazolyl, pyrazolinyl, pyrazolidinyl, imidazolyl, imidazolinyl, imidazolidinyl, pyridyl, tetrahydropyridyl, piperidinyl, homopiperidinyl, pyrazinyl, piperazinyl, pyrimidinyl, pyridazinyl, oxazolyl, oxazolinyl, oxazolidinyl, isoxazolyl, isoxazolidinyl, morpholinyl, thiomorpholinyl, thiazolyl, thiazolinyl, thiazolidinyl, isothiazolyl, isothiazolidinyl, indolyl, quinolinyl, isoquinolinyl, benzimidazolyl, benzothiazolyl, benzoxazolyl, oxetanyl, dihydrofuranyl, tetrahydrofuranyl, dihydropyranyl, tetrahydropyranyl, thienyl, dihydrothienyl, tetrahydrothienyl, triazolyl, triazolinyl, tetrazolyl, tetrazolinyl, isoxazolyl, 1,2,3-oxadiazolyl, 1,2,4-oxadiazolyl, 1,3,4-oxadiazolyl, 1,2,5-oxadiazolyl, oxadiazolinyl, 1,2,3-thiadiazolyl, 1,2,4-thiadiazolyl, 1,3,4-thiadiazolyl, 1,2,5-thiadiazolyl, thiadiazolinyl,1,3-dithiolinyl, 1,2-dithiolyl, 1,3-dithiolyl, 1,3-dioxolinyl, didehydrodioxolanyl, 1,3-oxathiolinyl, oxathiolyl, pyrimidyl, benzothienyl and the like. Heterocyclic groups also include compounds of the formula

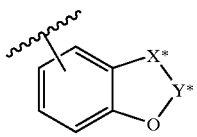

where $X^*$ is —$CH_2$ or —O— and $Y^*$ is —C(O)— or [—C($R^{92}$)$_2$—]$_v$ where $R^{92}$ is hydrogen or $C_1$–$C_4$ alkyl where v is 1, 2, or 3 such as 1,3-benzodioxolyl, 1,4-benzodioxanyl and the like. Heterocyclic groups also include bicyclic rings such as quinuclidinyl and the like.

Heterocyclic groups can be unsubstituted or substituted with from one to three substituents, each independently selected from loweralkyl, hydroxy, alkoxy, thioalkoxy, amino, alkylamino, dialkylamino and halogen. In addition, nitrogen containing heterocyclic rings can be N-protected.

The term "(heterocyclic)alkenyl" as used herein refers to a heterocyclic group appended to a lower alkenyl radical including, but not limited to, pyrrolidinylethenyl, morpholinylethenyl and the like.

The term "(heterocyclic)alkoxy" as used herein refers to the group having the formula, —$OR^{68}$, where $R^{68}$ is a (heterocyclic)alkyl group.

The term "(heterocyclic)alkyl" as used herein refers to a heterocyclic group appended to a loweralkyl radical including, but not limited to, pyrrolidinylmethyl, morpholinylmethyl and the like.

The term "(heterocyclic)alkynyl" as used herein refers to a heterocyclic group appended to a lower alkynyl radical including, but not limited to, pyrrolidinylacetylenyl, morpholinylpropynyl and the like.

The term "(heterocyclic)carbonylalkyl" as used herein refers to a heterocyclic group appended to an alkyl radical via a carbonyl group. Representative examples of (heterocyclic)carbonylalkyl include pyridylcarbonylmethyl, morpholinocarbonylethyl, piperazinylcarbonylmethyl and the like.

The term "(heterocyclic)carbonyloxyalkyl" as used herein refers to a heterocyclic group appended to an alkyl radical via a carbonyloxy group (i.e., —C(O)—O—). Representative examples of (heterocyclic)carbonylalkyl include pyridylcarbonylmethyl, morpholinocarbonylethyl, piperazinylcarbonylmethyl and the like.

The term "(heterocyclic)oxy" as used herein refers to a heterocyclic group appended to the parent molecular moiety through an oxygen atom (—O—).

The term "hydroxy protecting group", "hydroxyl protecting group" or "—OH protecting group" as used herein refers to refers to groups used to hydroxy groups against undesirable reactions during synthetic procedures. Commonly used hydroxy protecting groups are disclosed in T. H. Greene and P. G. M. Wuts, *Protective Groups in Organic Synthesis*, 2nd edition, John Wiley & Sons, New York (1991), which is incorporated herein by reference. Such hydroxy protecting groups include:

methyl ether;

substituted methyl ethers, including, but not limited to, methoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, t-butoxymethyl, 2-methoxyethoxymethyl, 2,2,2-trichloroethoxymethyl, 2-(trimethylsilyl)ethoxymethyl, tetrahydropyranyl, tetrahydrothiopyranyl, tetrahydrofuranyl, tetrahydrothiofuranyl ether and the like;

substituted ethyl ethers, including, but not limited to, 1-ethoxyethyl, 1-methyl-1-methoxyethyl, 1-methyl-1-benzyloxyethyl, 2,2,2-trichloroethyl, trimethylsilylethyl, t-butyl ether and the like;

benzyl ether;

substituted benzyl ethers, including, but not limited to, p-methoxybenzyl, 3,4-dimethoxybenzyl, o-nitorbenzyl, p-halobenzyl, p-cyanobenzyl, diphenylmethyl, triphenylmethyl ether and the like;

silyl ethers, including, but not limited to, trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, triphenylsilyl, diphenylmethylsilyl ether and the like;

esters, including, but not limited to, formate, acetate, chloroacetate, dichloroacetate, trichloroacetate, trifluoroacetate, methoxyacetate, phenoxyacetate, pivaloate, benzoate ester and the like; and the like.

Preferred hydroxy protecting groups include substituted methyl ethers, benzyl ether, substituted benzyl ethers, silyl ethers and esters.

The term "hydroxyalkyl" as used herein refers to the group having the formula, —$R^{65}$—OH, where $R^{65}$ is an alkylene group The term "leaving group" as used herein refers to a group which is easily displaced from the compound by a nucleophile. Examples of leaving groups include a halide (for example, Cl, Br or I) or a sulfonate (for example, mesylate, tosylate, triflate and the like) and the like.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in T. H. Greene and P. G. M. Wuts, *Protective Groups in Organic Synthesis*, 2nd edition, John Wiley & Sons, New York (1991), which is incorporated herein by reference. N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; sulfenyl groups such as phenylsulfenyl (phenyl-S—), triphenylmethylsulfenyl (trityl-S—) and the like; sulfinyl groups such as p-methylphenylsulfinyl (p-methylphenyl-S(O)—), t-butylsulfinyl (t-Bu-S(O)—) and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxy-carbonyl, benzhydryloxycarbonyl, t-butyloxycarbonyl, diisopropylmethoxy-carbonyl, isopropyloxycarbonyl, ethoxycarbonyl, methoxycarbonyl, allyloxycar-bonyl, 2,2,2-trichloroethoxycarbonyl, phenoxycarbonyl, 4-nitro-phenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, p-methoxybenzyl, triphenylmethyl, benzyloxymethyl and the like; p-methoxyphenyl and the like; and silyl groups such as trimethylsilyl and the like. Preferred N-protecting groups include formyl, acetyl, benzoyl, pivaloyl, t-butylacetyl, phenylsulfonyl, benzyl, t-butyloxycarbonyl (Boc) and benzyloxycar bonyl (Cbz).

The term "thioalkoxy" as used herein refers to groups having the formula —$SR^{98}$ wherein $R^{98}$ is an alkyl group. Preferred groups $R^{98}$ are loweralkyl groups.

The term "thio-substituted alkyl" as used herein refers to an alkyl radical to which is appended a thiol group (—SH).

As used herein, the terms "S" and "R" configuration are as defined by the IUPAC 1974 Recommendations for Section E, Fundamental Stereochemistry, Pure Appl. Chem. (1976) 45, 13–30.

The compounds of the invention can comprise asymmetrically substituted carbon atoms. As a result, all stereoisomers of the compounds of the invention are meant to be included in the invention, including racemic mixtures, mixtures of diastereomers, as well as individual optical isomers, including, enantiomers and single diastereomers of the compounds of the invention substantially free from their enantiomers or other diastereomers. By "substantially free" is meant greater than about 80% free of other enantiomers or diastereomers of the compound, more preferably greater than about 90% free of other enantiomers or diastereomers of the compound, even more preferably greater than about 95% free of other enantiomers or diastereomers of the compound, even more highly preferably greater than about 98% free of other enantiomers or diastereomers of the compound and most preferably greater than about 99% free of other enantiomers or diastereomers of the compound.

In addition, compounds comprising the possible geometric isomers of carbon-carbon double bonds and carbon-nitrogen double are also meant to be included in this invention.

Individual stereoisomers of the compounds of this invention can be prepared by any one of a number of methods which are within the knowledge of one of ordinary skill in the art. These methods include stereospecific synthesis, chromatographic separation of diastereomers, chromatographic resolution of enantiomers, conversion of enantiomers in an enantiomeric mixture to diastereomers and then chromatographically separating the diastereomers and regeneration of the individual enantiomers, enzymatic resolution and the like.

Stereospecific synthesis involves the use of appropriate chiral starting materials and synthetic reactions which do not cause racemization or inversion of stereochemistry at the chiral centers.

Diastereomeric mixtures of compounds resulting from a synthetic reaction can often be separated by chromatographic techniques which are well-known to those of ordinary skill in the art.

Chromatographic resolution of enantiomers can be accomplished on chiral chromatography resins. Chromatography columns containing chiral resins are commercially available. In practice, the racemate is placed in solution and loaded onto the column containing the chiral stationary phase. The enantiomers are then separated by HPLC.

Resolution of enantiomers can also be accomplished by converting the enantiomers in the mixture to diastereomers by reaction with chiral auxiliaries. The resulting diastereomers can then be separated by column chromatography. This technique is especially useful when the compounds to be separated contain a carboxyl, amino or hydroxyl group that will form a salt or covalent bond with the chiral auxiliary. Chirally pure amino acids, organic carboxylic acids or organosulfonic acids are especially useful as chiral auxiliaries. Once the diastereomers have been separated by chromatography, the individual enantiomers can be regenerated. Frequently, the chiral auxiliary can be recovered and used again.

Enzymes, such as esterases, phosphatases and lipases, can be useful for resolution of derivatives of the enantiomers in an enantiomeric mixture. For example, an ester derivative of a carboxyl group in the compounds to be separated can be prepared. Certain enzymes will selectively hydrolyze only one of the enantiomers in the mixture. Then the resulting enantiomerically pure acid can be separated from the unhydrolyzed ester.

In addition, solvates and hydrates of the compounds of Formula Ia, Ib, IIa, IIb, IIa, IIIb, IVa, IVb, Va, Vb, VIa, VIb, VIIa, VIIb, VIIIa, VIIIb, IXa, IXb, Xa, Xb, XIa, XIb , XIIa, XIIb, XIIIa, XIIIb, XIVa, XIVb, XVa or XVb are meant to be included in this invention.

When any variable (for example $R^1$, $R^2$, $R^3$, m, n, etc.) occurs more than one time in any substituent or in the compound of Ia, Ib, IIa, IIb, IIIa, IIIb, IVa, IVb, Va, Vb, VIa, VIb, VIIa, VIIb, VIIIa, VIIb, IXa, IXb, Xa, Xb, XIa, XIb, XIIa, XIIb, XIIIa, XIIIb, XIVa, XIVb, XVa or XVb or any other formula herein, its definition on each occurrence is independent of its definition at every other occurrence. In addition, combinations of substituents are permissible only if such combinations result in stable compounds. Stable compounds are compounds which can be isolated in a useful degree of purity from a reaction mixture.

This invention is intended to encompass compounds having Formula Ia, Ib, IIa, IIb, IIIa, IIIb, IVa, IVb, Va, Vb, VIa, VIb, VIIa, VIIb, VIIIa, VIIIb, IXa, IXb, Xa, Xb, XIa, XIb, XIIa, XIIb, XIIIa, XIIIb, XIVa, XIVb, XVa or XVb when prepared by synthetic processes or by metabolic processes. Preparation of the compounds of the invention by metabolic processes include those occurring in the human or animal body (in vivo) or processes occurring in vitro.

Compounds of the invention can be prepared according to the methods described in Schemes 1–11 as shown below.

Throughout the schemes, methods will be illustrated wherein $R^1$ is a carboxylic acid or carboxylic acid ester substituent. It will be understood by those skilled in the art that other $R^1$ substituents can (a) be obtained either from the carboxylic acid or carboxylic acid ester group, (b) can be introduced by similar methods to those used to introduce the carboxylic acid or carboxylic acid ester group or (c) can be introduced by other methods generally known in the art.

In adddition, throughout the schemes, methods will be illustrated wherein $R^4$, $R^6$, $R^7$, $R^8$, $R^9$ and $R^{10}$ are hydrogen. It will be understood by those skilled in the art that compounds wherein one or more of these substituents is other than hydrogen can be prepared by methods analogous to those disclosed in the schemes or by other methods generally known in the art.

In addition, unless otherwise noted, throughout the schemes methods will be illustrated for obtaining compounds of the invention having the preferred relative stereochemistry. It will be understood by those skilled in the art that compounds of the invention having other relative stereochemistry can be prepared by methods analogous to those disclosed in the schemes or by other methods generally known in the art.

In addition, throughout the schemes, methods will be illustrated wherein X is —C(=O)—NH—. It will be understood by those skilled in the art that other X groups can be prepared by methods analogous to those disclosed in the schemes or by other methods generally known in the art.

Compounds of the invention can be prepared according to the procedure described in Scheme 1. N-protected amino acid 1 ($P^1$ is an N-protecting group, for example, t-butoxycarbonyl or the like) can be prepared by N-protection of amino acid ((±)-(2R,3S)-2-Amino-bicyclo[2.2.1]hept-5-ene-3-carboxylic acid; Stajer, G. et al. *Tetrahedron*, 40, 2385 (1984)). Formation of an anhydride derivative of the acid (for example, by reaction with ethyl chloroformate or the like), followed by reduction (for example, with sodium borohydride or the like) provides alcohol 2. The alcohol group is oxidized (for example, by Swern oxidation or the like) to provide aldehyde 3. Reductive amination of the aldehyde (for example with benzyl amine and Na(AcO)$_3$BH or the like) provides N-protected amine 4 ($P^2$ is an N-protecting group, such as benzyl and the like). A second N-protecting group can be introduced to give 5 ($P^3$ is an N-protecting group, for example, benzyloxycarbonyl or the like). Optionally, the mono-protected amino group can be alkylated (for example, by reaction with a non-nucleophilic base and an alkyl halide). The bicyclic ring is oxidatively cleaved (for example, with RuO$_2$ and NaIO$_4$ or the like) to give a diacid which is esterified to give diester 6 ($P^4$ is a carboxylic acid protecting group, for example, loweralkyl, such as methyl, ethyl or the like). The N-protecting groups $P^2$ and $P^3$ are selectively removed (for example, by hydrogenation or the like) to provide amine 7. Amine 7 can be further functionalized to complete the introduction of the $R^2$—X— substituent (for example, by reaction of the amine with an acylating agent such as acetic anhydride or the like) to give 8. Removal of the acid protecting groups $P^4$ (for example, by base hydrolysis) provides diacid 9. Diacid 9 can be monoprotected (for example, by treatment with acetic anhydride, followed by methanol and triethylamine) and chromatographic separation to give 10 ($P^5$ is a carboxylic acid protecting group, for example, loweralkyl or the like). The acid group of 10 can also be transformed to a variety of substituents Y of the compounds of the invention using methods known to those skilled in the art to give 11, followed by N-deprotection, to give compounds of the invention 12.

As shown in Scheme 2, substituents $R^3$ can be introduced via reaction of aldehyde 3 with a Grignard reagent (for example, $R^3$MgBr or the like) to give alcohol 13. Oxidation of alcohol 13 (for example, Swern oxidation or the like) provides ketone 14. Reductive amination of ketone 14 (for example, by reaction with ammonium acetate and sodium cyanoborohydride in methanol or the like) gives amine 15. Amine 15 can be further functionalized to complete introduction of the $R^2$—X— substituent (for example, by reaction of the amine with an acylating agent such as acetic anhydride or the like or by other acylation methods), followed by chromatographic separation of the diastereomers to give 16a. The other diastereomer (16b) can also be isolated and further transformed according to the scheme.

Oxidation of 16a and esterification gives 17 (in a manner analogous to that disclosed in Scheme 1). Also similar to Scheme 1, the diacid resulting from hydrolysis of diester 17 can be selectively protected to give give 18, which can then be transformed to compounds of the invention 19.

As shown in Scheme 3, diol 20 is selectively diprotected (Culbertson, et al., Journal of the American Chemical Society 82, 2541–2547 (1960)) by reaction with one equivalent of a hydroxy protecting agent, followed by reaction with a second hydroxy protecting agent, to give 21 ($P^6$ is a hydroxy protecting group, for example, acetyl or the like and $P^7$ is a hydroxy protecting group, for example, benzyl or the like). Oxidation and esterification provide 22. Removal of protecting group $P^7$, followed by transformation of the hydroxy group to an amine, which is then N-protected, provides 24. Transformation of 24 in a manner analogous to the transformation of 2 to 11 or 12 in Scheme 1 provides compounds of the invention 27 or 28.

As shown in Scheme 4, alcohol 31 can be transformed to compounds of the invention 38 in a manner analogous to the transformation of 13 to 19 in Scheme 2.

As shown in Scheme 5, aldehyde 39 can be reacted with a Grignard reagent to introduce substituent $R^3$ to give 40. Oxidation (for example, by Swern oxidation or the like) provides 41a, which can be epimerized (for example, with sodium methoxide or the like) and 41b can be obtained by chromatography. Ketone 41 b can be transformed to compounds of the invention 47 in a manner analogous to the transformation of 14 to 19 in Scheme 2.

As shown in Scheme 6, olefin 48 ($P^8$ is a hydroxy protecting group) is converted to alcohol 48a (for example, by reaction with borane dimethylsulfide complex and hydrogen peroxide or the like). Oxidation of the alcohol to a carboxylic acid, followed by esterification with a carboxylic acid protecting group $P^9$ and deprotection of the diol, provides 49. Selective protection of the primary alcohol with a hydroxy protecting group $P^{10}$ gives 50. Oxidation of 50 (for example, Swern oxidation or the like) provides ketone 51. Reductive amination of ketone 51 (for example, by reaction with ammonium acetate and sodium cyanoborohydride in methanol or the like) gives amine 52. Amine 52 can be further functionalized to complete the introduction of the $R^2$—X— substituent (for example, by reaction with an acylating agent such as acetic anhydride or the like or by other acylation methods), followed by chromatographic separation of the diastereomers to give 53a. The other diastereomeric amide (53b) can also be isolated and further functionalized according to this scheme.

Selective removal of the $P^8$ hydroxy protecting group in 53a provides alcohol 54. Oxidation of the alcohol to an aldehyde (for example, Swern oxidation or the like) provides 55. The aldehyde can serve as a precursor for various substituents Y in the compounds of the invention. For example, olefination of 55 (for example, with Ph$_3$PCH$_2$, or triphenylphosine/methylene chloride/n-BuLi, or I$^-$Ph$_3$P$^+$CH$_2$CH$_3$/KOtBu, or the like) provides 56 wherein Y is an olefinic substituent. Removal of the $P^{10}$ hydroxy protecting group gives alcohol 57.

The alcohol can serve as a precursor for a variety of $R^3$ substituents in the compounds of the invention. For example, the alcohol of 57 can be oxidized to an aldehyde (for example, by Dess-Martin oxidation or the like) to give 58. Aldehyde 58 can be reacted with Grignard reagents ($R^{14}$MgBr or the like) or other organometallic reagents (for example, organolithium reagents such as $R^{14}$Li or the like) to provide 59 as a mixture of alcohol diastereomers which can be separated chromatographically to provide the major isomer 59a and the other isomer 59b. Isomer 59a or the mixture of isomers 59 can be oxidized (for example, by Dess-Martin oxidation or the like) to give ketone 62. Reduction of ketone 62 (for example, with sodium borohydride in ethanol or the like) provides alcohol 59b as the major isomer, which can be isolated by chromatography. Ester hydrolysis provides compounds of the invention 63a or 63b, respectively, wherein Y is an olefinic substituent.

Alkylation of alcohol 59a or 59b provides ethers 60a or 60b, respectively. Ester hydrolysis provides compounds of the invention 61a or 61b, respectively, wherein Y is an olefinic substituent.

As shown in Scheme 7, reaction of ketone 62 with with Grignard reagents ($R^{37a}$MgBr or the like) or other organometallic reagents (for example, organolithium reagents such as $R^{37a}$Li or the like) provides alcohols 64a and 64b as a mixture of alcohol diastereomers which can be separated chromatographically. Ester hydrolysis provides compounds of the invention 65a or 65b, respectively, wherein Y is an olefinic substituent.

Alkylation of alcohol 64a or 64b provides ethers 66a or 66b, respectively. Ester hydrolysis provides compounds of the invention 67a or 67b, respectively, wherein Y is an olefinic substituent.

Scheme 8 shows the preparation of precursor 74 for compounds of the invention which are substituted tetrahydrofurans. Alcohol 68 is oxidized to a ketone (for example, by Swern oxidation or the like), followed by oxidation of the olefin to a diol (for example, by treatment with $OsO_4$ and N-methylmorpholine N-oxide or the like) to give 69. Diol 69 is protected as the acetonide 70. Oxidation of 70 (for example, with MCPBA or the like) provides lactone 71. Iodination via the enolate of 71 provides 72. Reaction of 72 with potassium carbonate and methanol provides ester 73. Reduction of the ester provides aldehyde 74. The aldehyde provides a functional group via which substituents $R^3$ and $R^2$—X— can be introduced. Deprotection of the diol and oxidation of the diol provides functional groups via which substituents Y and $R^1$ can be introduced.

Esters or prodrugs of the compounds of the invention can be prepared by methods known in the art.

Scheme 9 illustrates a method for preparing enantiomerically enriched compounds of the invention having the preferred absolute stereochemistry. Cyclopentene 75 (wherein $P^4$ is a carboxylic acid protecting group, for example, loweralkyl, such as methyl, ethyl, t-butyl or the like) is reacted with 78 in the presence of phenyl isocyanate and triethylamine in an inert solvent, for example, benzene or the like, to provide 79. Hydrogenation of 79 (for example, by reaction with hydrochloric acid, $PtO_2$ and $H_2$ in methanol or the like), followed by reaction of the resulting amine with an acylating agent such as acetic anhydride or the like or by other acylation methods gives 80. Removal of protecting group $P^4$, for example, with sodium hydroxide in water or the like method, and deprotection of any protected functional groups in $R^3$ provides 81. Esters or prodrugs of 81 can be prepared by methods known in the art.

Dehydroxylation of 81, for example, by reaction with 1,1'-thiocarbonyldiimidazole, followed by reaction with tributyltin hydride and AIDN, or a like dehydroxylation method, provides 82. Removal of protecting group $P^4$, for example, with sodium hydroxide in water or the like method, and deprotection of any protected functional groups in $R^3$ provides 83. Esters or prodrugs of 83 can be prepared by methods known in the art.

In a similar manner, reaction of 75 with preferred nitro compound 85 provides 80a, which can be transformed according to the methods described above to provide 81 or 83 wherein $R^3$ is the preferred substituent comprised in 85.

Scheme 10 illustrates a method for the preparation of enantiomerically enriched compounds of the invention wherein Y is an amine or an amine-based substituent. Cyclopentene 84 (wherein $P^4$ is a carboxylic acid protecting group, for example, loweralkyl, such as methyl, ethyl, t-butyl or the like and $P^{11}$ is an N-protecting group, for example, t-butyloxycarbonyl or the like) is reacted with 85 (wherein $R^{37a}$, $R^{37c}$ and $R^{14}$ are as defined most broadly herein and wherein, preferably, $R^{37a}$ is loweralkyl or loweralkenyl, $R^{37c}$ is hydrogen, $C_1$–$C_3$ loweralkyl or allyl and $R^{14}$ is loweralkyl, loweralkenyl or alkoxy-substituted loweralkyl) in the presence of phenyl isocyanate and triethylamine in an inert solvent, for example, benzene, or the like, to provide 86. Hydrogenation of 86 (for example, by reaction with hydrochloric acid, $PtO_2$ and $H_2$ in methanol or the like), followed by reaction of the resulting amine with an acylating agent such as acetic anhydride or the like or by other acylation methods gives 87. Removal of protecting group $P^{11}$, for example by reaction with trifluoroacetic acid in methylene chloride or the like method, and removal of protecting group $P^4$, for example, with sodium hydroxide in water or the like method provides 88. For example, in those cases where $R^{37c}$ is hdyrogen, the hydroxy group may be protected throughout the process of Scheme 10. Esters or prodrugs of 88 can be prepared by methods known in the art.

Removal of protecting group $P^{11}$ in 87, for example by reaction with trifluoroacetic acid in methylene chloride or the like method, followed by reaction of the amine with N,N'-bis(tert-butoxycarbonyl)-thiourea, triethylamine and mercury(II) chloride in an inert solvent such as DMF or the like, or like method, followed by deprotection of the guanidino group, for example, with trifluoroacetic acid in methylene chloride or like method, and removal of protecting group $P^4$, for example, with sodium hydroxide in water or the like method provides guanidino compound 89. Esters or prodrugs of 89 can be prepared by methods known in the art.

Dehydroxylation of 87, for example, by reaction with 1,1'-thiocarbonyldiimidazole, followed by reaction with tributyltin hydride and AIDN, or a like dehydroxylation method, provides 90, which can be converted to 91 or 92 as described herein. Esters or prodrugs of 91 and 92 can be prepared by methods known in the art.

Scheme 11 illustrates a method for preparing preferred nitro compounds 85. Allylic alcohol 93 (wherein $R^{14}$a and the carbon to which it is bonded, when taken together, will become substituent $R^{14}$) is asymmetrically epoxidized, for example, by Sharpless epoxidation with t-butyl hydroperoxide, (–)-dimethyl D-tartrate and titanium tetraisopropoxide or the like in an inert solvent such as dichloromethane and the like and the alcohol is protected (for example, $P^{12}$ is benzoate or the like) to give 94. Epoxide 94 is reduced, for example, with lithium aluminum hydride or the like in an inert solvent such as THF or the like, followed by protection of the primary alcohol of 95 (for example, $P^{13}$ is benzyl or the like) to give 96. Where $R^{37c}$ is other than hydrogen, 96 is reacted with a non-nucleophilic strong base, for example, sodium bis(trimethylsilyl)amide or the like, and $R^{37c}$—X wherein X is a halide or other leaving group in an inert solvent such as THF or the like to provide 97. Where $R^{37c}$ is hydrogen, the hydroxy group is protected. Protecting group $P^{13}$ is removed, preferably, selectively if any other hydroxy protecting groups are present in the compound, for example, by hydrogenation when it is a benzyl group, and the resulting alcohol is oxidized to an aldehyde, for example, with pyridinium chlorochromate or the like to give aldehyde 98. Reaction of 98 with hydroxylamine gives oxime 99. Oxidation of the oxime 99, for example, with trifluoroacetic anhydride and hydrogen peroxide in acetonitrile or a like method, provides nitro compound 85.

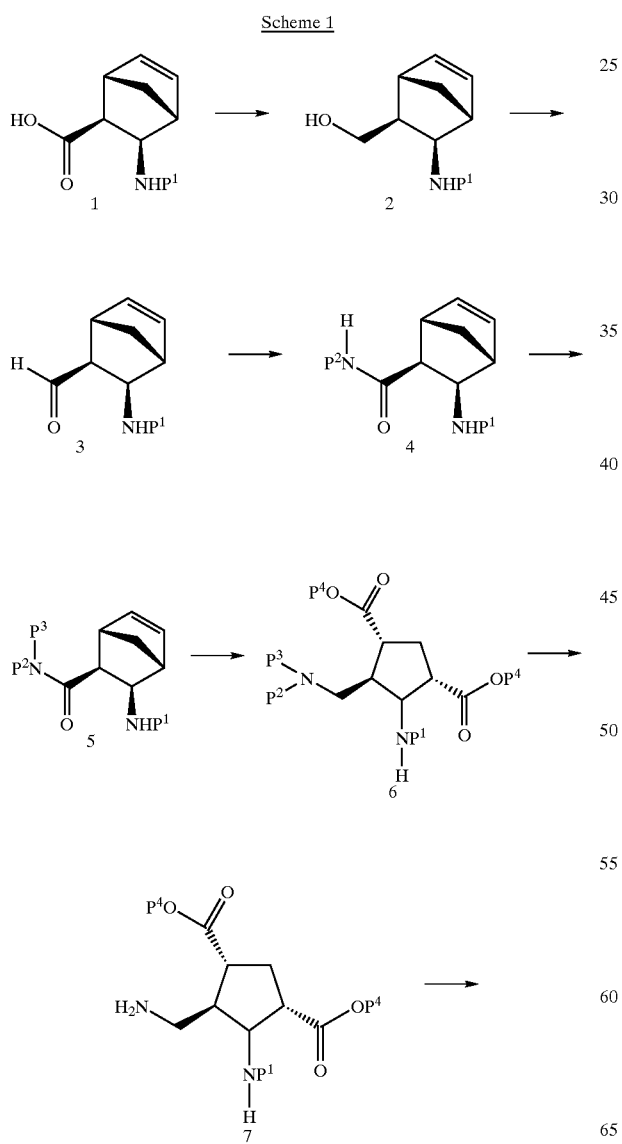

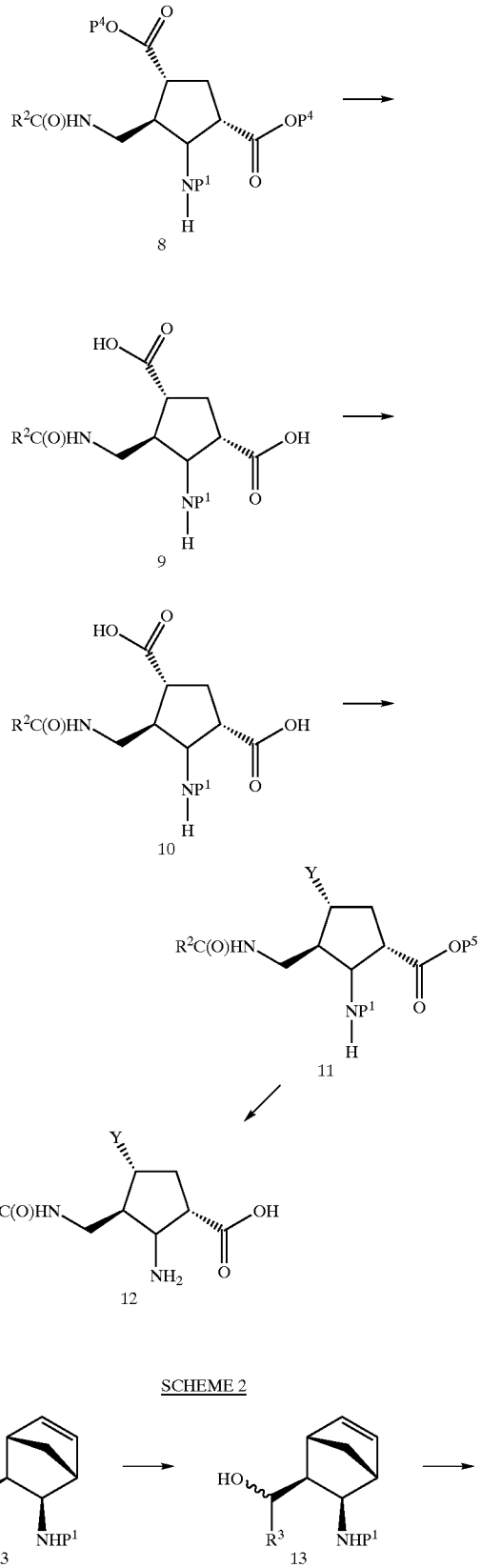

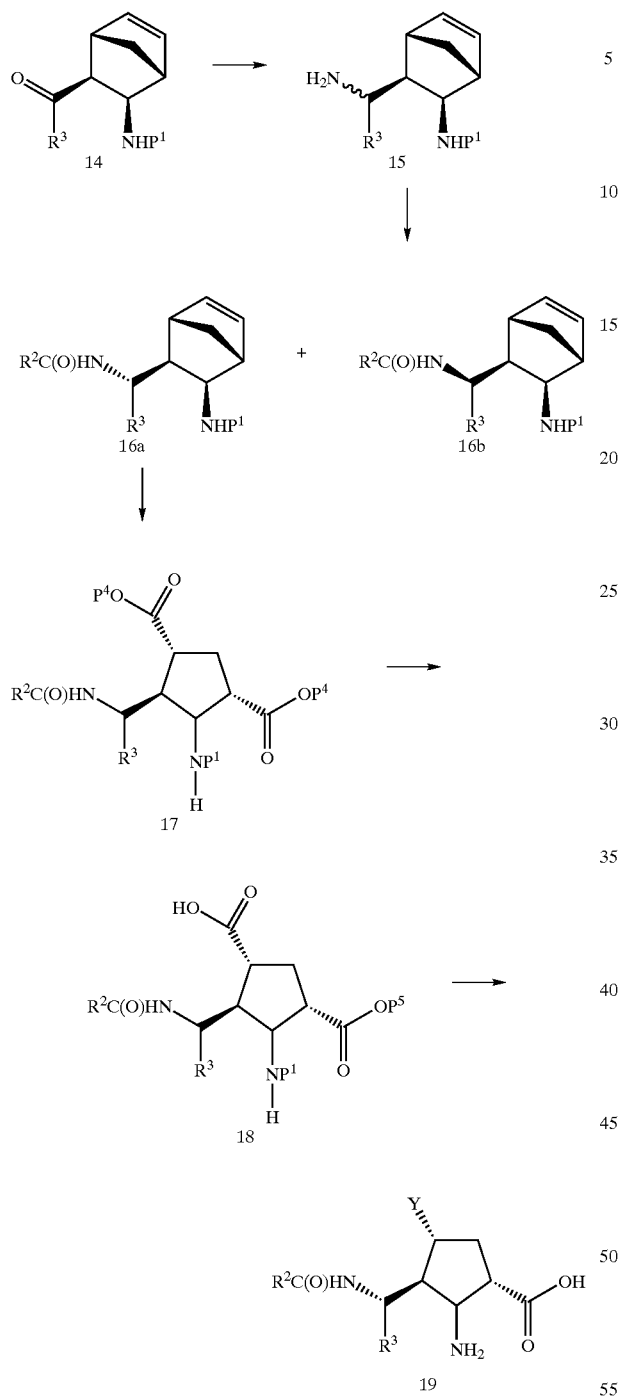
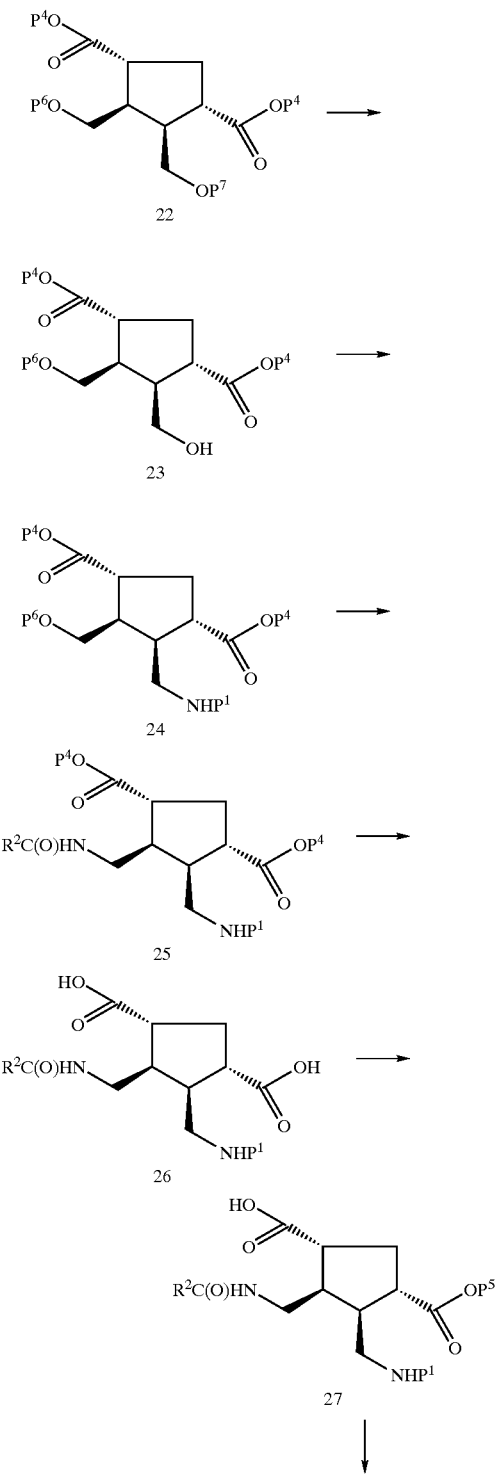
SCHEME 3
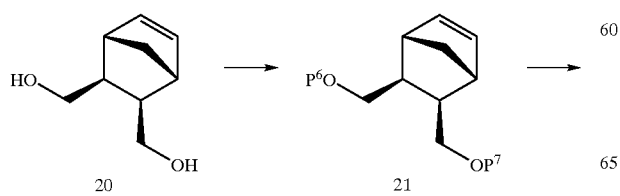

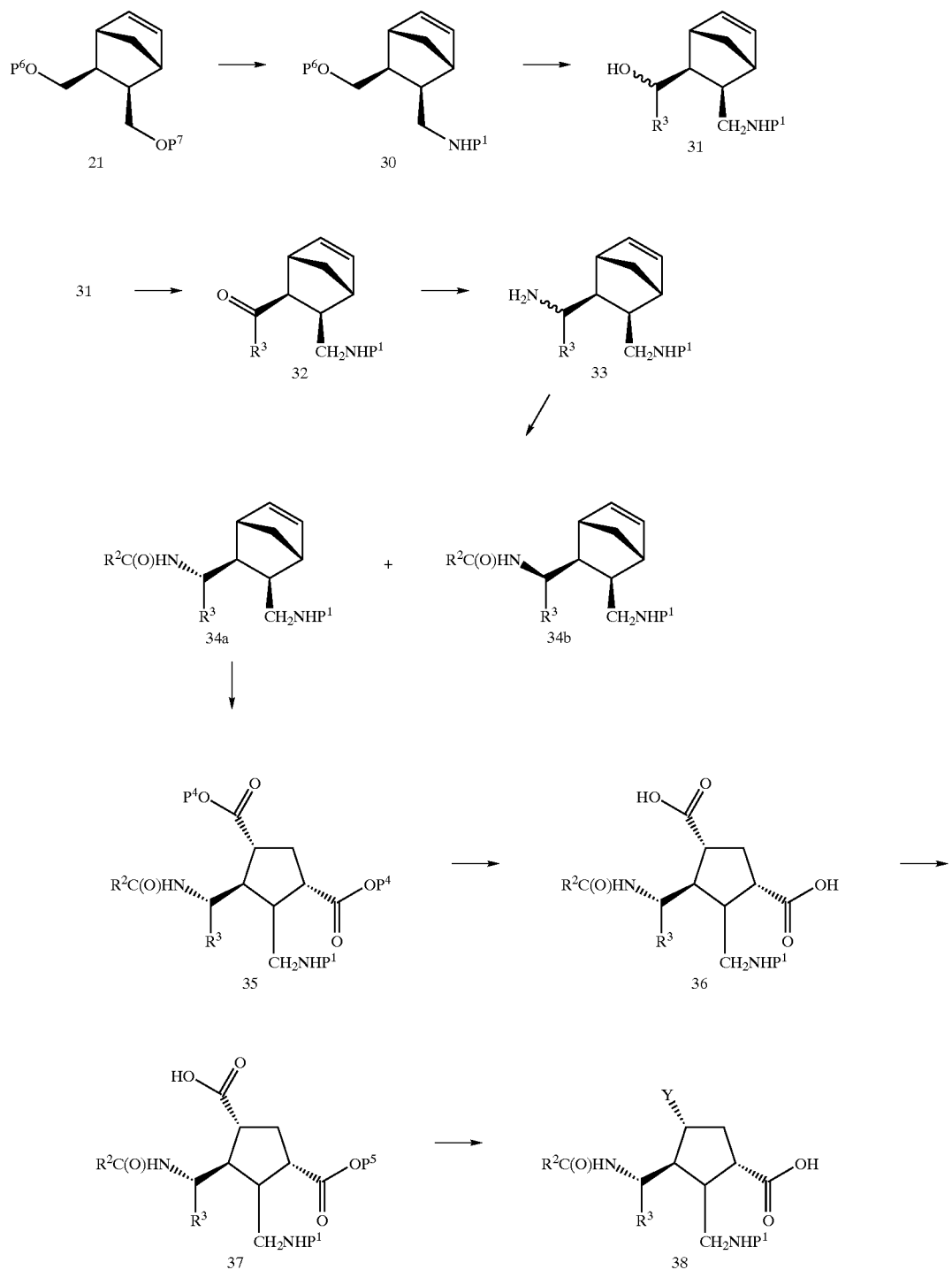

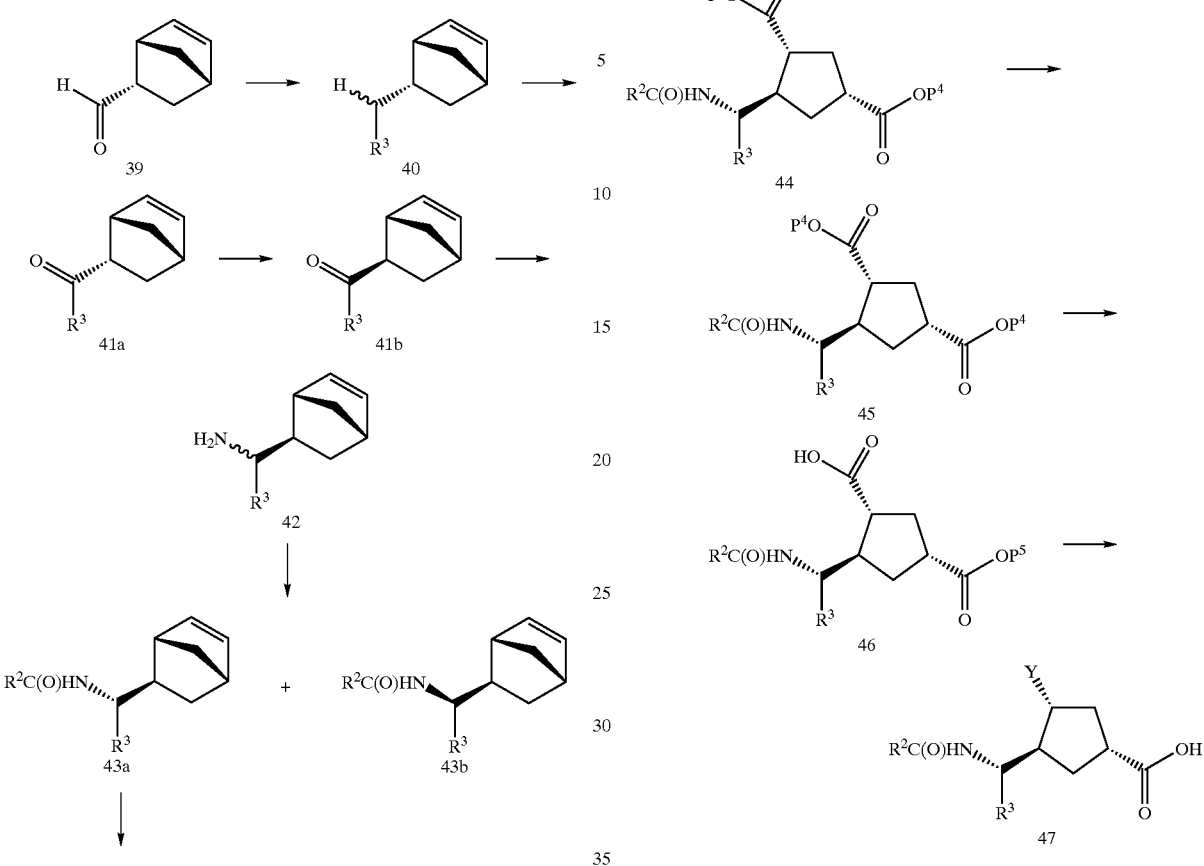
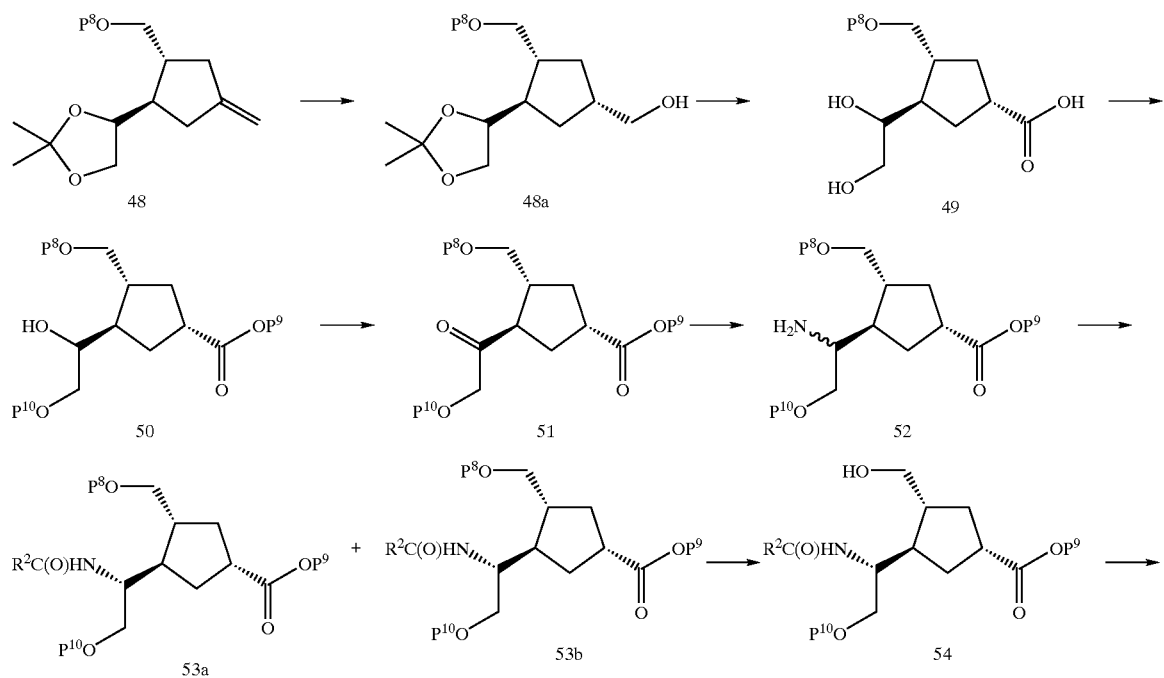

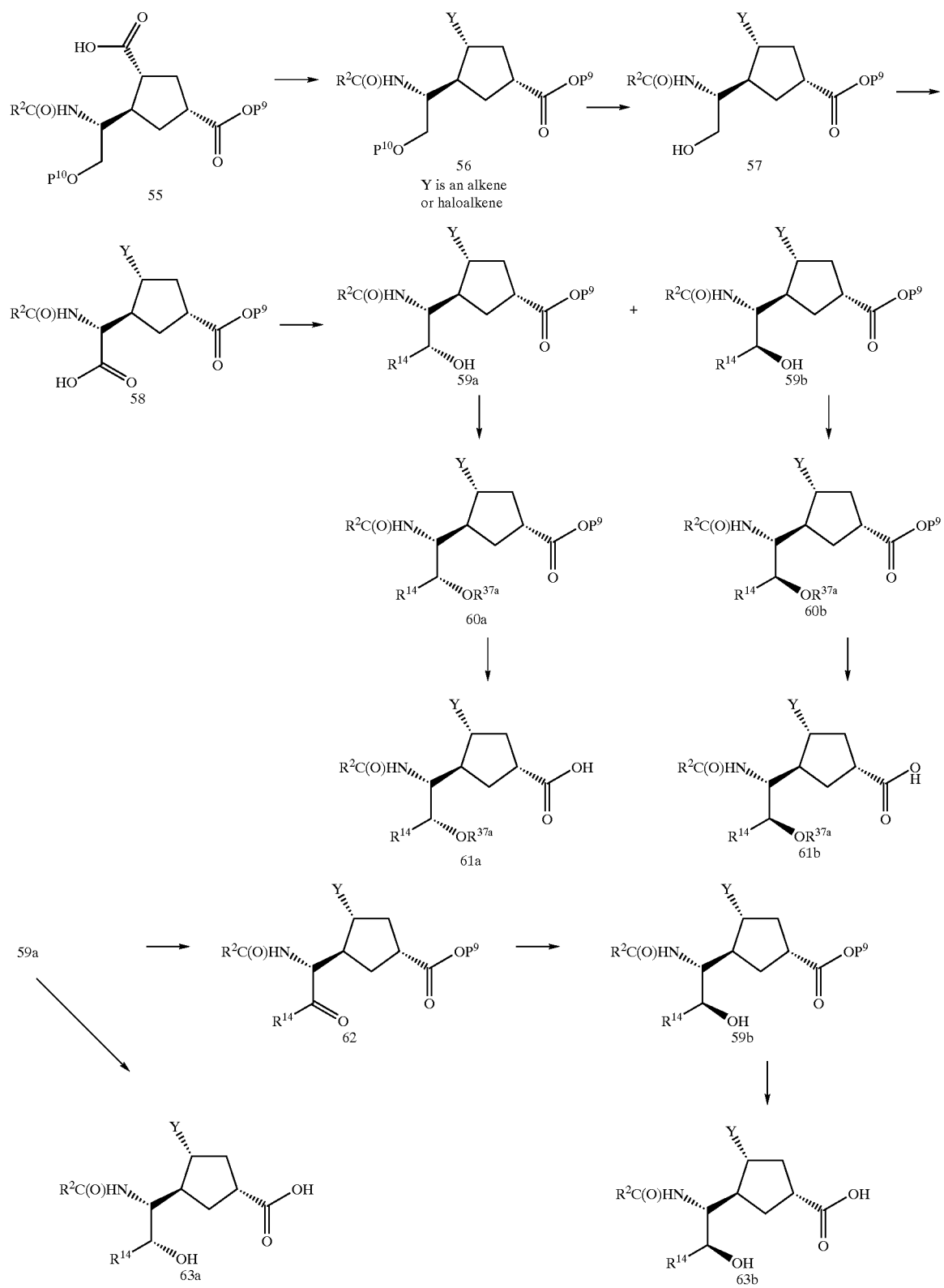

SCHEME 7
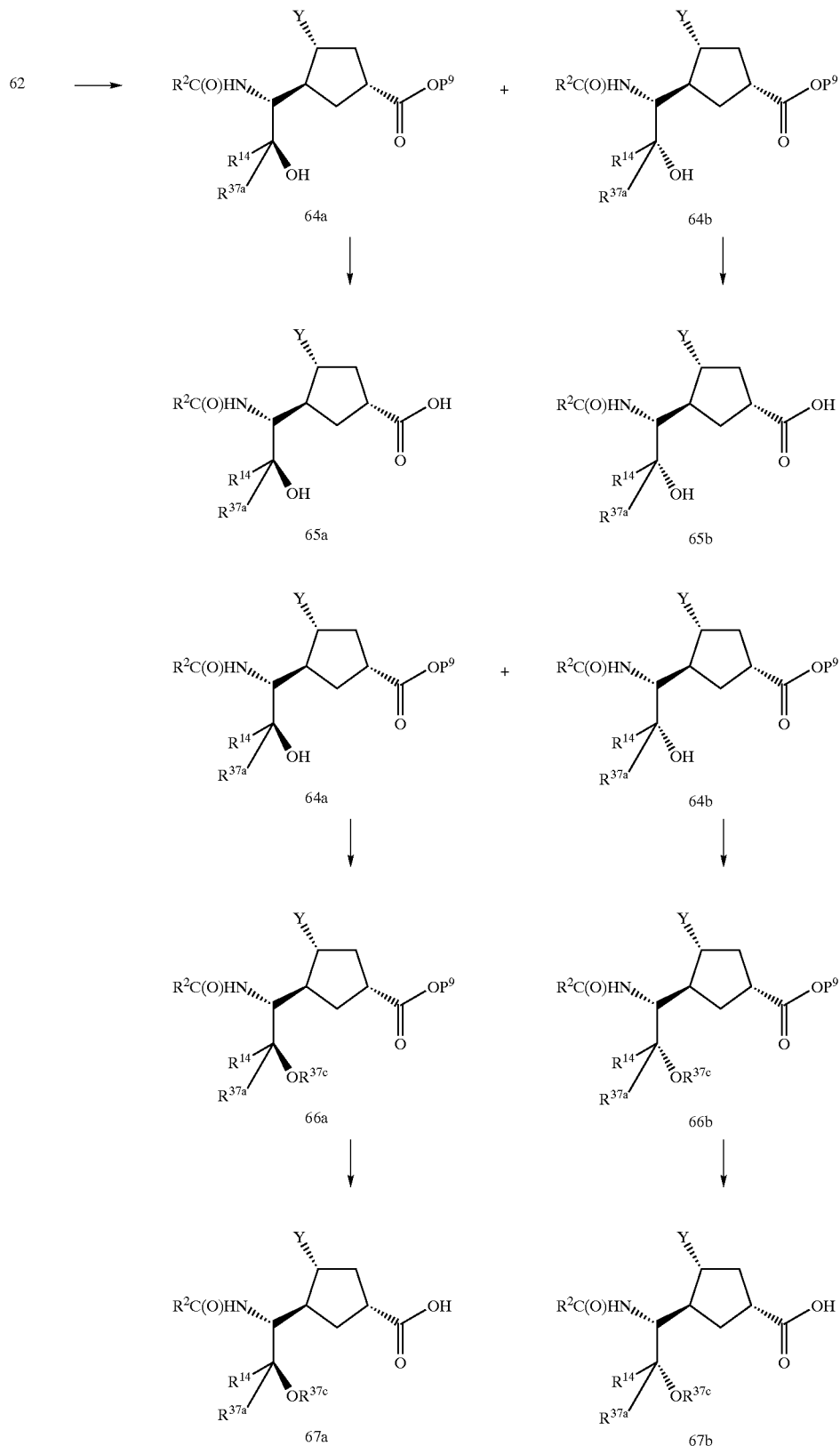

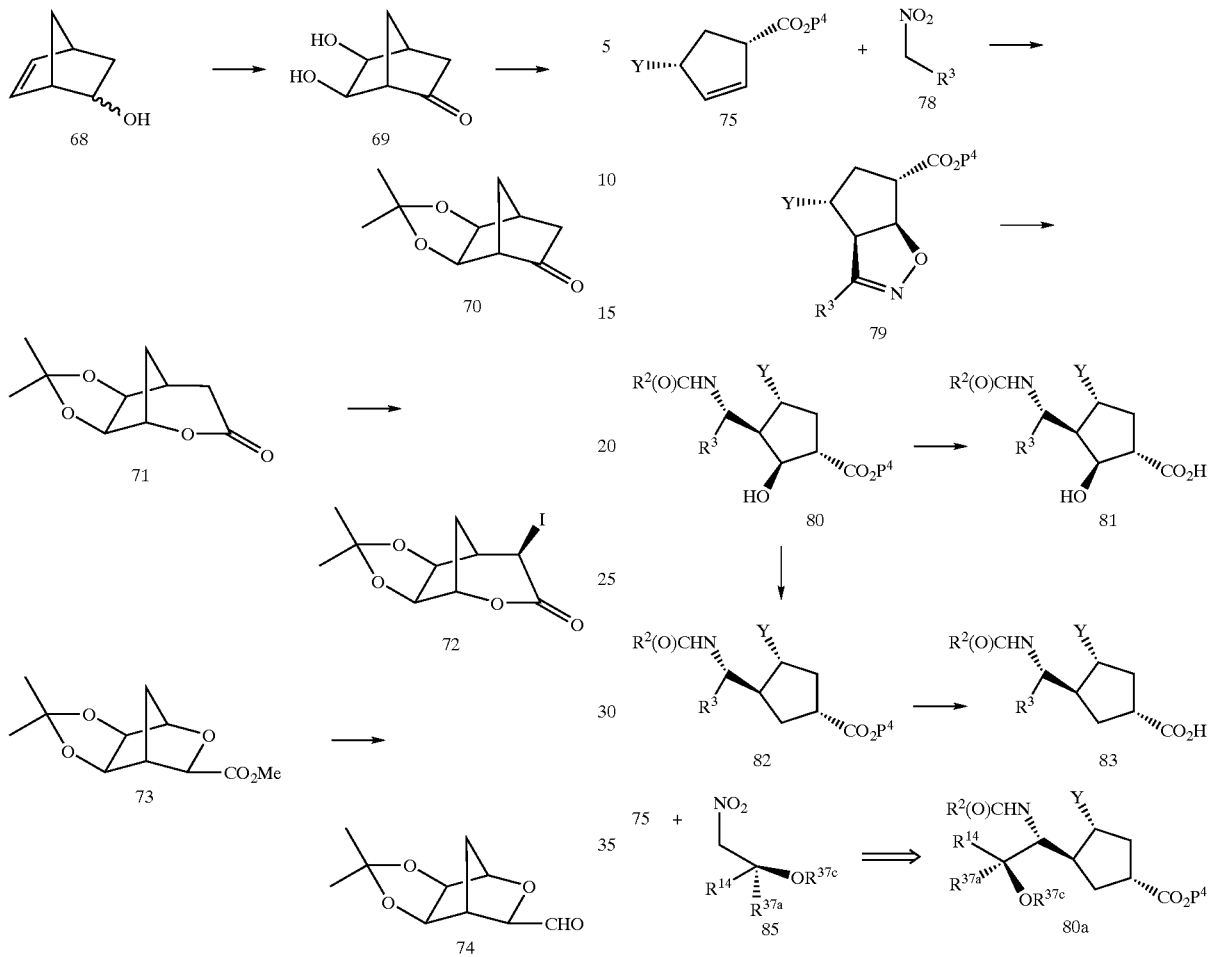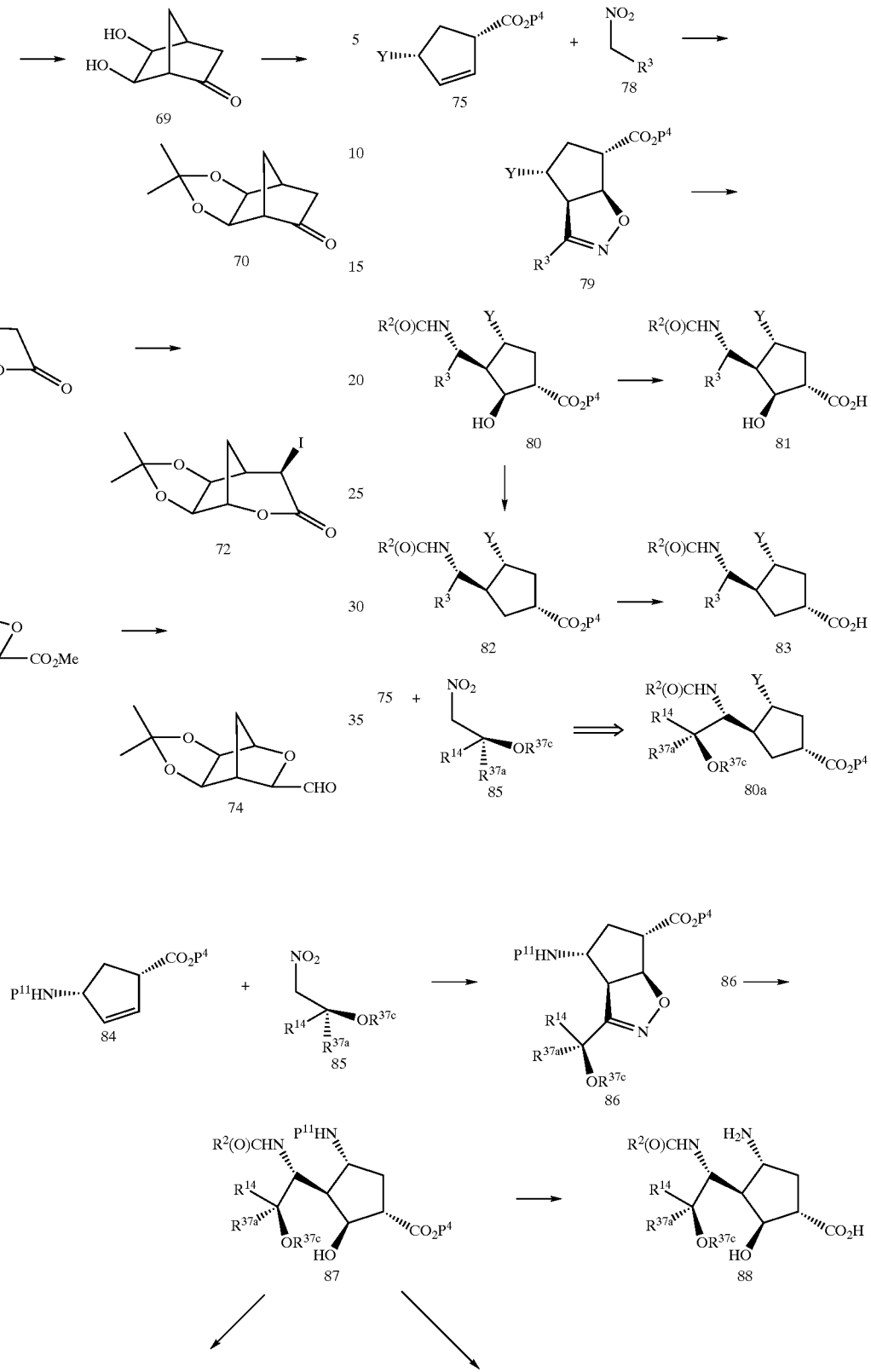

-continued

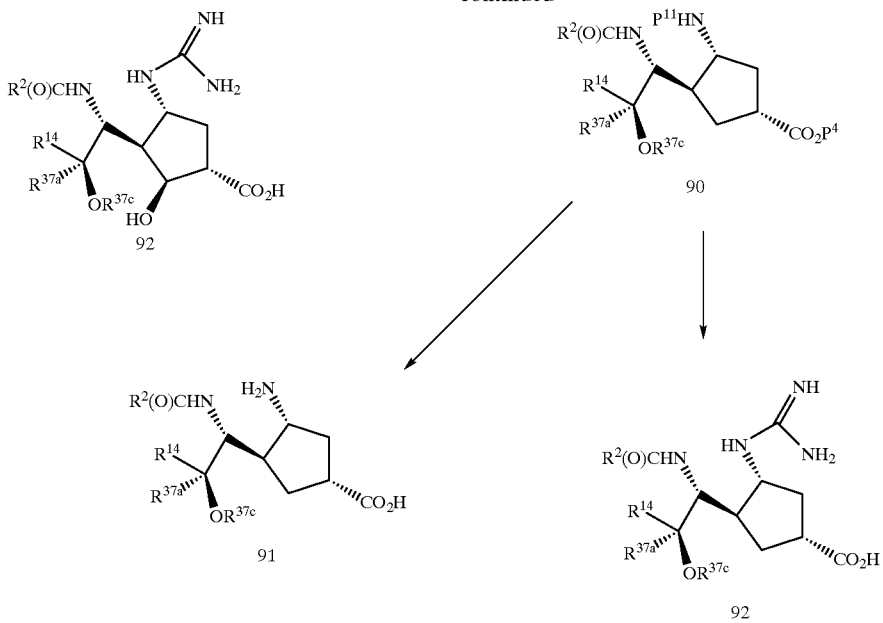

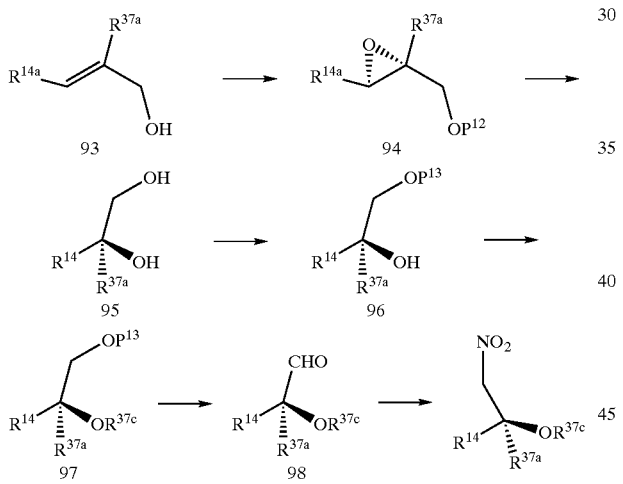

SCHEME 11

The other compounds of the invention can be readily prepared from the compounds available through commercial sources, in the chemical lliterature or as described herein using techniques well known in the chemical literature. The procedures required are well known and can be readily practiced by those having ordinary skill in the art.

The reagents required for the synthesis of the compounds of the invention are readily available from a number of commercial sources such as Aldrich Chemical Co. (Milwaukee, Wis., USA); Sigma Chemical Co. (St. Louis, Mo., USA); and Fluka Chemical Corp. (Ronkonkoma, N.Y., USA); Alfa Aesar (Ward Hill, Mass. 01835-9953); Eastman Chemical Company (Rochester, N.Y. 14652-3512); Lancaster Synthesis Inc. (Windham, N.H. 03087-9977); Spectrum Chemical Manufacturing Corp. (Janssen Chemical) (New Brunswick, N.J. 08901); Pfaltz and Bauer (Waterbury, Conn. 06708). Compounds which are not commercially available can be prepared by employing known methods from the chemical literature.

The following examples will serve to further illustrate the preparation of the compounds of the invention, without limitation.

EXAMPLE 1

(±)-(1S,2S,3R,4R)-2-(N-Methyl-N-t-butyloxycarbonylamino)-3-acetamidomethyl-4-methoxycarbonyl-cyclopentane-1-carboxylic Acid

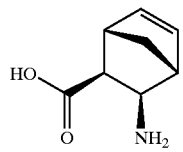

1A. (±)-(2R,3S)-2-Aminobicyclo[2.2.1]hept-5-ene-3-carboxylic Acid.

The title compound was synthesized from norbornadiene by a cycloaddition reaction with chlorosulfonyl isocyanate followed by a reduction and acidic hydrolysis as reported by Stajer, G. et al. *Tetrahedron*, 40, 2385 (1984).

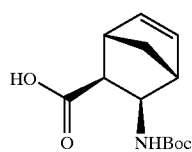

1B. (±)-(2R,3S)-2-(t-Butyloxycarbonylamino)bicyclo[2.2.1]hept-5-ene-3-carboxylic Acid.

A solution of (±)-(2R,3S)-2-aminobicyclo[2.2.1]hept-5-ene-3-carboxylic acid (6.3 g, 0.04 mole), NaOH (3.3 g, 0.082 mole), and di-tert-butyl dicarbonate (0.082 mmole) in water (200 mL) was stirred at room temperature for 48 hours. The reaction mixture was acidified using 1M aqueous HCl, while cooling the solution in an ice/water bath. The reaction mixture was extracted with dichloromethane (3×250 mL). The organic layer was dried over $MgSO_4$, filtered and concentrated to provide the title compound as a white solid (yield: 5.6 g, 55%).

$^1$H NMR (CDCl$_3$) δ 1.44 (s, 9H), 1.64 (d, 1H), 2.08 (d, 1H), 2.58 (m, 1H), 2.72 (s, 1H), 2.97 (s,1H), 6.18 (m, 2H), 6.96 (d, 1H).

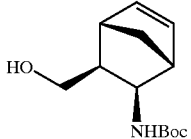

1C. (±)-(2R,3S)-2-(t-Butyloxycarbonylamino)-3-hydroxymethylbicyclo[2.2.1]hept-5-ene.

Ethyl chloroformate (2.3 mL, 23.7 mmole) was added slowly to a solution of (±)-(2R,3S)-2-(t-butyloxycarbonylamino)bicyclo[2.2.1]hept-5-ene-3-carboxylic acid (6 g, 23.7 mmole) and N-methylmorpholine (2.6 mL, 23.7 mmole) in THF (110 mL) at −20° C. The reaction mixture was warmed to 0° C., and the slurry-like reaction became nearly homogeneous. The reaction mixture was cooled to −20° C., and treated with sodium borohydride (3.7 g, 66 mmole). Methanol (10 mL) was added dropwise, over 20 minutes. The reaction mixture was neutralized with 1 N HCl and the reaction mixture was concentrated by removal of volatile materials, in vacuo. The residue was partitioned between ethyl acetate and water. The organic layer was washed with 1 N HCl, water, and brine, dried over MgSO$_4$, filtered and concentrated in vacuo. Purification by silica gel column chromatography using 15% ethyl acetate/hexanes provided the title compound (yield: 4.27 g, 75%).

$^1$H NMR (CDCl$_3$) δ 1.45 (s, 9H), 1.52 (m, 2H), 1.85 (q, 1H), 2.09 (bs, 1H), 2.68 (m, 2H), 3.66 (m, 3H), 4.83 (bs, 1H), 6.11 (m, 1H), 6.27 (m, 1H).

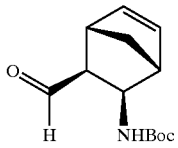

1D. (±)-(2R,3S)-2-(t-Butyloxycarbonylamino)-3-formylbicyclo[2.2.1]hept-5-ene.

DMSO (3.4 mL) in dichloromethane (5 mL) was added slowly to oxalyl chloride (2 mL, 22 mmole) in dichloromethane (50 mL) at −78° C. After 5 minutes, (±)-(2R,3S)-2-(t-butyloxycarbonylamino)-3-hydroxymethyl-bicyclo [2.2.1]hept-5-ene (4.27 g, 17.8 mmole) in 15 mL of dichloromethane and 10 mL of DMSO was added. Stirring was continued for 20 minutes at −78° C. The solution was treated with triethylamine (14 mL). After 5 minutes, the cooling bath was removed and the reaction stirred for an additional 30 minutes. The reaction mixture was partitioned with water (100 mL). The aqueous layer was extracted with dichloromethane (3×50 mL). The organic layers were combined, washed with brine, dried over MgSO$_4$, filtered and concentrated. The crude product was chromatographed on silica gel with 0–10% ethyl acetate/dichloromethane, to provide the title compound. (yield: 3.8 g, 90%)

$^1$H NMR (CDCl$_3$) δ 1.43 (s, 9H), 1.63 (m, 2H), 2.74 (m, 2H), 3.11 (s, 1H), 3.99 (t, 1H), 4.85 (d, 1H), 6.22 (m, 2H), 9.81 (s, 1H).

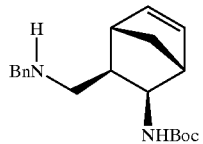

1E. (±)-(2R,3R)-2-(t-Butyloxycarbonylamino)-3-N-benzylaminomethylbicyclo-[2.2.1]hept-5-ene.

A solution of (±)-(2R,3S)-2-(t-butyloxycarbonylamino)-3-formyl-bicyclo[2.2.1]hept-5-ene (3.8 g, 16.0 mmole), benzylamine (1.9 mL, 17.6 mmole) and acetic acid (1 mL) in dichloromethane (80 mL) was stirred at 0 ° C. for 10 minutes followed by addition of Na(AcO)$_3$BH (5.09 g, 24 mmole). The reaction mixture was stirred at 0° C. for 2 hours then allowed to warm slowly to room temperature for 2 hours. After completion, the reaction mixture was washed with aqueous sodium bicarbonate, dried over MgSO$_4$, filtered and concentrated. The crude product was purified by silica gel chromatography using 0–2.5% methanol/chloroform to provide the title compound (yield: 4.0 g, 77%).

$^1$H NMR (CDCl$_3$) δ 1.47 (s, 9H), 1.51 (m, 2H), 1.78 (t, 1H), 2.72 (m, 4H), 3.57 (t, 1H), 3.78 (s, 1H), 6.10 (m, 1H), 6.21 (m, 1H), 7.30 (m, 5H). MS: (M+H)$^+$=329.

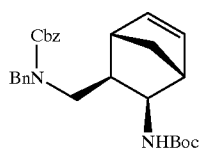

1F. (±)-(2R,3R)-2-(t-Butyloxycarbonylamino)-3-(N-benzyl-N-(benzyloxycarbonyl-amino)methyl)bicyclo[2.2.1]hept-5-ene.

A solution of (±)-(2R,3R)-2-(t-butyloxycarbonylamino)-3-N-benzylaminomethylbicyclo[2.2.1]hept-5-ene (2.8 g, 8.5 mmole) and N-(benzyloxycarbonyloxy)succinimide (2.3 g) in 50 mL of dichloromethane was reacted at room temperature for 6 hours. The reaction mixture was diluted with ethyl acetate, washed with saturated aqueous NaHCO$_3$ and brine, dried over MgSO$_4$ and concentrated in vacuo. The product was purified by silica gel chromatography using hexanes/ethyl acetate (3:1) to provide the title compound (yield: 3.37 g, 85%).

$^1$H NMR (CDCl$_3$) δ 1.32 (m, 2H), 1.36 (s, 9H), 1.56 (m, 1H), 1. 88 (m, 1H), 2.63 (m, 2H), 3.06 (m, 1H), 4.34 (m, 1H), 4.63 (m, 1H), 5.18 (m, 2H), 6.05 (bs, 2H), 7.2 8 (m, 11H).

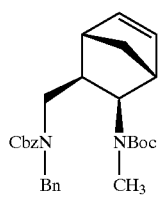

1G. (±)-(2R,3R)-2-(N-Methyl-N-t-butyloxycarbonylamino)-3-(N-benzyl-N-benzyloxycarbonylamino)methyl-bicyclo[2.2.1]hept-5-ene.

Sodium hydride (300 mg , 60% in oil) was added to a solution of (±)-(2R,3R)-2-(t-butyloxycarbonylamino)-3-(N-benzyl-N-benzyloxycarbonylamino)-methylbicyclo[2.2.1]hept-5-ene (3.37 g, 7.27 mmole) and iodomethane (0.9 mL) in anhydrous DMF (60 mL) at 0° C. After 4 hours, the reaction mixture was concentrated in vacuo and purified by silica gel chromatography using hexanes/ethyl acetate (4:1) to provide the title compound (yield: 3.3 g, 95%).

$^1$H NMR (CDCl$_3$) δ 1.40 (s, 9H), 1.82 (m, 2H), 2.26 (m, 1H), 2.78 (m, 1H), 2.85 (m, 1H), 2,90 (s, 3H), 2.94 (m, 2H), 3.63 (m, 1H), 4.22 (m, 2H), 5.34 (s, 2H), 5.60 (m, 2H), 7.15 (m, 10H). MS: (M+H)$^+$=477.

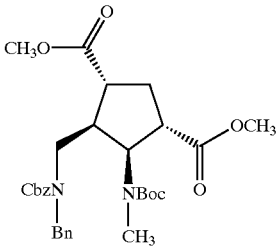

1H. (±)-(1S,2S,3R,4R)-2-(N-Methyl-N-t-butyloxycarbonylamino)-3-(N-benzyl-N-benzyloxycarbonylamino)methylcyclopentane-1,4-dicarboxylic Acid Dimethyl Ester.

A mixture of NaIO$_4$ (10 g, 47 mmole) and RuO$_2$ (45 mg, 0.3 mmol) in 25 mL of carbon tetrachloride 50 mL of acetonitrile, and 75 mL of water was rapidly stirred for 30 minutes. A solution of (±)-(2R,3R)-2-(N-methyl-N-t-butyloxycarbonylamino)-3-(N-benzyl-N-benzyloxycarbonylamino)methyl-bicyclo[2.2.1]hept-5-ene (3.3 g, 6.9 mmole) in 25 mL of carbon tetrachloride was added to the bright yellow mixture. The resultant black mixture was stirred at room temperature for 1.5 hours and diluted with 250 mL of water. The aqueous layer was extracted with ethyl acetate (5×200 mL). The combined organic layers were washed with brine, dried over MgSO$_4$, filtered and concentrated in vacuo. The residue was dissolved in ethyl acetate and treated with a solution of diazomethane in ethyl ether. The reaction mixture was concentrated in vacuo, and the crude product purified by silica gel chromatography using ethyl acetate/hexanes (1:1) to provide the title compound as a white solid (yield: 1.91 g, 50%).

$^1$H NMR (CDCl$_3$) δ 1.41 (s, 9H), 2.21 (m, 2H), 2.33 (m, 1H), 2.90 (s, 3H), 2.92 (m, 2H), 2.96 (m, 1H), 3.38 (t, 1H), 3.67 (s, 6H), 4.23 (m, 3H), 5.38 (s, 2H), 7.12 (m, 10H). MS: (M+H)$^+$=569.

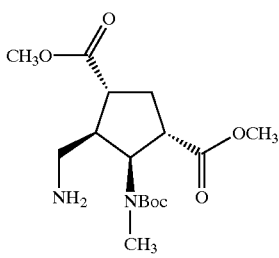

1I. (±)-(1S,2S,3R,4R)-2-(N-Methyl-N-t-Butyloxycarbonylamino)-3-aminomethyl-cyclopentane-1,4-dicarboxylic Acid Dimethyl Ester.

A mixture of (±)-(1S,2S,3S,4R)-2-(N-methyl-N-t-butyloxycarbonylamino)-3-(N-benzyl-N-benzyloxycarbonylamino)methyl-cyclopentane-1,5-dicarboxylic acid dimethyl ester (1.91 g, 3.36 mmole) and Pd(OH)$_2$ (380 mg, 20% on carbon) in 50 mL of isopropanol was stirred at room temperature under an hydrogen atmosphere, for 16 hours. The catalyst was removed by vacuum filtration through a bed of Celite®, and the filtrate concentrated in vacuo to provide the title compound (yield: 1.2 g 100%).

$^1$H NMR (CDCl$_3$) δ 1.48 (s, 9H), 2.00 (m, 2H), 2.42 (m, 1H), 2.64 (m, 2H), 2.90 (bs, 3H), 3.00 (m, 2H), 3.71 (s, 3H), 3.73 (s, 3H), 4.4 (bs, 1H), 5.4 (bs, 2H). MS: (M+H)$^+$=345.

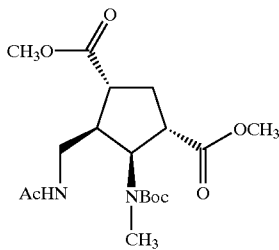

1J. (±)-(1S,2S,3R,4R)-2-(N-Methyl-N-t-butyloxycarbonylamino)-3-acetamidomethyl-cyclopentane-1,4-dicarboxylic Acid Dimethyl Ester.

A solution of (±)-(1S,2S,3R,4R)-2-(N-methyl-t-butyloxycarbonylamino)-3-aminomethylcyclopentane-1,5-dicarboxylic acid dimethyl ester (1.2 g, 3.5 mmole), acetic anhydride (0.5 mL) and triethylamine (1 mL) in 25 mL of dichloromethane was stirred at room temperature for 2 hours. The reaction mixture was diluted with ethyl acetate and washed successively with 1 N HCl, water and brine, dried over MgSO$_4$, and concentrated in vacuo. The residue was purified by silica gel chromatography using ethyl acetate/hexanes (1:1) to provide the title compound (yield: 790 mg, 58%).

$^1$H NMR (CDCl$_3$) δ 1.45 (s, 9H), 1.92 (s, 3H), 2.05 (m, 1H), 2.40 (m, 1H), 2.62 (m, 1H), 2.85 (s, 3H), 3.1 (m, 1H), 3.3 (m, 1H), 3.42 (m, 1H), 3.71 (s, 6H), 4.62 (bs, 1H), 6.38 (bs, 1H). MS: (M+H)$^+$=387.

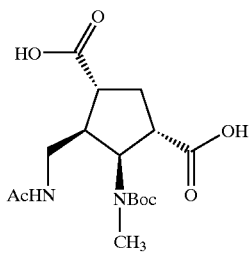

1K. (±)-(1S,2S 3R,4R)-2-(N-Methyl-N-t-butyloxycarbonylamino)-3-acetamidomethyl-cyclopentane-1,4-dicarboxylic Acid.

A solution of (±)-(1S,2S,3S,4R)-2-(N-methyl-N-t-butyloxycarbonylamino)-3-acetamidomethylcyclopentane-1,5-dicarboxylic acid dimethyl ester (720 mg, 1.86 mmole) and 5 equivalents of lithium hydroxide in methanol (40 mL) and H$_2$O (10 mL) was stirred at room temperature for two hours. The solution was concentrated in vacuo. The residue was partitioned between 1 N HCl and ethyl acetate. The aqueous layer was back extracted with ethyl acetate (3×50 mL). The organic layers were combined and washed with brine, dried over Na$_2$SO$_4$, filtered, and concentrated in vacuo to provide the title compound (yield: 500 mg, 75%).

$^1$H NMR (CDCl$_3$) δ 1.45 (s, 9H), 1.92 (s, 3H), 2.05 (m, 1H), 2.40 (m, 1H), 2.62 (m, 1H), 2.85 (s, 3H), 3.1 (m, 1H), 3.3 (m, 1H), 3.42 (m, 1H), 3.71 (s, 6H), 4.62 (bs, 1H), 6.38 (bs, 1H).

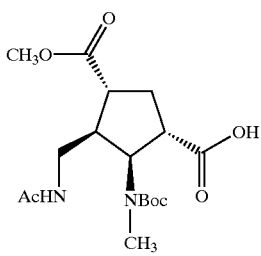

1L. (±)-(1S,2S,3R,4R)-2-(N-Methyl-N-t-butyloxycarbonylamino)-3-acetamidomethyl-4-methoxycarbonylcyclopentane-1-carboxylic Acid

A solution of (±)-(1S,2S,3R,4R)-2-(N-methyl-N-t-butyloxycarbonylamino)-3-acetamidomethylcyclopentane-1,5-dicarboxylic acid (500 mg, 11.4 mmole), in 5 mL of dichloromethane and 5 mL of acetic anhydride, was stirred at room temperature for two hours. The solution was concentrated in vacuo, at 20° C. The residue was dissolved in 10 mL of methanol and 0.2 mL of triethylamine and reacted for 16 hours at room temperature, under a nitrogen atmosphere. The reaction mixture was diluted with 100 mL of chloroform, and washed successively with 0.1 N HCl and brine. The solution was dried over $MgSO_4$, filtered and concentrated in vacuo. The residue was purified by silica gel chromatography using chloroform/methanol/acetic acid (97:2:1) to provide the title compound (yield: 155 mg, 30%).

$^1$H NMR ($CDCl_3$) δ 1.47 (s, 9H), 1.95 (s, 3H), 2.10 (m, 2H), 2.43 (m, 1H), 2.64 (m, 1H), 2.88 (m, 4H), 3.20 (m, 1H), 3.30 (m, 1H), 3.44 (m, 1H), 3.72 (s, 3H), 4.66 (t, 1H), 6.48 (bs, 1H). MS $(M+H)^+$=373.

EXAMPLE 2

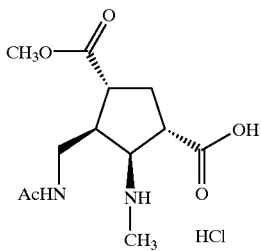

(±)-(1S,2S,3R,4R)-2-N-Methyl-3-acetamidomethyl-4-methoxycarbonylcyclopentanecarboxylic Acid Hydrochloride

A solution of (±)-(1S,2S,3R,4R)-2-(N-methyl-N-t-butyloxycarbonylamino)-3-acetamidomethyl-4-methoxycarbonylcyclopentanecarboxylic acid (130 mg, 0.35 mmole) in 4.5 mL of dichloromethane was reacted with trifluoroacetic acid (1.5 mL) for 1 hr, at room temperature. The solution was concentrated in vacuo, at 25° C. The residue was treated with 1 N HCl and concentrated in vacuo to provide the title compound as a white solid (yield: 100 mg, 92%).

$^1$H NMR ($D_2O$) δ 2.02 (s, 3H), 2.08 (m, 1H), 2.54 (m, 2H), 2.76 (s, 3H), 2.85 (m, 2H), 3.36 (m, 2H), 3.76 (s, 3H), 3.81 (t, 1H).

EXAMPLE 3

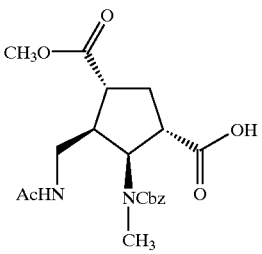

(±)-(1S,2S,3R,4R)-2-(N-Methyl-N-benzyloxycarbonylamino)-3-acetamidomethyl-4-methoxycarbonyl-cyclopentanecarboxylic Acid

A solution of (±)-(1S,2S,3R,4R)-2-N-methyl-3-acetamidomethyl-4-methoxycarbonyl-cyclopentanecarboxylic acid hydrochloride (100 mg), N-(benymoxycarbonyloxy)succinimide (183 mg) and triethylamine (0.160 mL) in dichloromethane (10 mL) was stirred at room temperature for 16 hours. The mixture was diluted with ethyl acetate and washed successively with 1 N HCl, and brine, dried over $MgSO_4$, and concentrated in vacuo. The residue was purified by silica gel chromatography using chloroform/methanol/acetic acid (97:2:1) to provide the title compound as a white solid.

$^1$H NMR ($CDCl_3$) δ 1.88 (s, 3H), 2.08 (m, 2H), 2.46 (m, 1H), 2.66 (m, 1H), 2.92 (m, 1H), 2.96 (s, 3H), 3.18 (m, 1H), 3.35 (m, 1H), 3.70 (s, 3H), 4.64 (bs, 1H), 5.14 (s, 2H), 6.29 (bs, 1H), 7.34 (m, 5H). MS: $(M+H)^+$=407.

EXAMPLE 4

(±)-(1S,2S,3R,4R)-2-(t-Butyloxycarbonylamino)-3-(acetamidomethyl)-4-(methoxycarbonyl)-cyclopentane-1-carboxylic Acid

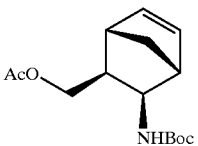

4A. (±)-(2R,3S)-2-t-Butyloxycarbonylamino-3-acetoxymethylbicyclo[2.2.1]hept-5-ene.

A solution of (±)-(2R,3S)-2-(t-butyloxycarbonylamino)-3-hydroxymethylbicyclo[2.2.1]hept-5-ene (1.0 g, 4.18 mmole), acetic anhydride (0.55 mL), triethylamine (2 mL) and N,N-dimethylaminopyridine (catalytic) in 50 mL of dichloromethane was reacted for 2 hours, at room temperature. The reaction mixture was diluted with 200 mL of ethyl acetate, washed with 0.5 N HCl, water, saturated sodium bicarbonate, and brine. The organic layer was dried over $MgSO_4$, filtered and concentrated. The crude product was purified by silica gel chromatography using 10% ethyl acetate/hexanes to provide the title compound. (yield: 0.92 g, 78%) MS: $(M+H)^+$=282.

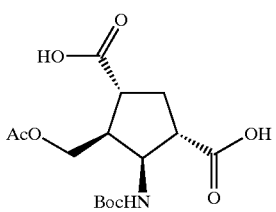

4B. (±)-(1S,2S,3S,4R)-2-(t-Butyloxycarbonylamino)-3-(acetoxymethyl)-cyclopentane-1,4-dicarboxylic Acid

Ruthenium dioxide hydrate (43 mg, 0.32 mmole) was added to a vigorously stirred mixture of NaIO$_4$ (7.12 g, 33 mmole) in 33 mL of acetonitrile, 33 mL of carbon tetrachloride and 58 mL of water. The mixture was stirred at room temperature for 5 minutes or until a homogeneous yellow color was attained. A solution of (±)-(2R,3S)-2-(t-butyloxycarbonylamino)-3-acetoxymethyl-bicyclo[2.2.1]hept-5-ene (2.28 g, 8.11 mmole) in 10 mL of (1:1) acetonitrile:carbon tetrachloride was added rapidly to the reaction mixture. The mixture was stirred vigorously for 1 hour at room temperature. The reaction mixture was partitioned between ethyl acetate and 0.5 N HCl. The organic layer was washed with brine, dried over Na$_2$SO$_4$, filtered and concentrated to provide the diacid compound which was used in the following reaction without additional purification.

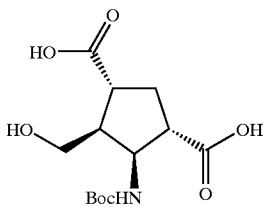

4C. (±)-(1S,2S,3S,4R)-2-(t-Butyloxycarbonylamino)-3-(hydroxymethyl)-cyclopentane-1,4-dicarboxylic Acid.

The crude diacid, (±)-(1S,2S,3S,4R)-2-(t-butyloxycarbonylamino)-3-(acetoxymethyl)-cyclopentane-1,4-dicarboxylic acid, prepared in example 4B, and sodium hydroxide (1.2 g) in 45 mL of water was reacted for 6 hours, at room temperature. The reaction mixture was acidified to pH 1 with and extracted with ethyl acetate (3×40 mL). The organic layer was washed with brine and dried over Na$_2$SO$_4$, filtered and concentrated. The crude diacid-alcohol was used in the following reaction without additional purification.

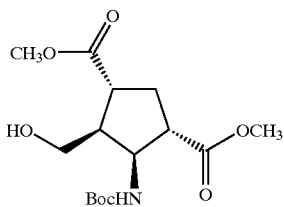

4D. (±)-(1S,2S,3S,4R)-2-(t-Butyloxycarbonylamino)-3-(hydroxymethyl)-cyclopentane-1,4-dicarboxylic Acid Dimethyl Ester.

The diacid-alcohol, (±)-(1S,2S,3S,4R)-2-(t-butyloxycarbonylamino)-3-(hydroxymethyl)-cyclopentane-1,5-dicarboxylic acid, prepared in Example 4C, was dissolved in 40 mL of tetrahydrofuran (THF) and reacted with diazomethane in ethyl ether until complete conversion to the dimethyl ester. The reaction mixture was monitored by TLC, using 10% methanol in chloroform with 1% acetic acid. The reaction was concentrated in vacuo to provide the title compound as a colorless oil (yield: 1.3 g, 85%). MS: (M+H)$^+$=331.

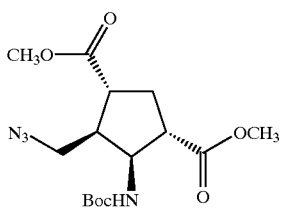

4E. (±)-(1S,2S,3R,4R)-2-(t-Butyloxycarbonylamino)-3-(azidomethyl)-cyclopentane-1,4-dicarboxylic Acid Dimethyl Ester.

Methanesulfonyl chloride (1.3 mL, 17.0 mmole) was added slowly to a solution of (±)-(1S,2S,3S,4R)-2-(t-butyloxycarbonylamino)-3-(hydroxymethyl)-cyclopentane-1,4-dicarboxylic acid dimethyl ester (2.76 g, 8.34 mmole) and triethylamine (2.4 mL, 17.0 mmole) in 80 mL of 1:1 dichloromethane:tetrahydrofuran, maintained at −30° C. The reaction mixture was stirred for 2.5 hours, at −30° C. then diluted with ethyl acetate washed with 0.1 N HCl and brine, dried over MgSO$_4$, filtered and concentrated in vacuo to provide the crude mesylate. The mesylate and lithium azide (4 g) were reacted in 35 mL of N,N-dimethylformamide for 1 hour, at 90° C. The reaction mixture was partitioned between ethyl acetate and water. The organic layer was washed with brine, dried over MgSO$_4$, filtered and concentrated. The crude product was purified by silica gel chromatography using 20% ethyl acetate in hexanes to provide the title compound. (yield: 1.8 g, 48%) MS: (M+H)$^+$=373.

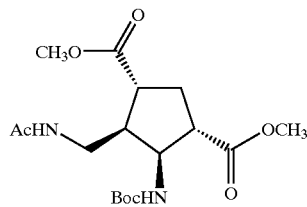

4F. (±)-(1S,2S,3R,4R)-2-(t-Butyloxycarbonylamino)-3-(acetamidomethyl)-cyclopentane-1,5-dicarboxylic Acid Dimethyl Ester.

(±)-(1S,2S,3R,4R)-2-(t-Butyloxycarbonylamino)-3-(azidomethyl)-cyclopentane-1,4-dicarboxylic acid dimethyl ester (506 mg, 1.42 mmole) and thiolacetic acid (0.4 mL) were reacted at room temperature for 6 hours. The reaction mixture was concentrated in vacuo and the crude product was purified by silica gel chromatography using 3% methanol in chloroform to provide the title compound (yield: 255 mg, 48%). MS: (M+H)$^+$=373.

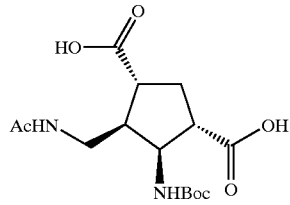

4G. (±)-(1S,2S,3R,4R)-2-(t-Butyloxycarbonylamino)-3-(acetamidomethyl)-cyclopentane-1,4-dicarboxylic Acid (±)-(1S,2S,3R,4R)-2-(t-Butyloxycarbonylamino)-3-(acetamidomethyl)-cyclopentane-1,4-dicarboxylic acid dimethyl ester (255 mg, 0.68 mmole) and lithium hydroxide (2.2 equivalents) in 15 mL of 4:1 methanol:water were reacted at room temperature for 2 hours. The reaction was acidified with dilute HCl and extracted with ethyl acetate (3×60 mL). The organic layers were combined, dried over $Na_2SO_4$, filtered and concentrated to provide the title compound.

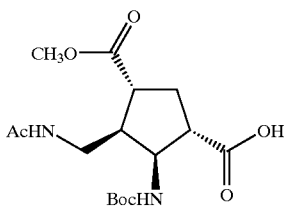

4H. (±)-(1S,2S,3R,4R)-2-(t-Butyloxycarbonylamino)-3-(acetamidomethyl)-4-(methoxcyarbonyl)-cyclopentane-1-carboxylic Acid The crude diacid, (±)-(1S,2S,3R,4R)-2-(t-butyloxycarbonylamino)-3-(acetamidomethyl)-cyclopentane-1,4-dicarboxylic acid, prepared in Example 4G was reacted with acetic anhydride (20 mL) for approximately 1 hour at 60° C. to provide the bicyclic anhydride. The reaction mixture was concentrated in vacuo and the crude anhydride was treated with methanol (50 mL) and triethylamine (2–3 equivalents) at room temperature for 3 hours. The reaction mixture was diluted with ethyl acetate and washed with 0.5N HCl and brine. The organic solution was dried over $Na_2SO_4$, filtered and concentrated. Chromatographic separation of the diastereomers was accomplished by silica gel chromatography using 25% ethyl acetate in hexanes and 0.5% acetic acid to provide the title compound (yield: 146 mg, 60%).

$^1$H NMR (methanol-d4) δ 1.44 (s, 9H), 1.90 (s, 3H), 2.04 (m, 1H), 2.32 (m, 1H), 2.54 (m, 1H), 2.72 (m, 2H), 3.11 (m, 1H), 3.36 (m, 1H), 4.38 (m, 1H), 6.92 (broad d, 1H), 7.8 (broad s, 1H). MS: $(M+H)^+$=359.

EXAMPLE 5

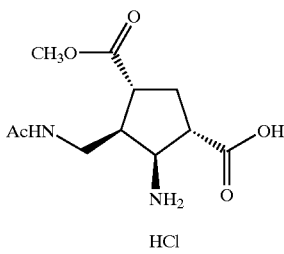

(±)-(1S,2S,3R,4R)-2-Amino-3-(acetamidomethyl)-4-(methoxycarbonyl)-cyclopentane-1-carboxylic Acid Hydrochloride A solution of (±)-(1S,2S,3R,4R)-2-(t-butyloxycarbonylamino)-3-(acetamidomethyl)-4-(methoxycarbonyl)-cyclopentane-1-carboxylic acid (66 mg, 0.18 mmole) in 3 mL of dichloromethane was reacted with trifluoroacetic acid (1.0 mL) for 1 hr, at room temperature. The solution was concentrated in vacuo at 25° C. The crude product was treated with 1 N HCl and concentrated in vacuo to provide the title compound as a white solid.

$^1$H NMR ($D_2O$) δ 2.01 (s, 3H), 2.19 (m, 1H), 2.58 (m, 1H), 2.81 (t, 1H), 2.95 (m, 1H), 3.15 (m, 1H), 3.38 (m, 3H), 3.75 (s, 3H), 4.08 (t, 1H). MS=$(M+H)^+$=259.

EXAMPLE 6

(±)-(1S,2S,3R,4R)-3-Acetamidomethyl-2-(N-t-butoxycarbonylamino)methyl-4-methoxycarbonyl-cyclopentane-1-carboxylic Acid

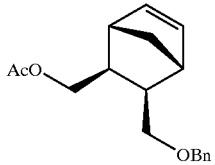

6A. (±)-exo-exo-3-Acetoxymethyl-2-benzyloxymethyl-bicyclo[2.2.1]hept-5-ene.

(±)-exo-exo-2,3-Dihydroxymethylbicyclo[2.2.1]hept-5-ene (620 mg, 4.0 mmole), prepared according to the procedure described by Culberson, C. et al., *Journal of the American Chemical Society* 82, 2541–2547, (1960), was reacted with sodium hydride (300 mg, 60% oil dispersion) in 10 mL of N,N-dimethylformamide (DMF) for 15 min, at 0° C. This was followed by treatment of the dianion with benzyl bromide (0.5 mL) for an additional 2 hours. The reaction mixture was diluted with ethyl acetate washed with water, and brine, dried over $MgSO_4$, filtered and concentrated in vacuo.

The crude benzylated product was reacted with acetic anhydride (0.7 mL), triethylamine (3 mL) and N,N-dimethylaminopyridine (catalytic) in dichloromethane (20 mL) at room temperature for 1 hour. The reaction mixture was concentrated in vacuo and purified by silica gel chromatography using 10% ethyl acetate in hexanes to provide the title compound (yield: 0.845 g, 74%).

$^1$H NMR ($CDCl_3$) δ 1.41 (m, 2H), 1.85 (m, 2H), 2.05 (s, 3H), 2.73 (brs, 1H), 2.78 (brs, 1H), 3.38 (m, 1H), 3.57 (m, 1H), 3.95 (m, 1H), 4.31 (m, 1H), 4.51 (m, 2H), 6.18 (m, 2H), 7.33 (m, 5H). MS: $(M+H)^+$=287.

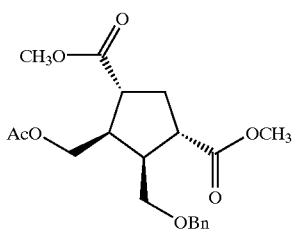

6B. (±)-(1S,2S,3R,4R)-3-Acetoxymethyl-2-benzyloxymethyl-cyclopentane-1,4-dicarboxylic Acid Dimethyl Ester.

A rapidly stirred mixture of $NaIO_4$ (10 g) and $RuO_2$ (45 mg) in 25 mL of carbon tetrachloride, 50 mL of acetonitrile, and 75 mL of water was reacted for 30 minutes. A solution of (±)-(2R,3S)-2-acetoxymethyl-3-benzyloxymethyl-bicyclo[2.2.1]hept-5-ene (3.3 g, 11.5 mmole) in 25 mL of carbon tetrachloride was added to the bright yellow mixture. The resultant black mixture was stirred for 1.5 hours, at room temperature. Water (250 mL) was added to the reaction mixture and the aqueous layer was extracted with ethyl acetate (5×200 mL). The combined organic layers were washed with brine, dried over $MgSO_4$, and concentrated in vacuo.

The residue was dissolved in ethyl acetate and treated with a solution of diazomethane in ethyl ether. The reaction mixture was concentrated in vacuo, and the crude product purified by silica gel chromatography using ethyl acetate-:hexanes (1:1) to provide the title compound as a white solid (yield: 1.91 g, 44%).

$^1$H NMR (CDCl$_3$) δ 2.00 (s, 3H), 2.14 (m, 1H), 2.34 (m, 1H), 2.77 (m, 3H), 2.89 (m, 1H), 3.51 (m, 2H), 3.67 (s, 3H), 3.70 (s, 3H), 4.18 (m, 2H), 4.47 (s, 2H), 7.32 (m, 5H). MS: (M+H)$^+$=379.

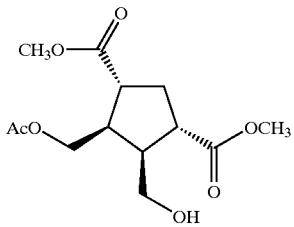

6C. (±)-(1S,2S,3R,4R)-3-Acetoxymethyl-2-hydroxymethyl-cyclopentane-1,4-dicarboxylic Acid Dimethyl Ester.

A mixture of (±)-(1S,2S,3R,4R)-3-acetoxymethyl-2-benzyloxymethylcyclopentane-1,4-dicarboxylic acid dimethyl ester (3.3 g, 8.72 mmole) and palladium (600 mg, 10% on carbon) in ethanol (100 mL) was stirred vigorously at room temperature under an hydrogen atmosphere. Upon completion, as determined by TLC, the reaction mixture was filtered and concentrated in vacuo to provide the title compound (yield: 2.56 g, 100%).

$^1$H NMR (CDCl$_3$) δ 1.84 (t, 1H), 2.05 (s, 3H), 2.16 (m, 1H), 2.36 (m, 1H), 2.75 (m, 4H), 3.70 (s, 3H), 3.71 (s, 3H), 3.73 (m, 1H), 4.19 (m, 2H). MS=(M+H)$^+$=289.

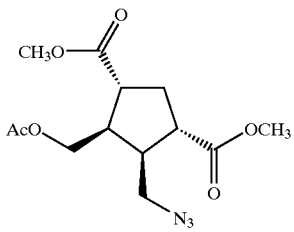

6D. (±)-(1S,2S,3R,4R)-3-Acetoxymethyl-2-azidomethylcyclopentane-1,4-dicarboxylic Acid Dimethyl Ester.

Methanesulfonyl chloride (2.1 mL, 26.6 mmole) was added slowly to a solution of (±)-(1S,2S,3R,4R)-3-acetoxymethyl-2-hydroxymethylcyclopentane-1,4-dicarboxylic acid dimethyl ester (2.56 g, 8.72 mmole) and triethylamine (3.7 mL, 26.6 mmole) in 100 mL of dichloromethane at −30° C. The reaction mixture was stirred at −30° C. for 0.5 hour then allowed to warm to 0° C. over 1 hour. The reaction mixture was diluted with ethyl acetate washed with 0.1 N HCl and brine, dried over MgSO$_4$, filtered and concentrated in vacuo to provide 4.32 g of crude mesylate.

The crude mesylate, prepared above, and lithium azide (4.2 g, 87.2 mmole) were reacted at 90° C. in 50 mL of N,N-dimethylformamide for 1 hour. The reaction mixture was cooled and partitioned between ethyl acetate and water. The organic layer was washed with brine, dried over MgSO$_4$, filtered and concentrated. The crude product was purified by silica gel chromatography using 25% ethyl acetate in hexanes to provide the title compound (yield: 2.0 g, 72%).

$^1$H NMR (CDCl$_3$) δ 2.07 (s, 3H), 2.17 (m, 1H), 2.37 (m, 1H), 2.76 (m, 4H), 3.47 (m, 2H), 3.71 (s, 3H), 3.73 (s, 3H), 4.16 (m, 2H).

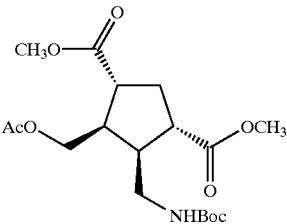

6E. (±)-(1S,2S,3R,4R)-3-Acetoxymethyl-2-(N-t-butoxycarbonylamino)methylcyclopentane-1,4-dicarboxylic Acid Dimethyl Ester.

A mixture of (±)-(1S,2S,3R,4R)-3-acetoxymethyl-2-azidomethylcyclopentane-1,4-dicarboxylic acid dimethyl ester (2.0 g, 6.6 mmole), di-t-butyldicarbonate (3.79 g), and palladium (900 mg, 10% on carbon) in 100 mL of ethyl acetate was stirred vigorously at room temperature under an hydrogen atmosphere. Upon completion, as determined by TLC, the reaction mixture was filtered and concentrated in vacuo. The residue was purified by chromatography on silica gel using 50% ethyl acetate in hexanes to provide the title compound (yield: 2.3 g, 94%).

$^1$H NMR (CDCl$_3$) δ 1.43 (s, 9H), 2.06 (s, 3H), 2.17 (m, 1H), 2.35 (m, 1H), 2.72 (m, 4H), 3.21 (m, 2H), 3.70 (s, 3H), 3.72 (s, 3H), 4.12 (m, 2H), 4.74 (t, 1H). MS=(M+H)$^+$=388.

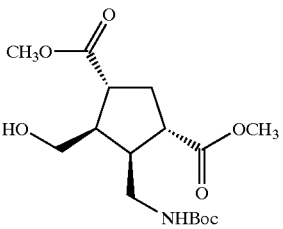

6F. (±)-(1S,2S,3R,4R)-2-(N-t-Butoxycarbonylamino)methyl-3-hydroxymethylcyclopentane-1,4-dicarboxylic Acid Dimethyl Ester.

(±)-(1S,2S,3R,4R)-3-Acetoxymethyl-2-(N-t-butoxycarbonylamino)-methylcyclopentane-1,4-dicarboxylic acid dimethyl ester (600 mg, 11.55 mmole) was treated with potassium carbonate (catalytic) in 10 mL of methanol, at room temperature for 6 h. The reaction mixture was concentrated in vacuo. The residue was partitioned between ethyl acetate and brine. The organic layer was dried over MgSO$_4$, filtered and concentrated to provide the title compound. (yield: 510 mg, 95%)

$^1$H NMR (CDCl$_3$) δ 1.44 (s, 9H), 2.24 (m, 2H), 2.59 (m, 2H), 2.77 (m, 2H), 3.28 (m, 2H), 3.73 (m, 8H), 5.04 (t, 1H).

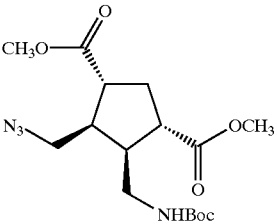

6G. (±)-(1S,2S,3R,4R)-3-Azidomethyl-2-(N-t-butoxycarbonylamino)methylcyclopentane-1,4-dicarboxylic Acid Dimethyl Ester.

Methanesulfonyl chloride (0.35 mL, 4.5 mmole) was added slowly to a solution of (±)-(1S,2S,3R,4R)-2-(N-t-butoxycarbonylamino)methyl-3-hydroxymethyl-cyclopentane-1,4-dicarboxylic acid dimethyl ester (560 mg, 1.48 mmole) and triethylamine (0.6 mL) in dichloromethane (10 mL) at −30° C. The reaction mixture was stirred at −30° C. for 2 hours then allowed to warm to 0° C. over 1 hour. The reaction mixture was then diluted with ethyl acetate washed with 0.1 N HCl and brine, dried over MgSO$_4$, filtered and concentrated in vacuo to provide the crude mesylate.

The crude mesylate, prepared above, and lithium azide (0.7 g, 14.3 mmoles) were reacted at 85° C. in 10 mL of N,N-dimethylformamide for 1 hour. The reaction mixture was cooled to room temperature and partitioned between ethyl acetate and water. The organic layer was washed with brine, dried over MgSO$_4$, filtered and concentrated. The crude product was purified by silica gel chromatography using 25% ethyl acetate in hexanes to provide the title compound (yield: 386 mg, 70%).

$^1$H NMR (CDCl$_3$) δ 1.43 (s, 1H), 2.26 (m, 2H), 2.69 (m, 4H), 3.23 (m, 2H), 3.46 (m, 2H), 3.70 (s, 3H), 3.71 (s, 3H), 4.74 (bs, 1H).

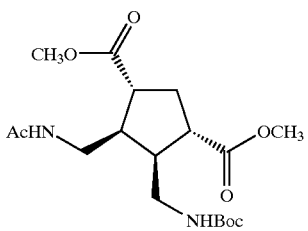

6H. (±)-(1S,2S,3R,4R)-3-Acetamidomethyl-2-(N-t-butoxycarbonylamino)methylcyclopentane-1,4-dicarboxylic Acid Dimethyl Ester.

A mixture of (±)-(1S,2S,3R,4R)-3-azidomethyl-2-(N-t-butoxycarbonylamino)methylcyclopentane-1,4-dicarboxylic acid dimethyl ester (386 mg, 1.04 mmole), acetic anhydride (0.25 mL) and palladium (25 mg, 10% on carbon) in 10 mL of ethyl acetate was stirred vigorously at room temperature under an hydrogen atmosphere. Upon completion, as determined by TLC, the reaction mixture was filtered and concentrated in vacuo. The residue was purified by chromatography on silica gel using 75% ethyl acetate in hexanes to provide the title compound. (yield: 232 mg, 58%).

$^1$H NMR (CDCl$_3$) δ 1.44 (s, 9H), 1.97 (s, 3H), 2.27 (m, 2H), 2.64 (m, 2H), 3.18 (m, 2H), 3.32 (t, 1H), 3.71 (s, 3H), 3.73 (s, 3H), 7.78 (bs, 1H), 6.19 (bs, 1H). MS=(M+H)$^+$=387.

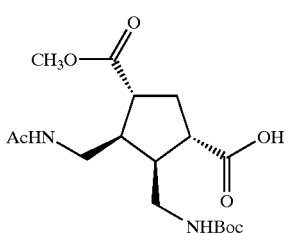

6I. (±)-(1S,2S,3R,4R)-3-Acetamidomethyl-2-(N-t-butoxycarbonylamino)methyl-4-methoxycarbonylcyclopentane-1-carboxylic Acid.

(±)-(1S,2S,3R,4R)-3-Acetamidomethyl-2-(N-t-butoxycarbonylamino)methylcyclopentane-1,4-dicarboxylic acid dimethyl ester (232 mg, 0.60 mmole) was reacted with 5 equivalents of lithium hydroxide in 5 mL of (4:1) methanol:water for 2 hours, at room temperature. The reaction mixture was neutralized with 0.1 N HCl and partitioned between ethyl acetate and brine. The organic layer was concentrated to provide 194 mg of crude diacid.

The crude diacid (190 mg), prepared above, was reacted with acetic anhydride (10 mL) for 3 hours, at room temperature. The reaction mixture was concentrated in vacuo. The crude product was treated with methanol (10 mL) and triethylamine (0.250 mL) for 16 hours. The reaction mixture was concentrated and partitioned between ethyl acetate and 0.1 N HCl. The organic layer was dried over Na$_2$SO$_4$, filtered and concentrated. The diastereomeric mixture of methyl esters (174 mg) was chromatographed on silica gel using (5–10%) methanol in chloroform and acetic acid (0.5%) to provide the title compound. (yield: 72 mg, 32%)

$^1$H NMR (CD$_3$OD) δ 1.44 (s, 9H), 1.93 (s, 3H), 2.24 (m, 2H), 2.64 (m, 4H), 3.12 (m, 3H), 3.67 (s, 3H). MS=(M+H)$^+$=373.

EXAMPLE 7

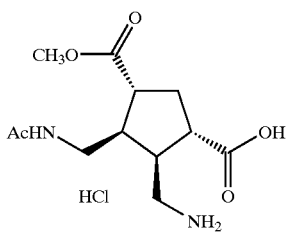

(±)-(1S,2S,3R,4R)-2-Aminomethyl-3-acetamidomethyl-4-methoxycarbonyl-cyclopentane-1-carboxylic Acid Hydrochloride A solution of (±)-(1S,2S,3R,4R)-3-Acetamidomethyl-2-(N-t-butoxycarbonylamino)methyl-4-methoxycarbonylcyclopentane-1-carboxylic acid (62 mg, 0.16 mmol) in of dichloromethane (4 mL) was reacted with trifluoroacetic acid (1.0 mL) for 1 hour, at room temperature. The solution was concentrated in vacuo, at 25° C. The residue was treated with 1 N HCl and concentrated in vacuo to provide the title compound as a white solid (yield: 39 mg, 75%).

$^1$H NMR (D$_2$O) δ 1.95 (s, 3H), 2.22 (m, 1H), 2.46 (m, 1H), 2.71 (m, 2H), 2.83 (m, 1H), 2.96 (q, 1H), 3.10 (m, 2H), 2.31 (m, 2H), 3.72 (s, 3H). MS: (M+H)$^+$=273.

EXAMPLE 8

(±)-(1S,2S,3R,4R)-2-N-t-Butoxycarbonylamino-3-(acetamidomethyl)-4-carbamoylcyclopentane-1-carboxylic Acid

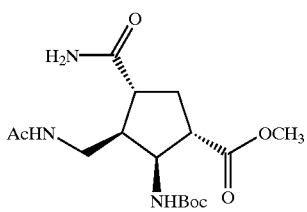

8A. (±)-(1S,2S,3R,4R)-2-N-t-Butoxycarbonylamino-3-(acetamidomethyl)-4-carbamoyl-cyclopentane-1-carboxylic Acid Methyl Ester.

The title compound was prepared in two steps starting by reacting (±)-(1S,2S,3R,4R)-2-(N-t-butyloxycarbonylamino)-3-(acetamidomethyl)-cyclopentane-1,4-dicarboxylic acid in place of (±)-(1S,2S,3R,4R)-2-(t-butyloxycarbonylamino)-3-(acetamidomethyl)-cyclopentane-1,4-dicarboxylic acid, according to the method described in Example 4H, and substituting anhydrous liquid ammonia for methanol and triethylamine.

In the second step the crude product (54 mg, 0.16 mmole), prepared above, in 4 ml of THF was cooled to 0° C. and treated with an ethereal solution of $CH_2N_2$ until the yellow reaction color persisted. The reaction mixture was warmed slowly to room temperature and concentrated in vacuo to provide a colorless oil. Purification using flash chromatography eluting with 5% methanol/chloroform provided the title compound as a white solid (yield: 16 mg, 28%).

$^1$H NMR (CDCl$_3$) δ 1.43 (s, 9H), 1.90 (s, 3H), 2.03 (m, 1H), 2.24 (m, 1H), 2.65 (m, 4H), 3.68 (s, 3H), 4.30 (m, 2H). MS: (M+H)$^+$=358.

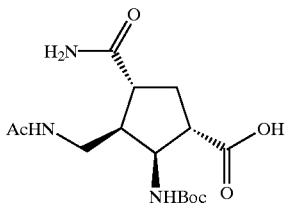

8B. (±)-(1S,2S,3R,4R)-2-N-t-Butoxycarbonylamino-3-(acetamidomethyl)-4-carbamoyl-cyclopentane-1-carboxylic Acid.

A solution of (±)-(1S,2S,3R,4R)-2-N-t-butoxycarbonylamino-3-(acetamidomethyl)-4-carbamoyl-cyclopentane-1-carboxylic acid methyl ester (16 mg, 0.045 mmole) in 0.2 ml methanol/H$_2$O (3:1) was treated with (1 mg, 0.045 mmole) of LiOH. After stirring at room temperature overnight, the reaction mixture was quenched with 5% HCl and extracted 3 times with ethyl acetate. The combined extracts were dried over Na$_2$SO$_4$, filtered and concentrated in vacuo to provide the title compound as a white solid (yield: 11 mg, 73%).

$^1$H NMR (methanol-d4) δ 1.44 (s, 9H), 1.91 (s, 3H), 2.02 (m, 1H), 2.24 (m, 1H), 2.60 (m, 5H), 4.32 (m, 1H), 6.90 (br d, 1H). MS (M−H)$^−$=342.

EXAMPLE 9

(±)-(1S,2S,3R,4R)-2,3-Acetamidomethyl-4-methoxycarbonylcyclopentane-1-carboxylic Acid

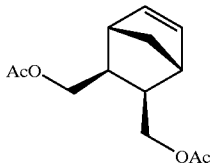

9A. (±)-exo-exo-2,3-diacetoxymethyl-bicyclo[2.2.1]hept-5-ene.

(±)-exo-exo-2,3-dihydroxymethyl-bicyclo[2.2.1]hept-5-ene was treated with acetic anhydride and triethylamine in dichloromethane. Standard workup provided the title compound. MS: (M+H)$^+$=329.

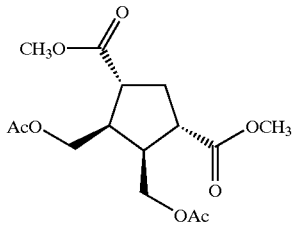

9B. (±)-(1S,2S,3R,4R)-2,3-Diacetoxymethylcyclopentane-1,4-dicarboxylic Acid Dimethyl Ester.

The title compound was prepared according to the method described in Example 6B, substituting (±)-exo-exo-2,3-diacetoxymethylbicyclo[2.2.1]hept-5-ene (1 g, 4.2 mmol) in place of (±)-(2R,3S)-2-acetoxymethyl-3-benzyloxymethyl-bicyclo[2.2.1]hept-5-ene. Purification, using flash chromatography eluting with 50% ethyl acetate/hexanes, provided the title compound as a colorless oil. (yield: 0.8 g, 58%).

$^1$H NMR (CDCl$_3$) δ 2.05 (s, 6H), 2.29 (m, 2H), 2.79 (m, 4H), 3.72 (s, 6H), 4.14 (m, 4H). MS: (M+H)$^+$=331.

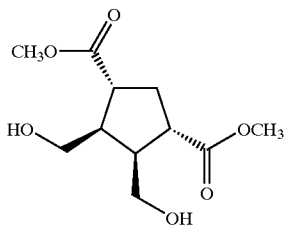

9C. (±)-(1S,2S,3R,4R)-2,3-Dihydroxymethylcyclopentane-1,4-dicarboxylic Acid Dimethyl Ester.

A solution of (±)-(1S,2S,3R,4R)-2,3-diacetoxymethylcyclopentane-1,4-dicarboxylic acid dimethyl ester (5.0 g, 0.015 mole) in 60 ml of methanol was treated with a catalytic amount of K$_2$CO$_3$. The reaction mixture was stirred, under a nirogen amosphere, at room temperature, for 16 hours. The reaction mixture was diluted with ethyl acetate and quenched with 5% HCl. The organic layer was separated, dried over Na$_2$SO$_4$, filtered, and concentrated in vacuo, at 30° C. to provide the title compound as a colorless oil. (yield: 3.3 g, 89%)

$^1$H NMR (CDCl$_3$) δ 2.06 (m, 1H), 2.29 (m, 2H), 2.54 (m, 3H), 2.80 (m, 2H), 3.67 (m, 8H). MS: (M+H)$^+$=247.

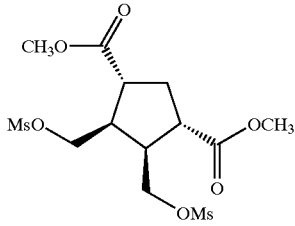

9D. (±)-(1S,2S,3R,4R)-2,3-Dimethansulfonyloxymethylcyclopentane-1,4-dicarboxylic Acid Dimethyl Ester.

A solution of (±)-(1S,2S,3R,4R)-2,3-dihydroxymethylcyclopentane-1,4-dicarboxylic acid dimethyl ester (200 mg, 0.81 mmole) in 4 ml of THF and 4 ml of dichloromethane was cooled to −30° C. and treated with methanesulfonyl chloride (0.19 mL, 2.4 mmole) followed by dropwise addition of triethylamine (0.34 mL, 2.4 mmole).

After 30 minutes of stirring under a nirogen amosphere, at −30° C., the mixture was diluted with ethyl acetate and washed with water and brine. The organic layer was dried over Na$_2$SO$_4$, filtered and concentrated in vacuo to provide the title compound as a colorless oil (yield: 302 mg, 93%).

$^1$H NMR (CDCl$_3$) δ 2.16 (m, 1H), 2.45 (m, 1H), 2.87 (m, 4H), 3.06 (s, 6H), 3.72 (s, 6H), 4.38 (m, 4H). MS: (M+H)$^+$=403.

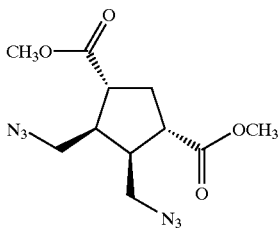

9E. (±)-(1S,2S,3R,4R)-2,3-Diazidomethyl-cyclopentane-1,4-dicarboxylic Acid Dimethyl Ester.

A solution of (±)-(1S,2S,3R,4R)-2,3-dimethansulfonyloxymethyl-cyclopentane-1,4-dicarboxylic acid dimethyl ester (300 mg, 0.75 mmole) in 3 mL of DMF was treated with LiN$_3$ (400 mg, 8.2 mmole) and heated to 100° C. under a nitrogen amosphere. After heating for 1 hour, the reaction mixture was diluted with ethyl acetate and washed twice with water, brine, dried over Na$_2$SO$_4$, filtered and concentrated in vacuo to provide the title compound as a copper colored oil (yield: 204 mg, 92%).

$^1$H NMR (CDCl$_3$) δ 2.12 (m, 1H), 2.37 (m, 1H), 2.71 (m, 4H), 3.50 (m, 4H), 3.72 (m, 6H). MS: (M+H)$^+$=297.

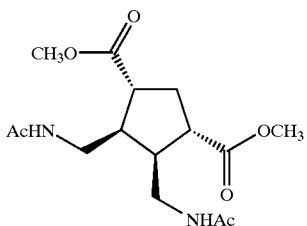

9F. (±)-(1S,2S,3R,4R)-2,3-Acetamidomethyl-cyclopentane-1,4-dicarboxylic Acid Dimethyl Ester.

A solution of (±)-(1S,2S,3R,4R)-2,3-diazidomethyl-cyclopentane-1,4-dicarboxylic acid dimethyl ester (145 mg, 0.49 mmole) in 2 ml of isopropyl alcohol was treated with Pd/C. The reaction mixture stirred vigorously overnight under a hydrogen atmosphere, at room temperature. The reaction mixture was filtered over Celite® and concentrated in vacuo to provide a pale yellow oil. The crude product was then taken up in dichloromethane and treated with excess acetic anhydride and N,N-dimethylaminopyridine. The reaction mixture was stirred at room temperature for 1 hour before concentrating in vacuo to provide a pale yellow oil. Purification, by flash chromatography eluting with 10% methanol/chloroform provided the title compound as a colorless oil (yield: 40 mg, 25%).

$^1$H NMR (CDCl$_3$) δ 1.98 (s, 6H), 2.30 (m, 1H), 2.36 (m, 1H), 2.56 (m, 2H), 2.68 (m, 2H), 3.30 (m, 4H), 3.71 (s, 6H), 6.16 (br s, 2H). MS: (M+H)$^+$=329.

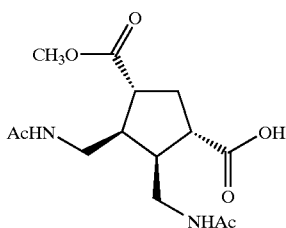

9F. (±)-(1S,2S,3R,4R)-2,3-Acetamidomethyl-4-methoxycarbonylcyclopentane-1-carboxylic Acid.

A solution of (±)-(1S,2S,3R,4R)-2,3-acetamidomethyl-cyclopentane-1,4-dicarboxylic acid dimethyl ester (100 mg, 0.33 mmole) in 1 ml of a mixture of methanol/H$_2$O (3:1) was treated with LiOH (16 mg, 0.66 mmole). After stirring for 1 hour, at room temperature, the reaction mixture was acidified with 5% HCl and extracted three times with ethyl acetate. The organic extracts were dried over Na$_2$SO$_4$, filtered and concentrated in vacuo to provide the diacid intermediate as a white solid (69 mg, 70%). The diacid was taken up in acetic anhydride (2 ml) and heated for 1 hour at 60° C. The reaction mixture was then concentrated in vacuo, taken up in 1 mL of methanol and treated with triethyl amine. The mixture was stirred at room temperature for 3 hours, under a nitrogen atmosphere. The reaction mixture was diluted with ethyl acetate and washed 3 times with 5% HCl. The organic layer was dried over Na$_2$SO$_4$, filtered and concentrated in vacuo. Purification, using flash chromatography, eluting with 20% ethyl acetate/hexanes with 1% acetic acid provided the title compound as a white solid. (yield: 6 mg, 6%)

$^1$H NMR (methanol-d$_4$) δ 1.92 (d, J=3 Hz, 6H), 2.15 (m, 2H), 2.35 (m, 2H), 2.67 (m, 4H), 3.15 (m, 2H), 3.67 (s, 3H). MS: (M+H)$^+$=315.

EXAMPLE 10

(±)-(1S,2S,3R,4R)-2-N-t-Butoxycarbonylamino-3-(acetamidomethyl)-4-N-methylcarboxamido-cyclopentane-1-carboxylic Acid and (±)-(1R,2R,3S,4S)-3-N-t-Butoxycarbonylamino-2-(acetamidomethyl)-4-N-methylcarboxamido-cyclopentane-1-carboxylic Acid

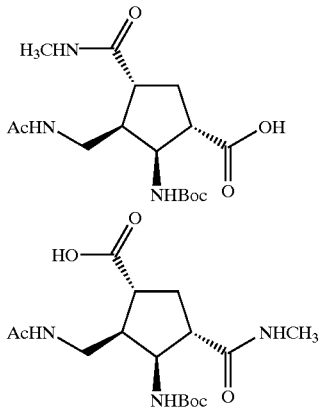

10A. (±)-(1S,2S,3R,4R)-2-N-t-butoxycarbonylamino-3-(acetamidomethyl)-4-N-methylcarboxamido-cyclopentane-1-carboxylic Acid Methyl Ester and (±)-(1R,2R,3S,4S)-3-N-t-butoxycarbonylamino-2-(acetamidomethyl)-4-N-methylcarboxamido-cyclopentane-1-carboxylic Acid Methyl Ester.

A solution of (±)-(1S,2S,3R,4R)-2-N-t-butoxycarbonylamino-3-(acetamidomethyl)-4-N-methylcarboxamido-cyclopentane-1-carboxylic acid methyl ester and (±)-(1R,2R,3S,4S)-3-N-t-butoxycarbonylamino-2-(acetamidomethyl)-4-N-methylcarboxamido-cyclopentane-1-carboxylic acid methyl ester (1:1) (260 mg, 0.72 mmole) in 3 ml of dichloromethane was treated with hydroxybenzotriazole (1 equiv.), 1-(3-dimethylaminopropyl)-3-ethylcarbodiimide (1.5 equivalents), and methylamine (5 equivalents). After stirring at room temperature for 2 hours, the reaction mixture was diluted with ethyl acetate and washed 3 times with 5% HCl. The organic layer was dried over $Na_2SO_4$, filtered and concentrated in vacuo to provide the title ester-amide compounds as a white solid. (yield: 111 mg, 42%) MS: $(M+H)^+=372$.

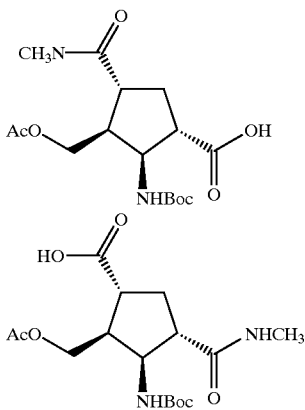

10B. (±)-(1S,2S,3R,4R)-2-N-t-Butoxycarbonylamino-3-(acetamidomethyl)-4-N-methylcarboxamido-cyclopentane-1-carboxylic Acid and (±)-(1R,2SR,3S,4S)-3-N-t-butoxycarbonylamino-2-(acetamidomethyl)-4-N-methylcarboxamido-cyclopentane-1-carboxylic Acid.

A solution of the ester-amide mixture (125 mg, 0.34 mmole) prepared in Example 10A, in 1 ml of methanol/$H_2O$ (3:1) was treated with LiOH (8 mg, 0.34 mmole). After stirring for 1 hour at room temperature, the reaction mixture was quenched with 5% HCl and extracted 3 times with ethyl acetate. The combined organic extracts were dried over $Na_2SO_4$, filtered and concentrated in vacuo to provide the title compound as a white solid. (yield: 85 mg, 70%)

1H NMR (methanol-$d_4$) δ 1.44 (brd, 18H), 1.91 (d, J=5 Hz, 6H), 2.00 (m, 2H), 2.20 (m, 2H), 2.60 (m, 6H), 2.72 (br s, 6H), 3.08 (m, 4H), 4.35 (m, 2H). MS: $(M+H)^+=358$.

EXAMPLE 11

(±)-(1S,2S,3R,4R)-3-Acetamidomethyl-2,4-diamino-cyclopentane-1-carboxylic Acid Hydrochloride

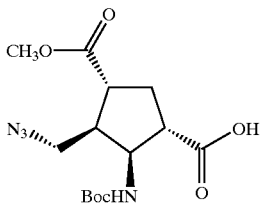

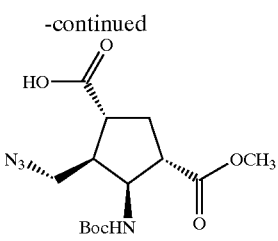

11A. (±)-(1S,2S,3R,4R)-2-(t-Butyloxycarbonylamino)-3-(azidomethyl)-4-methoxycarbonyl-cyclopentane-1-carboxylic Acid and (±)-(1S,2S,3R,4R)-2-(t-Butyloxycarbonylamino)-3-(azidomethyl)-1-methoxycarbonyl-cyclopentane-4-carboxylic Acid.

The title compound was prepared, in two steps, first following the procedure described in Example 4G and 4H substituting (±)-(1S,2S,3R,4R)-2-(t-butyloxycarbonylamino)-3-(azidomethyl)-cyclopentane-1,4-dicarboxylic acid dimethyl ester (98 mg, 0.28 mmole) in place of (±)-(1S,2S,3R,4R)-2-(t-butyloxycarbonylamino)-3-(acetamidomethyl)-cyclopentane-1,4-dicarboxylic acid dimethyl ester (yield: 76 mg, 79%). MS: $(M+H)^+=343$

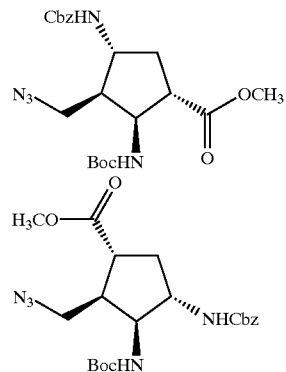

11B. (±)-(1S,2S,3S,4R)-2-(t-Butyloxycarbonylamino)-3-(azidomethyl)-4-benzyloxycarbonylamino-cyclopentane-1-carboxylic Acid Methyl Ester and (±)-(1R,2R,3S,4S)-3-(t-Butyloxycarbonylamino)-2-(azidomethyl)-4-benzyloxycarbonylamino-cyclopentane-1-carboxylic Acid Methyl Ester.

A solution of (250 mg, 0.73 mmole) of the above mixture of regioisomers of methyl ester azide cyclopentanes, prepared in Example 11A, was treated with diphenylphosphorylazide, in 8 ml of toluene, $Et_3N$, (0.2 mL) and 0.75 mL of benzyl alcohol, under a nitrogen atmosphere, and heated to 80° C. for 3 hours. The reaction mixture was diluted with ethyl acetate and washed 3 times with 5% HCl. The organic layer was dried over $Na_2SO_4$, filtered and concentrating in vacuo to provide a pale yellow oil. Purification using flash chromatography on silica gel eluting with 20% ethyl acetate/hexanes provided the title compounds (mixture of regioisomers) as a white solid (yield: 278 mg, 85%) MS: $(M+H)^+=448$.

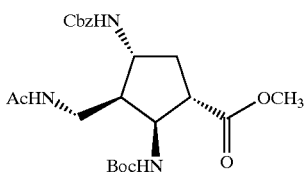

11C. (±)-(1S,2S,3S,4R)-2-(t-Butyloxycarbonylamino)-3-(acetamido)methyl-4-benzyloxycarbonylamino-cyclopentane-1-carboxylic Acid Methyl Ester.

A solution of the methyl ester diastereomers (278 mg, 0.62 mmole), prepared in Example 11B, in 0.2 ml of thiolacetic acid was stirred under a nitrogen atmosphere at room temperature for 6 hours. The reaction mixture was concentrated in vacuo to provide a yellow oil. The crude oil was purified using flash chromatography, eluting with 50% ethyl acetate/hexanes to provide the title compound as a white solid. (yield: 70 mg, 24%) MS: (M+H)$^+$=464.

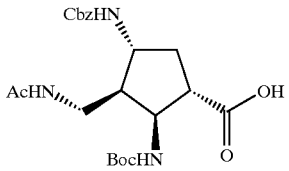

11D. (±)-(1S,2S,3S,4R)-2-(t-Butyloxycarbonylamino)-3-(acetamido)methyl-4-benzyloxycarbonylamino-cyclopentane-1-carboxylic Acid.

A solution of (±)-(1S,2S,3S,4R)-2-(t-butyloxycarbonylamino)-3-(acetamido)methyl-4-benzyloxycarbonylamino-cyclopentane-1-carboxylic acid methyl ester (70 mg, 0.15 mmole) in 1 mL of methanol/H$_2$O (3:1) was treated with (4 mg, 0.15 mmole) of LiOH. After stirring at room temperature for 2 hours the reaction mixture was quenched with 5% HCl and extracted 3 times with ethyl acetate. Standard workup, as described above, provided the title compound as a white solid (yield: 51 mg, 76%). MS: (M+H)$^+$=450.

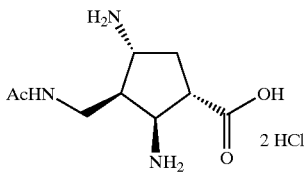

11E. (±)-(1S,2S,3S,4R)-3-Acetamidomethyl-2,4-diaminocyclopentane-1-carboxylic Acid Dihydrochloride

A solution of (±)-(1S,2S,3S,4R)-2-(t-butyloxycarbonylamino)-3-(acetamido)methyl-4-benzyloxycarbonylaminocyclopentane-1-carboxylic acid (51 mg, 0.11 mmole) in 0.2 ml of isopropyl alcohol and Pd/C was reacted under 1 atmosphere of hydrogen for 18 hours. The reaction mixture was filtered through Celite® and concentrated in vacuo to provide the title compound as a tan foam. (yield: 30 mg, 86%)

MS: (M+H)$^+$=216.

EXAMPLE 12

(±)-(1R,2R,4R,1'S)-4-(1'-Acetamido-3'-ethyl)pentyl-3-methoxycarbonylcyclopentane-1-carboxylic Acid

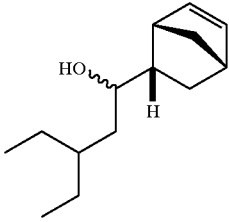

12A. (±)-(exo,1'RS) and (endo,1'RS)-2-(3-Ethyl-1-hydroxy)pentylbicyclo[2.2.1]hept-5-ene.

1-bromo-2-ethylbutane (12.5 mL) and a catalytic amount of 1,2-dibromoethane were added to a suspension of 2.1 g Mg turnings in 200 mL of tetrahydrofuran. This mixture was heated to 50° C. for 2 hours, and cooled to −78° C. A solution of 5.4 mL (±)-endo-2-formylbicyclo[2.2.1]hept-5-ene, in 75 mL tetrahydrofuran, was added dropwise to the Grignard solution. The mixture was warmed to 0° C. and stirred for 1 hour. The reaction was quenched by addition of 20 mL saturated ammonium chloride and ethyl acetate. The organic layer was separated, washed with brine, dried over magnesium sulfate, filtered and the solvent is evaporated. The crude material was purified by flash chromatography using 10% ethyl acetate:hexanes (1:9) to provide the title compounds. (yield: 4.9 g, 53%)

$^1$H NMR (CDCl$_3$) δ 0.78–0.91 (m, 6H), 1.15–1.50 (m, 11H), 1.70–2.10 (m, 1H), 2.60–2.95 (m, 2H), 2.95–3.55 (m, 1H), 6.0–6.2(m, 2H), MS: (M+H)$^+$=208.

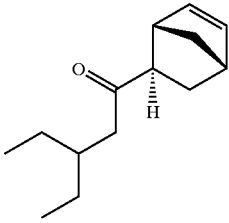

12B. (±)-exo and endo-2-(1'-oxo-3'-Ethyl)pentyl-bicyclo[2.2.1]hept-5-ene.

A solution of of oxalyl chloride, (2.3 mL) in 100 mL dichloromethane, maintained at −78° C., was treated dropwise with dimethyl sulfoxide, (4.0 mL). The mixture was stirred under nitrogen for 20 minutes and a solution of (±)-(2S,1'R) and (2S,1'S)-2-(1'-hydroxy-3'ethyl)pentyl-bicyclo[2.2.1]hept-5-ene (4.9 g) in 50 mL of dichloromethane was added. The mixture was stirred at −78° C. for 0.5 hours warmed to 0° C. for 15 minutes, treated with 16.4 mL triethylamine at 0° C. and stirred for 10 minutes. Water (100 mL), at 25° C., was added over 10 minutes. The organic layer was separated, washed with brine, dried over MgSO$_4$, filtered and the solvent evaporated. The crude ketone mixture was purified by flash chromatography using chloroform:hexanes (1:3) to provide the products (yield: 3.72 g, 77%).

The ketone mixture prepared above (3.1 g, 14.9 mmole) was dissolved in 50 mL of methanol and combined with 22 mL of 1 M sodium methoxide. This mixture is heated to 70° C. for 18 hours. The solvent was evaporated and the residue dissolved in 300 mL ethyl acetate. The organic layer was washed with 100 mL of 0.5M HCl, brine, dried over magnesium sulfate, filtered, and the solvent is evaporated. The ketones were separated by flash chromatography using chloroform:hexanes (1:3) to provide title compound (±) (2R)-2-(3-ethyl-1-oxo)pentyl-bicyclo[2.2.1]hept-5-ene (yield: 0.99 g, exo ketone) (higher Rf) and (±) (2S)-2-(3-ethyl-1-oxo)pentyl-bicyclo[2.2.1]hept-5-ene (yield: 1.7 g, endo ketone, 87%).

$^1$H NMR (CDCl$_3$) δ 0.85 (2t, 6H), 1.19–1.42 (m, 7H), 1.70–1.92 (m, 2H), 2.32–2.39 (m, 1H), 2.39–2.47 (2d, 2H), 2.88–2.98 (d,2H), 6.10–6.17 (m, 2H).

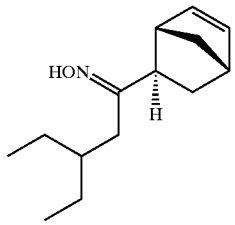

12C. (±)-(2R)-2-(1-Hydroxyimino-3-ethyl)pentyl-bicyclo[2.2.1]hept-5-ene.

A solution of (±) (2R)-2-(1'-oxo-3'ethyl)pentyl-bicyclo[2.2.1]hept-5-ene (1.1 g, 5.4 mmole) in 45 mL methanol was reacted with hydroxylamine hydrochloride (1.5 g, 21.6 mmole) and 1 N NaOH (16.3 mL). This mixture was heated at 40° C. for 2 days. The solvent was evaporated and the residue was partitioned between ethyl acetate and brine. The organic layer was dried over MgSO$_4$, filtered, and the solvent evaporated to provide the title compound (yield: 1.16 g, 97%).

$^1$H NMR (CDCl$_3$) δ 0.87 (2t, 6H), 1.24–1.40 (m, 8H), 1.50 (d, 1H), 1.65 (m, 1H), 1.78 (m, 1H), 2.15 (m, 1H), 2.35 (m, 2H), 2.90 (m, 2H), 6.13 (m, 2H), 2.87 (m, 1H), 3.68 (s, 3H), 3.85 (m, 1H). MS: (M+H)$^+$=222

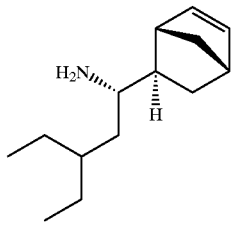

12D. (±)-(2R,1'S)-2-(1-Amino-3-ethyl)pentyl-bicyclo[2.2.1]hept-5-ene.

The crude (±)-(2R)-2-(1-hydroxyimino-3-ethyl)pentylbicyclo[2.2.1]hept-5-ene (0.49 g, 2.13 mmole), prepared in Example 12C, in 10 mL toluene, was treated with 1 M lithium aluminum hydride bis(tetrahydrofuran) (4.3 mL). The mixture was heated to 100° C. for 2 hours, under a nitrogen atmosphere. The mixture was cooled to 0° C., and consecutively combined with water (0.16 mL), 15% NaOH (0.16 mL), and water (0.49 mL). The solids were filtered, and the solution diluted with 150 mL ethyl acetate. The organic layer was washed with water, and brine, dried over MgSO$_4$, filtered and the solvent evaporated. The crude amines were separated by flash chromatography using ether:methanol:ammonium hydroxide (98:2:0.2) to provide the title compound, (±)-(2R,1'S)-2-(1-amino-3-ethyl)pentylbicyclo[2.2.1]hept-5-ene (yield: 79 mg), and the (±)-(2R, 1'R)-isomer (77 mg) and 77 mg of a mixture of the amines overall yield 52%.

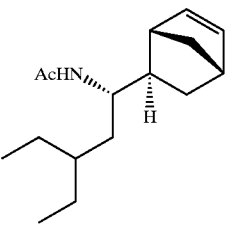

12E. (±)-(2R, 1'S)-2-(1-Acetamido-3-ethyl-)pentyl-bicyclo[2.2.1]hept-5-ene.

(±)-(2R,1'S)-2-(1'-amino-3'-ethyl-)pentyl-bicyclo[2.2.1]hept-5-ene (78 mg, 0.38 mmole) was dissolved in 3 mL dichloromethane. Triethylamine (0.16 mL) and acetic anhydride (0.07 mL) were added to the mixture. After 1 hour at 25° C. the solvent was evaporated and the residue purified by flash chromatography using ethyl acetate:hexanes (1:4) to provide the title compound (yield: 78 mg, 83%).

$^1$H NMR (CDCl$_3$, 300 MHz) δ 0.77–0.88 (m, 6H), 1.10–1.57 (m, 11H), 2.02 (s, 3H), 2.65 (s, 1H), 2.84 (s, 1H), 3.80–3.95 (m, 1H), 5.0–5.15 (m, 1H), 6.05 (s, 2H). MS: (M+H)$^+$=250.

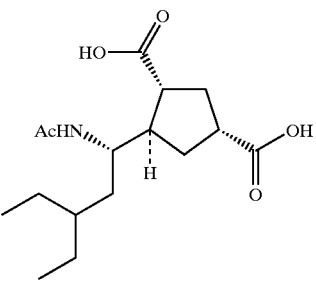

12F. (±)-(1R,3R,4R,1'S)-4-(1-Acetamido-3-ethyl)pentylcyclopentane-1,3-dicarboxylic Acid.

A solution of ruthenium tetroxide was prepared from 5.5 mg of ruthenium dioxide, suspended in carbon tetrachloride:acetonitrile (2:1), and 219 mg sodium periodate in 3 mL of water. The mixture was stirred 15 minutes at 0° C. A solution of (±)-(2R,1'S)-2-(1'-Acetamido-3'-ethyl)pentylbicyclo[2.2.1]hept-5-ene (64 mg, 0.256 mmol) in 1 mL of carbon tetrachloride was added to the ruthenium mxture. The reaction mixture was allowed to warm to 25° C. and stirred for 3 hours. 1 M Sodium bicarbonate (2 mL) was added and the aqueous layer was separated and acidified with 5 mL 1M HCl and extracted with ethyl acetate. The organic layer was filtered through Celite® and the solvents were evaporated in vacuo. The crude mixture was purified by flash chromatography using methanol:dichloromethane acetic acid (3:20:0.5) to provide the title compound (yield: 50 mg, 62%).

$^1$H NMR (CD$_3$OD) δ 0.78–0.92 (2t, 6H), 1.14–1.47 (m, 7H), 1.62–1.75 (m, 1H), 1.92 (s, 3H), 1.95–2.03 (m, 1H), 2.08–2.20 (m, 1H), 2.22–2.33 (m, 1H), 2.35–2.49 (m, 1H), 2.58–2.68 (m, 1H), 2.82–2.94 (m, 1H), 3.83–3.95 (m, 1H),. MS: (M+H)$^+$=314

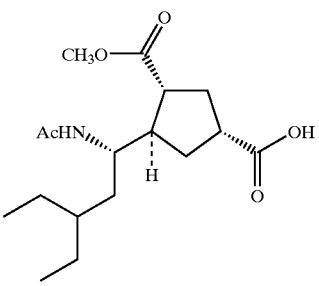

12G. (±)-(1R,3R,4R,1'S)-4-(1'-Acetamido-3'-ethyl)pentyl-3-methoxycarbonylcyclopentane-1-carboxylic Acid.

(±)-(1R,3R,4R,1'S)-2-(1-Acetamido-3-ethyl)pentylcyclopentane-1,3-dicarboxylic acid was reacted with acetic anhydride (0.1 mL), suspended in 3 mL of chloroform, in a sealed tube, and heated to 70° C. for 3 hours. The solvents were evaporated and the residue was added to 1 mL of methanol and 0.1 mL of triethylamine, and heated for 1 hour, at 70° C. The solvents were evaporated and the crude acid/ester purified by flash chromatography using ethyl acetate:methanol:acetic acid (97:2:1) to provide of the mixture of acid/esters (yield: 30 mg, 57%). The two isomers were separated by preparative thin layer chromatography using ethyl acetate:methanol:acetic acid (97:2:1) to provide the title compound (yield: 6.9 mg, 13%).

$^1$H NMR (CD$_3$OD, 300 MHz) δ 0.83 (2t, 6H), 1.14–1.48 (m, 8H), 1.67 (m, 1H), 1.91 (s, 3H), 1.98 (m, 1H), 2.11 (m, 1H), 2.25 (m, 1H), 2.42 (m, 1H), 2.62 (m, 1H), 2.92 (m, 1H), 3.68 (s, 3H), 3.89 (m, 1H). MS: (M+H)$^+$=328

EXAMPLE 13

(1R,3R,4R,1'S)-3-Hydroxymethyl-4-(1'-Acetamido-3'-ethyl)pentyl-cyclopentane-1-carboxylic Acid

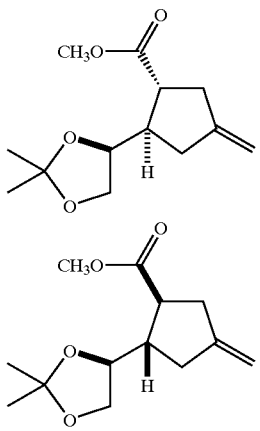

13A. (±)-1R,2R,4'S) and (±)-(1S,2S,4'S)-2-(2,2-Dimethyl-1,3-dioxolan-4-yl)-4-methylenecyclopentane-1-carboxylic Acid Methyl Ester.

A solution of 2-[(trimethylsilyl)methyl]-2-propen-1-yl-acetate (5 g, 26.9 mmole), methyl (S)-(+)-3-(2,2-dimethyl-1,3-dioxolan-4-yl)-trans-2-propenoate (5 g, 26.9 mmole), Pd(OAc)$_2$ (0.42 g, 1.8 mmole) and (i-PrO)$_3$P (2 mL, 8.1 mmole) in 27 mL of toluene was heated under an argon atmosphere for 24 hours. The reaction was cooled and concentrated in vacuo. The crude product was chromatographed on silica gel with 5–15% ethyl acetate in hexanes to provide the title compound (yield: 4.68 g, 73%).

$^1$H NMR (CDCl$_3$) δ 4.88 (m, 2H), 4.18–3.95 (m, 2H), 3.70 (s), 3.69 (s) [3H overall], 3.68–3.55 (m, 1H), 2.78–2.29 (m, 6H), 1.40 (s), 1.38 (s) [3H, overall], 1.34 (s), 1.32 (s) [3H, overall]. MS: (M+H)$^+$=241.

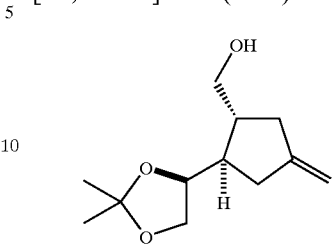

13B. (1R,2R,4'S)-2-Hydroxymethyl-1-(2,2-dimethyl-1,3-dioxolan-4-yl)-4-methylene-cyclopentane Lithium aluminum hydride (0.63 g, 16.6 mmole) was added to a solution of (1R,2R,4'S) and (1R,2S,4'S)-methyl 2-(2,2-dimethyl-1,3-dioxolan-4-yl)-4-methylene-cyclopentane-1-carboxylate (2.0 g, 8.33 mmole) in 40 mL of THF maintained at −78° C. The reaction was allowed to warm to 0° C. and stirred for 1 hour. The reaction was quenched (at 0° C.) by adding sequentially H$_2$O (1.9 mL), 10% NaOH (2.8 mL), and H$_2$O (2.8 mL). The reaction was allowed to warm to room temperature then dried over MgSO$_4$. The reaction was filtered and the solids were washed with ethyl acetate (200 mL). The filtrate was concentrated in vacuo to provide 1.83 g of the crude product mixture. Preparative HPLC on silica gel with (0–75%) ethyl acetate in hexanes provided the title compound (yield; 1.15 g, 65%).

$^1$H NMR (CDCl$_3$) δ 4.84 (m, 2H), 4.21 (m, 1H), 4.03 (dd, J=6, 8 Hz, 1H), 3.64 (t, J=8 Hz, 1H), 3.56 (m, 2H), 2.60–2.05 (m, 6H), 1.44 (s, 3H), 1.36 (s, 3H). MS: (M+H)$^+$=213.

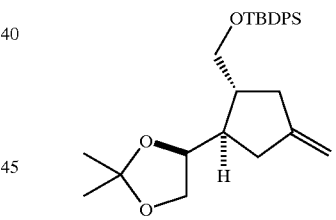

13C. (1R,2R,4'S)-2-(t-Butyldiphenylsilyloxymethyl)-1-(2,2-dimethyl-1,3-dioxolan-4-yl)-4-methylenecyclopentane A solution of (1R,2R,4'S)-2-hydroxymethyl-1-(2,2-dimethyl-1,3-dioxolan-4-yl)-4-methylenecyclopentane (1.15 g, 5.4 mmole), t-butyldiphenylsilyl chloride (1.6 mL, 6.8 mmole) and imidazole (1.11 g, 16.3 mmole) in 30 mL of dichloromethane was stirred at room temperature for 1.5 hours. The reaction mixture was quenched with methanol (0.2 mL) and stirred for 1 hour. The mixture was partitioned between ethyl acetate and 10% citric acid. The organic layer was washed with water and saturated NaHCO$_3$, dried over MgSO$_4$, filtered and concentrated to provide the title compound.

$^1$H NMR (CDCl$_3$) δ 7.65 (m, 4H), 7.39 (m, 6H), 4.82 (m, 2H), 4.00 (m, 1H), 3.89 (dd, J=6, 8 Hz, 1H), 3.62–3.48 (m, 3H), 2.51–1.98 (m, 6H), 1.37 (s, 3H), 1.31 (s, 3H), 1.05 (s, 9H). MS: (M+H)$^+$=451.

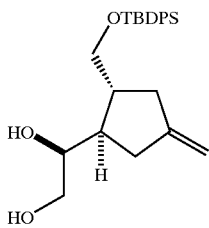

13D. (1R,2R,1'S)-2-(t-Butyldiphenylsilyloxymethyl)-1-(1,2-dihydroxy)ethyl-4-methylene-cyclopentane (1R,2R,4'S)-2-(t-Butyldiphenylsilyloxymethyl)-1-(2,2-dimethyl-1,3-dioxolan-4-yl)-4-methylene-cyclopentane and pyridinium p-toluenesulfonate (0.68 g, 2.7 mmole) in 110 mL of methanol were heated to 45° C. for 16 hours. The reaction was cooled, concentrated in vacuo and partitioned between dichloromethane and water. The organic layer was washed with brine, dried over MgSO$_4$, filtered and concentrated. The crude product was chromatographed on silica gel with 15% ethyl acetate in hexanes to provide the title compound and recovered starting material (yield: 1.2 g, 54%).

$^1$H NMR (CDCl$_3$) δ 7.65 (m, 4H), 7.39 (m, 6H), 4.81 (m, 2H), 3.75–3.46 (m, 5H), 2.54–1.89 (m, 6H), 1.06 (s, 9H). MS: (M+H)$^+$=411.

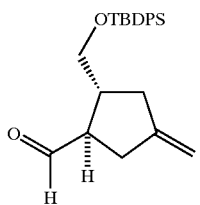

13E. (1R,2R)-2-(t-Butyldiphenylsilyloxymethyl)-1-formyl-4-methylene-cyclopentane A solution of (1R,2R,1'S)-2-(t-butyldiphenylsilyloxymethyl)-1-(1,2-dihydroxy)ethyl-4-methylene-cyclopentane (1.2 g, 2.92 mmole), NaIO$_4$ (2.5 g, 11.6 mmole) in ethanol (4 mL) and water (4 mL) was stirred at 0° C. for 4 hours. The reaction was diluted with ethyl ether (90 mL) and filtered through a celite pad. The filtrate was concentrated in vacuo. The crude product was dissolved in toluene and concentrated in vacuo to azeotropically remove water. The reaction was redissolved in ethyl ether and filtered again followed by concentration to provide the title compound as a crude oil.

$^1$H NMR (CDCl$_3$) δ 9.68 (d, J=3 Hz, 1H), 7.65 (m, 4H), 7.39 (m, 6H), 4.87 (m, 2H), 3.68 (dd, J=5, 10 Hz, 1H), 3.56 (dd, J=7, 10 Hz, 1H), 2.83–2.09 (m, 6H), 1.04 (s, 9H). MS: (M+H)$^+$=379.

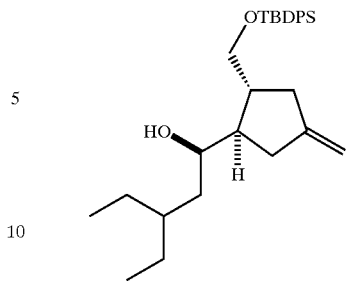

13F. (1R,2R,1'R)-2-(t-Butyldiphenylsilyloxymethyl)-1-(3-ethyl-1-hydroxy)pentyl-4-methylene-cyclopentane A 0.9 M solution of 2-ethylbutyl magnesium bromide (15.3 mL), prepared from 1-bromo-2-ethylbutane (3.8 mL, 27.1 mmole), magnesium (1 g, 41.6 mmole) and iodine (170 mg) in ethyl ether (30 mL) and stirred overnight at room temperature, was added to a solution of (1R,2R)-2-(t-butyldiphenylsilyloxy-methyl)-1-formyl-4-methylene-cyclopentane (2.92 mmole) in ethyl ether (15 mL) at 0° C. for 20 minutes. The reaction was quenched with saturated ammonium chloride and stirred for 30 minutes. The reaction was partitioned between ethyl acetate and water. The organic layer was washed with brine, dried over MgSO$_4$, filtrered and concentrated. The crude product was purified by preparative HPLC on silica gel with (5–50%) ethyl acetate in hexanes to provide the title compound (yield: 0.7 g, 51%).

$^1$H NMR (CDCl$_3$) δ 7.65 (m, 4H), 7.39 (m, 6H), 4.80 (m, 2H), 3.79 (m, 1H), 3.64 (dd, J=5, 10 Hz, 1H), 3.56 (dd, J=7, 10 Hz, 1H), 2.46–1.9 (m, 6H), 1.5–1.21 (m, 7H), 1.05 (s, 9H), 0.84 (t, J=8 Hz, 3H), 0.83 (t, J=8 Hz, 3H). MS: (M+H)$^+$=465.

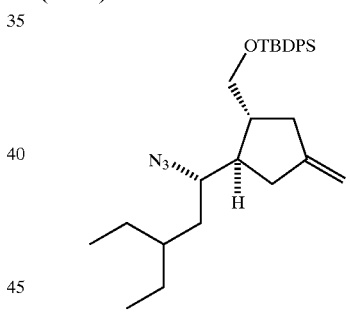

13G. (1R,2R,1'S)-1-(t-Butyldiphenylsilyloxymethyl)-2-(3-ethyl-1-azido)pentyl-4-methylene-cyclopentane A solution of (1R,2R,1'R)-2-(t-butyldiphenylsilyloxymethyl)-1-(3-ethyl-1-hydroxy)pentyl-4-methylene-cyclopentane (0.7 g, 1.51 mmole), methanesulfonyl chloride (0.25 mL, 3.23 mmole) and triethylamine (1 mL) in dichloromethane (15 mL) was stirred for 0.5 hours, at 0° C. The reaction was quenched with saturated NaHCO$_3$ solution (3 mL) and then partitioned between ethyl acetate and 10% citric acid. The organic layer was washed with saturated NaHCO$_3$ and brine, dried over MgSO$_4$, filtered and concentrated in vacuo to provide the intermediate mesylate. A solution of the crude mesylate and sodium azide (1 g, 15.3 mmole) in dimethylformamide (15 mL) was reacted at 65° C. for 16 hours. The reaction was cooled and diluted with ethyl acetate. The organic layer was washed with water and brine, dried over MgSO$_4$, filtered and concentrated to provide the title compound.

$^1$H NMR (CDCl$_3$) δ 7.66 (m, 4H), 7.39 (m, 6H), 4.81 (m, 2H), 3.64 (dd, J=6, 10 Hz, 1H), 3.52 (dd, J=7, 10 Hz, 1H), 3.22 (m, 1H), 2.58–2.0 (m, 6H), 1.48–1.11 (m, 7H), 1.05 (s, 9H), 0.86 (t, J=7 Hz, 3H), 0.80 (t, J=7 Hz, 3H).

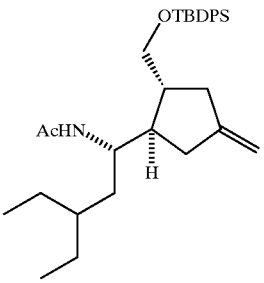

13H. (1R,2R,1'S)-1-(t-Butyldiphenylsilyloxymethyl)-2-(1'-Acetamido-3'-ethyl)pentyl-4-methylene-cyclopentane A solution of the crude (1R,2R,1'S)-1-(t-butyldiphenylsilyloxymethyl)-2-(3-ethyl-1-azido)pentyl-4-methylene-cyclopentane (~1.5 mmole), prepared in Example 13G, and triphenylphosphine (1.39 g, 5.3 mmole) in 20% H$_2$O in THF (25 mL) was stirred at 75° C. for 16 hours. The reaction was cooled and concentrated in vacuo to provide the crude amine. The amine, acetic anhydride (0.25 mL) and pyridine (0.55 mL) in dichloromethane (13 mL) were stirred at room temperature for 2 hours. The reaction was quenched with methanol (2 mL) and stirred for an additional 1 hour. The reaction was diluted with ethyl acetate and washed sequentially with 10% citric acid, saturated NaHCO$_3$, and brine, dried over MgSO$_4$, filtered and concentrated. Chromatography on silica gel with 2.5–10% ethyl acetate in dichloromethane provided the title compound (yield: 0.404 g, 60%).

$^1$H NMR (CDCl$_3$) δ 7.65 (m, 4H), 7.39 (m, 6H), 4.93 (d, J=10 Hz, 1H), 4.77 (m, 2H), 3.92 (m, 1H), 3.60 (dd, J=6, 10 Hz, 1H), 3.52 (dd, J=6, 10 Hz, 1H), 2.54–1.83 (m, 6H), 1.71 (s, 3H), 1.40–1.10 (m, 7H), 1.07 (s, 9H), 0.83 (t, J=7 Hz, 3H), 0.77 (t, J=7 Hz, 3H). MS: (M+H)$^+$=506.

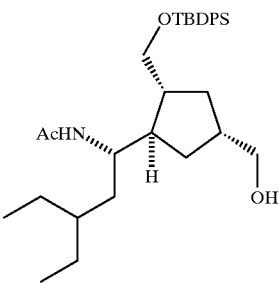

13I. (1R,2R,4R,1'S)-1-(t-Butyldiphenylsilyloxymethyl)-2-(1'-Acetamido-3'-ethyl)pentyl-4-hydroxymethyl-cyclopentane A solution of (1R,2R,1'S)-1-(t-butyldiphenylsilyloxymethyl)-2-(1'-Acetamido-3'-ethyl)pentyl-4-methylene-cyclopentane (50 mg, 0.1 mmole) and 2M borane dimethylsulfide complex, in THF (75 uL, 0.15 mmole) in THF (1 mL) was stirred at 0° C. for 7 hours. Water (0.1 mL) and 1N NaOH (0.2 mL) were added and the reaction allowed to warm to room temperature. After 15 minutes, 30% hydrogen peroxide (2 mL) was added and the reaction was stirred for an additional 0.5 hour. The reaction was diluted with ethyl acetate washed with water (2×) and with brine. The organic layer was dried over MgSO$_4$, filtered and concentrated in vacuo. The crude product was purified by chromatography using preparative HPLC in silica gel using 0–15% ethyl acetate in dichloromethane to provide the title compound (yield: 22 mg, 42%).

$^1$H NMR (CDCl$_3$) δ 7.65 (m, 4H), 7.43 (m, 6H), (m, H), 5.00 (d, J=10 Hz, 1H), 3.84 (m, 1H), 3.66–3.54 (m, 2H), 3.52 (d, J=7 Hz, 2H), 2.20–1.04 (m, 14H, 1.66 (s, 3H), 1.08 (s, 9H), 0.83 (t, J=7 Hz, 3H), 0.78 (t, J=7 Hz, 3H). MS: (M+H)$^+$=524.

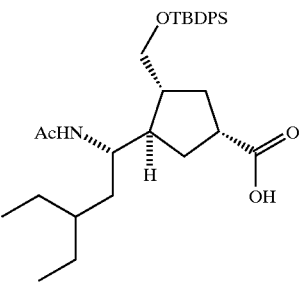

13J. (1R,3R,4R,1'S) 3-(t-Butyldiphenylsilyloxymethyl)-4-(1'-Acetamido-3'-ethyl)pentyl-cyclopentane-1-carboxylic Acid A solution of (1R,2R,4R,1'S)-1-(t-butyldiphenylsilyloxymethyl)-2-(1'-Acetamido-3'-ethyl)pentyl-4-hydroxymethyl-cyclopentane (22 mg, 0.042 mmole) and pyridinium dichromate (100 mg, 0.26 mmole) in N,N-dimethylformamide (0.75 mL) was stirred at room temperature for 48 hours. The reaction was partitioned between ethyl acetate and 10% citric acid. The organic layer was separated and washed with brine, dried over MgSO$_4$, filtered and concentrated to provide the title compound, which was used without further purification.

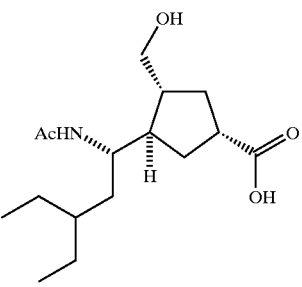

13K. (1R,3R,4R,1'S) 3-Hydroxymethyl-4-(1'-Acetamido-3'-ethyl)pentyl-cyclopentane-1-carboxylic Acid A solution of (1R,3R,4R,1'S) 3-(t-butyl-diphenylsilyloxymethyl)-4-(1'-Acetamido-3'-ethyl)pentyl-cyclopentane-1-carboxylic acid from 1L and 1M tetrabutylammonium fluoride in THF (0.8 mL) in THF (2 mL) was stirred for 16 hours at room temperature. The reaction was partitioned between ethyl acetate and 10% citric acid. The organic layer was separated and washed with brine, dried over MgSO$_4$, filtered and concentrated in vacuo. The crude product was chromatographed using a C-18 reverse phase column with 10–25% acetonitrile in water to provide the title compound (yield: 6.6 mg, 52%).

$^1$H NMR (CD$_3$OD) δ 7.81 (d, J=10 Hz, 1H), 3.88 (m, 1H), 3.61 (dd, J=5, 11 Hz, 1H), 3.38 (dd, J=8, 11 Hz, 1H), 2.75 (m, 1H), 2.19–1.00 (m, 13H), 1.95 (s, 3H), 0.87 (t, J=7 Hz, 3H), 0.83 (t, J=7 Hz, 3H). MS: (M+H)$^+$=300.

EXAMPLE 14

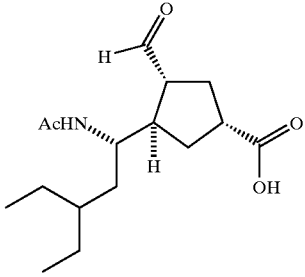

(1R,3R,4R,1'S) 3-Formyl-4-(1'-Acetamido-3'-ethyl)pentyl-cyclopentane-1-carboxylic Acid A solution of (1R,3R,4R,1'S)-3-hydroxymethyl-2-(1'-Acetamido-3'-ethyl)-pentyl-cyclopentane-1-carboxylic acid (34 mg, 0.11 mmole) and pyridinium dichromate (40 mg, 0.1 mmole) in dichloromethane (1.5 mL) was stirred at room temperature for 0.5 hours. The reaction was partitioned between ethyl acetate and 10% citric acid. The organic layer was separated and washed with brine, dried over MgSO$_4$, filtered and concentrated. The crude product was chromatographed on a C18 column with 10–50% acetonitrile in water to provide the title compound.

EXAMPLE 15

(1R,3R,4R,1'S)-3-(Imidazol-2-yl)-4-(1-Acetamido-3-ethyl)pentyl-cyclopentane-1-carboxylic Acid

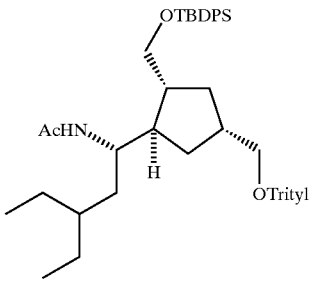

15A. (1R,2R,4R,1'S)-1-(t-Butyldiphenylsilyloxymethyl)-2-(1'-Acetamido-3'-ethyl)pentyl-4-triphenylmethyloxymethyl-cyclopentane A solution of (1R,2R,4R,1'S) 1-(t-butyldiphenylsilyloxymethyl)-2-(1-Acetamido-3-ethyl)pentyl-4-hydroxymethylcyclopentane (0.357 g, 0.682 mmol) in pyridine (0.165 mL, 2.05 mmol) and dichloromethane (2 mL) was reacted with trityl chloride (0.248 g, 0.89 mmol) and DMAP (16.3 mg, 0.13 mmol) at room temperature for 16 hours. The reaction was partitioned between ethyl acetate and 10% citric acid. The organic layer was separated and washed with brine, dried over MgSO$_4$, filtered and concentrated in vacuo. The residue was purified by chromatography on silica gel using 2% methanol/dichloromethane to provide the title compound (yield: 0.5 g, 95%).

$^1$H NMR (CDCl$_3$) δ 7.62 (m, 4H), 7.4 (m, 12H), 7.23 (m, 9H), 3.57 (s, 2H), 2.96 (s, 2H), 2.26 (m, 1H), 1.97 (m, 2H), 1.62 (m, 3H), 1.52 (s, 3H), 1.25–1.5 (m, 7H), 1.06 (s, 9H), 0.83 (br s, 6H). MS: (M+Na)$^+$=788.

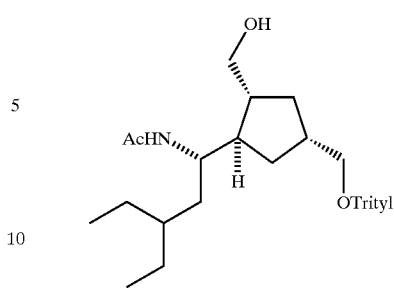

15B. (1R,2R,4R,1'S)-1-Hydroxymethyl-2-(1'-Acetamido-3'-ethyl)pentyl-4-(triphenylmethyloxy)methylcyclopentane The title compound was prepared according to the method described in Example 13K substituting (1R,2R,4R,1'S)-1-(t-butyldiphenylsilyloxymethyl)-2-(1'-Acetamido-3'-ethyl)pentyl-4-(triphenylmethyloxy)methyl-cyclopentane for (1R,3R,4R,1'S) 3-(t-butyldiphenylsilyloxymethyl)-4-(1'-Acetamido-3'-ethyl)pentyl-cyclopentane-1-carboxylic acid (yield: 0.33 g, 98%).

$^1$H NMR (CDCl$_3$) δ 7.42 (m, 6H), 7.26 (m, 9H), 5.59 (d, 1H), 3.86 (m, 1H), 3.6 (2d, 1H), 3.42 (2d, 1H), 3.95 (2d, 2H), 2.25 (m, 1H), 1.95 (s, 3H), 1.7–2.02 (m, 2H), 1.5–1.7 (m, 4H), 1.1–1.5 (m, 9H), 0.83 (2t, 6H). MS: (M–H)$^-$=526, (M+35)$^-$=562; (M+Na)$^+$=550.

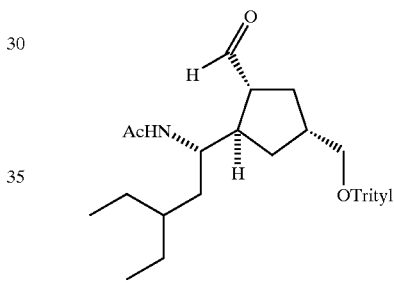

15C. (1R,2R,4R,1'S)-1-Formyl-5-(1'-Acetamido-3'-ethyl)pentyl-3-(triphenylmethyloxy)methyl-cyclopentane The title compound was prepared according to the method described in Example 13L substituting (1R,2R,4R,1'S)-1-hydroxymethyl-2-(1'-Acetamido-3'-ethyl)pentyl-4-(triphenylmethyloxy)methyl-cyclopentane for (1R,3R,4R,1'S)-3-hydroxymethyl-4-(1'-Acetamido-3'-ethyl)pentyl-cyclopentane-1-carboxylic acid (yield: 0.3 g, 91%).

$^1$H NMR (CDCl$_3$) δ 9.56 (d, 1H), 7.42 (m, 6H), 7.27 (m, 9H), 5.13 (d, 1H), 3.86 (m, 1H), 2.94 (m, 2H), 2.72 (m, 1H), 2.42 (m, 1H), 2.16 (m, 2H), 1.90 (s, 3H), 1.1–1.7 (m, 10H), 0.83 (2t, 6H). MS: (M–H)$^-$=524.

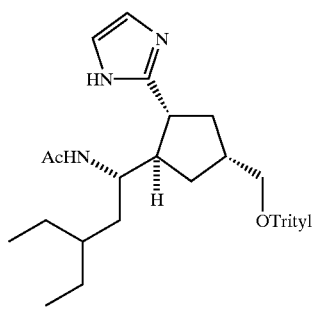

15D. (1R,3R,4R,1'S)-3-(Imidazol-2-yl)-4-(1-Acetamido-3-ethyl)pentyl-1-(triphenylmethyloxy)methyl-cyclopentane (1R,3R,4R,1'S)-1-Formyl-2-(1'-Acetamido-3'-ethyl)pentyl-4-(triphenylmethyloxy)methyl-cyclopentane (80 mg, 0.15 mmol) was reacted with ammonia and 40% glyoxal (0.264 mL, 7.5 mmol) in methanol (7 mL) according the procedure of Rothenberg, A. and coworkers in Angew. Chem. Int. Ed. 1983, 22, p. 560 to provide the title compound (yield: 60 mg, 70%).

$^1$H NMR (CDCl$_3$) δ 7.7 (d, 1H), 7.42 (m, 7H), 7.27 (m, 9H), 5.72 (d, 1H), 3.86 (m, 1H), 3.2 (m, 2H), 3.08 (m, 2H), 2.54 (m, 1H), 2.42 (m, 2H), 1.77 (s, 3H), 1.1–1.7 (m, 10H), 0.78 (2t, 6H). MS: (M–H)$^-$=562, (M+35)$^-$=598; (M+H)$^+$=564, (M+Na)$^+$=586.

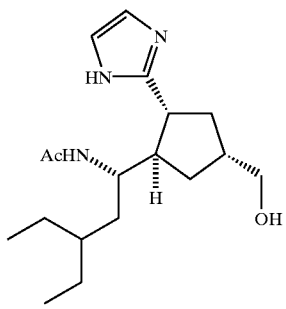

15E. (1R,3R,4R,1'S)-3-(Imidazol-2-yl)-4-(1'-Acetamido-3'-ethyl)pentyl-1-hydroxymethyl-cyclopentane (1R,3R,4R,1'S)-3-(imidazol-2-yl)-4-(1'-Acetamido-3-ethyl)pentyl-1-(triphenylmethyloxy)methyl-cyclopentane (60 mg, 0.106 mmol) was reacted with p-toluenesulfonic acid monohydrate (61 mg, 0.32 mmol) in MeOH (1 mL) for 1 hour. The reaction was quenched with water (10 mL) and diluted with ethyl acetate (25 mL). The organic layer was washed with water, and brine, dried over MgSO$_4$, filtered and concentrated in vacuo. The residue was purified by chromatography on silica gel using 10% methanol/dichloromethane to provide the title compound (yield: 30 mg, 88%).

$^1$H NMR (CDCl$_3$) δ 7.83 (d, 1H), 7.2 (d, 1H), 6.47 (d, 1H), 3.86 (m, 1H), 3.6 (m, 2H), 3.2 (m, 1H), 2.61 (m, 1H), 2.32 (m, 2H), 1.82 (m, 1H), 1.72 (s, 3H), 1.62 (m, 2H), 1.1–1.4 (m, 7H), 0.78 (2t, 6H). MS: (M–H)$^-$=320, (M+35)$^-$=356; (M+H)$^+$=322, (M+Na)$^+$=344.

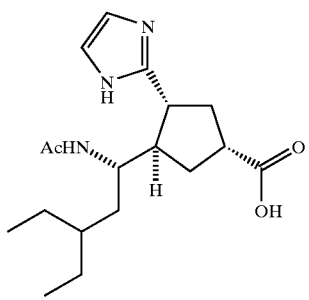

15F. (1R,3R,4R,1'S)-3-(Imidazol-2-yl)-4-(1-Acetamido-3-ethyl)pentyl-cyclopentane-1-carboxylic Acid The title compound was prepared according to the procedure described ing Example 13J substituting (1R,3R,4R,1'S)-3-(imidazol-2-yl)-4-(1-Acetamido-3-ethyl)pentyl-1-hydroxymethylcyclopentane for (1R,2R,4R,1'S) 1-(t-butyldiphenylsilyloxymethyl)-2-(1'-Acetamido-3'-ethyl)pentyl-4-hydroxymethyl-cyclopentane (yield: 5.2 mg, 17%).

$^1$H NMR (d$_6$-MeOH) δ 7.12 (br s, 2H), 3.92 (m, 1H), 2.95 (m, 1H), 2.42 (m, 1H), 2.22 (m, 1H), 1.96 (m, 1H), 1.82 (m, 1H), 1.72 (s, 3H), 1.15–1.45 (m, 7H), 0.82 (2t, 6H). MS: (M–H)$^-$=334, (M+35)$^-$=370; (M+H)$^+$=336, (M+Na)$^+$=358.

EXAMPLE 16

(1R,3R,4R,1'S)-3-(Oxazol-5-yl)-4-(1'-Acetamido-3'-ethyl)pentyl-cyclopentane-1-carboxylic Acid

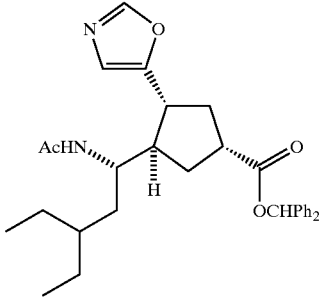

16A. (1R,3R,4R,1'S)-Diphenylmethyl 3-(Oxazol-5-yl)-4-(1'-Acetamido-3'-ethyl)pentylcyclopentane-1-carboxylate (1R,3R,4R,1'S)- Diphenylmethyl 3-formyl-4-(1'-Acetamido-3'-ethyl)pentyl-cyclopentane-1-carboxylate is reacted with p-toluensulfonylmethylisocyanide following the procedure of van Leusen and coworkers in Tetrahedron Letters, 2369 (1977) to provide the title compound.

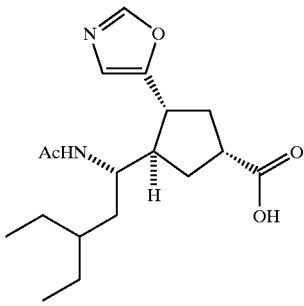

16B. (1lR,3R,4R,1'S)-3-(Oxazol-5-yl)-4-(1'-Acetamido-3'-ethyl)pentyl-cyclopentane-1-carboxylic Acid (1R,3R,4R,1'S)-diphenylmethyl 3-(oxazol-5-yl)-4-(1'-Acetamido-3'-ethyl)pentyl-cyclopentane-1-carboxylate is reacted with anhydrous trifluoroacetic acid in dichloromethane concentration in vacuo provides the title compound.

EXAMPLE 17

(1R,3R,4R,1'S)-3-(N,N-Dimethylcarbamoyl)-4-(1'-Acetamido-3'-ethyl)pentyl-cyclopentane-1-carboxylic Acid

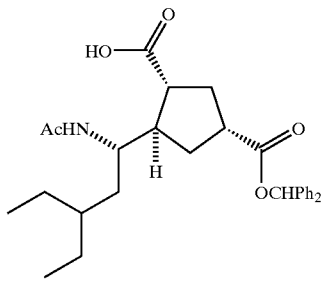

17A. (1R,3R,4R,1'S)-Diphenylmethyl 3-carboxy-4-(1'-Acetamido-3'-ethyl)pentyl-cyclopentane-1-carboxylate The title compound is prepared according to the procedure described in Example 14J substituting (1R,3R,4R,1'S)-diphenylmethyl-3-hydroxymethyl-4-(1'-Acetamido-3'-ethyl)pentyl-cyclopentane-1-carboxylate for (1R,2R,4R,1'S) 1-(t-butyldiphenylsilyloxymethyl)-2-(1'-Acetamido-3'-ethyl)pentyl-4-hydroxymethyl-cyclopentane.

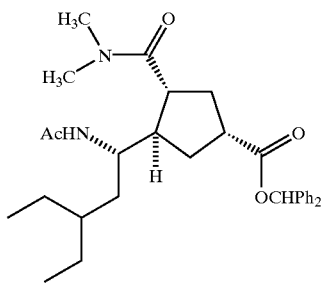

17B. (1R,3R,4R,1'S)-Diphenylmethyl 3-(N,N-Dimethylcarbamoyl)-4-(1'-Acetamido-3'-ethyl)pentyl-cyclopentane-1-carboxylate (1R,3R,4R,1'S)-Diphenylmethyl 3-carboxy-4-(1'-Acetamido-3'-ethyl)pentyl-cyclopentane-1-carboxylate is reacted with isobutyl chloroformate in the presence of N-methylmorpholine at 0° C. The intermediate activated ester is reacted with N,N-dimethylamine to provide the title compound.

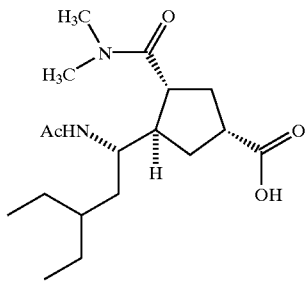

17B. (1R,3R,4R,1'S)-3-(N,N-dimethylcarbamoyl)-4-(1'-Acetamido-3'-ethyl)pentyl-cyclopentane-1-carboxylic Acid The title compound is prepared according to the procedure described in Example 16B substituting (1R,3R,4R,1'S)-diphenylmethyl-3-(N,N-dimethylcarbamoyl)-4-(1'-Acetamido-3'-ethyl)pentyl-cyclopentane-1-carboxylate for (1R,3R,4R,1'S)-diphenylmethyl-3-(imidazol-2-yl)-4-(1'-Acetamido-3'-ethyl)pentyl-cyclopentane-1-carboxylate.

EXAMPLE 18

(1R,3R,4R,1'S)-3-Propionyl-4-(1'-Acetamido-3'-ethyl)pentyl-cyclonentane-1-carboxylic Acid

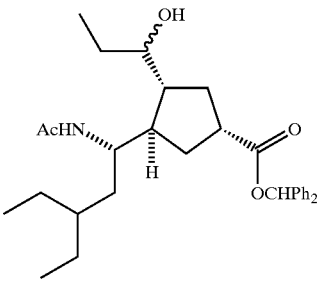

18A. (1R,3R,4R,1'S,1"S)- and (1R,3R,4R,1'S,1"R)-Diphenylmethyl 3-(1-Hydroxypropyl)-4-(1'-Acetamido-3'-ethyl)pentyl-cyclopentane-1-carboxylate (1R,3R,4R,1'S)- Diphenylmethyl 3-formyl-4-(1'-Acetamido-3'-ethyl)pentyl-cyclopentane-1-carboxylate is reacted with ethyl magnesium bromide in THF at 0° C. The reaction is quenched with aqueous ammonium chloride and partitioned between ethyl acetate and water. The organic layer is dried over $MgSO_4$, filtered, and concentrated in vacuo to provide the title compound.

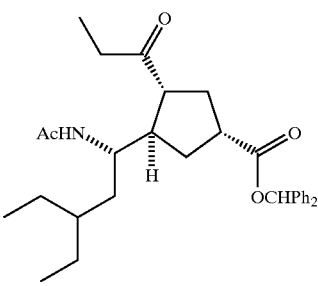

18B. (1R,3R,4R,1'S)-Diphenylmethyl 3-propionyl-4-(1'-Acetamido-3'-ethyl)pentyl-cyclopentane-1-carboxylate The title compound is prepared according to the procedure of Example 12B substituting (1R,3R,4R,1'S,1"S)- and (1R,3R,4R,1'S,1"R)-diphenylmethyl3-(1-hydroxypropyl)-4-(1'-Acetamido-3'-ethyl)pentyl-cyclopentane-1-carboxylate for (±)-(2S,1'R) and (2S,1'S)-2-(3'ethyl-1'-hydroxy)pentyl-bicyclo[2.2.1]hept-5-ene.

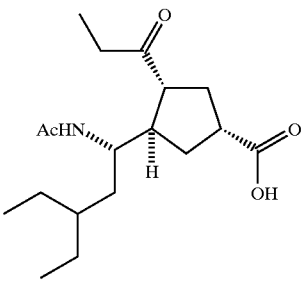

18C. (1R,3R,4R,1'S)-3-Propionyl-4-(1'-Acetamido-3'-ethyl)pentyl-cyclopentane-1-carboxylic Acid The title compound is prepared according to the procedure described in Example 16B substituting (1R,3R,4R,1'S)-diphenylmethyl 3-propionyl-4-(1'-Acetamido-3'-ethyl)pentyl-cyclopentane-1-carboxylate for (1R,3R,4R,1'S)-diphenylmethyl 3-(imidazol-2-yl)-4-(1'-Acetamido-3'-ethyl)pentyl-cyclopentane-1-carboxylate.

EXAMPLE 19

(±)-(2R,3R,5R,1'S)-2-(1'-Acetamido-3'-Methyl)butyl-3-methoxycarbonyl-tetrahydrofuran-5-carboxylic Acid

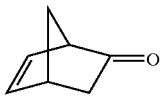

19A (±)-Bicyclo[2.2.1]hept-5-en-2-one

In a three-necked flask equipped with a mechanical stirrer, a $N_2$ inlet and an additional funnel, a solution of oxalyl chloride (2.0 M in dichloromethane, 136 mL, 0.272 mole) in dichloromethane (250 mL) was cooled to −78° C. and a solution of DMSO (40 mL) in 40 mL of dichloromethane was added dropwise over 30 min. After stirring for 5 additional minutes, a solution of 5-norbornen-2-ol (24 g, 0.218 mole) in 40 mL of dichloromethane was added dropwise. The solution was stirred for another 10 minutes and triethylamine (150 mL) was added over 40 minutes. The mixture was then stirred for 10 minutes at −78° C. and allowed to warm up to 0° C. over 1 hour. Water (250 mL) was added. Following the separation of two layers, the organic layer was washed with 0.2 N HCl (4×200 mL) and brine (2×200 mL). After drying (MgSO$_4$), the solution was concentrated to about 80 mL. The residue was distilled with a 12" Vigreux column at reduced pressure to give the title compound b.p. 100–105° C./15 mmHg, (yield: 20.1 g, 86%).

$^1$H NMR (CDCl$_3$): 1.85 (dd, 1H), 1.90–2.00 (m, 2H), 3.00 (brs, 1H), 3.20 (b.s, 1H), 6.01 (t, 1H), 6.58 (t, 1H).

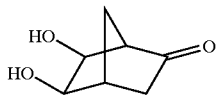

19B (±)-exo,exo-5,6-Dihydroxybicyclo[2.2.1]heptan-2-one

A solution of (±)-bicyclo[2.2.1]hept-5-en-2-one (10.8 g, 0.1 mole) and N-methyl morpholine oxide (12.7 g, 0.12 mole) in 300 mL of 90% THF-water was reacted with a solution of osmium tetroxide (2.5% wt in t-BuOH, 8.0 mL) for 5 hours at ambient temperature. The solvents were evaporated and the resulting residue was dried in vacuo. The residue was then taken up in 100 mL of ethyl acetate, dried (MgSO$_4$) and filtered. The filtrate was passed through a short silica gel plug, eluting with ethyl acetate. Concentration gave the title compound as a thick oil (14.5 g) which was used directly for the next step.

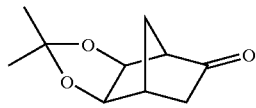

19C (±)-exo,exo-5,6-Dihydroxyacetonide-bicyclo[2.2.1]heptan-2-one

A solution of (±)-exo,exo-5,6-dihydroxybicyclo[2.2.1]heptan-2-one (14.5 g, crude) in 250 mL of 2,2-dimethoxypropane was cooled to 0° C. and p-toluensulfonic acid (125 mg) was added. The solution was stirred for 30 minutes when TLC indicated complete reaction. The solution was loaded on an aluminum oxide (neutral) column and eluted with 15–30% ethyl acetate in hexane, to give the title compound as a white solid (yield: 11.9 g, 65% for two steps).

MS (DCI-NH$_3$): m/z 200 for (M+NH$_4$), base peak. $^1$H NMR (CDCl$_3$): δ 1.34 (s, 3H), 1.50 (s, 3H), 1.63–1.74 (m, 2H), 2.12–2.20 (m, 2H), 2.70–2.76 (m, 2H), 4.28 (d, 1H), 4.34 (d, 1H). $^{13}$C NMR (CDCl$_3$): δ 21.1, 25.3, 31.2, 39.4, 39.5, 55.3, 76.8, 81.2, 111.2, 214.0. Analysis: C$_{10}$H$_{14}$O$_3$, calc. 65.92% C, 7.75% H; found, 66.01% C, 7.79% H.

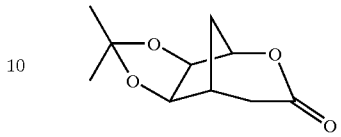

19D (±)-exo,exo-6,7-Dihydroxyacetonide-2-oxabicyclo[3.2.1]octan-3-one

To a solution of (±)-exo,exo-5,6-dihydroxyacetonide-bicyclo[2.2.1]heptan-2-one (14.76 g, 0.081 mole) in 500 mL of dichloromethane was added NaHCO$_3$ (13.6 g, 0.16 mole). The mixture was cooled with a water bath and MCPBA (30.3 g, ~60%) was added portionwise over 30 minutes. The solution was then stirred for 2 hours at ambient temperature and washed with 10% aqueous Na$_2$S$_2$O$_5$ (500 mL), saturated NaHCO$_3$ solution (3×200 mL) and brine (3×200 mL). The organic solution was then dried (MgSO$_4$), filtered and concentrated. The residue was loaded on an aluminum oxide (neutral) column for 30 minutes, then eluted with 10–25% ethyl acetate in hexane to give the title compound as a white solid (yield: 7.7 g, 50%)

MS (DCI-NH$_3$): m/z 216 for (M+NH$_4$)$^+$, base peak. $^1$H NMR (CDCl$_3$): δ 1.30 (s, 3H), 1.45 (s, 3H), 1.84 (d, 1H), 2.10–2.20 (m, 1H), 2.48–2.56 (m, 2H), 2.80 (dd, 1H), 4.56 (d, 1H), 4.60 (s, 1H), 4.70 (d, 1H). $^{13}$C NMR (CDCl$_3$): 23.79, 25.58, 29.17, 35.97, 36.51, 80.70, 82.49, 82.55, 83.24, 110.83, 167.95. Analysis: C$_{10}$H$_{14}$O$_4$, cal. 60.59% C, 7.12% H; found, 60.52% C, 6.97% H.

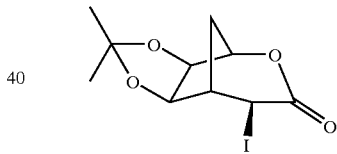

19E (±)-exo,exo-6,7-Dihydroxyacetonide-4-exo-iodo-2-oxabicyclo[3.2.1]octan-3-one To a mixture of lithium bis(trimethylsilyl)amide (1.0 M in THF, 32.6 mL) and distilled THF (60 mL), cooled to −78° C., was added a solution of (±)-exo,exo-6,7-dihydroxyacetonide-2-oxabicyclo[3.2.1]octan-3-one (5.87 g, 29.6 mmol) in 60 mL of THF over 30 minutes. After stirring for another 30 minutes, the solution was then cannulated into a flask containing a solution of iodine (8.3 g, 32.6 mmol) in 60 mL of THF cooled to −78° C. over 30 minutes. The resulting solution was stirred for another 10 minutes and quenched with 300 mL of 5% aqueous citric acid. The mixture was then extracted with ethyl acetate (3×100 mL). The combined ethyl acetate solution was washed with 10% aqueous Na$_2$S$_2$O$_3$ solution (2×100 mL) and brine (2×200 mL), and dried (MgSO$_4$). After filtration, the solution was evaporated and the residue chromatograhed on a silica gel column eluting with 15–25% ethyl acetate in hexane, to give a white crystalline solid (yield: 7.55 g, 79%).

MS (DCI-NH$_3$): m/z=342 for (M+NH$_4$)$^+$, base peak. $^1$H NMR (CDCl$_3$): δ 1.30 (s, 3H), 1.45 (s, 3H), 1.55 (s, 1H), 2.12–2.20 (m, 1H), 2.42 (d, 1H), 2.80 (m, 1H), 4.56 (d, 1H), 4.54 (d, 1H), 4.70 (m, 2H). Analysis: C$_{10}$H$_{13}$IO$_4$, cal.

37.06% C, 4.04% H, 39.15% I; found, 37.08% C, 3.98% H, 39.55% I.

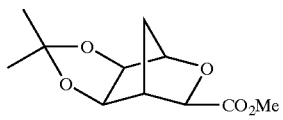

19F (±)-Methyl-exo,exo-5,6-dihydroxyacetonide-2-oxabicyclo[2.2.1]heptane-3-exo-carboxylate.

To a solution of (±)-exo,exo-6,7-dihydroxyacetonide-4-exo-iodo-2-oxabicyclo[3.2.1]octan-3-one (7.55 g, 23.3 mmol) in 300 mL of methanol (pre-dried with 4 Å sieves) was added $K_2CO_3$ (3.54 g, 25.6 mmol). The mixture was stirred vigorously for 30 min. The undissolved potassium carbonate was removed by filtration and the filtrate was concentrated to dryness. The residue was triturated with ethyl acetate several times until complete extraction of the product (TLC). The ethyl acetate solution was then concentrated and directly chromatographed on a silica gel column eluting with 10–25% ethyl acetate in hexane, giving 4.86 g of the title compound as a white solid. Yield: 92.0%.

MS (DCI-NH$_3$): m/z 246 for (M+NH$_4$), base peak. $^1$H NMR (CDCl$_3$): δ 1.30 (s, 3H), 1.45 (s, 3H), 1.62 (d, 1H), 1.85 (d, 1H), 2.82 (s, 1H), 3.78 (s, 3H), 3.80 (s, 1H), 4.20 (d, 1H), 4.30 (d, 1H), 4.40 (s, 1H). Analysis: $C_{11}H_{16}O_5$, calc.: 57.88% C, 7.07% H; found: 57.98% C, 7.10% H.

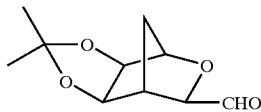

19G (±)-exo-3-Formyl-exo,exo-5,6-dihydroxyacetonide-2-oxabicyclo[2.2.1]heptane

To a well-stirred solution of (±)-methyl-exo,exo-5,6-dihydroxyacetonide-2-oxabicyclo[2.2.1]heptane-exo-3-carboxylate (0.82 g, 3.62 mmol) in 30 mL of anhydrous dichloromethane at −78° C. was added a solution of diisobutylaluminum hydride in toluene (1.0 M, 5.77 mL) dropwise. The mixture was then stirred at −78° C. for 1 hour and quenched with 2 mL of methanol and 15 mL of saturated aqueous sodium potassium tartrate solution. The mixture was then stirred vigorously and allowed to warm to ambient temperature over 1 hour. The phases were separated and the aqueous phase was extracted with Et$_2$O (5×50 mL). After drying, solvent removal gave the title compound as an oil (0.8 g) which was used directly for the next step.

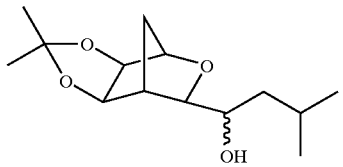

19H (±)-(1'RS)-exo-3-(1'-Hydroxy-3'-Methyl)butyl-exo,exo-5,6-dihydroxyacetonide-2-oxabicyclo[2.2.1]heptane.

To a solution of (±)-exo-3-formyl-exo,exo-5,6-dihydroxyacetonide-2-oxabicyclo[2.2.1]heptane (0.99 g, 5.0 mmol) in 50 mL of anhydrous THF at −78° C. was added a solution of isobutylmagnesium chloride (2.0 M in ether, 30 mL) dropwise over 30 minutes. The mixture was then allowed to warm up to ambient temperature over 2 hours and quenched with 100 mL of saturated aqueous NH$_4$Cl solution. The solution was then extracted with Et$_2$O (3×100 mL). The combined organic layers were washed with brine (3×100 mL) and dried. After filtration, evaporation of solvent gave title compound as an oil (1.28 g) which was used directly for the next step.

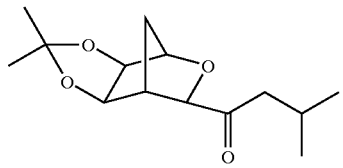

19I (±)-exo-3-(1'-oxo-3'-Methyl)butyl-exo, exo-5,6-dihydroxyacetonide-2-oxabicyclo[2.2.1]heptane A solution of oxalyl chloride (2.0 M in dichloromethane, 3.76 mL, 7.3 mmol) was mixed with 10 mL of anhydrous dichloromethane and the solution was cooled to −78° C. A solution of DMSO (1.06 mL) in 10 mL of anhydrous dichloromethane was then added dropwise. After stirring for 10 minutes, a solution of (±)-(1'RS)-exo-3-(1'-hydroxy-3'-Methyl)butyl-exo,exo-5,6-dihydroxyacetonide-2-oxabicyclo[2.2.1]heptane (1.28 g, 5.0 mmol) in anhydrous dichloromethane (10 mL) was added dropwise and the solution was stirred for another 10 minutes. Triethylamine (4.3 mL) in 10 mL of dichloromethane was then added. The mixture was then stirred at −78° C. for 2 hours and allowed to warm up to ambient temperature. The solution was washed with water (100 mL), 5% aqueous citric acid (100 mL), saturated NaHCO$_3$ (100 mL) and brine. After drying and concentration, the crude material was purified by flash chromatography on a silica gel column using 5%–20% ethyl acetate-hexane to give the title compound as a white solid, 0.65 g, 51% for three steps.

MS (DCI-NH$_3$): m/z 272 for (M+NH$_4$)$^+$ base peak. $^1$H NMR (CDCl$_3$): δ 0.84 (dd, 6H), 1.30 (s, 3H), 1.34,1.38 (bd, 1H), 1.43 (s, 3H), 1.77, 1.82 (dd, 1H), 2.10–2.10 (m, 1H), 2.30–2.50 (dq, 2H), 2.86 (s, 1H), 3.62 (s, 1H), 4.16–4.20 (m, 1H), 4.28–4.32 (bd, 1H), 4.37 (s, 1H). Analysis: $C_{14}H_{22}O_4$, cal. 66.12% C, 8.72% H; found, 65.99% C, 8.58% H.

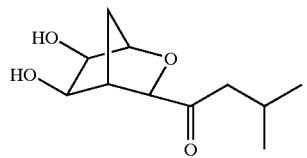

19J (±)-exo-3-(1'-oxo-3'-Methyl)butyl-exo,exo-5,6-dihydroxy-2-oxabicyclo[2.2.1]heptane.

(±)-exo-3-(1'-Oxo-3'-Methyl)butyl-exo,exo-5,6-dihydroxyacetonide-2-oxabicyclo[2.2.1]heptane (0.64 g, 0.25 mmol) was dissolved in 12.5 mL of methanol and 12.5 mL of 2M HCl. The solution was stirred at 60° C. for 2.5 hours. After cooling to ambient temperature, the solution was partially concentrated and then extracted with ethyl acetate (4×50 mL). The combined ethyl acetate solution was washed with saturated aqueous NaHCO$_3$ solution (2×50 mL) and brine (2×50 mL), and dried. After filtration, removal of solvent gave the title compound as an off-white crystalline solid, (yield: 0.53 g, 98.0%).

MS (DCI-NH$_3$): m/z 232 for (M+NH$_4$)$^+$, base peak. $^1$H NMR (CDCl$_3$): δ 0.92 (dd, 6H), 1.34, 1.44 (bd, 1H), 1.77, 1.82 (dd, 1H), 2.10–2.20 (m, 1H), 2.30–2.45 (dq, 2H), 2.65 (d, 1H), 2.74–2.80 (m, 2H), 3.72 (s, 1H), 3.94–4.00 (m, 1H), 4.00–4.05 (bd, 1H), 4.24 (s, 1H).

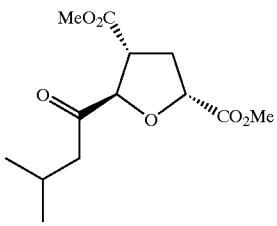

19K (±)-(2R,3R,5R)-Dimethyl 2-(1'-oxo-3'-Methyl)butyltetrahydrofuran-3,5-dicarboxylate (±)-exo-3-(1'-Oxo-3'-Methyl)butyl-exo,exo-5,6-dihydroxy-2-oxabicyclo[2.2.1]heptane.(0.50 g, 2.3 mmol) was dissolved in a mixture of acetonitrile (6.5 mL), carbon tetrachloride (6.5 mL) and water (10 mL). To this solution was added sodium periodate (2.1 g, 10 mmol) and $RuCl_3 \cdot H_2O$ (10 mg). The solution was stirred at ambient temperature for 3 hours and filtered to remove the solid. The filtrate was loaded on a short silica gel column, eluted with 5% methanol in ethyl acetate containing 5% acetic acid. The resulting crude diacid (yellow oil, 0.53 g) was dissolved in ethyl acetate (25 mL). N,N-diisopropylethylamine (1.73 mL, 12 mmol) and methyl iodide (2.98 mL, 46 mmol) were added and the mixture was stirred at 50° C. for 2 hours. The mixture was filtered to remove the solid and the filtrate was concentrated. The residue was purified by flash chromatography on a silica gel column eluting with 10–40% ethyl acetate in hexane, giving the title compound as a colorless liquid (0.40 g, 68.0% for two steps).

MS (DCI-NH$_3$): m/z 290 for (M+NH$_4$)$^+$, base peak. $^1$H NMR (CDCl$_3$): δ 0.92 (d, 3H, CH$_3$), 0.93 (d, 3H, CH$_3$), 2.19 (m, 1H, H$_7$), 2.40–2.60 (m, 4H, H$_{6a}$, H$_{6b}$, H$_{3a}$, H$_{3b}$), 3.30 (m, 1H, H$_3$), 3.75 (s, 3H, OCH$_3$), 3.78 (s, 3H, OCH$_3$), 4.65 (dd, 1H, H$_5$), 4.85 (d, 1H, H$_2$).

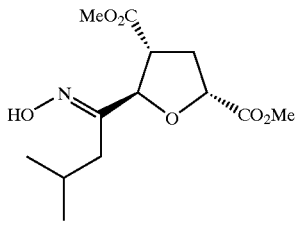

19L (±)-(2R,3R,5R)-Dimethyl-2-(1'-N-hydroxyimino-3'-Methyl)butyl-tetrahydrofuran-3,5-dicarboxylate A solution of (±)-(2R,3R,5R)-dimethyl-2-(1'-oxo-3'-Methyl)butyl-tetrahydrofuran-3,5-dicarboxylate(0.3 g, 1.09 mole), hydroxylamine hydrochloride (0.23 g, 3.3 mmol), diisopropylethylamine (0.57 mL, 3.3 mmol) and tetrabutylammonium iodide in 10 mL of methanol was stirred at 40° C. for 2 hours. The solution was concentrated and purified directed on a 10-g silica gel cartridge, eluting with 30% ethyl acetate in hexane, giving the title compound as a mixture of cis and trans oximes.

MS (DCI-NH$_3$): m/z 287 (M+H), 305 (M+NH$_4$)$^+$. $^1$H NMR (CDCl$_3$): δ 0.95–1.0 (m, 6H), 2.19 (m, 1H), 2.40–2.60 (m, 4H,), 3.45 (m, 1H), 3.65–3.80 (4 s, 6H), 4.50–4.60 (bs, 1H), 4.70 (m, 1H), 5.0 (bs, 1H).

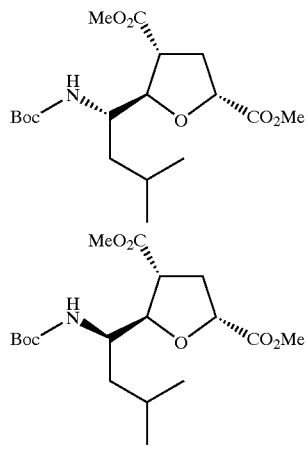

19M (±)-(2R,3R,5R,1'S) and (±)-(2R,3R,5R,1'R)Dimethyl 2-(1'-t-Butoxycarbonylamino-3'-Methyl)butyl-tetrahydrofuran-3,5-dicarboxylate.

A solution of (±)-(2R,3R,5R)-dimethyl-2-(1'-N-hydroxyimino-3'-Methyl)butyl-tetrahydrofuran-3,5-dicarboxylate (0.27 g, 0.94 mmol) and Boc$_2$O (2.11 mL, 10×) in 70 mL of isopropanol was hydrogenated with Raney Nickel at 4 atm of hydrogen for 15 hours. After concentration of the solution, separation on a silica gel column with 10% ethyl acetate in hexane gave (±)-(2R,3R,5R,1'S) isomer (137 mg) and (±)-(2R,3R,5R,1'R) isomer (176 mg).

(±)-(2R,3R,5R,1'S) MS (DCI-NH$_3$): m/z 374, 391, 317, 335. $^1$H NMR (CDCl$_3$): 0.9–0.95 (2d, 6H), 1.22–1.31 (m, 1H), 1.49 (s, 9H), 1.50–1.55 (m, 1H), 1.62–1.75 (m, 1H), 2.40–2.60 (m, 2H), 2.95–3.10 (m, 1H), 3.70 (s, 3H), 3.75 (s, 3H), 4.20 (t, 1H), 4.37 (bd, 1H), 4.60 (dd, 1H).

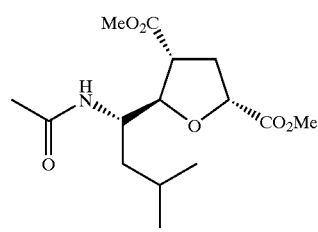

19N (±)-(2R,3R,5R,1S)-Dimethyl 2-(1'-Acetamido-3'-Methyl)butyl-tetrahydrofuran-3,5-dicarboxylate.

A solution of (±)-(2R,3R,5R,1'S) dimethyl 2-(1'-t-butoxycarbonylamino-3'-Methyl)butyl-tetrahydrofuran-3,5-dicarboxylate (40 mg, 0.11 mmol) in 2 mL of 50% trifluoroacetic acid/dichloromethane was stirred at ambient temperature for 1 hours. The solution was then evaporated to dryness. The residue was dissolved in 0.5 mL of dichloromethane. Acetic anhydride (104 mL, 10.0 eq.) and diisopropylethylamine (192 mL, 10.0 eq.) were added. After stirring for 2 hours, the mixture was directly loaded on a 5-g silica gel cartridge and eluted with 60% ethyl acetate in hexane, giving the title compound as a solid (34 mg, 100%).

MS (DCI-NH$_3$): m/z 316 (M+H)$^+$, 333 (M+NH$_4$)$^+$. $^1$H NMR (CDCl$_3$): δ 0.9–0.95 (2d, 6H), 1.25–1.35 (m, 1H), 1.50–1.70 (m, 2H), 1.99 (s, 3H), 2.40–2.60 (m, 2H), 2.95–3.10 (m, 1H), 3.70 (s, 3H), 3.75 (s, 3H), 4.20–4.40 (m, 2H), 4.60 (dd, 1H), 5.30 (bd, 1H).

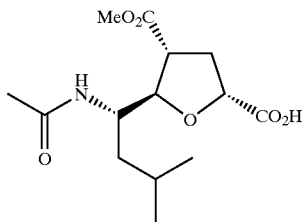

19O (±)-(2R,3R,5R,1'S)-2-(1'-Acetamido-3'-Methyl)butyl-3-methoxycarbonyl-tetrahydrofuran-5-carboxylic Acid To a solution of (±)-(2R,3R,5R,1'S)-dimethyl 2-(1'-Acetamido-3'-Methyl)butyl-tetrahydrofuran-3,5-dicarboxylate (32 mg, 0.1 mmol) in 1.0 mL of THF cooled to 0° C. was added a solution of LiOH (0.1 M, 1.0 mL) slowly dropwise. The solution was then stirred for 15 minutes and quenched with 1.0 mL of acetic acid. After extracting with ethyl acetate (3×1 mL), the organic solution was dried (MgSO$_4$) and purified on a 5-g silica gel cartridge, eluting with 0–20% methanol/ethyl acetate containing 5% acetic acid. The product obtained was further purified by recrystallization from ethyl acetate and isopropanol. (yield: 22 mg, 71%).

HRMS: $C_{14}H_{24}O_6N$, calculated: 302.1604, found: 302.1592. $^1H$ NMR (CDCl$_3$): δ 0.9–0.95 (2d, 6H), 1.25–1.35 (m, 1H), 1.50–1.70 (m, 2H), 1.99 (s, 3H), 2.40–2.50 (m, 1H), 2.60–2.70 (m, 1H), 2.95–3.10 (m, 1H), 3.70 (s, 3H), 4.10–4.40 (m, 2H), 4.60 (dd, 1H), 5.30 (bd, 1H). The relative stereochemistry was confirmed by the X-ray structure of a single crystal.

EXAMPLE 20

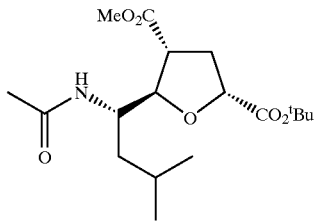

20A (±)-(2R,3R,5R,1'S)-2-(1'-Acetamido-3'-Methyl)butyl-3-methoxycarbonyl-tetrahydrofuran-5-carboxylic Acid t-Butyl Ester.

To a solution of (±)-(2R,3R,5R,1'S)-2-(1'-Acetamido-3'-Methyl)butyl-3-methoxycarbonyltetrahydrofuran-5-carboxylic acid (25 mg, 0.08 mmol) in 1.0 mL of dichloromethane was added a solution of tert-butyl 2,2,2-trichloroacetimidate (54 mg, 0.24 mmol) in 0.3 mL of cyclohexane. After cooling to 0° C., 3 drops of boron trifluoride etherate was added. The mixture was stirred for another 40 minutes and quenched with 2 mL of 5% NaHCO$_3$ solution. After diluting with 10 mL of dichloromethane, the mixture was filtered to remove insoluble by-product and the organic phase was further washed with 5% NaHCO$_3$ solution, dried, and concentrated. The residue was purified on a 5-g silica gel cartridge to give the title compound as an oil (26 mg) which was used directly for the next step.

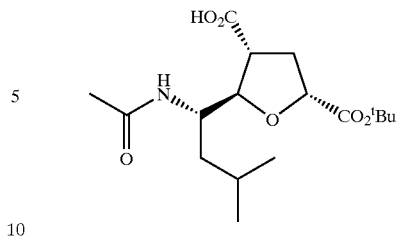

20B (±)-(2R,3R,5R,1'S)-2-(1'-Acetamido-3'-Methyl)butyl-3-carboxyl-tetrahydrofuran 5-Carboxylic Acid t-Butyl Ester A solution of (±)-(2R,3R,5R,1'S)-2-(1'-Acetamido-3'-Methyl)butyl-3-methoxycarbonyl-tetrahydrofuran-5-carboxylic acid t-butyl ester (26 mg, 0.073 mmol) in 1.5 mL of THF was cooled to 0° C. and a solution of 0.1 N LiOH (0.73 mL) was added. The mixture was allowed to warm up to ambient temperature over 90 minutes, then acidified to pH 2–3 with 1N HCl and extracted with ethyl acetate. The combined ethyl acetate solution was dried and concentrated. The residue was purified on a 5-g silica gel cartridge to give the title compound (10 mg) as a solid.

MS (DCI-NH$_3$): m/z 344 (M+H)$^+$, 361 (M+NH$_4$)$^+$. $^1H$ NMR (methanol-d$_4$): δ 0.87, 0.89 (d, 3H), 0.92, 0.94 (d, 3H), 1.35–1.45 (m, 1H), 1.47 (s, 9H), 1.50–1.70 (m, 2H), 1.92 (s, 3H), 2.30–2.37 (m, 1H), 2.45–2.55 (m, 1H), 2.90–2.97 (m, 1H), 4.00–4.07 (m, 1H), 4.20 (t, 1H), 4.45 (dd, 1H).

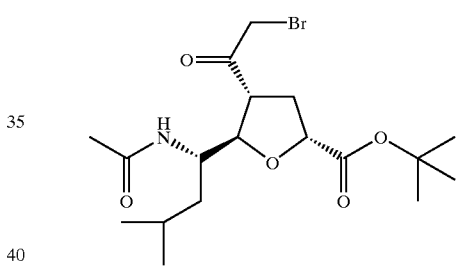

20C (±)-(2R,3R,5R,1'S)-2-(1'-Acetamido-3'-Methyl)butyl-3-(1"-oxo-2"-bromo)ethyl-tetrahydrofuran-5-carboxylic Acid t-Butyl Ester To a solution of (±)-methyl (2R,3R,5R,1'S)-2-(1'-Acetamido-3'-Methyl)butyl-3-carboxyl-tetrahydrofuran-5-carboxylic acid t-butyl ester (10 mg, 0.029 mmol) in 1.0 mL of THF, cooled to 0° C., was added N-methyl morpholine (0.13 mL) and iso-butyl chloroformate (0.15 mL, 0.12 mmol). The mixture was stirred at 0° C. for 1 h. A solution of diazomethane generated from Diazald (0.21 g, 1.0 mmol) and KOH (0.8 g) in 2 mL of Et$_2$O was then added via a syringe until the yellow color persisted. The solution was then stirred for 3 hours, washed with brine (2×2.0 mL) and dried (MgSO$_4$). Evaporation of solvent gave a yellow solid which was redissolved in 1.5 mL of dioxane. To this solution was added 48% HBr (aq.) solution (0.125 mL) and the mixture was stirred for 10 minutes. Saturated NaHCO$_3$ solution (0.5 mL) was then added slowly and the mixture was extracted with ethyl acetate (5×1.0 mL). The combined ethyl acetate solution was dried (MgSO$_4$), filtered and concentrated. Chromatography on a 5-g silica gel cartridge eluting with 60% ethyl acetate-hexane give the title compound (7.3 mg) as a solid which was used directly for the next step.

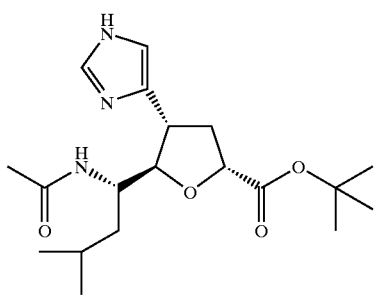

20D (±)-(2R,3S,5R,1'S)-2-(1'-Acetamido-3'-Methyl)butyl-3-(imidazol-4-yl)-tetrahydrofuran-5-carboxylic Acid t-Butyl Ester

To a vial containing (±)-(2R,3R,5R,1'S)-2-(1'-Acetamido-3'-Methyl)butyl-3-(1″-oxo-2″-bromo)ethyl-tetrahydrofuran-5-carboxylic acid t-butyl ester (7 mg, 0.014 mmol) and formamidine acetate (30 mg, excess) was added liquid ammonia (2.0 mL). The vial was sealed and stirred at 45° C. overnight. The ammonia was allowed to evaporate slowly. The residue was taken up in 5% $Na_2CO_3$ (aq. 1.0 mL) and extracted with ethyl acetate (4×1.0 mL). The combined ethyl acetate solution was dried and concentrated. The residue was chromatographed on a 2-g silica gel cartridge eluting with ethyl acetate to give the title compound as a solid (1.0 mg).

MS (APCI+): m/z 366 (M+H)$^+$, 310 (M–$C_4H_9$)$^+$, base peak. $^1$H NMR (methanol-$d_4$): δ 0.87, 0.89 (d, 3H), 0.95, 0.97 (d, 3H), 1.27–1.37 (m, 1H), 1.47 (s, 9H), 1.42–1.67 (m, 2H), 1.84 (s, 3H), 2.10–2.17 (dt, 1H), 2.77–2.87 (dt, 1H), 3.50 (q, 1H), 4.02–4.06 (m, 1H), 4.16 (t, 1H), 4.55 (t, 1H), 7.34 (s, 1H), 8.64 (s, 1H).

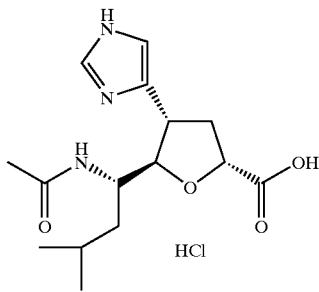

20E (±)-(2R,3S,5R,1'S)-2-(1'-Acetamido-3'-Methyl)butyl-3-(imidazol-4-yl)-tetrahydrofuran 5-Carboxylic Acid

A solution of (±)-(2R,3S,5R,1'S)-2-(1'-Acetamido-3'-Methyl)butyl-3-(imidazol-4-yl)-tetrahydrofuran-5-carboxylic acid t-butyl ester (1.0 mg) in 1.0 mL of 6N aqueous HCl was stirred for 1 h. The solution was then concentrated to give the title compound as a white solid (0.8 mg).

$^1$H NMR ($D_2O$): δ 0.81, 0.83 (d, 3H), 0.87, 0.89 (d, 3H), 1.30–1.58 (m, 4H), 1.84 (s, 3H), 2.10–2.22 (m, 1H), 2.85–2.95 (m, 1H), 3.58 (q, 1H), 3.90–3.94 (m, 1H), 4.00–4.04 (m, 1H), 4.20 (t, 1H), 7.32 (s, 1H), 8.64 (s, 1H).

EXAMPLE 21

(1S,3R,4S,1'S)-3-(1'-Acetamido-3'-ethyl)pentyl-4-vinyl-cyclopentane-1-carboxylic Acid

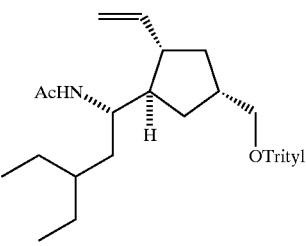

21A. (1S,3R,4S,1'S)-3-(1'-Acetamido-3'-ethyl-)pentyl-1-(triphenylmethyloxy)methyl-4-vinyl-cyclopentane

A solution of (1R,2R,4R,1'S)-1-formyl-2-(1'-Acetamido-3'-ethyl)pentyl-4-(triphenylmethyloxy)methyl-cyclopentane (60 mg, 0.11 mmol) prepared according to the method of Example 15C in THF (1 mL) was added to a mixture prepared from the reaction of methyltriphenylphosphonium iodide (69 mg, 0.17 mmol) and 2.5M n-BuLi/hexane (64 mg, 0.16 mmol) in THF (1 mL) for 2 hours at room temperature. After 1.5 hours, the reaction was partitioned between ethyl acetate and 10% citric acid. The organic layer was separated and washed with brine, dried over $MgSO_4$, filtered and concentrated in vacuo. The residue was purified by chromatography on silica gel using 3% methanol/dichloromethane to provide the title compound (yield: 29 mg, 49%).

$^1$H NMR (CDCl$_3$) δ 7.52 (m, 6H), 7.24 (m, 9H), 5.64 (m, 1H), 4.84–5.04 (m, 3H), 3.98 (m, 1H), 2.95 (m, 2H), 2.7 (m, 2H), 2.0 (m, 1H), 1.88 (m, 2H), 1.66 (m, 1H), 1.56 (s, 3H), 1.1–1.5 (m, 9H), 0.83 (m, 6H). MS: (M–H)$^-$=522, (M+35)$^-$=558; (M+Na)$^+$=546.

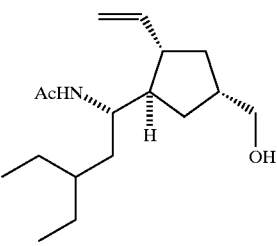

21B. (1S,3R,4S,1'S) 3-Vinyl-4-(1-Acetamido-3-ethyl)pentyl-1-hydroxymethyl-cyclopentane

The title compound was prepared according to the method described in Example 1 5E substituting (1S,3R,4S,1'S)-3-(1-Acetamido-3-ethyl)pentyl-1-(triphenylmethyloxy)methyl-4-vinyl-cyclopentane for (1R,3R,4R,1'S)-3-(imidazol-2-yl)-4-(1'-Acetamido-3'-ethyl)pentyl-1-(triphenylmethyloxy)methyl-cyclopentane (yield: 7 mg, 87%).

$^1$H NMR (CDCl$_3$) δ 5.68 (m, 1H), 4.84–5.05 (m, 3H), 3.98 (m, 1H), 3.54 (2d, 2H), 2.4 (m, 1H), 2.18 (m, 1H), 1.92 (s, 3H), 1.1–1.5 (m, 10H), 0.83 (2t, 6H). MS: (M+H)$^+$=282, (M+18)$^+$=299.

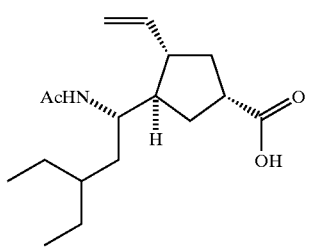

21C. (1S,3R,4S,1'S)-3-(1-Acetamido-3-ethyl-)pentyl-4-vinyl-cyclopentane-1-carboxylic Acid The title compound was prepared according to the procedure described in Example 13J substituting (1S,3R,4S,1'S) 3-(1-Acetamido-3-ethyl)pentyl-1-hydroxymethyl-4-vinyl-cyclopentane for (1R,2R,4R,1'S)-1-(t-butyldiphenylsilyloxymethyl)-2-(1'-Acetamido-3'-ethyl)pentyl-4-hydroxymethyl-cyclopentane (yield: 4.2 mg, 33%).

$^1$H NMR (CDCl$_3$) δ 5.65–5.78 (m, 1H), 5.05 (d, 1H), 5.02 (2d, 1H), 4.92 (2d, 1H), 3.99 (q, 1H), 2.88 (m, 1H), 2.43 (m, 1H), 2.15 (m, 2H), 1.91 (s, 3H), 1.87 (m, 1H), 1.71 (m, 1H), 1.1–1.5 (m, 8H), 0.83 (2t, 6H). MS: (M–H)$^-$=294; (M+H)$^+$=296, (M+Na)$^+$=318.

EXAMPLE 22

(±)-(1R,3R,4R,1'S)-3-N-Methylcarbamoyl-4-(1'-Acetamido-3'-ethyl)pentyl-cyclopentane-1-carboxylic Acid

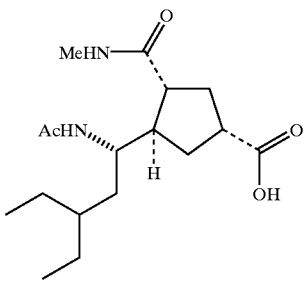

The title compound was prepared according to the procedure described ing Example 12G substituting methylamine for methanol (yield: 0.029 g, 30%).

$^1$H NMR (CD$_3$OD) δ 7.52 (d, 1H), 3.78–3.90 (m, 1H), 2.80–2.95 (m, 1H), 2.71 (s, 3H), 2.46–2.50 (m, 2H), 2.09–2.24 (m, 2H), 1.87 (s, 3H), 1.59–1.72 (m, 1H), 1.10–1.49 (m, 7H), 0.82, 0.87 (2t, 6H). MS: (M+H)$^+$=327, (M+NH4)$^+$=344.

EXAMPLE 23

(1R,3R,4R,1'S)-3-(Imidazol-4-yl)-4-(1'-Acetamido-3'-Methyl)butyl-cyclopentane-1-carboxylic Acid

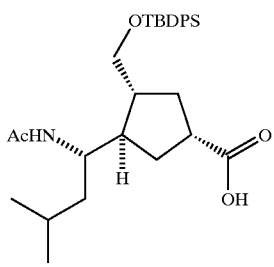

23A. (1R,3R,4R,1'S) 3-(t-Butyldiphenylsilyloxymethyl)-4-(1'-Acetamido-3'-Methyl)butyl-cyclopentane-1-carboxylic Acid.

The title compound was prepared by the methods described in Examples 13F–13J substituting isobutylmagnesium bromide for 3-pentylmagnesium bromide in Example 13F and substituting the resulting products in the subsequent steps.

$^1$H NMR (d$_4$-methanol) δ 7.68 (m, 4H), 7.42 (m, 6H), 3.88 (m, 1H), 3.74 (2d, 1H), 3.48 (2d, 1H), 2.77 (m, 1H), 2.15–2.27 (m, 2H), 1.68–2.05 (m, 3H), 1.80 (s, 3H), 1.5 (m, 1H), 1.1–1.32 (m, 2H), 1.03 (s, 9H), 0.84 (2d, J=6.44 Hz, 6H).

MS: (M–H)$^-$=508; (M+H)$^+$=510, (M+Na)$^+$=532.

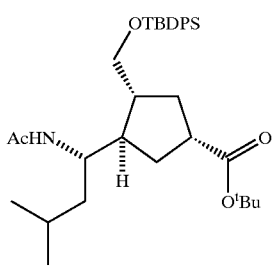

23B. (1R,3R,4R,1'S)-3-(t-Butyldiphenylsilyloxymethyl)-4-(1'-Acetamido-3'-Methyl)butyl-cyclopentane-1-carboxylic Acid t-Butyl Ester.

(1R,3R,4R,1'S)-3-(t-Butyldiphenylsilyloxymethyl)-4-(1'-Acetamido-3'-Methyl)butyl-cyclopentane-1-carboxylic acid (0.65 g, 1.27 mmol) was reacted with t-butyl trichloroacetimidate (1.36 mL, 7.56 mmol) in toluene at 100° C. for 16 hours. The reaction was quenched with water (20 mL) and diluted with ethyl acetate (50 mL). The organic layer was washed with water, and brine, dried over MgSO$_4$, filtered and concentrated in vacuo. The residue was purified by chromatography on silica gel using 7% methanol/dichloromethane to provide the title compound (yield: 0.65 g, 90%).

$^1$H NMR (d$_4$-methanol) δ 7.65 (m, 4H), 7.4 (m, 6H), 3.88 (m, 1H), 3.72 (2d, 1H), 3.46 (2d, 1H), 2.68 (m, 1H), 2.12 (m, 1H), 1.76–2.0 (m, 2H), 1.79 (s, 3H), 1.68 (m, 1H), 1.48 (m, 1H), 1.42 (s, 9H), 1.1–1.32 (m, 2H), 0.84 (2d, J=6.44 Hz, 6H). MS: (M–H)$^-$=564, (M+35)$^-$=600; (M+H)$^+$=566, (M+Na)$^+$=588.

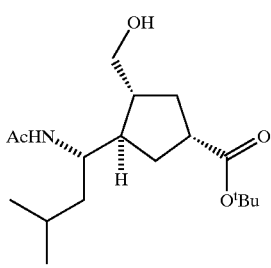

23C. (1R,3R,4R,1'S)-3-Hydroxymethyl-4-(1'-Acetamido-3'-Methyl)butyl-cyclopentane-1-carboxylic Acid t-Butyl Ester The title compound was prepared according to the method described in Example 13K substituting (1R,3R,4R,1'S) 3-(t-butyldiphenylsilyloxymethyl)-4-(1'-Acetamido-3'-Methyl)butyl-cyclopentane-1-carboxylic acid t-butyl ester for (1R,3R,4R,1'S)-3-(t-butyldiphenylsilyloxymethyl)-4-(1'-Acetamido-3'-ethyl)pentyl-cyclopentane-1-carboxylic acid (yield: 0.35 g, 93%).

$^1$H NMR ($d_4$-methanol) δ 3.88 (m, 1H), 3.58 (2d, 1H), 3.35 (2d, 1H), 2.7 (m, 1H), 2.08 (m, 1H), 1.95 (s, 3H), 1.94 (m, 1H), 1.78 (m, 1H), 1.5–1.7 (m, 3H), 1.43 (s, 9H), 1.2–1.4 (m, 2H), 0.9 (2d, J=6.44 Hz, 6H). MS: (M–H)$^-$=326, (M+35)$^-$=362; (M+H)$^+$=328, (M+Na)$^+$=350.

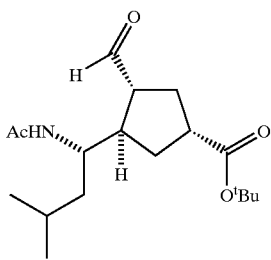

23D. (1R,3R,4R,1'S)-3-Formyl-4-(1'-Acetamido-3'-Methyl)butyl-cyclopentane-1-carboxylic Acid t-Butyl Ester The title compound was prepared according to the method described in Example 1D substituting (1R,3R,4R,1'S)-3-hydroxymethyl-4-(1'-Acetamido-3'-Methyl)butyl-cyclopentane-1-carboxylic acid t-butyl ester for (±)-(2R,3S)-2-(t-butyloxycarbonylamino)-3-hydroxymethylbicyclo[2.2.1]hept-5-ene (yield: 0.32 g, 92%).

$^1$H NMR ($d_4$-methanol) δ 9.5 (d, 1H), 7.85 (d, 1H), 3.88 (m, 1H), 2.85 (m, 1H), 2.62 (m, 1H), 2.47 (m, 1H), 2.05 (m, 2H), 1.91 (m, 1H), 1.87 (s, 3H), 1.5–1.72 (m, 2H), 1.44 (s, 9H), 1.23–1.4 (m, 2H), 0.9 (2d, J=6.44 Hz, 6H). MS: (M–H)$^-$=324; (M+H)$^+$=326, (M+Na)$^+$=348.

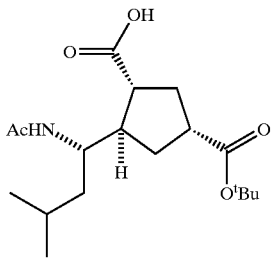

23E. (1R,3R,4R,1'S)-3-Carboxyl-4-(1'-Acetamido-3'-Methyl)butyl-cyclopentane-1-carboxylic Acid t-Butyl Ester A solution of (1R,3R,4R,1'S)-3-formyl-4-(1'-Acetamido-3'-Methyl)butyl-cyclopentane-1-carboxylic acid t-butyl ester (0.3 g, 0.93 mmol) and 2-methyl-2-butene (1.5 mL, 14.15 mmol) dissolved in t-BuOH (7.5 mL) and acetonitrile (7.5 mL) was reacted with a solution of NaClO$_2$ (0.3 g, 3.31 mmol) and NaH$_2$PO$_4$·H$_2$O (0.3 g, 2.17 mmol) in water (6 mL) at 0° C. for 1 hour. The reaction was quenched with 10% aqueous Na$_2$S$_2$O$_3$ and extracted with dichloromethane. The organic layer was washed with water and brine, dried (MgSO$_4$) and concentrated in vacuo. The residue was purified by chromatography on silica gel using 9% methanol/dichloromethane to provide the title compound (yield: 0.286 g, 90.8%).

$^1$H NMR ($d_4$-methanol) δ 3.86 (m, 1H), 2.8 (m, 1H), 2.7 (m, 1H), 2.4 (m, 1H), 2.22 (m, 1H), 2.08 (m, 1H), 1.97 (m, 1H), 1.90 (s, 3H), 1.5–1.68 (m, 2H), 1.44 (s, 9H), 1.23–1.4 (m, 2H), 0.9 (2d, J=6.44 Hz, 6H). MS: (M–H)$^-$=340, (M+35)$^-$=376; (M+H)$^+$=342, (M+Na)$^+$=364.

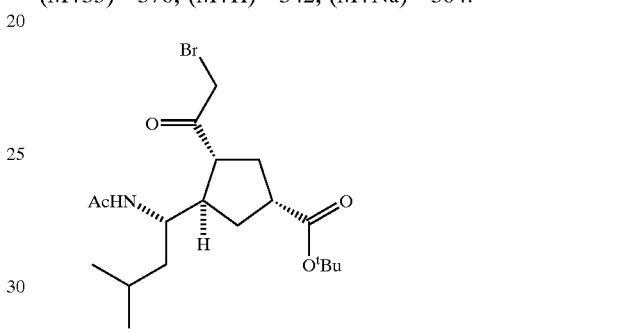

23F. (1R,3R,4R,1'S) 3-(2-Bromo-1-oxo)ethyl-4-(1-Acetamido-3-Methyl)butyl-cyclopentane-1-carboxylic Acid t-Butyl Ester (1R,3R,4R,1'S)-3-Carboxyl-4-(1'-Acetamido-3'-Methyl)butyl-cyclopentane-1-carboxylic acid t-butyl ester (286 mg, 0.84 mmol) and N-methylmorpholine (111 μL, 1.01 mmol) in ether (15 mL) was reacted with isobutyl chloroformate (120 μL, 0.93 mmol) at 0° C. for 45 minutes. To the reaction flask was cannulated a distilled diazomethane solution in ether prepared from the reaction of Diazald (2.4 g) in ether (60 mL) with a solution of potassium hydroxide (2.4 g) in ethanol (15 mL) and water (15 mL). The reaction was stirred for 8 hours at room temperature then diluted with ether. The organic layer was washed with brine, dried (Na$_2$SO$_4$) and concentrated to give the intermediate diazo ketone. The diazoketone was reacted with 48% HBr (90 μL) in dioxane (10 mL) at 23° C. for 45 minutes. The reaction was quenched with water (50 mL) and diluted with ethyl acetate (200 mL). The organic layer was washed with water, and brine, dried over MgSO$_4$, filtered and concentrated in vacuo. The residue was purified by chromatography on silica gel using 20% ethyl acetate/hexane to provide the title compound (yield: 105 mg, 33%).

$^1$H NMR ($d_4$-methanol) δ 4.18 (2d, J=14.07 Hz, 2H), 3.8 (m, 1H), 3.08 (m, 1H), 2.83 (m, 1H), 2.48 (m, 1H), 2.3 (m, 1H), 2.07 (m, 1H), 1.89 (s, 3H), 1.45 (m, 1H), 1.5–1.7 (m, 2H), 1.15–1.46 (m, 2H), 1.43 (s, 9H), 1.2–1.4 (m, 3H), 0.88 (2d, J=6.44 Hz, 6H). MS: (M–H)$^-$=372; (M+H)$^+$=374.

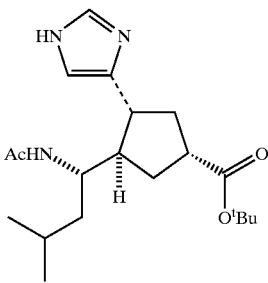

23G. (1R,3R,4R,1'S)-3-(Imidazol-4-yl)-4-(1'-Acetamido-3'-Methyl)butyl-cyclopentane-1-carboxylic Acid t-Butyl Ester (1R,3R,4R,1'S)-3-(2-Bromo-1-oxo)ethyl-4-(1'-Acetamido-3'-Methyl)butyl-cyclopentane-1-carboxylic acid t-butyl ester (105 mg, 0.28 mmol) was reacted with formamidine acetate (0.52 g, 4.99 mmol) in liquid ammonia (5 mL) and heated at 45° C. in a sealed tube for 18 hours. The reaction was concentrated in vacuo. The residue was treated with aqueous NaHCO$_3$ and extracted with dichloromethane (5×20 mL). The combined organic layers were washed with brine, dried over sodium sulfate, filtered and concentrated in vacuo. The residue was purified by chromatography on silica gel using 10% methanol in dichloromethane to provide the title compound as an oil (40 mg, 39%).

$^1$H NMR(d$_4$-methanol) δ 7.57 (br s, 1H), 6.81 (br s, 1H), 3.93 (m, 1H), 2.96 (m, 1H), 2.7 (m, 1H), 2.1–2.4 (m, 3H), 1.85 (m, 1H), 1.72 (s, 3H), 1.48 (m, 1H), 1.43 (s, 9H), 1.15–1.46 (m, 2H), 0.85 (2d, J=6.44 Hz, 6H). MS: (M–H)$^-$=362, (M+35)$^-$=398; (M+H)$^+$=364, (M+Na)$^+$=386.

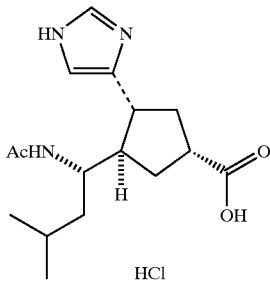

23G. (1R,3R,4R,1'S)-3-(Imidazol-4-yl)-4-(1'-Acetamido-3'-Methyl)butyl-cyclopentane-1-carboxylic Acid Hydrochloride (1R,3R,4R,1'S) 3-(imidazol-4-yl)-4-(1'-Acetamido-3'-Methyl)butyl-cyclopentane-1-carboxylic acid t-butyl ester (40 mg, 0.11 mmol) was reacted with 6N HCl (4 mL) for 1 hour. The reaction concentrated in vacuo to provide the title compound (yield: 37 mg, 98%).

$^1$H NMR (d$_4$-methanol) δ 8.83 (d, J=1.01 Hz, 1H), 7.36 (d, J=1.01 Hz, 1H), 3.92 (m, 1H), 3.18 (m, 1H), 2.98 (m, 1H), 2.49 (m, 2H), 2.22 (m, 1H), 1.90 (m, 2H), 1.77 (s, 3H), 1.53 (m, 1H), 1.41 (m, 1H), 1.25 (m, 1H), 0.86 (2d, J=6.45 Hz, 6H). MS: (M–H)$^-$=306, (M+35)$^-$=342; (M+H)$^+$=308, (M+Na)$^+$=330.

EXAMPLE 24

(3R,4R,1'S)-4-(Imidazol-2-yl)-3-(1'-Acetamido-3'-ethyl)pentyl-cyclopent-1-ene-1-carboxylic Acid

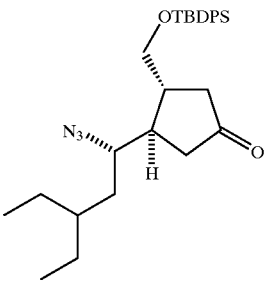

24A. (3R,4R,1'S)-3-(t-Butyldiphenylsilyloxymethyl)-4-(1'-azido-3'-ethyl)pentyl-cyclopentan-1-one (3R,4R,1'S)-3-(t-Butyldiphenylsilyloxymethyl)-4-(1'-azido-3'-ethyl)pentyl-1-methylene-cyclopentane (0.455 g, 0.93 mmol) was reacted with 4% osmium tetroxide in water (0.59 mL, 0.093 mmol) and sodium periodate (0.8 g, 3.73 mmol) in THF (15 mL) and water (3 mL) at room temperature for 3 hours. The mixture was filtered and the filtrate was diluted with ethyl acetate, washed with 10% Na$_2$S$_2$O$_3$ solution, water, dried over MgSO$_4$, filtered, and concentrated in vacuo. Chromatography on silica gel using 10% ethyl acetate/hexane afforded the title compound (yield: 240 mg, 52%).

$^1$H NMR (CDCl$_3$) δ 7.64 (m, 4H), 7.4 (m, 6H), 3.68 (m, 2H), 3.36 (m, 1H), 2.3–2.6 (m, 4H), 2.23 (2d, 1H), 2.08 (m, 1H), 1.16–1.52 (m, 6H), 1.05 (s, 9H), 0.78–0.88 (2t, J=7.12 Hz, 6H). MS: (M+18)$^+$=509, (M+Na)$^+$=514.

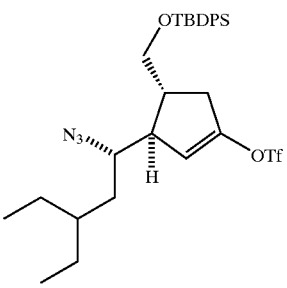

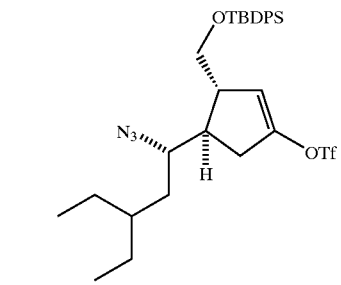

24B. (3R,4R,1'S)4-(t-Butyldiphenylsilyloxymethyl)-3-(1'-azido-3'-ethyl)pentyl-1-trifluoromethansulfonyloxy-cyclopent-1-ene and (3R,4R,1'S)-3-(t-Butyldiphenylsilyloxamethyl)-4-(1'-azido-3'-ethyl)pentyl-1-trifluoromethansulfonyloxy-cyclopent-2-ene (3R,4R,1'S)-3-(t-Butyldiphenylsilyloxymethyl)-4-(1-azido-3-ethyl)pentyl-cyclopentan-1-one (230 mg, 0.468 mmol) was reacted with 1M lithium hexamethyldisilazide (1.17 mL) in THF (1 mL) at −78° C. for 45 minutes. The reaction mixture was treated with N-phenyltrifluoromethanesulfonimide (0.2 g, 0.56 mmol) and reacted at 0° C. for 0.5 hour. The reaction was quenched with water (10 mL) and diluted with ethyl acetate (50 mL). The organic layer was washed with water, brine, dried over MgSO₄, filtered and concentrated in vacuo. The residue was purified by chromatography on silica gel using 5% ethyl acetate/hexane to provide a mixture of the title compounds in a ratio of 3:2 (yield: 280 mg, 96%).

$^1$H NMR (CDCl₃) δ 7.64 (m, 4H), 7.4 (m, 6H), 5.58–5.5 (m, 1H), 3.55–3.72 (m, 2H), 3.36 (m, 1H), 2.7–2.83 (m, 2H), 2.3–2.47 (m, 2H), 1.16–1.5 (m, 6H), 1.05 (s, 9H), 0.78–0.9 (m, 6H).

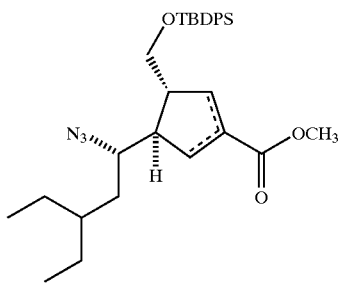

24C. (3R,4R,1'S)-4-(t-Butyldiphenylsilyloxymethyl)-3-(1'-azido-3'-ethyl)pentyl-cyclopent-1-ene-1-carboxylic Acid Methyl Ester and (3R,4R,1'S)-3-(t-Butyldiphenylsilyloxymethyl)-4-(1'-azido-3'-ethyl)pentyl-1-cyclopent-1-ene1-carboxylic Acid Methyl Ester Carbon monoxide was bubbled into a mixture consisting of (3R,4R,1'S)-4-(t-Butyldiphenylsilyloxymethyl)-3-(1'-azido-3'-ethyl)pentyl-1-trifluoromethansulfonyloxy-cyclopent-1-ene and (3R,4R,1'S)-3-(t-Butyldiphenylsilyloxymethyl)-4-(1'-azido-3'-ethyl)pentyl-1-trifluoromethansulfonyloxy-cyclopent-1-ene (280 mg, 0.45 mmol), triethylamine (0.125 mL, 0.9 mmol), bis(acetato)bis(triphenylphosphine)palladium(II) (34 mg, 0.045 mmol) in DMF (4 mL) and methanol (2 mL) at 40° C. for 2 hours. The reaction was quenched with water (10 mL) and diluted with ethyl acetate (50 mL). The organic layer was washed with water, brine, dried over MgSO₄, filtered and concentrated in vacuo. The residue was purified by chromatography on silica gel using 5% ethyl acetate/hexane to provide the title compounds in a ratio of 3:2 as a mixture (yield: 181 mg, 75%).

$^1$H NMR (CDCl₃) δ 7.64 (m, 4H), 7.4 (m, 6H), 6.58–6.7 (2 br s, 1H), 3.74 (brs, 3H), 3.25–3.62 (m, 3H), 2.7–2.95 (m, 2H), 2.22–2.49 (m, 2H), 1.16–1.5 (m, 6H), 1.05 (s, 9H), 0.78–0.9 (m, 6H). MS: (M+18)⁺=551, (M+Na)⁺=556.

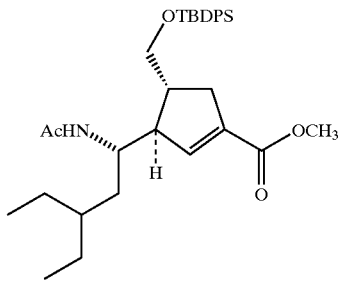

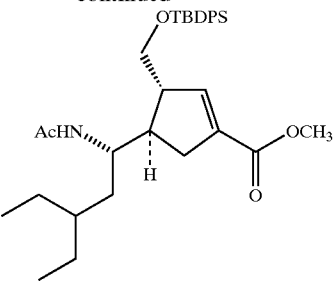

24D. (3R,4R,1'S)4-(t-Butyldiphenylsilyloxymethyl)-3-(1'-Acetamido-3'-ethyl)pentyl-cyclopent-1-ene-1-carboxylic Acid Methyl Ester and (3R,4R,1'S)-3-(t-Butyldiphenylsilyloxymethyl)-4-(1'-Acetamido-3'-ethyl) pentyl-cyclopent-1-ene-1-carboxylic Acid Methyl Ester A solution of the mixture of (3R,4R,1'S)-4-(t-butyldiphenylsilyloxymethyl)-3-(1'-azido-3'-ethyl)pentyl-1-trifluoromethansulfonyloxy-cyclopent-1-ene-1-carboxylic acid methyl ester and (3R,4R,1'S)-3-(t-butyldiphenylsilyloxymethyl)-4-(1'-azido-3'-ethyl)pentyl-1-trifluoromethansulfonyloxy-cyclopent-1-ene-1-carboxylic acid methyl ester (0.18 g, 0.33 mmol) in THF (12 mL) and water (3 mL) was reacted with triphenylphosphine (0.265 mg, 1.01 mmol) at 65° C. for 4 hours. The reaction mixture was concentrated in vacuo, redissolved in chloroform, dried over MgSO₄, filtered and concentrated in vacuo. The crude amine was reacted with acetic anhydride (64 μL, 0.67 mmol) in pyridine (0.135 mL, 1.67 mmol) and dichloromethane (1 mL) at room temperature for 2 hours. The reaction was quenched with 10% citric acid solution (10 mL) and diluted with ethyl acetate (50 mL). The organic layer was washed with water, and brine, dried over MgSO₄, filtered and concentrated in vacuo. The residue was purified by chromatography on silica gel using 40% ethyl acetate/hexane to provide the title compounds (3R,4R,1'S)-4-(t-butyldiphenylsilyloxymethyl)-3-(1'-Acetamido-3'-ethyl) pentyl-cyclopent-1-ene-1-carboxylic acid methyl ester (yield: 109 mg, 60%) and (3R,4R,1'S)-3-(t-butyldiphenylsilyloxymethyl)-4-(1'-Acetamido-3'-ethyl) pentyl-cyclopent-1-ene-1-carboxylic acid methyl ester (yield: 37 mg, 20%).

(3R,4R,1'S)-4-(t-butyldiphenylsilyloxymethyl) $^1$H NMR (CDCl₃) δ 7.63 (m, 4H), 7.4 (m, 6H), 6.58 (s, 1H), 4.95 (br s, 1H), 4.0 (br s, 1H), 3.73 (s, 3H), 3.57 (d, 2H), 2.72 (m, 2H), 1.78 (s, 3H), 1.47 (m, 3H), 1.18 (m, 3H), 1.06 (s, 9H), 0.74–0.88 (2t, J=7.12 Hz, 6H). MS: (M−H)⁻=548, (M+35)⁻=584; (M+H)⁺=550, (M+Na)⁺=572.

(3R,4R,1'S)-3-(t-butyldiphenylsilyloxymethyl) $^1$H NMR (CDCl₃) δ 7.63 (m, 4H), 7.4 (m, 6H), 6.64 (d, 1H), 4.72 (d, 1H), 3.95 (m, 1H), 3.74 (s, 3H), 3.73 (2d, 1H), 3.57 (2d, 1H), 2.9 (m, 1H), 2.75 (m, 1H), 2.3 (m, 1H), 2.14 (m, 1H), 1.71 (s, 3H), 1.45 (m, 3H), 1.18 (m, 3H), 1.05 (s, 9H), 0.72–0.86 (2t, J=7.12 Hz, 6H). MS: (M−H)⁻=548, (M+35)⁻=584; (M+H)⁺=550, (M+Na)⁺=574.

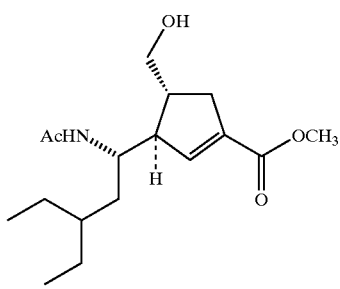

24E. (3R,4R,1'S)-4-Hydroxymethyl-3-(1'-Acetamido-3'-ethyl)pentyl-cyclopent-1-ene1-carboxylic Acid Methyl Ester The title compound was prepared according to the method described in Example 13K substituting (3R,4R,1'S)-4-(t-butyldiphenylsilyloxymethyl)-3-(1-Acetamido-3-ethyl)pentyl-1-trifluoromethansulfonyloxy-cyclopent-1-ene-1-carboxylic acid methyl ester for (1R,3R,4R,1'S)-3-(t-butyldiphenylsilyloxymethyl)-4-(3-ethyl-1-acetamido)pentyl-cyclopentane-1-carboxylic acid (yield: 53 mg, 85%).

$^1$H NMR (CDCl$_3$) δ 6.63 (m, 1H), 5.49 (d, 1H), 3.98 (m, 1H), 3.74 (s, 3H), 3.5–3.7 (m, 2H), 2.87 (m, 1H), 2.75 (m, 1H), 2.2–2.4 (m, 2H), 1.99 (s, 3H), 1.17–1.48 (m, 8H), 0.78–0.87 (2t, J=7.12 Hz, 6H). MS: (M–H)$^-$=310, (M+35)$^-$=346; (M+H)$^+$=312, (M+Na)$^+$=334.

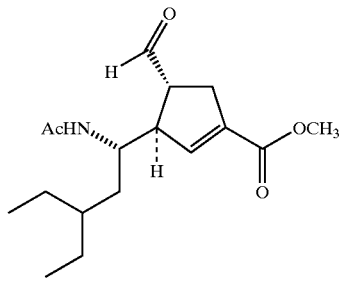

24F. (3R,4R,1'S)-4-Formyl-3-(1-Acetamido-3-ethyl)pentyl-cyclopent-1-ene-1-carboxylic Acid Methyl Ester The title compound was prepared according to the method described in Example 1D substituting (3R,4R,1'S)-4-hydroxymethyl-3-(1'-Acetamido-3'-ethyl)pentyl-cyclopent-1-ene-1-carboxylic acid methyl ester for (±)-(2R,3S)-2-(t-butyloxycarbonylamino)-3-hydroxymethyl-bicyclo[2.2.1]hept-5-ene (yield: 38 mg, 72%).

$^1$H NMR (CDCl$_3$) δ 9.71 (s, 1H), 6.62 (m, 1H), 5.2 (d, 1H), 4.06 (m, 1H), 3.75 (s, 3H), 3.25 (m, 1H), 3.1 (m, 1H), 2.96 (m, 1H), 2.83 (m, 1H), 1.96 (s, 3H), 1.2–1.5 (m, 8H), 0.77–0.9 (2t, J=7.12 Hz, 6H). MS: (M–H)$^-$=308; (M+H)$^+$=310.

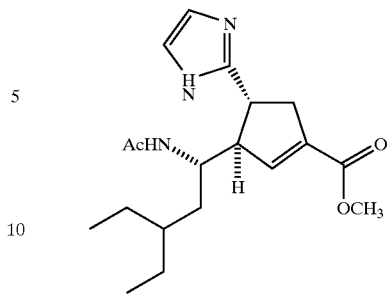

24G. (3R,4R,1'S)-4-(Imidazol-2-yl)-3-(1'-Acetamido-3'-ethyl)pentyl-cyclopent-1-ene1-carboxylic Acid Methyl Ester The title compound was prepared according to the method described in Example 15D substituting (3R,4R,1'S)-4-formyl-3-(1'-Acetamido-3'-ethyl)pentyl-cyclopent-1-ene1-carboxylic acid methyl ester for (1R,3R,4R,1'S)-1-formyl-2-(1'-Acetamido-3'-ethyl)pentyl-4-(triphenylmethyloxy)methyl-cyclopentane (yield: 6 mg, 14%).

$^1$H NMR (CDCl$_3$) δ 7.06 (s, 2H), 6.69 (s, 1H), 3.95 (m, 1H), 3.74 (s, 3H), 3.5–3.7 (m, 2H), 3.23 (m, 1H), 2.8 (m, 1H), 1.90 (s, 3H), 1.1–1.5 (m, 8H), 0.73–0.87 (2t, J=7.12 Hz, 6H). MS: (M–H)$^-$=346, (M+35)$^-$=382; (M+H)$^+$=348, (M+Na)$^+$=370.

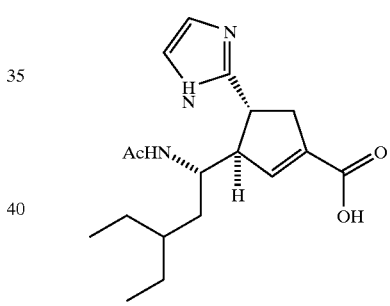

24H. (3R,4R,1'S)-4-(Imidazol-2-yl)-3-(1'-Acetamido-3'-ethyl)pentyl-cyclopent-1-ene-1-carboxylic Acid (3R,4R,1'S)4-(imidazol-2-yl)-3-(1'-Acetamido-3'-ethyl)pentyl-cyclopent-1-ene-1-carboxylic acid methyl ester (6 mg, 0.017 mmol) was reacted with lithium hydroxide (1 mg, 0.026 mmol) in THF (0.5 mL) and water (0.2 mL) at 0° C. for 4 hours. The reaction was quenched with 10% citric acid (1 mL) and diluted with 25% isopropanol/dichloromethane (10 mL). The organic layer was washed with water, and brine, dried over MgSO$_4$, filtered and concentrated in vacuo. The residue was purified by chromatography on silica gel using 1:3:1:1 water/ethyl acetate/n-butanol/acetic acid followed by extraction into 25% isopropanol/dichloromethane to provide the title compound (yield: 4.3 mg, 74%).

$^1$H NMR (d$_4$-methanol) δ 7.06 (br s, 2H), 6.48 (br s, 1H), 4.08 (m, 1H), 3.45–3.7 (m, 2H), 3.1 (m, 1H), 2.62 (m, 1H), 1.98 (br s, 2H), 1.82 (br s, 3H), 1.1–1.42 (m, 8H), 0.73–0.87 (m, 6H). MS: (M–H)$^-$=332, (M+35)$^-$=368; (M+H)+334, (M+Na)$^+$356.

EXAMPLE 25

(1S,2S,3R,4R,1'R,2'S)-3-(1'-Acetamido-2'-methoxy-2'-Methyl)pentyl-4-amino-2-hydroxycyclopentan-1-carboxylic Acid

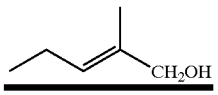

25A (2E)-2-Methyl-2-penten-1-ol

A solution of methyl 2-methyl-2-pentenoate (6.37 g, 49.6 mmol) in ether (120 mL) was added to a mixture of lithium aluminum hydride (4.72 g, 124.2 mmol) in ether (180 mL) at 0° C. and stirred at 25° C. for 1.5 h. After recooling to 0° C. the reaction was quenched (water, 4.7 mL; 15% NaOH, 4.7 mL; water, 14.1 mL). The mixture was filtered, dried, refiltered, and the solvent was evaporated. The crude product was distilled (55 torr, 85–87° C.) to give the allylic alcohol (3.96 g, 80%).

$^1$H NMR (CDCl$_3$) δ 5.44–5.38 (m, 1H), 4.0 (d, J=5.42 Hz, 2H), 2.10–2.00 (m, 2H), 1.67 (s, 3H), 1.0–0.95 (t, J=5.09 Hz, 3H).

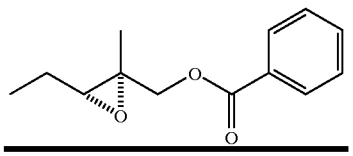

25B 3,4-Anhydro-1,2-dideoxy-4-methyl-D-threo-pentitol

A solution of the product of example 25A (5.1 g, 51 mmol) in dichloromethane (35 mL) was added to a mixture of (−)-dimethyl D-tartrate (0.545 g, 3.06 mmol), titanium tetraisopropoxide (0.76 g, 2.55 mmol), molecular sieves (4A, 1.8 g), and t-butyl hydroperoxide (5M solution in decane, 20 mL) in dichloromethane (180 mL) at −20° C., and the reaction mixture was stirred for 3.5 h. To this mixture was added trimethyl phosphite (9 mL, 76.5 mmol), triethylamine (8.5 mL, 61.2 mmol), and benzoyl chloride (5.92 mL, 51 mmol), and was stirred for 1.5 h before being washed with 10% tartaric acid (200 mL×2), saturated sodium bicarbonate (150 mL×3), and brine. The organic layer was dried, the solvent was evaporated and the residue was purified using hexanes-85% hexanes/ethyl acetate to give the title compound (7.35 g, 65%).

$^1$H NMR (CDCl$_3$) δ 8.18–7.42 (m, 5H), 4.31 (dd, J=1.87 and 6.45 Hz, 1H), 2.94 (t, J=6.45 Hz, 1H), 1.71–1.53 (m, 2H), 1.40 (s, 3H), 1.06 (t, J=7.46 Hz, 3H).

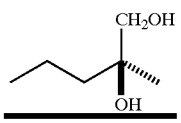

25C (2S)-2-Methyl-1,2-pentanediol

To a solution of lithium aluminum hydride (3.8 g, 0.1 mol) at 0° C. in tetrahydrofuran (THF) (160 mL) was added the product of example 25B (7.35 g, 0.033 mol) in THF (40 mL). After 0.5 h, the mixture is warmed to 25° C., recooled to 0° C. and quenched (water, 5 mL; 15% NaOH, 5 mL; water, 15 mL). The mixture was filtered, and the solvent was evaporated. The residue was purified using hexanes-60% hexanes/ethyl acetate to give the title compound (2.48 g, 63%).

$^1$H NMR (CDCl$_3$) δ 3.50–3.38 (m, 2H), 1.50–1.31 (m, 4H), 1.17 (s, 3H), 0.94 (t, J=7.1 Hz, 3H).

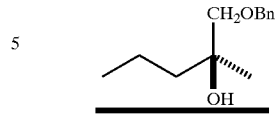

25D (2S)-1-(Benzyloxy)-2-methyl-2-pentanol

To a suspension of sodium hydride (95% powder, 5.08 g, 0.212 mol) in THF (210 mL) at 0° C. was added the product of example 25C (10.02 g, 0.085 mol) in THF (85 mL). After 1 h, benzyl bromide (12.1 mL, 0.102 mol) was added, and the reaction mixture was warmed to 25° C. for 16 h. The mixture was quenched with sat. NH$_4$Cl (30 mL), and the solvent was evaporated. The residue was partitioned between water and ether, the ether was separated and dried.

The crude product was purified using 100–85% hexanes-hexanes/ethyl acetate to give the title compound (17.26 g, 98%).

$^1$H NMR (CDCl$_3$) δ 7.39–7.27 (m, 5H), s(4.56, 2H), 3.31 (dd, J=8.82 and 16.96 Hz, 2H), 1.52–1.23 (m, 4H), 1.17 (s, 3H), 0.92 (t, J=7.12, 3H).

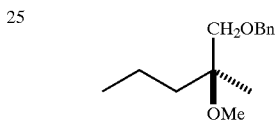

25E ((((2S)-2-Methoxy-2-methylpentyl)oxy)methyl)benzene

To a solution of the product of example 25D (17.26 g, 0.0829 mol) in THF (280 mL) at 0° C. was added sodium bis(trimethylsilyl)amide (NaHMDS) (1M in THF, 166 mL, 0.166 mol). After 1 h methyl iodide (25.8 mL, 0.415 mol) was added, and the mixture was warmed to 25° C. for 16 h. The mixture was quenched with sat. NH$_4$Cl (25 mL) and water (250 mL), the organic layer was separated and the aqueous layer was extracted with ether. The organic layers were combined, washed with brine, and dried. The solvent was evaporated, and the residue was purified using hexanes-90% hexanes/ethyl acetate to give the title compound (18.03 g, 98%).

$^1$H NMR (CDCl$_3$) δ 7.35–7.26 (m, 5H), 4.55 (s, 2H), 3.32 (dd, J=9.8 and 12.5 Hz, 2H), 3.22 (s, 3H), 1.58–1.42 (m, 2H), 1.34–1.22 (m, 2H), 1.14 (s, 3H), 0.90 (t, J=7.12 Hz, 3H).

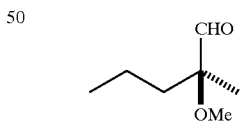

25F (2S)-2-Methoxy-2-methylpentanal

To a solution of the product of example 25E (5 g, 22.5 mmol) in dichloromethane (75 mL) was added Pd(OH)$_2$ (20% on carbon, 1.6 g) and the flask fitted with a hydrogen balloon. The mixture was stirred for 3.5 h after which the catalyst was filtered and rinsed with dichloromethane (75 mL). This solution was reacted directly with pyridinium chlorochromate (14.5 g, 67.5 mmol) at 0° C. with molecular sieves (4 A, 5 g) and Celite (5 g). The mixture was stirred for 1.5 h at 25° C. Ether (200 mL) was added and this solution was filtered through a short pad of silica gel with additional ether. The solvent was evaporated in a short-path distillation apparatus, and the product was distilled (60 torr, 72–75° C.) to give the title compound (1.4 g, 48% for two steps).

$^1$H NMR (CDCl$_3$) δ 9.21 (s, 1H), 3.28 (s, 3H), 1.64–1.51 (m, 2H), 1.38–1.23 (m, 2H), 1.22 (s, 3H), 0.92 (t, J=7.12 Hz, 3H).

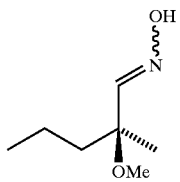

25G (2S)-2-Methoxy-2-methylpentyl-1-oxime

The product of example 25F is reacted with hydroxylamine hydrochloride and acetic acid sodium salt in ethanol as by the procedure of Elgamal, M. H. A. et. al., *Pol. J. Chem.* 1998, 72, 735–745 to give the title compound.

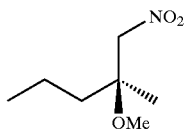

25H (2S)-2-Methoxy-2-methyl-1-nitropentane

The product of example 25G is reacted with trifluoroacetic anhydride and hydrogen peroxide in acetonitrile by the procedure of Kiess, F.-M. et. al, *J.C.S. Chem. Commun.* 1998, 119–120 to give the title compound.

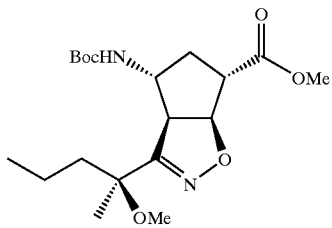

25I

The title compound is prepared by reacting a refluxing solution of (1 S,4R)-(−)-methyl-4-tert-butoxycarbonylaminocyclopent-2-en-1-carboxylate and phenyl isocyanate (3.5 equivalents) in benzene, with a solution of (2S)-2-methoxy-2-methyl-1-nitropentane (1.5 eq) and triethylamine (0.1 eq) in benzene by dropwise addition over a 3 hr period. The resulting reaction mixture is stirred at reflux overnight and then let cool to room temperatue. Any precipitate that forms during cooling is removed by filtration, the filtrate is concentrated in vacuo and purified by chromatography on silica gel providing the title compound.

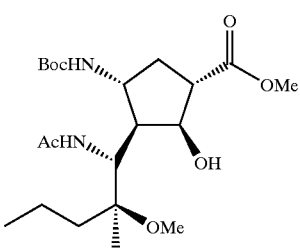

25J (1S,2S,3R,4R,1'R,2'S)-Methyl 3-(1'-Acetamido-2'-methoxy-2'-Methyl)pentyl-4-tert-butoxycarbonyl-amino-2-hydroxycyclopentan-1-carboxylate The product of example 25I (1 eq) is reacted with conc. hydrochloric acid (1 eq), and Adam's catalyst (PtO$_2$) in methanol under an atmosphere of 100 psi hydrogen . When complete, the catalyst is removed by filtration and the filtrate concentrated to (1S,2S,3R,4R,1'R,2'S)-methyl 3-(1'-amino-2'-methoxy-2'-Methyl)pentyl-4-tert-butoxycarbonylamino-2-hydroxycyclopentan-1-carboxylate hydrochloride which is used directly for acetylation.

To the above amine hydrochloride (1 eq) in dichloromethane, is added triethylamine (1 eq) and acetic anhydride (1.1 eq) at room temperature. When complete, the reaction is quenched with saturated NH$_4$Cl and diluted with ethyl acetate. The organic layer is washed with water, and brine, dried over MgSO$_4$, filtered and concentrated in vacuo. The residue is then purified by chromatography on silica gel to provide the title compound.

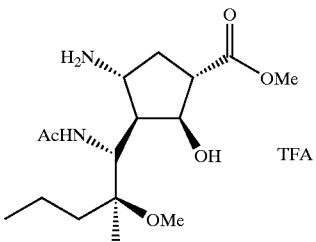

25K (1S,2S,3R,4R,1'R,2'S)-Methyl 3-(1'-Acetamido-2'-methoxy-2'-Methyl)pentyl-4-amino-2-hydroxycyclopentan-1-carboxylate Trifluoroacetic Acid Salt The product of example 25J is reacted with 80% trifluoroacetic acid in dichloromethane at room temperature. When complete, the reaction is concentrated in vacuo to provide the title compound.

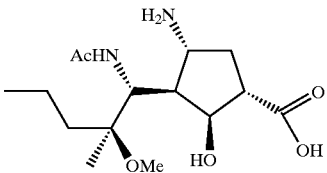

25L (1S,2S,3R,4R,1'R,2'S)-3-(1'-Acetamido-2'-methoxy-2'-Methyl)pentyl-4-amino-2-hydroxycyclopentan-1-carboxylic Acid.

The product of example 25K is dissolved in a mixture of 1 N aqueous sodium hydroxide and water in a 1 to 2 ratio respectively. This solution is stirred at room temperature for 3 h followed by adjustment of the solution to pH=2 by the addition of 1N aqueous hydrochloric acid solution. The solution is then concentrated in vacuo and purified by cation-exchange chromatography on Dowex 50W-X8 providing the title compound.

EXAMPLE 26

(1S,2S,3R,4R,1'R,2'S)-3-(1'-Acetamido-2'-methoxy-2'-Methyl)pentyl-4-[(amino-imino)methyl]amino-2-hydroxycyclopentan-1-carboxylic Acid

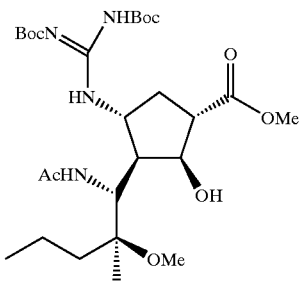

26A (1S,2S,3R,4R,1'R,2'S)-Methyl 3-(1'-Acetamido-2'-methoxy-2'-Methyl)pentyl-4-[(N-tert-butoxycarbonylamino-N'-tert-butoxycarbonylimino)methyl]amino-2-hydroxycyclopentan-1-carboxylate The product of example 25K is reacted with N,N'-bis(tert-butoxycarbonyl)-thiourea (1.5 eq.), triethylamine (5.0 eq.), and mercury(II) chloride (1.5 eq.) in dimethylformamide at room temperature. When complete, the reaction is diluted with ethyl acetate and filtered through a pad of celite. The organic solution is washed with water, and brine, dried over MgSO$_4$, filtered and concentrated in vacuo. The residue is then purified by chromatography on silica gel providing the title compound.

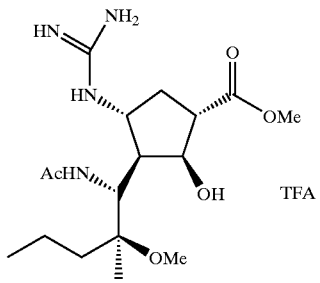

26B (1S,2S,3R,4R,1'R,2'S)-Methyl 3-(1'-Acetamido-2'-methoxy-2'-Methyl)pentyl-4-[(amino-imino)methyl]amino-2-hydroxycyclopentan-1-carboxylate Trifluoroacetic Acid Salt.

The title compound is prepared according to the procedure of example 25K substituting the product of example 26A for the product of example 25J.

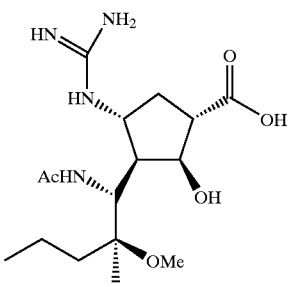

26C (1S,2S,3R,4R,1'R,2'S)-3-(1'-Acetamido-2'-methoxy-2'-Methyl)pentyl-4-[(amino-imino)methyl]amino-2-hydroxycyclopentan-1-carboxylic Acid.

The title compound is prepared according to the procedure of example 25L substituting the product of example 26B for the product of example 25K.

EXAMPLE 27

(1R,3R,4R,1'R,2'S)-3-(1'-Acetamido-2'-methoxy-2'-Methyl)pentyl-4-amino-cyclopentan-1-carboxylic Acid

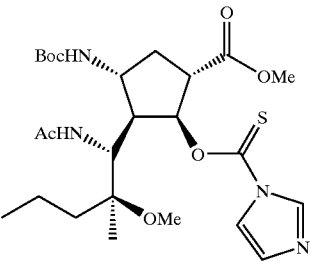

27A (1S,2S,3R,4R,1'R,2'S)-Methyl 3-(1'-Acetamido-2'-methoxy-2'-Methyl)pentyl-4-tert-butoxycarbonyl-amino-2-(N-imidazolyl-thiocarbonyloxy)cyclopentan-1-carboxylate.

The product of example 25J is reacted with 1,1'-thiocarbonyldiimidazole (2 eq.) in anhydrous THF at reflux. When complete, the solvent was concentrated in vacuo and the residue dissolved in ethyl acetate. The resulting solution is washed with 0.5 N aqueous HCl, the organic layer dried over MgSO$_4$, filtered and concentrated in vacuo. The residue is then purified by chromatography on silica gel to provide the title compound.

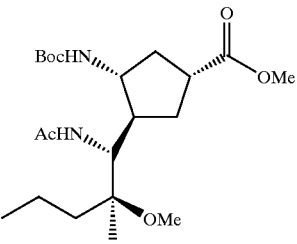

27B (1R,3R,4R,1'R,2'S)-Methyl 3-(1'-Acetamido-2'-methoxy-2'-Methyl)pentyl-4-tert-butoxycarbonylaminocyclopentan-1-carboxylate.

The product of example 27A is reacted with tributyltin hydride (1.5 eq.) and azobisisobutyronitrile (AIBN, 0.1 eq.) in toluene at 70° C. When complete, the reaction is diluted with ethyl acetate, the organic layer is washed with water, and brine, dried over MgSO$_4$, filtered and concentrated in vacuo. The residue is then purified by chromatography on silica gel to provide the title compound.

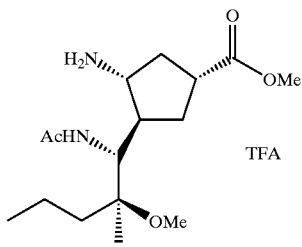

27C (1R,3R,4R,1'R,2'S)-Methyl 3-(1'-Acetamido-2'-methoxy-2'-Methyl)pentyl-4-aminocyclopentan-1-carboxylate Trifluoroacetic Acid Salt.

The title compound is prepared according to the procedure of example 25K substituting the product of example 27B for the product of example 25J.

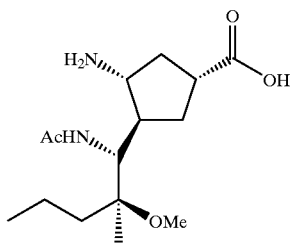

27D (1R,3R,4R,1'R,2'S)-3-(1'-Acetamido-2'-methoxy-2'-Methyl)pentyl-4-aminocyclopentan-1-carboxylic Acid.

The title compound is prepared according to the procedure of example 25L substituting the product of example 27C for the product of example 25K.

EXAMPLE 28

(1S,2S,3R,4R,1'R,2'S)-3-(1'-Acetamido-2'-methoxy-2'-Methyl)pentyl-4-[(amino-imino)methyl] aminocyclopentan-1-carboxylic Acid

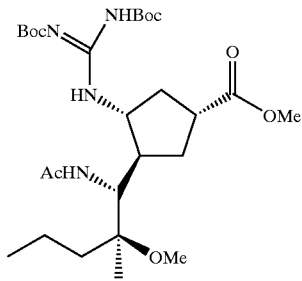

28A (1R,3R,4R,1'R,2'S)-Methyl 3-(1'-Acetamido-2'-methoxy-2'-Methyl)pentyl-4-[(N-tert-butoxycarbonylamino-N'-tert-butoxycarbonylimino) methyl]aminocyclopentan-1-carboxylate The title compound is prepared according to the procedure of example 26A substituting the product of example 27C for the product of example 25K.

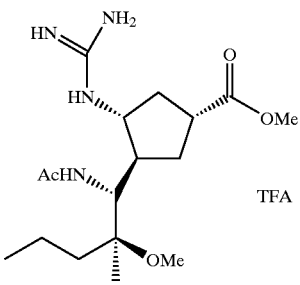

28B (1R,3R,4R,1'R,2'S)-Methyl 3-(1'-Acetamido-2'-methoxy-2'-Methyl)pentyl-4-[(amino-imino)methyl] aminocyclopentan-1-carboxylate Trifluoroacetic Acid Salt.

The title compound is prepared according to the procedure of example 25K substituting the product of example 28A for the product of example 25J.

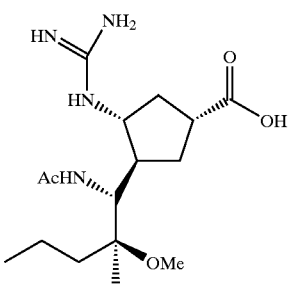

28C (1R,3R,4R,1'R,2'S)-3-(1'-Acetamido-2'-methoxy-2'-Methyl)pentyl-4-[(amino-imino)methyl]aminocyclopentan-1-carboxylic Acid.

The title compound is prepared according to the procedure of example 25L substituting the product of example 28B for the product of example 25K.

EXAMPLE 29

(3R,4R,1'R,2'S)-3-(1'-Acetamido-2'-methoxy-2'-Methyl)pentyl-4-aminocyclopent-1-ene-1-carboxylic Acid

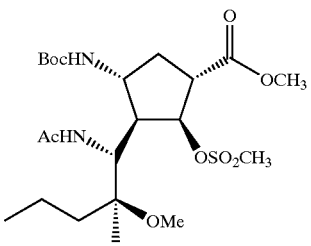

29A (1S,2S,3R,4R,1'R,2'S)-Methyl 3-(1'-Acetamido-2'-methoxy-2'-Methyl)pentyl-4-tert-butoxycarbonylamino-2-methylsulfonyloxy-cyclopentane-1-carboxylate.

The product of example 25J is reacted with methanesulfonyl chloride (2 eq.) and triethylamine in anhydrous dichloromethane at 0° C. When complete, the solvent was concentrated in vacuo and the residue dissolved in ethyl acetate. The resulting solution is washed with 0.5 N aqueous HCl, the organic layer dried over MgSO$_4$, filtered and concentrated in vacuo. The residue is then purified by chromatography on silica gel to provide the title compound.

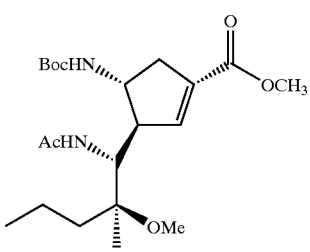

29B (3R,4R,1'R,2'S)-Methyl 3-(1'-Acetamido-2'-methoxy-2'-Methyl)pentyl-4-tert-butoxycarbonylaminocyclopent-1-ene-1-carboxylate.

The product of example 29A is reacted with sodium methoxide in methanol at 0° C. When complete, reaction was neutralized with 0.01N HCl and diluted with ethyl acetate. The organic layer was washed with water, brine and dried over MgSO$_4$, filtered and concentrated in vacuo. The residue is then purified by chromatography on silica gel to provide the title compound.

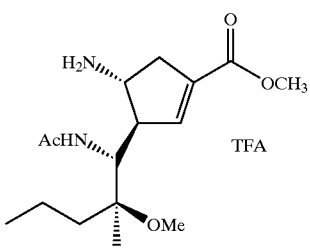

29C (3R,4R,1'R,2'S)-Methyl 3-(1'-Acetamido-2'-methoxy-2'-Methyl)pentyl-4-aminocyclopent-1-ene-1-carboxylate Trifluoracetic Acid Salt The title compound is prepared according to the procedure of example 25K substituting the product of example 29B for the product of example 25J.

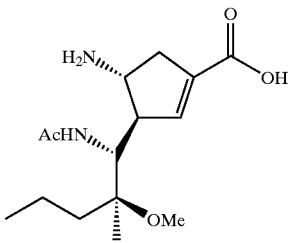

29D (3R,4R,1'R,2'S)-Methyl 3-(1'-Acetamido-2'-methoxy-2'-Methyl)pentyl-4-aminocyclopent-1-ene-1-carboxylic Acid The title compound is prepared according to the procedure of example 25L substituting the product of example 29C for the product of example 25K.

EXAMPLE 30

(3R,4R,1'R,2'S)-3-(1'-Acetamido-2'-methoxy-2'-Methyl)pentyl-4-[(amino-imino)methyl]aminocyclopent-1-ene-1-carboxylic Acid

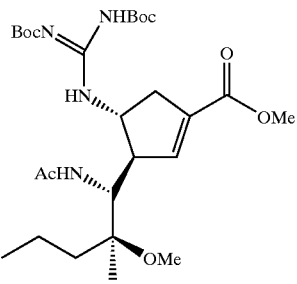

30A (3R,4R,1'R,2'S)-Methyl 3-(1'-Acetamido-2'-methoxy-2'-Methyl)pentyl-4-[(N-tert-butoxycarbonylamino-N'-tert-butoxycarbonylimino)methyl]aminocyclopent-1-ene-1-carboxylate The product of example 29C is reacted with 1,3-bis-(tert-butoxycarbonyl)-2-methyl-2-thiopseudourea (1.5 eq.), triethylamine (5.0 eq.), and mercury(II) chloride (1.5 eq.) in dimethylformamide at room temperature. When complete, the reaction is diluted with ethyl acetate and filtered through a pad of celite. The organic solution is washed with water, and brine, dried over MgSO$_4$, filtered and concentrated in vacuo. The residue is then purified by chromatography on silica gel providing the title compound.

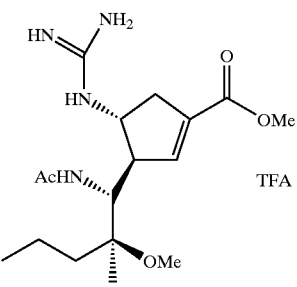

30B (3R,4R,1'R,2'S)-Methyl 3-(1'-Acetamido-2'-methoxy-2'-Methyl)pentyl-4-[(amino-imino)methyl]aminocyclopent-1-ene-1-carboxylate Trifluoroacetic Acid Salt.

The title compound is prepared according to the procedure of example 25K substituting the product of example 30A for the product of example 25J.

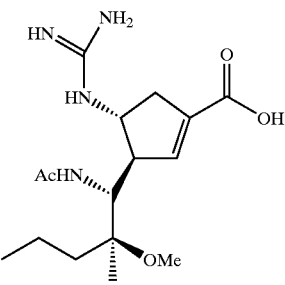

30C (3R,4R,1'R,2'S)-3-(1'-Acetamido-2'-methoxy-2'-Methyl)pentyl-4-[(amino-imino)methyl]aminocyclopent-1-ene-1-carboxylic Acid.

The title compound is prepared according to the procedure of example 25L substituting the product of example 30B for the product of example 25K.

Using the methods described above and the general knowledge of one skilled in the art, compounds of the invention (having the indicated relative stereochemistry or enantiomerically enriched and having the indicated absolute stereochemistry) can be prepared which are represented by taking one core from Table 1 (wherein Ac is acetyl), one Y substituent from Table 2a, one R substituent from Table 3, one $R^3$ substituent from Table 4a, 4b, 4c, 4d, 4e, 4f, 4 g or 4h and one $R^5$ substituent from Table 5; or one core from Table 1 (wherein Ac is acetyl), one Y substituent from Table 2b, one R substituent from Table 3, one $R^3$ substituent from Table 4f, 4 g or 4h or 4b69–4b84 and one $R^5$ substituent from Table 5.

TABLE 1

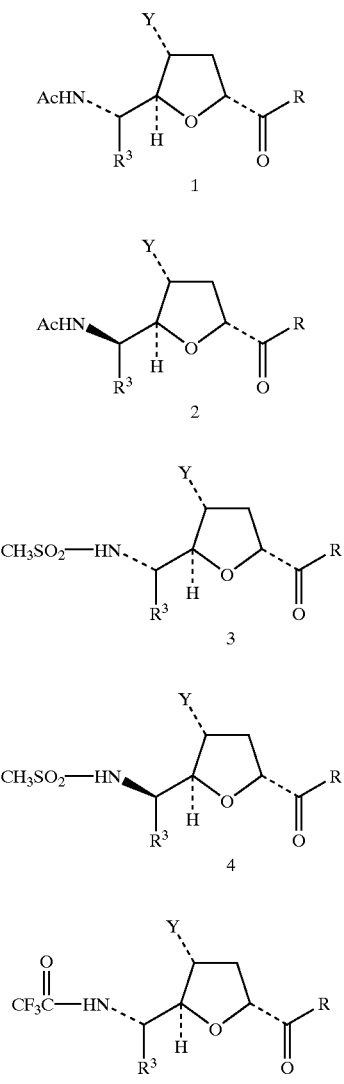

TABLE 1-continued

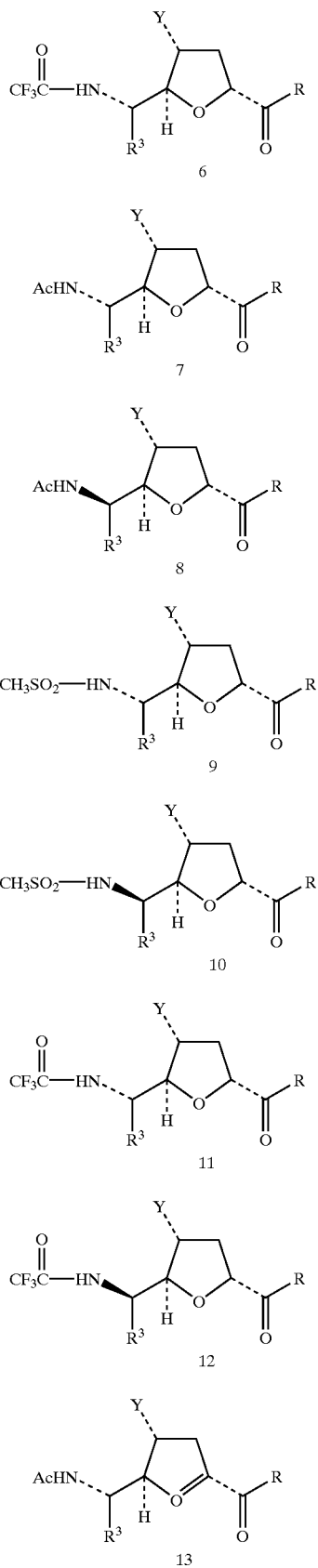

TABLE 1-continued
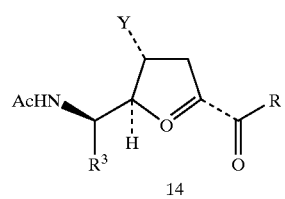
14
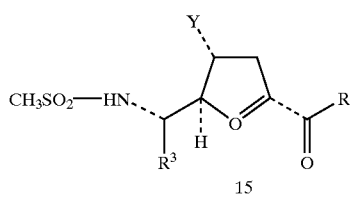
15
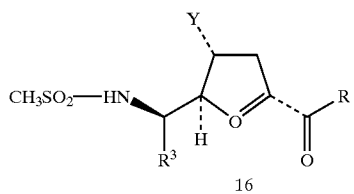
16
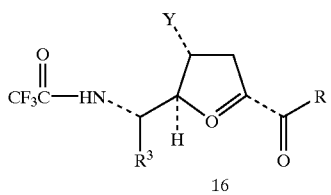
16
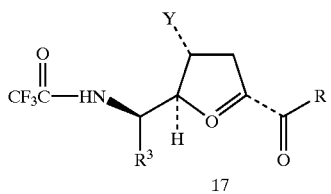
17
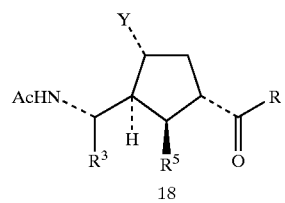
18
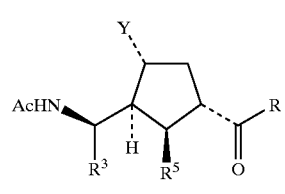
19
TABLE 1-continued
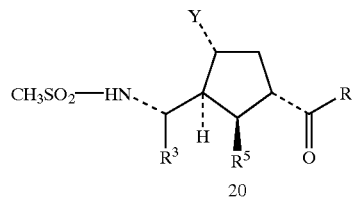
20
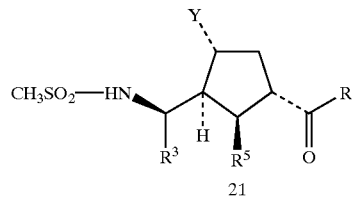
21
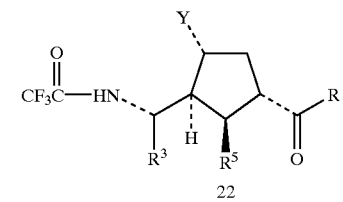
22
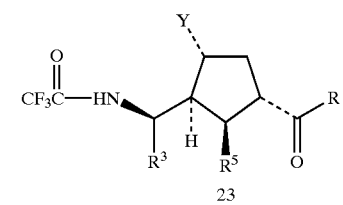
23
TABLE 2A
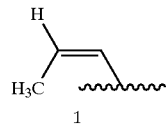
1
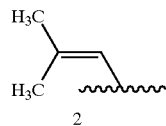
2
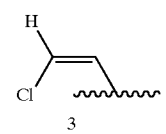
3
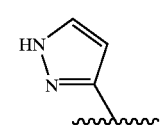
4

TABLE 2A-continued
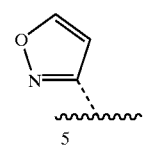
5
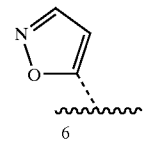
6
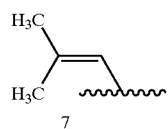
7
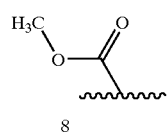
8
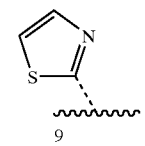
9
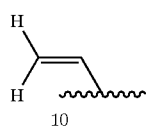
10
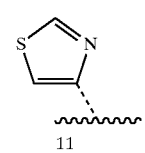
11
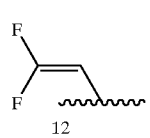
12
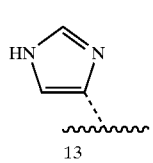
13
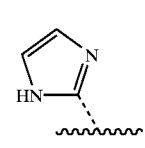
14
TABLE 2A-continued
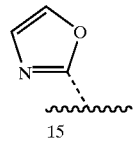
15
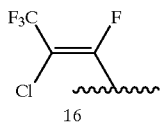
16
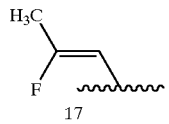
17
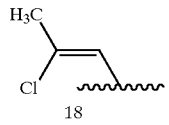
18
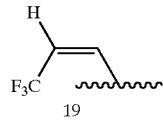
19
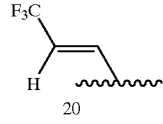
20
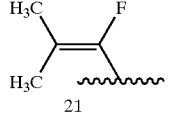
21
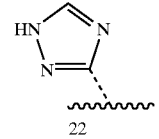
22
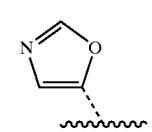
23
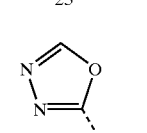
24
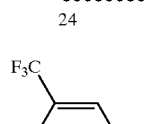
25

TABLE 2A-continued
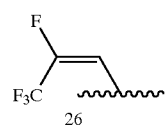
26
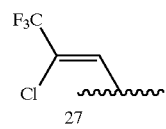
27
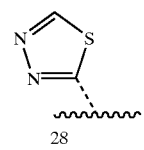
28
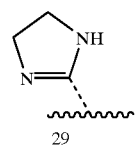
29
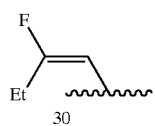
30
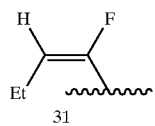
31
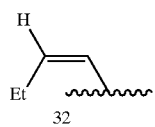
32
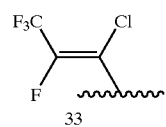
33
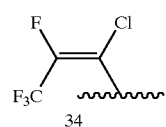
34
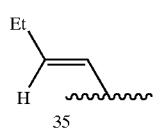
35
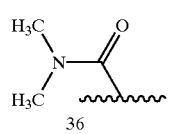
36
TABLE 2A-continued
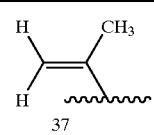
37
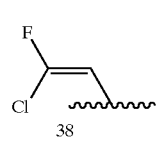
38
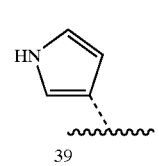
39
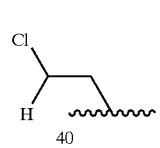
40
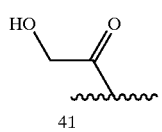
41
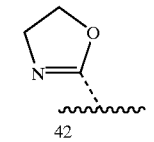
42
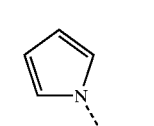
43
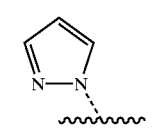
44
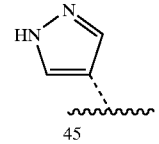
45
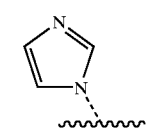
46

TABLE 2A-continued
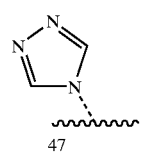
47
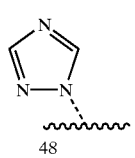
48
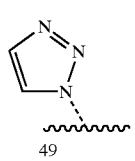
49
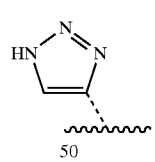
50
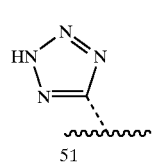
51
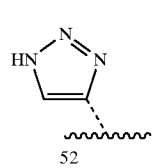
52
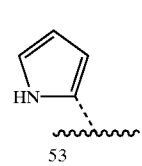
53
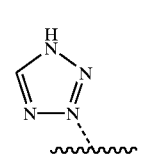
54
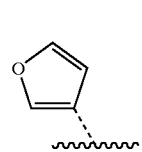
55
TABLE 2A-continued
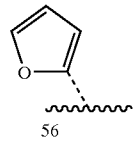
56
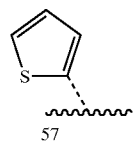
57
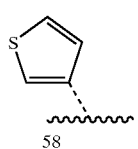
58
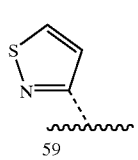
59
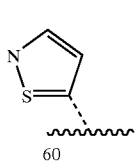
60
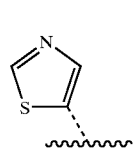
61
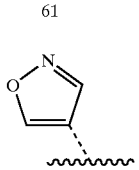
62
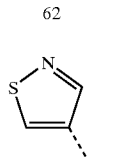
63
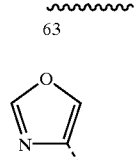
64
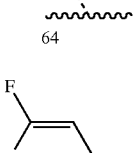
65

TABLE 2A-continued
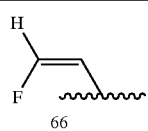
66
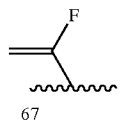
67
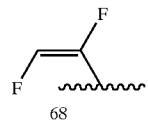
68
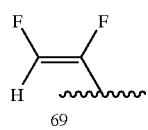
69
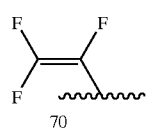
70
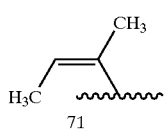
71
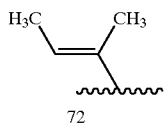
72
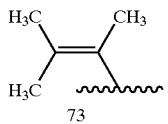
73
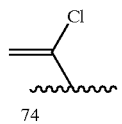
74
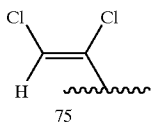
75
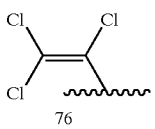
76
TABLE 2A-continued
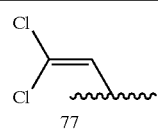
77
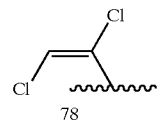
78
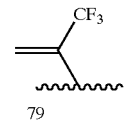
79
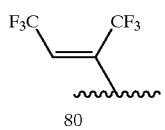
80
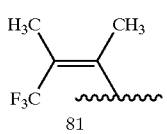
81
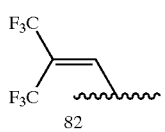
82
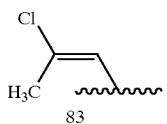
83
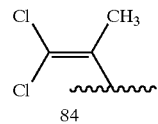
84
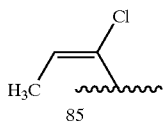
85
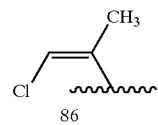
86
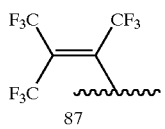
87

TABLE 2A-continued
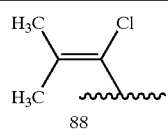
88
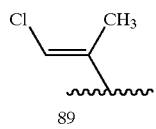
89
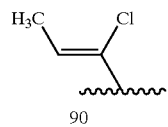
90
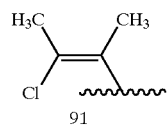
91
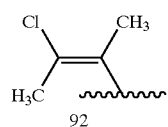
92
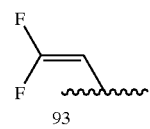
93
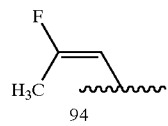
94
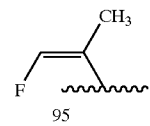
95
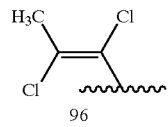
96
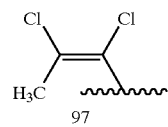
97
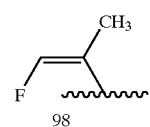
98
TABLE 2A-continued
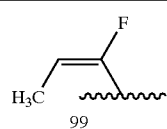
99
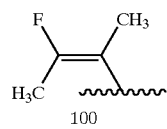
100
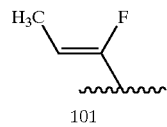
101
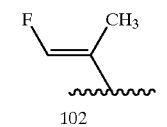
102
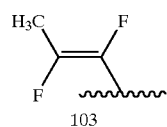
103
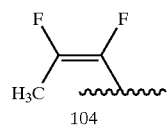
104
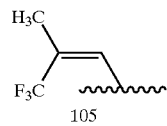
105
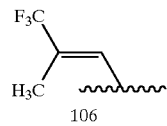
106
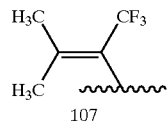
107
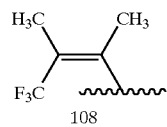
108
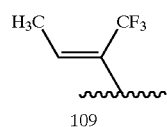
109

TABLE 2A-continued
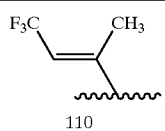
110
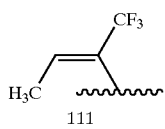
111
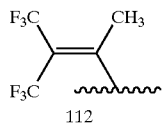
112
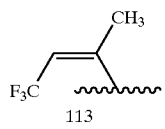
113
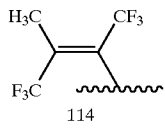
114
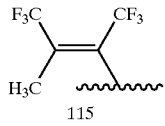
115
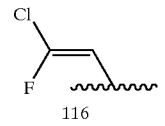
116
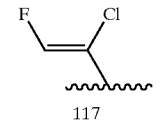
117
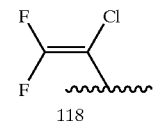
118
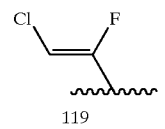
119
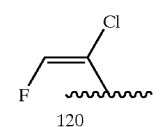
120
TABLE 2A-continued
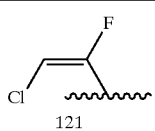
121
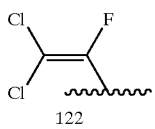
122
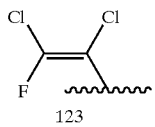
123
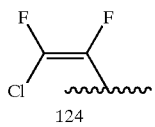
124
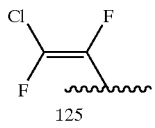
125
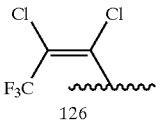
126
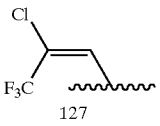
127
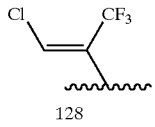
128
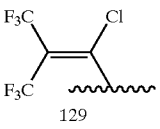
129
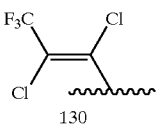
130
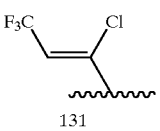
131

TABLE 2A-continued
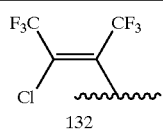
132
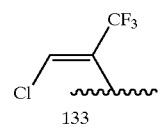
133
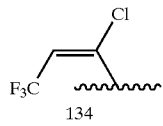
134
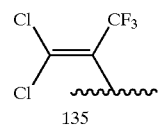
135
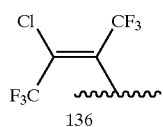
136
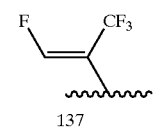
137
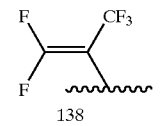
138
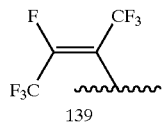
139
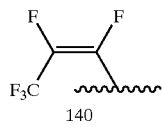
140
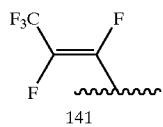
141
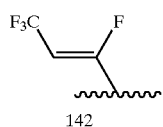
142
TABLE 2A-continued
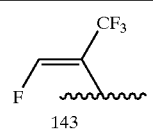
143
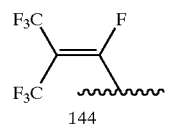
144
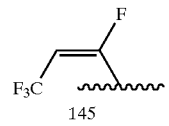
145
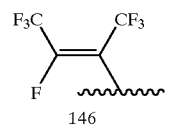
146
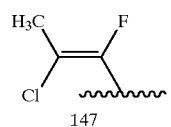
147
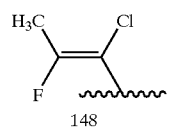
148
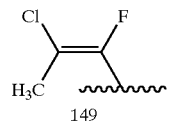
149
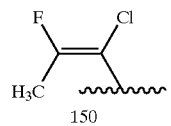
150
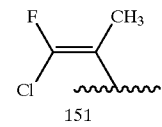
151
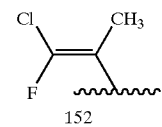
152
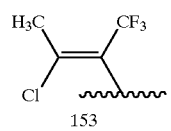
153

TABLE 2A-continued
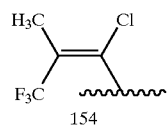
154
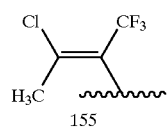
155
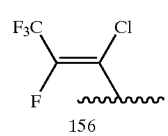
156
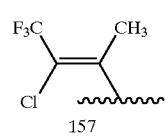
157
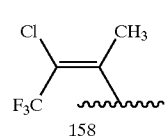
158
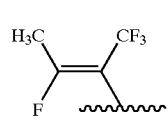
159
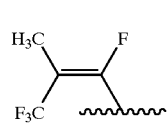
160
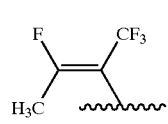
161
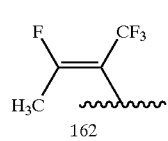
162
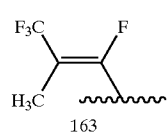
163
TABLE 2A-continued
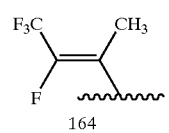
164
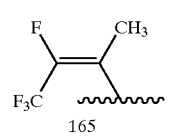
165
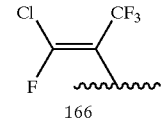
166
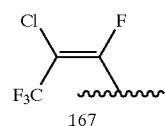
167
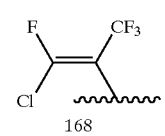
168
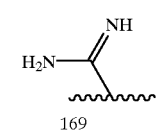
169
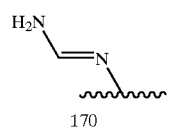
170
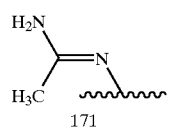
171
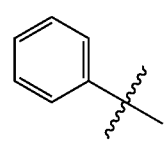
172

TABLE 2B

1. H₂N– (primary amine)

2. Guanidine group: H₂N–C(=NH)–NH–

TABLE 3

1. —OH
2. —OCH₃
3. —OCH₂CH₃
4. —OCH₂CH₂CH₃
5. —OCH(CH₃)₂
6. —OCH₂CH₂CH₂CH₃
7. —OC(CH₃)₃
8. —OCH₂CH(CH₃)₂
9. —OCH₂C(CH₃)₃
10. —OCH₂CH₂CH(CH₃)₂
11. —O–(S)–CH(CH₃)CH₂CH₃
12. —O–(R)–CH(CH₃)CH₂CH₃
13. —OCH₂C(CH₃)₂CH₃
14. —OCH₂CH₂N(CH₃)₂
15. —OCH₂CH₂N(CH₂CH₃)₂
16. —OCH₂–phenyl
17. —OCH₂–(2-pyridyl)
18. —OCH₂–(3-pyridyl)
19. —O–cyclohexyl
20. —O–cyclopropyl
21. —O–(1-methylpiperidin-4-yl)
22. —OCH₂CH₂–(piperidin-1-yl)

TABLE 3-continued
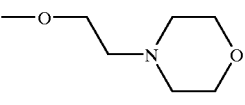
23
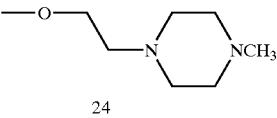
24
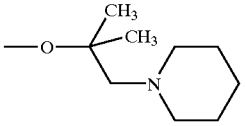
25
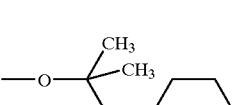
26
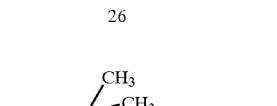
27
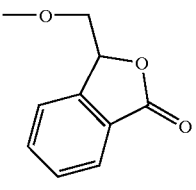
28
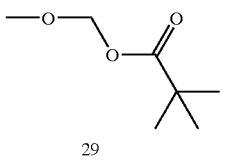
29
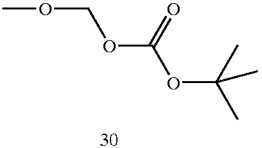
30
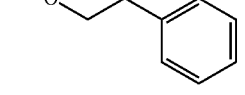
31
TABLE 3-continued
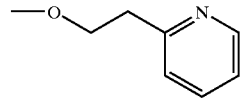
32
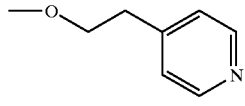
34
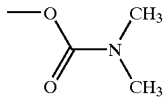
35
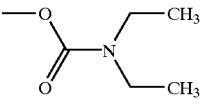
36
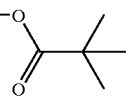
37
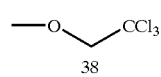
38
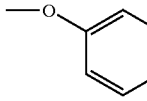
39
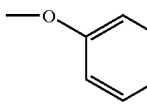
40
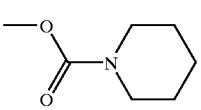
41
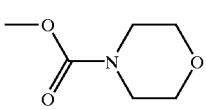
42
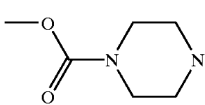
43

TABLE 3-continued
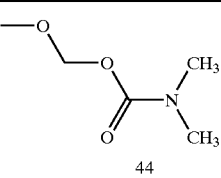
44
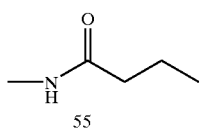
45
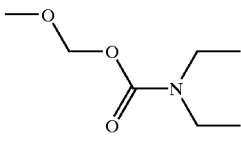
46
—NH₂
47
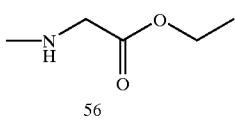
48
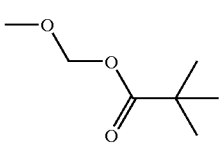
49
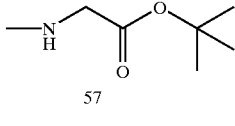
50
51
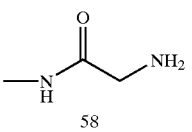
52
53
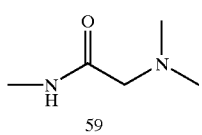
54
TABLE 3-continued
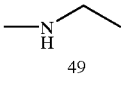
55
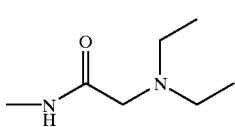
56
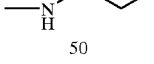
57
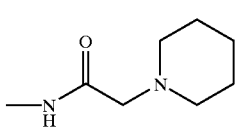
58
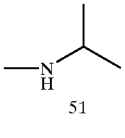
59
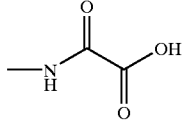
60
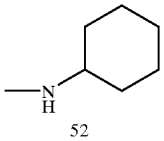
61
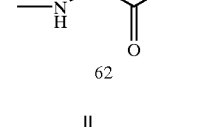
62
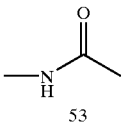
63
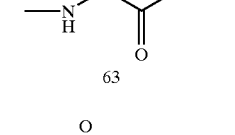
64
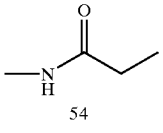
65

TABLE 3-continued

—N(H)—Ala-OCH₃
66

—N(H)—Ala-OEt
67

—N(H)—Val-OH
68

—N(H)—Val-OCH₃
69

—N(H)—Val-OEt
70

—N(H)—Leu-OH
71

—N(H)—Leu-OCH₃
72

—N(H)—Leu-OEt
73

—N(H)—Ile-OH
74

—N(H)—Ile-OCH₃
75

—N(H)—Ile-OEt
76

—N(H)—Phe-OH
77

—N(H)—Phe-OCH₃
78

—N(H)—Phe-OEt
79

—N(H)—Tyr-OH
80

—N(H)—Tyr-OCH₃
81

—N(H)—Tyr-OEt
82

—N(H)—Asn-OH
83

—N(H)—Asn-OCH₃
84

TABLE 3-continued

—N(H)—Asn-OEt
85

—N(H)—Glu-OH
86

—N(H)—Glu-OCH₃
87

—N(H)—Glu-OEt
88

—N(H)—Gln-OH
89

—N(H)—Gln-OCH₃
90

—N(H)—Gln-OEt
91

—N(H)—Asp-OH
92

—N(H)—Asp-OCH₃
93

—N(H)—Asp-OEt
94

—N(H)—Lys-OH
95

—N(H)—Lys-OCH₃
96

—N(H)—Lys-OEt
97

—N(H)—Ser-OH
98

—N(H)—Ser-OCH₃
99

—N(H)—Ser-OEt
100

—O—CH(CH₂CH₃)(CH₂CH₃)
101

TABLE 4A
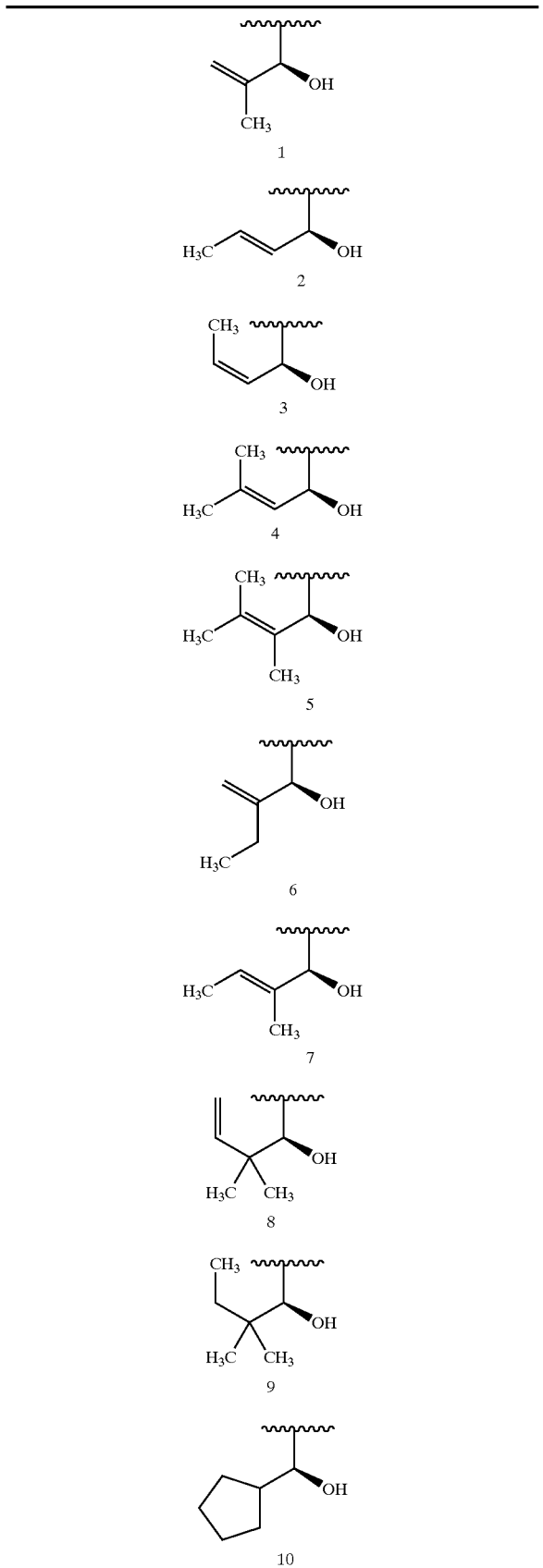
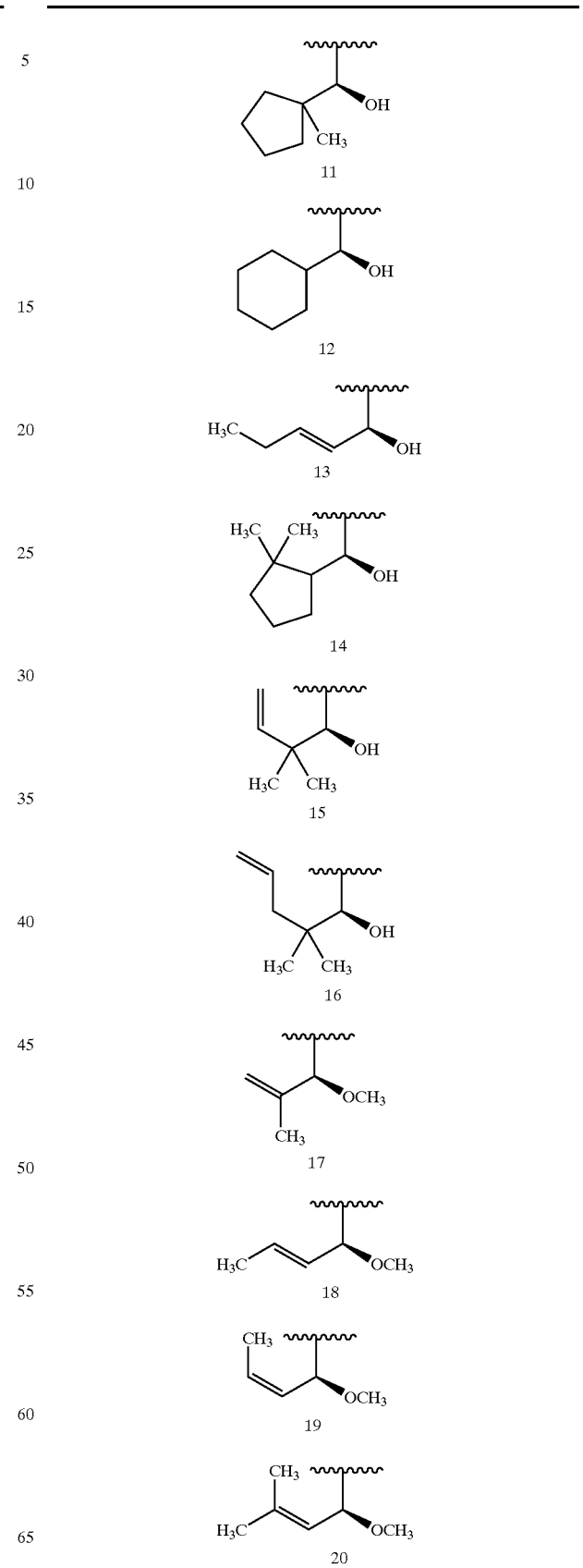

TABLE 4A-continued
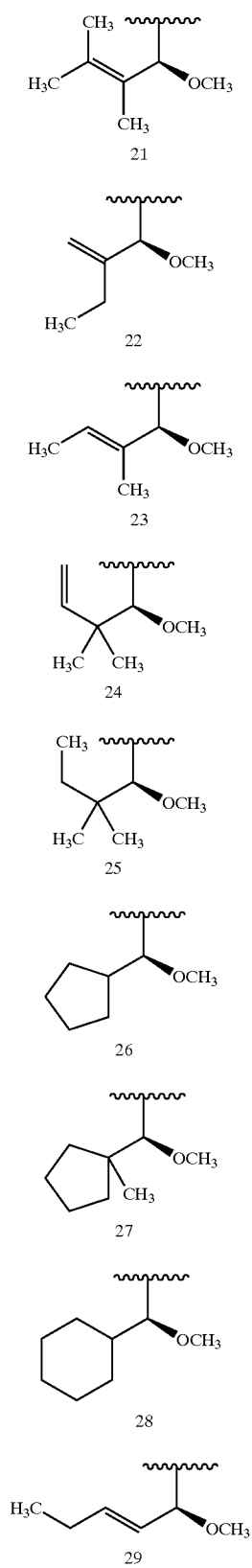
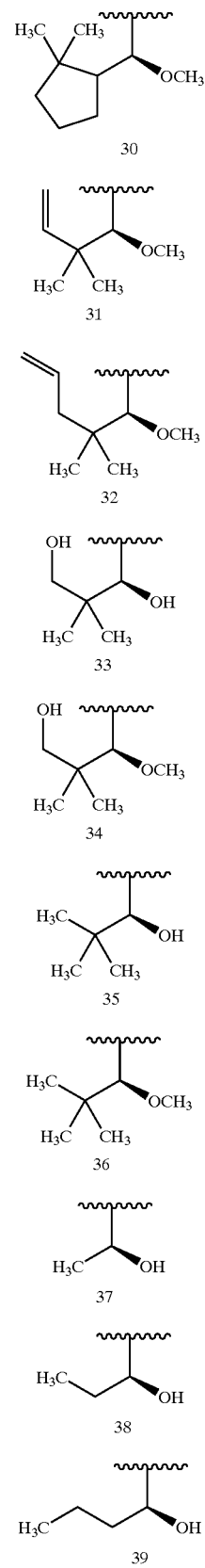

TABLE 4A-continued
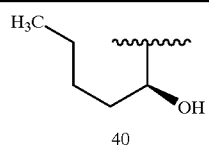
40
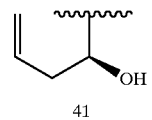
41
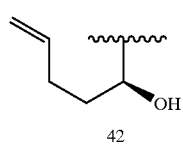
42
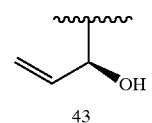
43
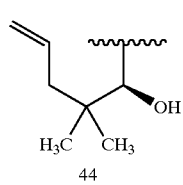
44
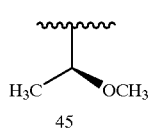
45
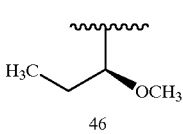
46
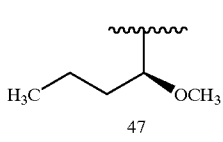
47
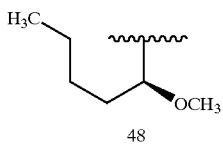
48
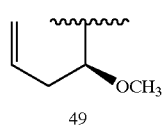
49
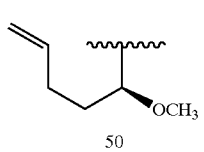
50
TABLE 4A-continued
51
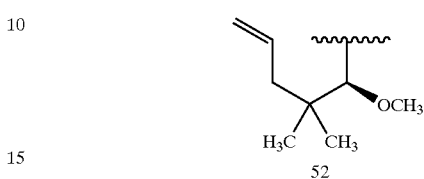
52
TABLE 4b
1
2
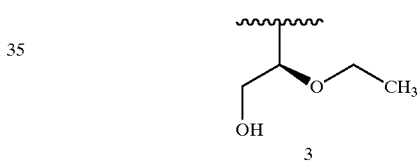
3
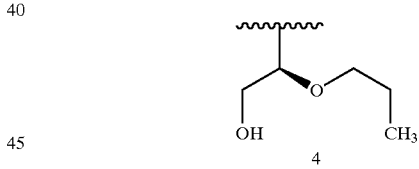
4
5
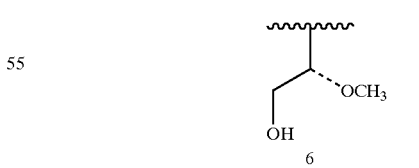
6
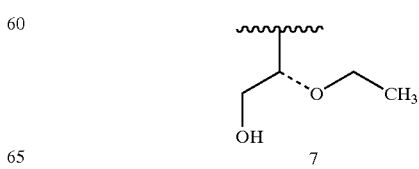
7

TABLE 4b-continued
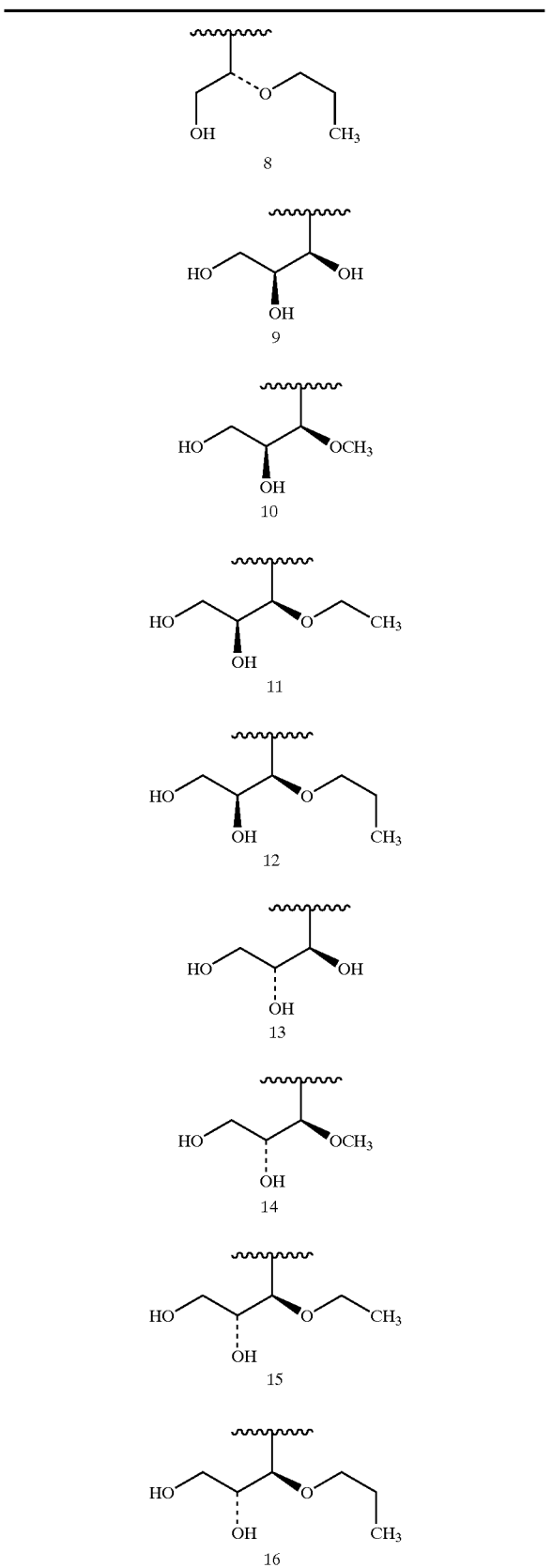
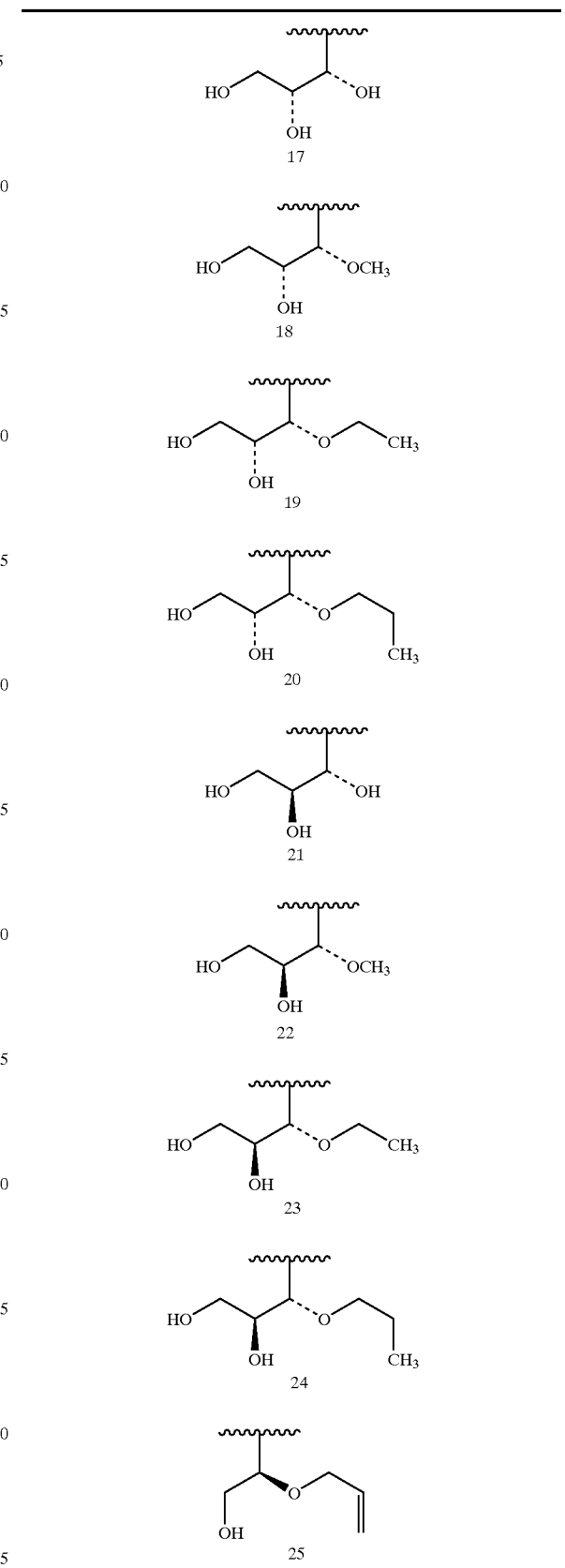

TABLE 4b-continued
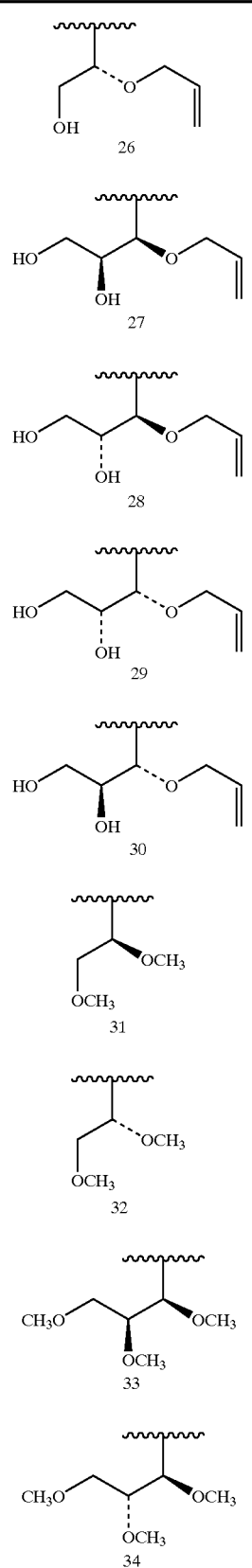
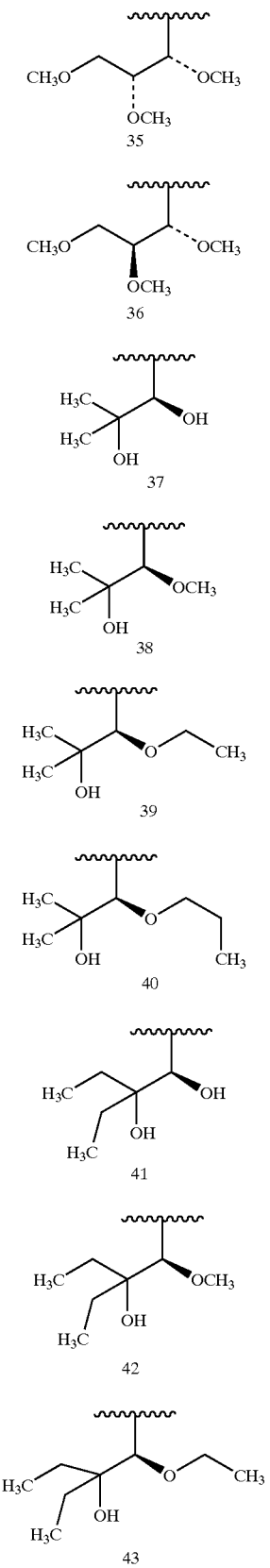

TABLE 4b-continued
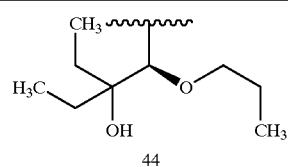
44
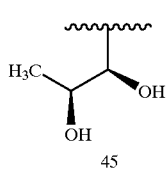
45
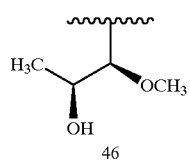
46
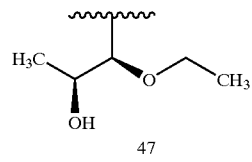
47
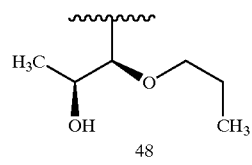
48
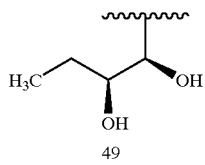
49
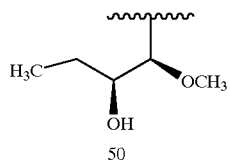
50
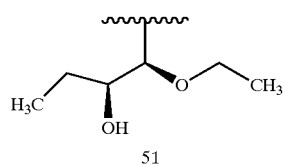
51
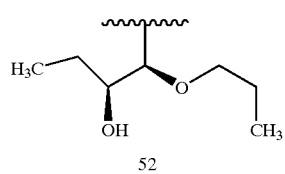
52
TABLE 4b-continued
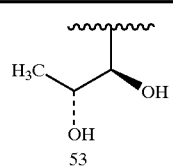
53
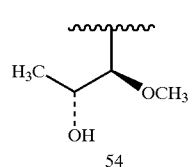
54
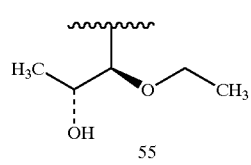
55
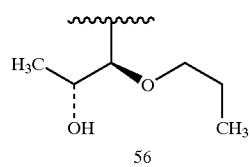
56
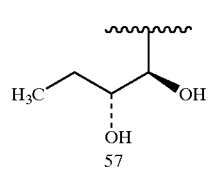
57
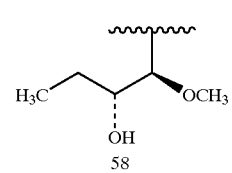
58
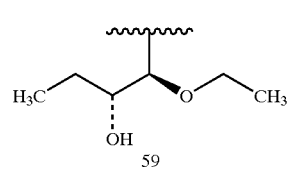
59
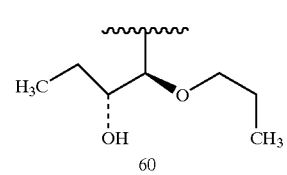
60
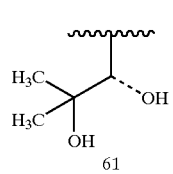
61

TABLE 4b-continued
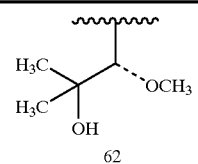
62
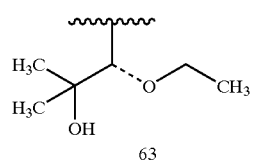
63
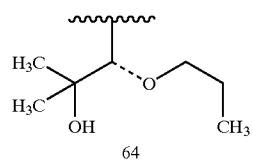
64
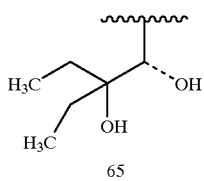
65
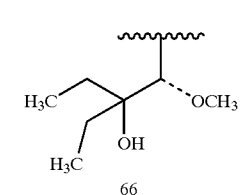
66
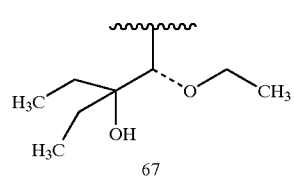
67
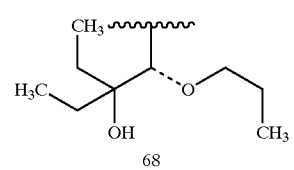
68
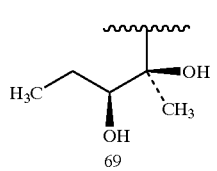
69
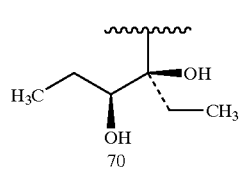
70
TABLE 4b-continued
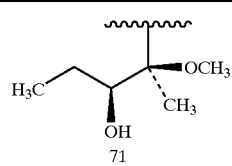
71
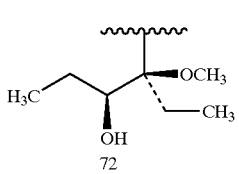
72
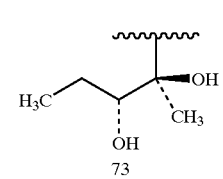
73
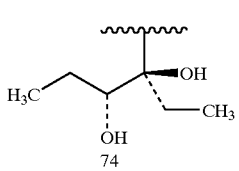
74
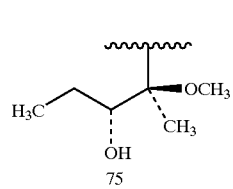
75
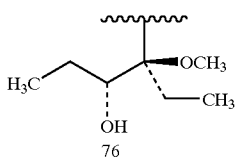
76
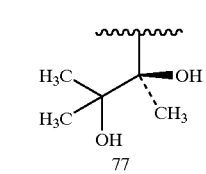
77
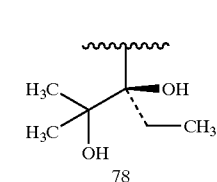
78
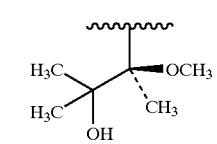
79

TABLE 4b-continued

[Structures 80, 81, 82, 83, 84]

TABLE 4C

[Structures 1–5]

TABLE 4C-continued

[Structures 6–15]

TABLE 4C-continued
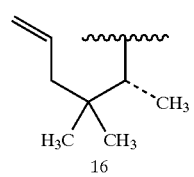
16
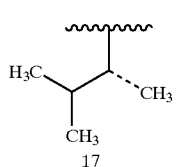
17
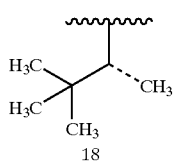
18
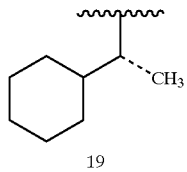
19
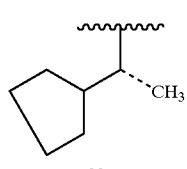
20
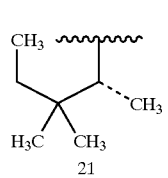
21
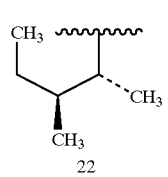
22
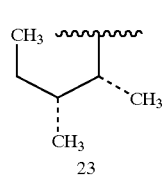
23
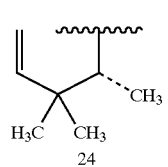
24
TABLE 4C-continued
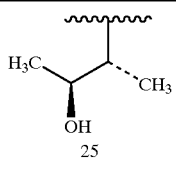
25
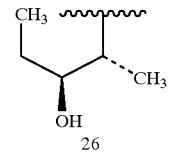
26
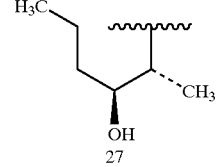
27
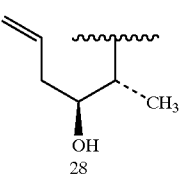
28
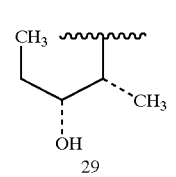
29
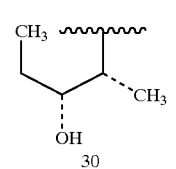
30
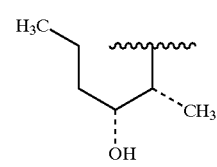
31
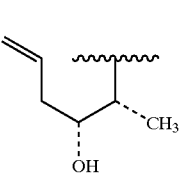
32
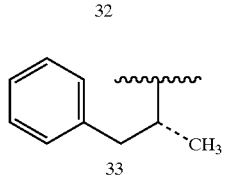
33

TABLE 4C-continued
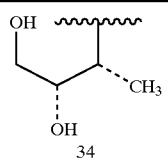
34
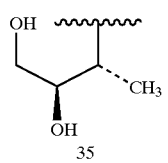
35
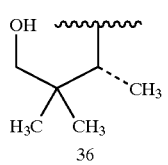
36
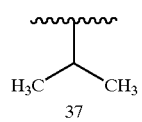
37
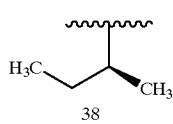
38
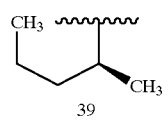
39
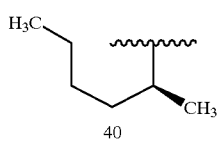
40
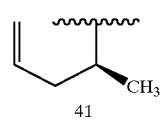
41
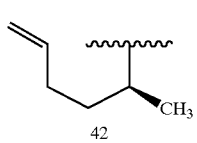
42
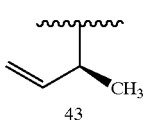
43
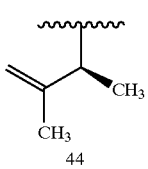
44
TABLE 4C-continued
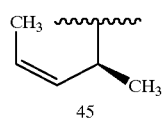
45
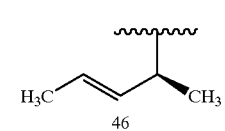
46
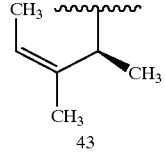
43
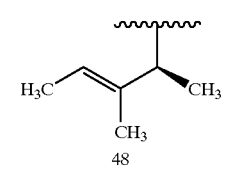
48
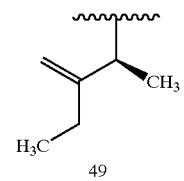
49
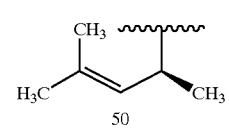
50
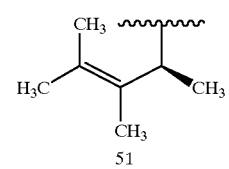
51
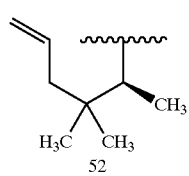
52
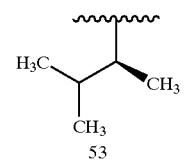
53

TABLE 4C-continued
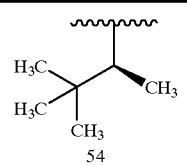
54
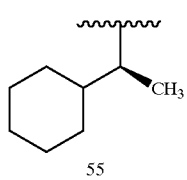
55
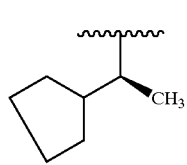
56
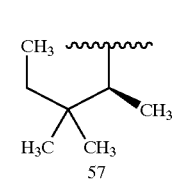
57
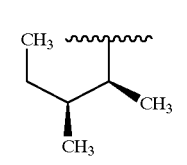
58
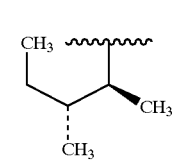
59
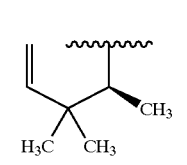
60
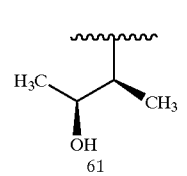
61
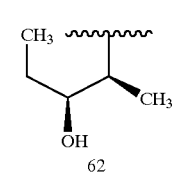
62
TABLE 4C-continued
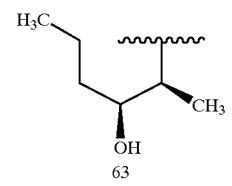
63
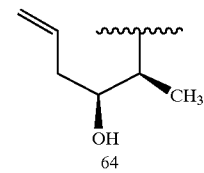
64
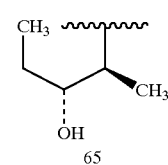
65
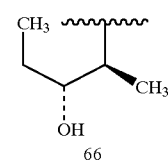
66
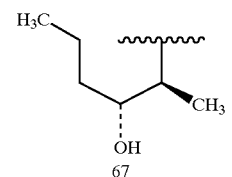
67
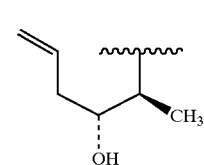
68
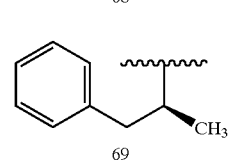
69
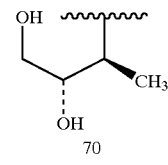
70
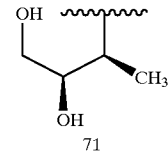
71

TABLE 4C-continued
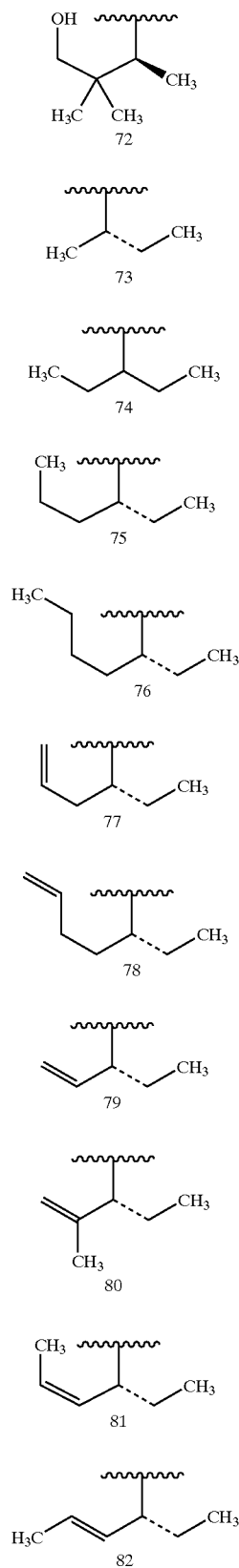
TABLE 4C-continued
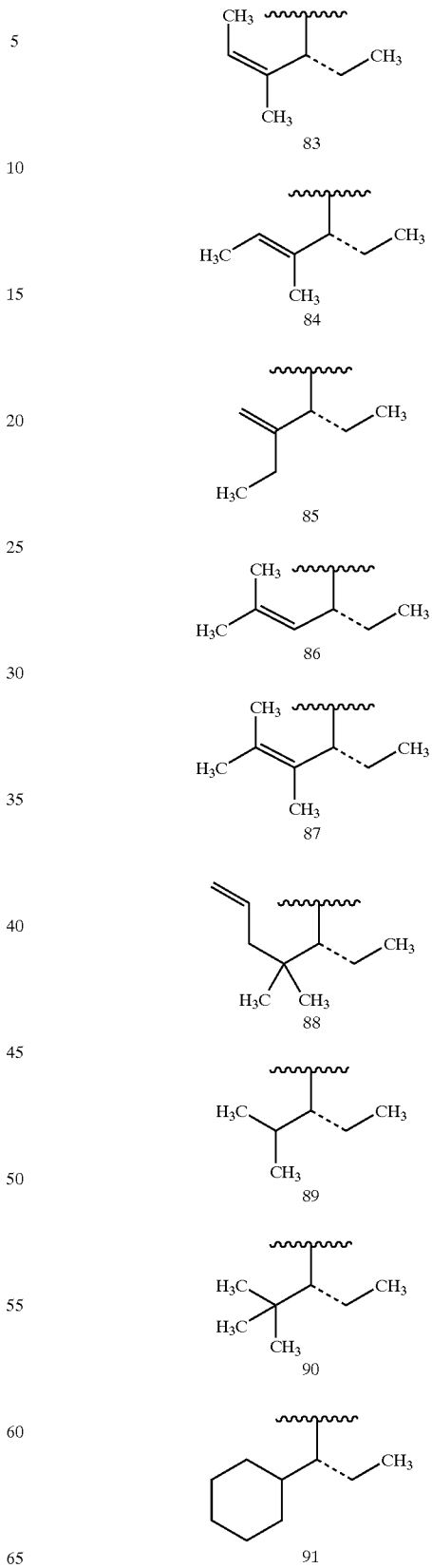

TABLE 4C-continued
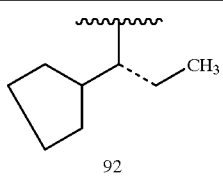
92
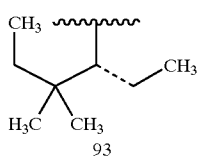
93
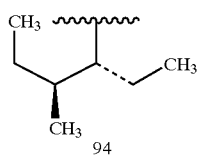
94
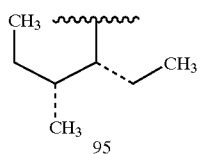
95
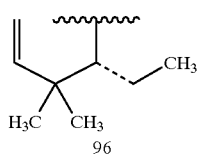
96
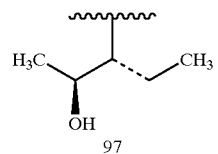
97
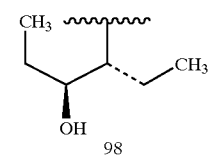
98
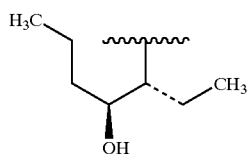
99
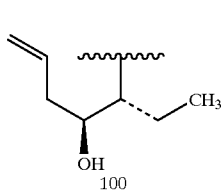
100
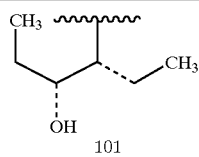
101
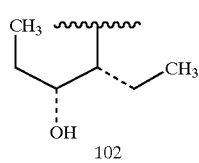
102
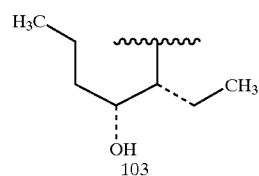
103
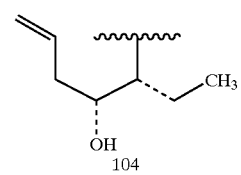
104
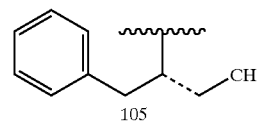
105
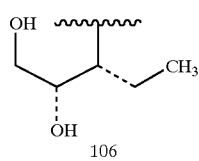
106
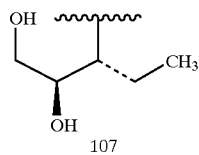
107
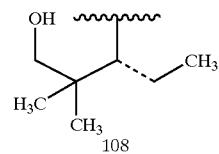
108
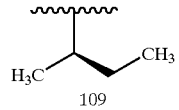
109
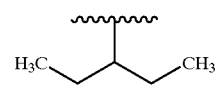
110

TABLE 4C-continued
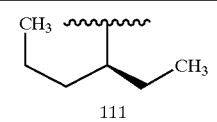
111
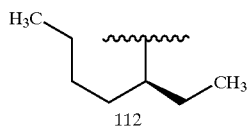
112
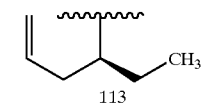
113
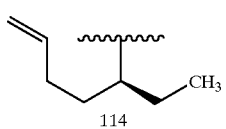
114
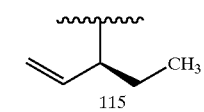
115
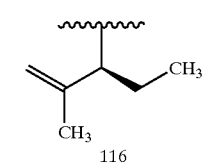
116
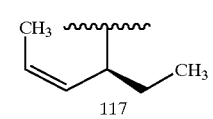
117
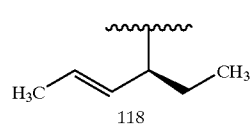
118
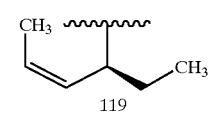
119
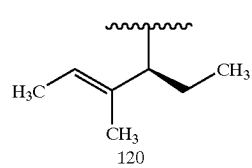
120
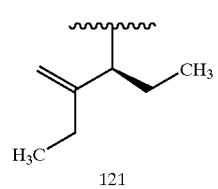
121
TABLE 4C-continued
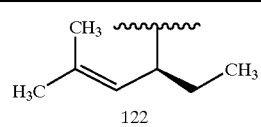
122
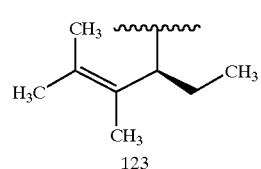
123
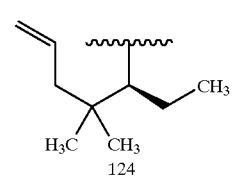
124
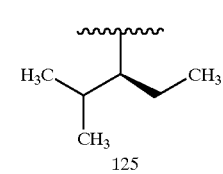
125
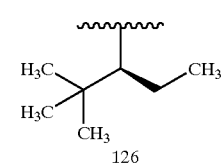
126
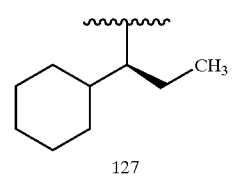
127
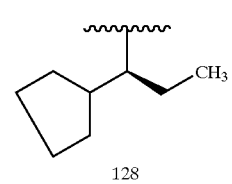
128
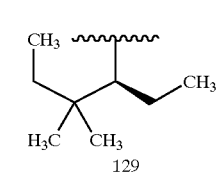
129
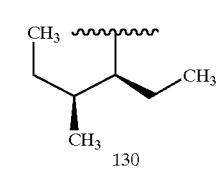
130

TABLE 4C-continued
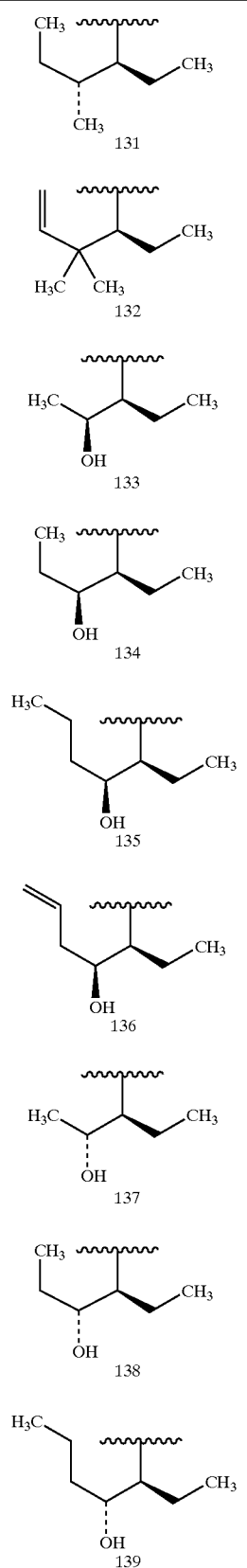
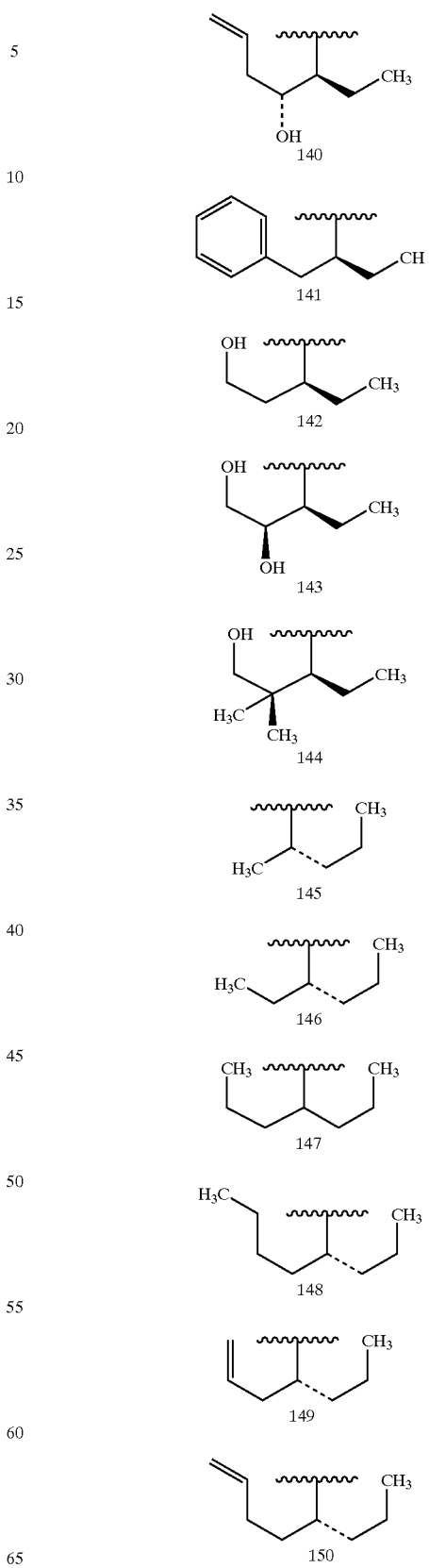

TABLE 4C-continued
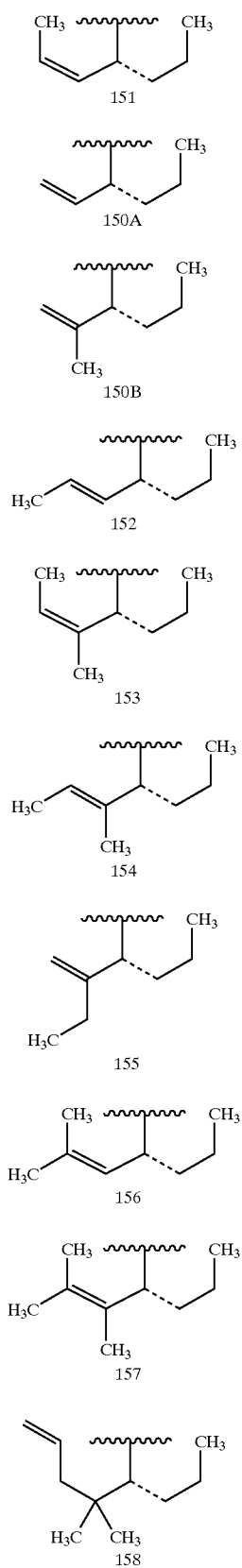
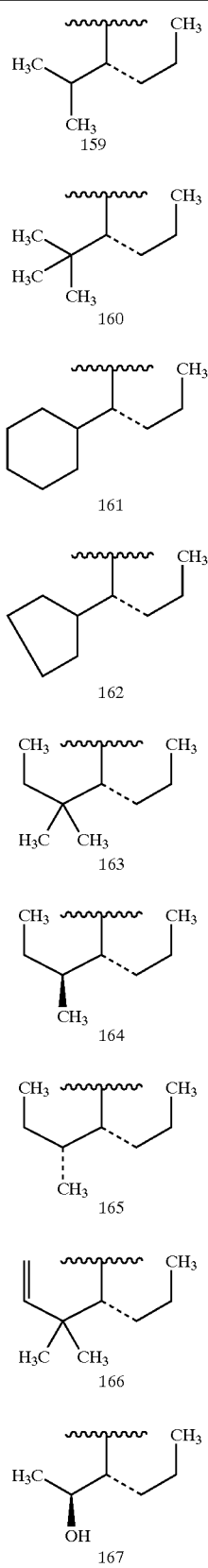

TABLE 4C-continued

TABLE 4C-continued
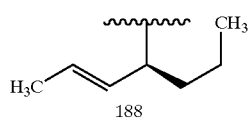
188
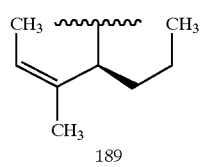
189
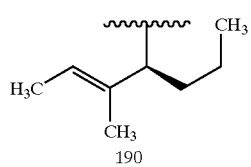
190
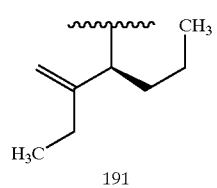
191
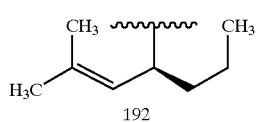
192
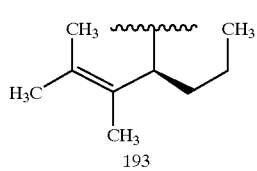
193
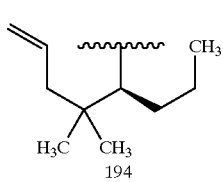
194
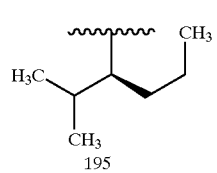
195
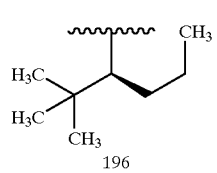
196
TABLE 4C-continued
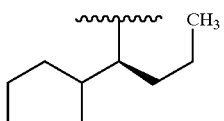
197
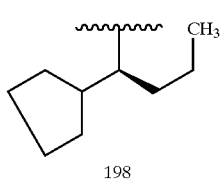
198
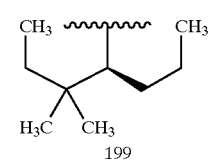
199
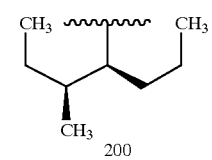
200
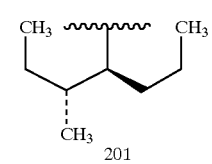
201
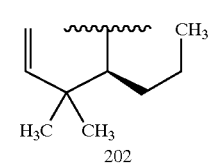
202
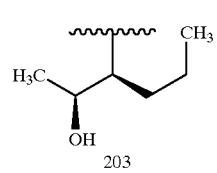
203
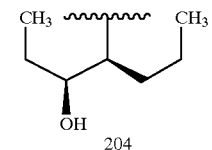
204
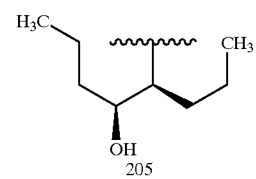
205

TABLE 4C-continued
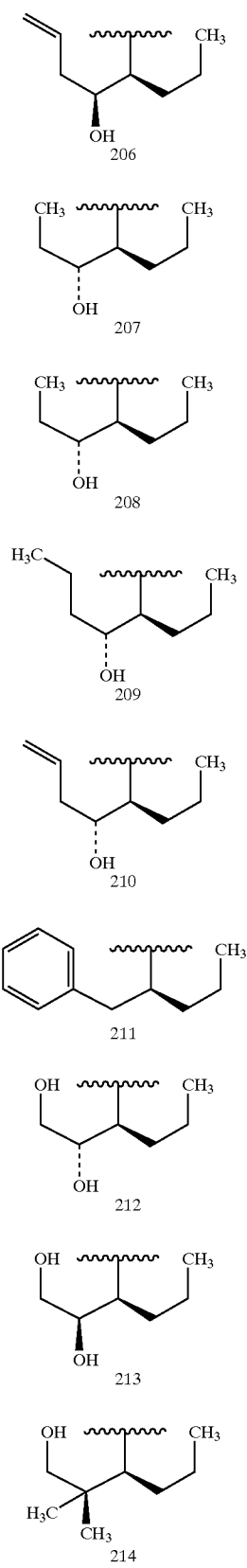
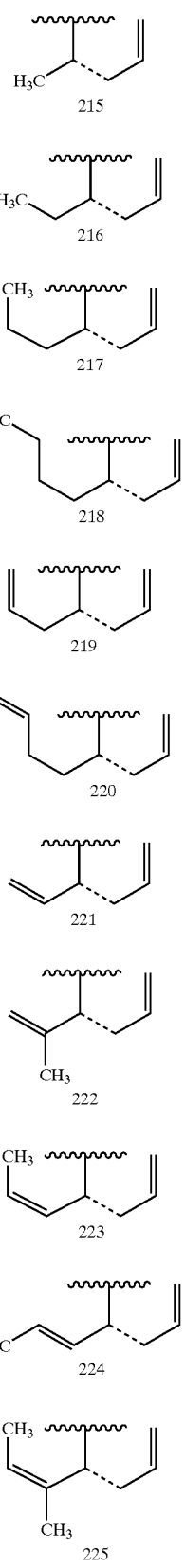

TABLE 4C-continued
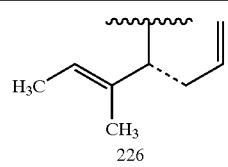
226
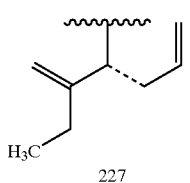
227
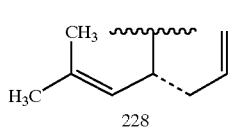
228
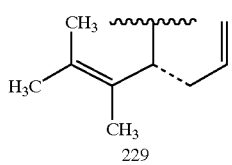
229
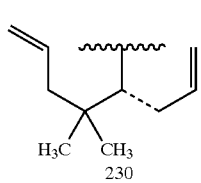
230
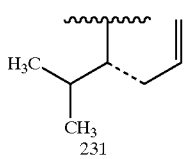
231
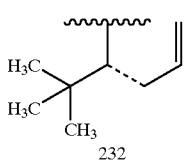
232
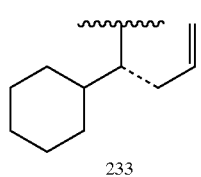
233
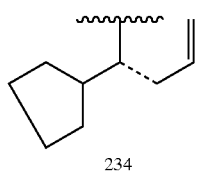
234
TABLE 4C-continued
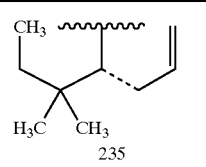
235
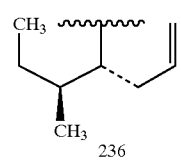
236
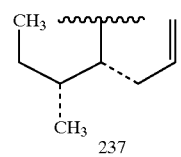
237
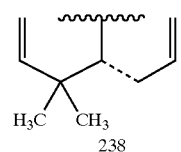
238
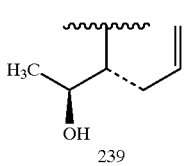
239
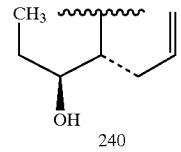
240
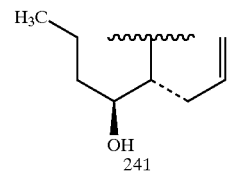
241
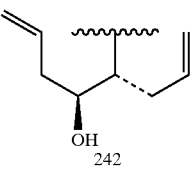
242
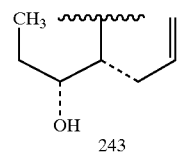
243

TABLE 4C-continued
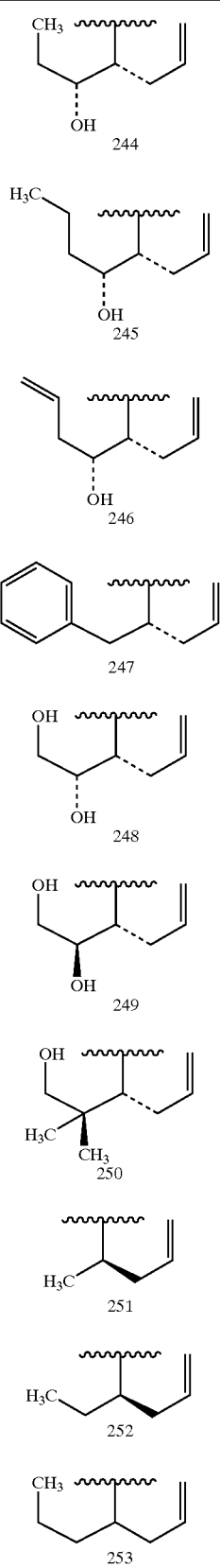
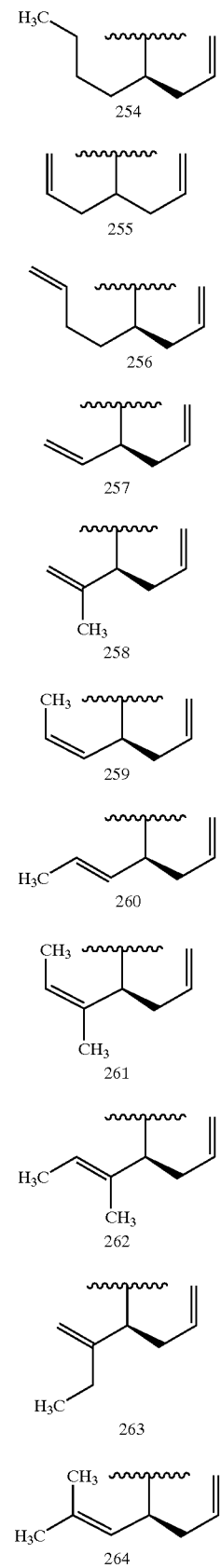

TABLE 4C-continued
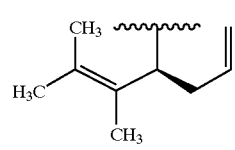
265
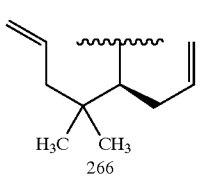
266
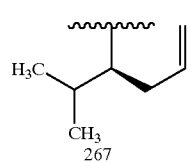
267
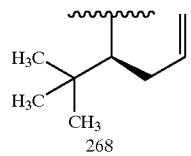
268
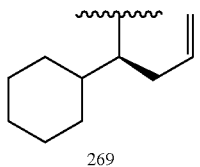
269
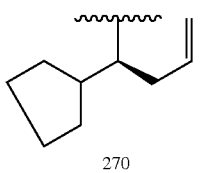
270
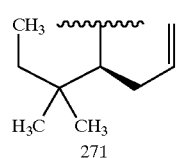
271
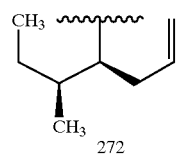
272
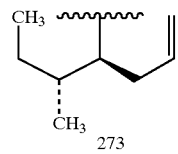
273
TABLE 4C-continued
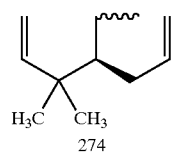
274
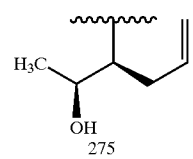
275
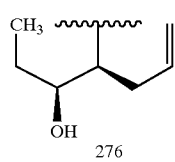
276
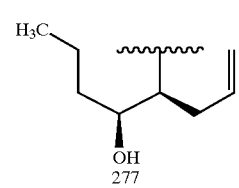
277
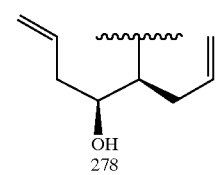
278
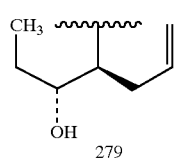
279
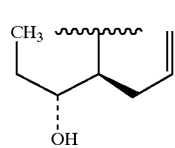
280
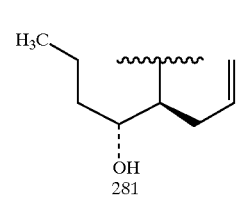
281
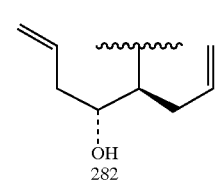
282

TABLE 4C-continued
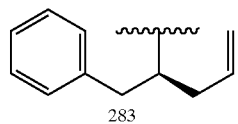
283
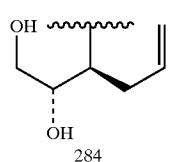
284
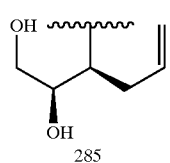
285
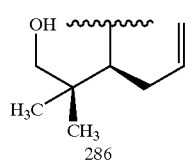
286
287
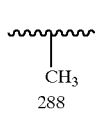
288
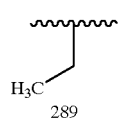
289
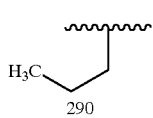
290
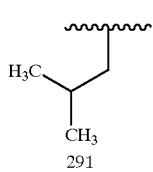
291
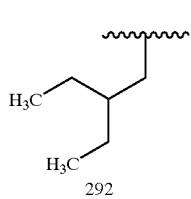
292
TABLE 4d
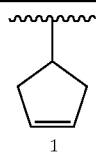
1
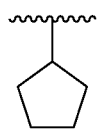
2
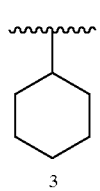
3
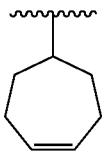
4
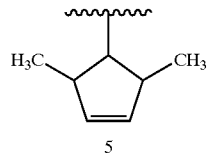
5
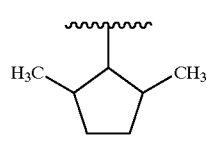
6
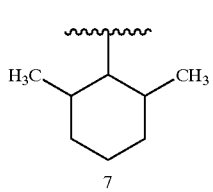
7
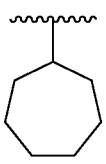
8
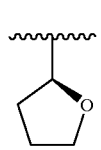
9

TABLE 4d-continued

TABLE 4d-continued

TABLE 4e

TABLE 4e-continued
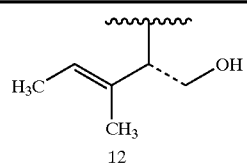
12
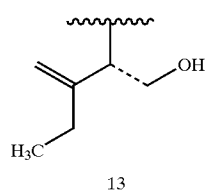
13
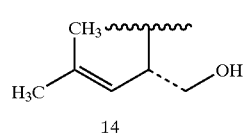
14
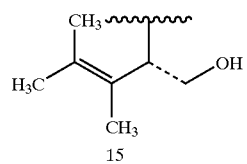
15
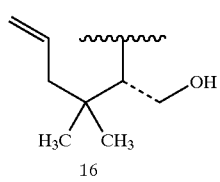
16
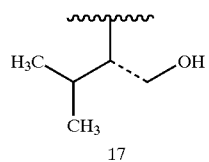
17
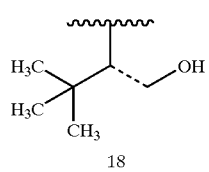
18
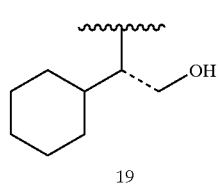
19
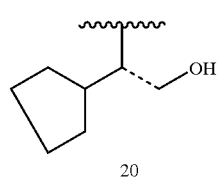
20
TABLE 4e-continued
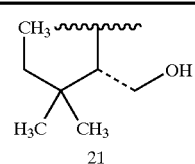
21
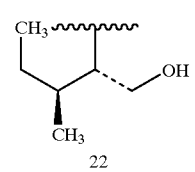
22
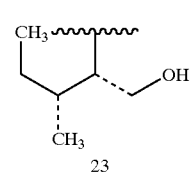
23
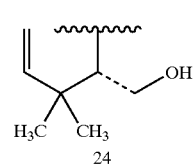
24
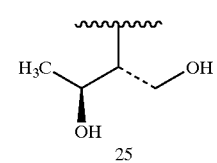
25
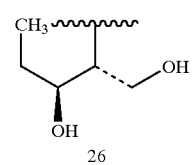
26
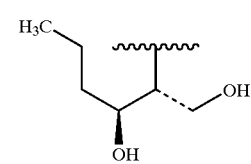
27
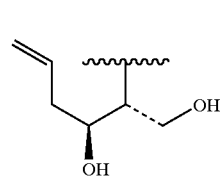
28
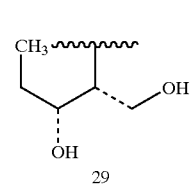
29

TABLE 4e-continued
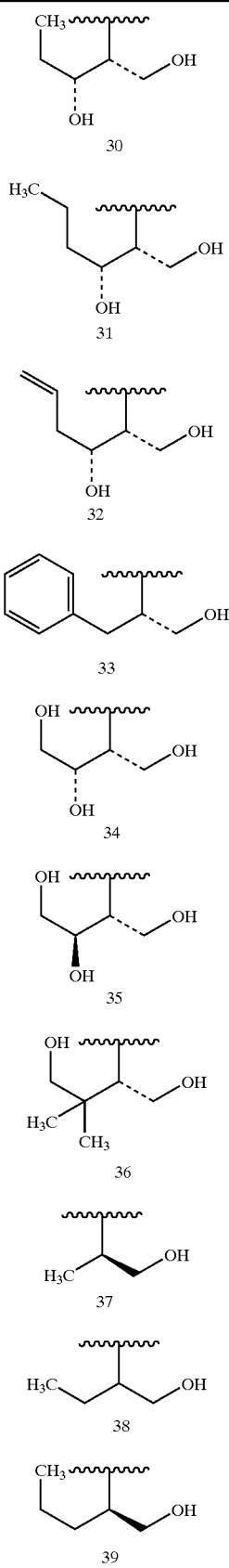
TABLE 4e-continued
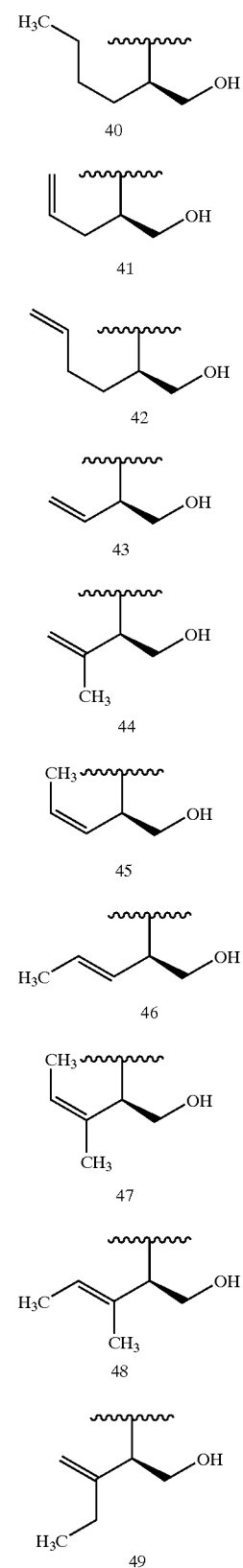

TABLE 4e-continued
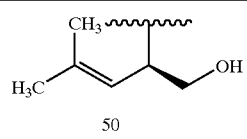
50
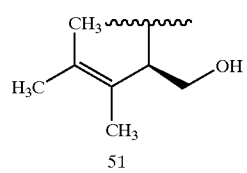
51
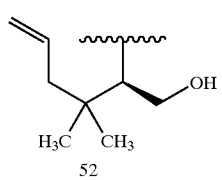
52
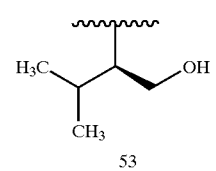
53
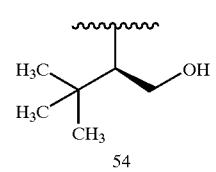
54
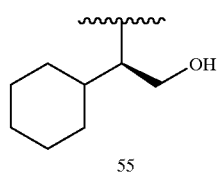
55
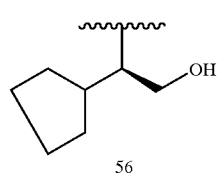
56
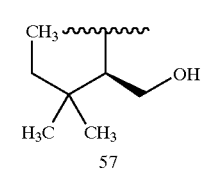
57
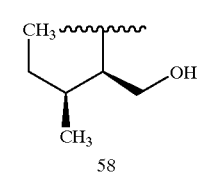
58
TABLE 4e-continued
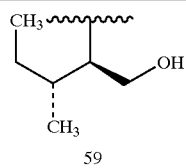
59
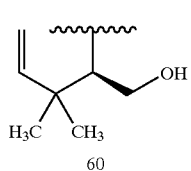
60
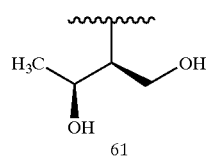
61
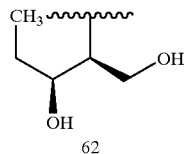
62
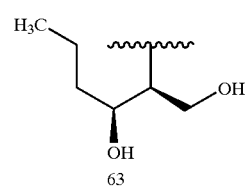
63
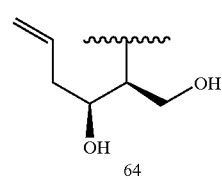
64
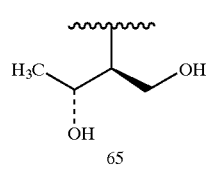
65
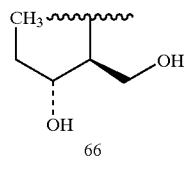
66
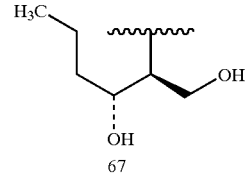
67

TABLE 4e-continued

Structures 68-75 (chemical structures of diols and related compounds)

TABLE 4f

Structures 1-12 (chemical structures with methyl/alkyl substituents)

TABLE 4f-continued
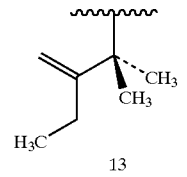
13
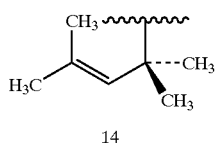
14
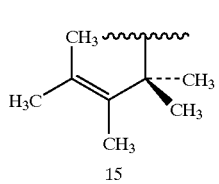
15
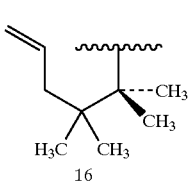
16
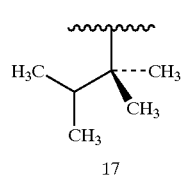
17
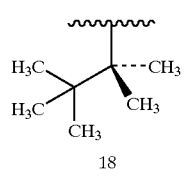
18
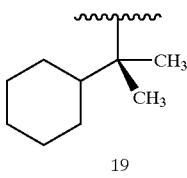
19
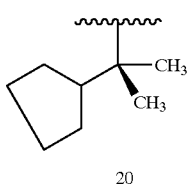
20
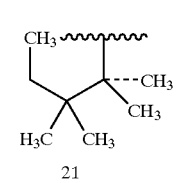
21
TABLE 4f-continued
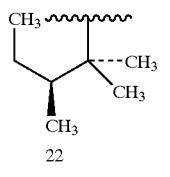
22
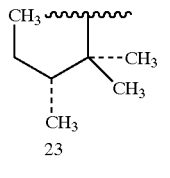
23
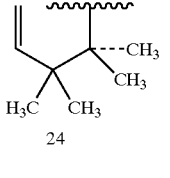
24
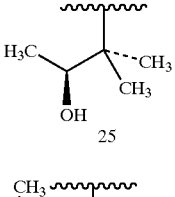
25
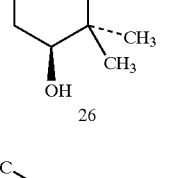
26
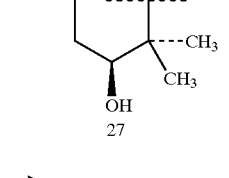
27
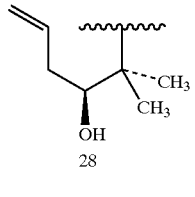
28
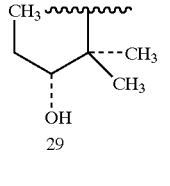
29
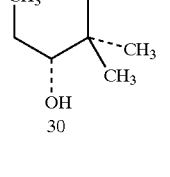
30

TABLE 4f-continued
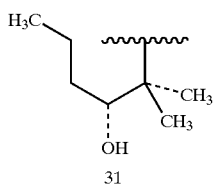
31
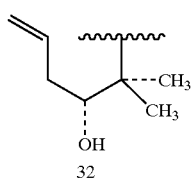
32
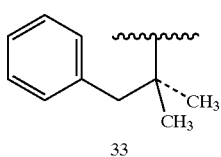
33
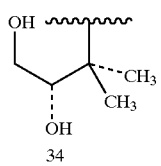
34
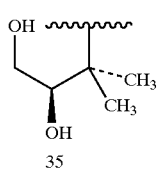
35
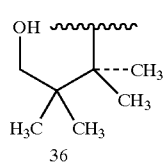
36
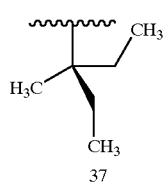
37
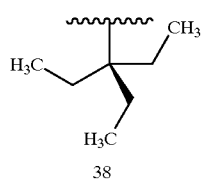
38
TABLE 4f-continued
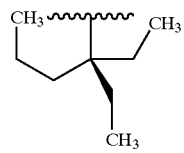
39
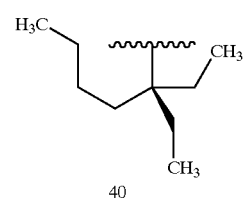
40
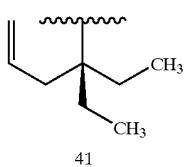
41
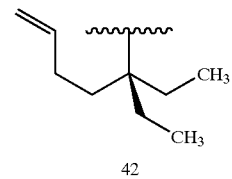
42
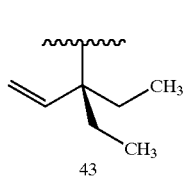
43
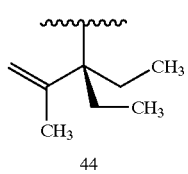
44
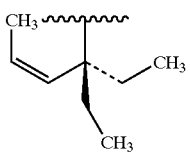
45
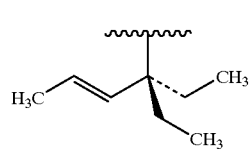
46

TABLE 4f-continued
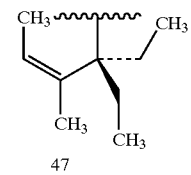
47
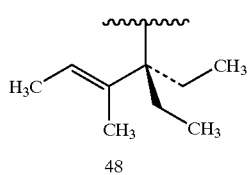
48
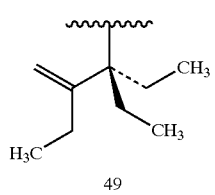
49
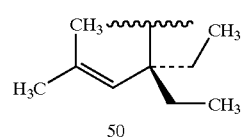
50
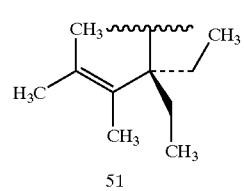
51
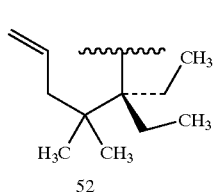
52
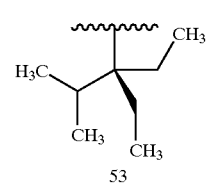
53
TABLE 4f-continued
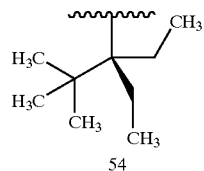
54
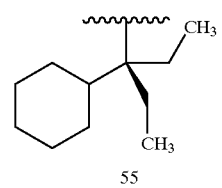
55
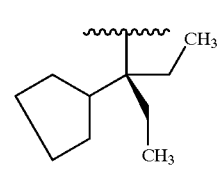
56
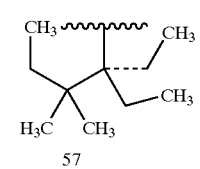
57
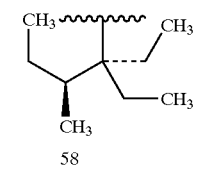
58
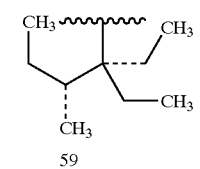
59
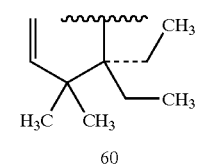
60
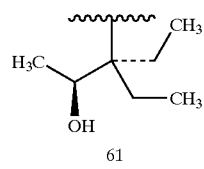
61
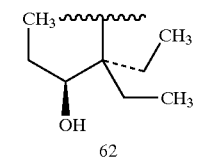
62

TABLE 4f-continued
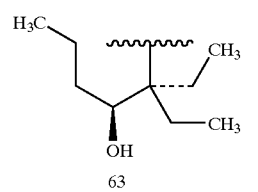
63
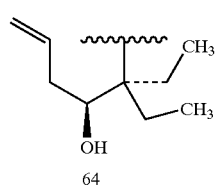
64
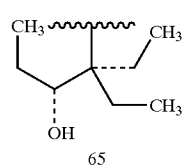
65
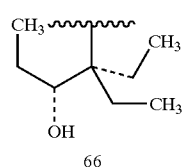
66
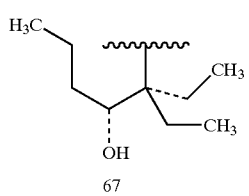
67
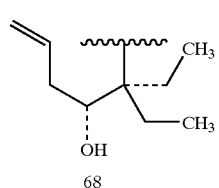
68
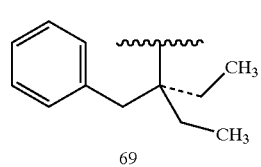
69
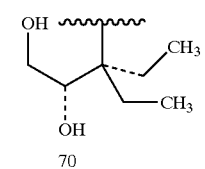
70
TABLE 4f-continued
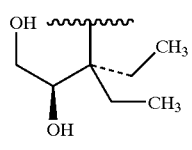
71
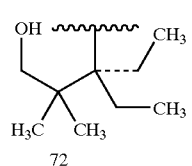
72
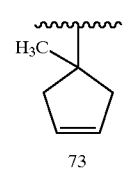
73
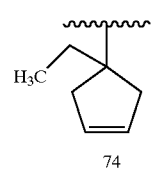
74
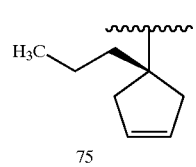
75
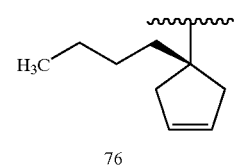
76
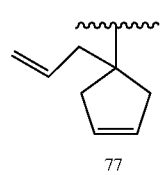
77
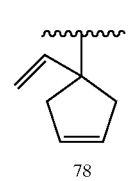
78
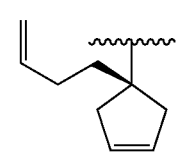
79

TABLE 4f-continued
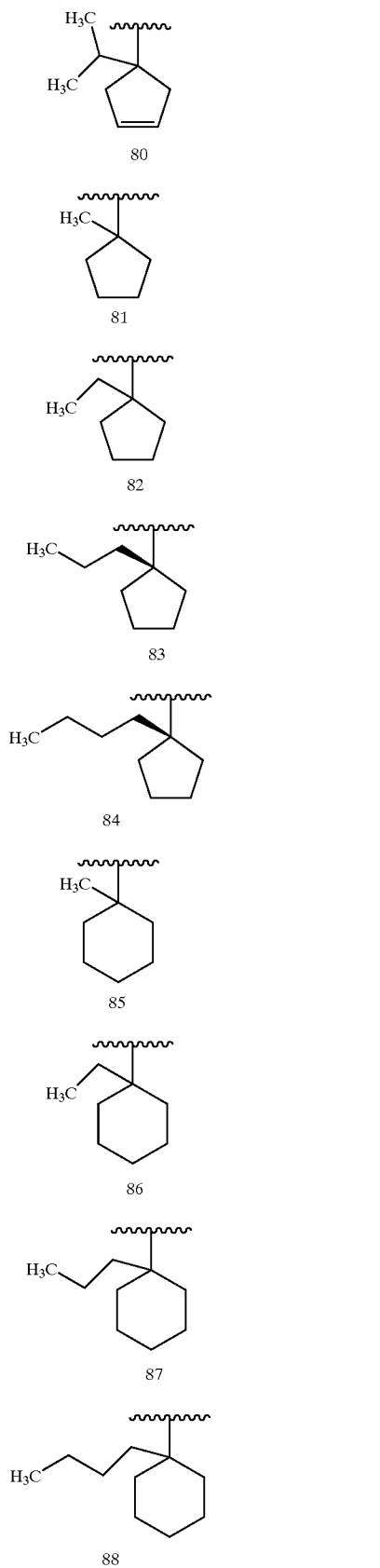
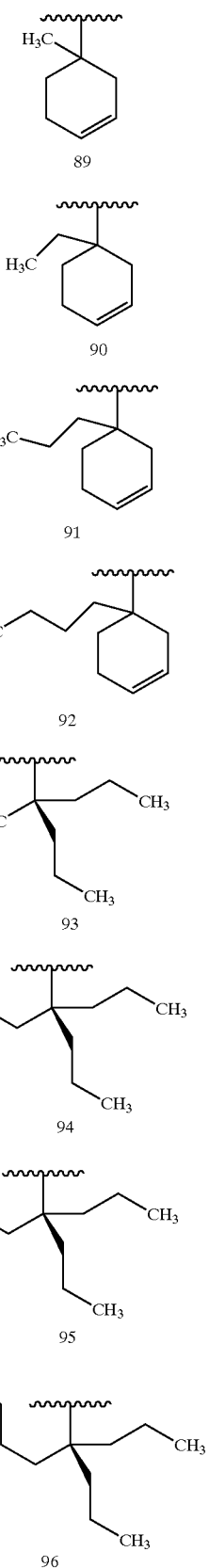

TABLE 4f-continued
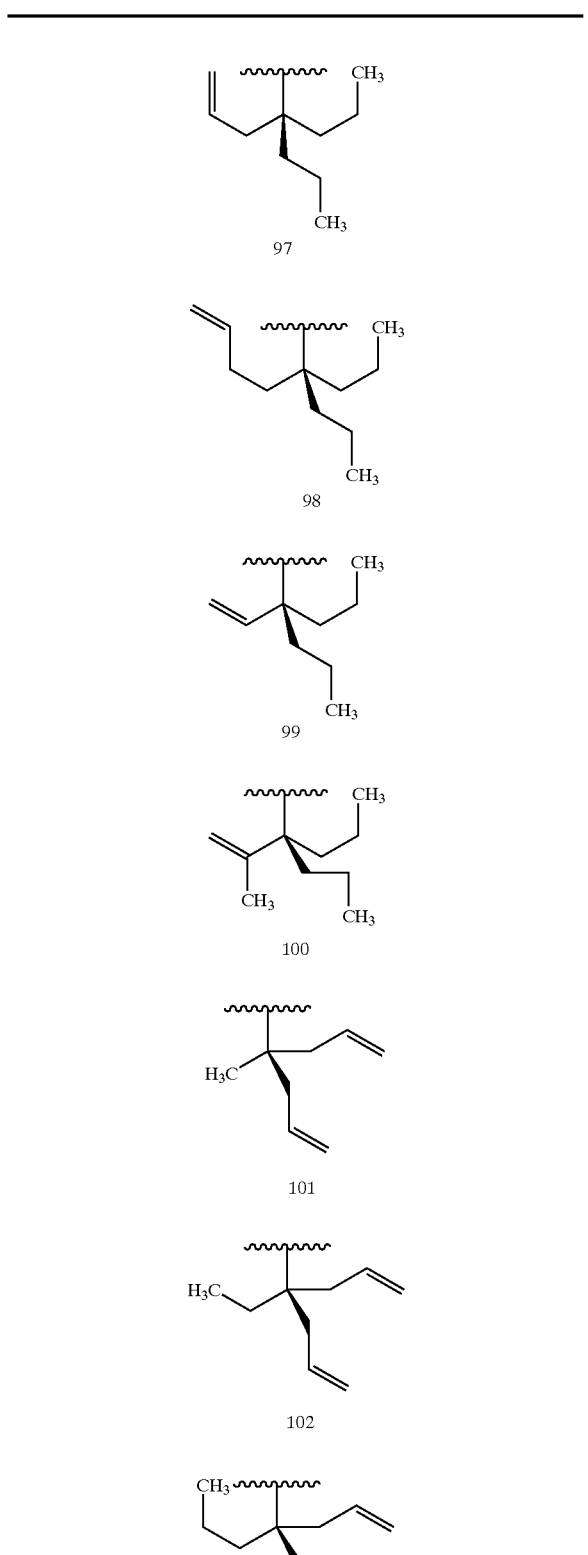
TABLE 4f-continued
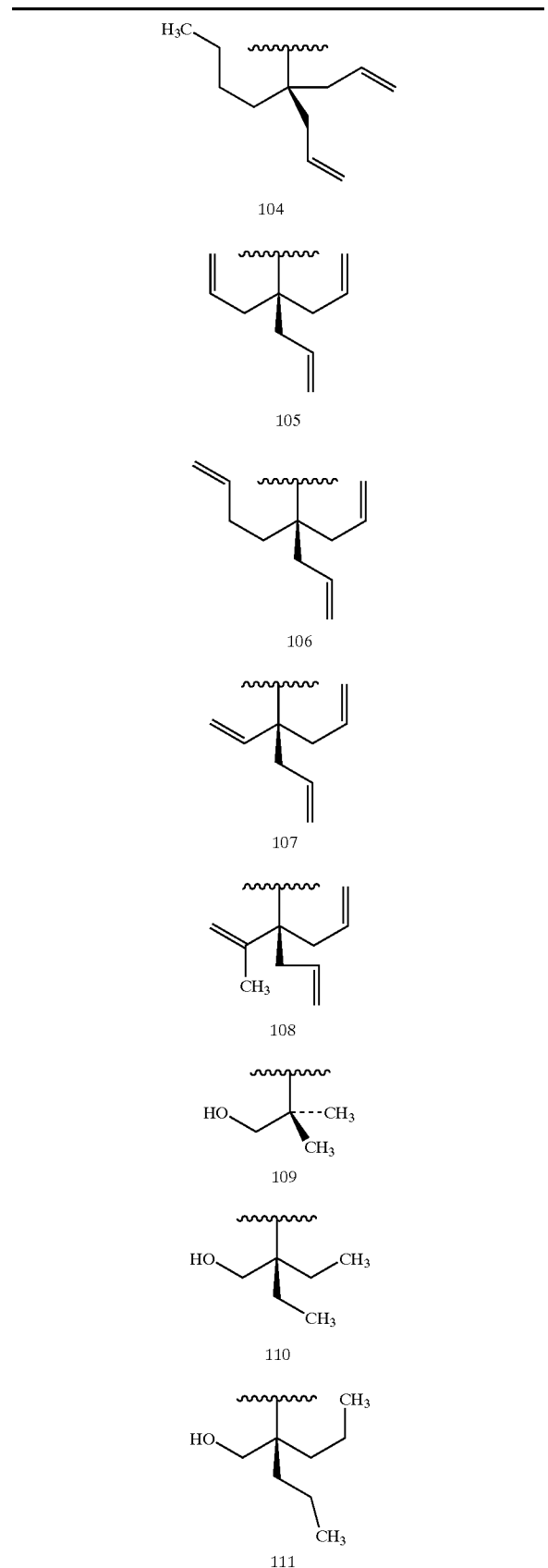

TABLE 4f-continued
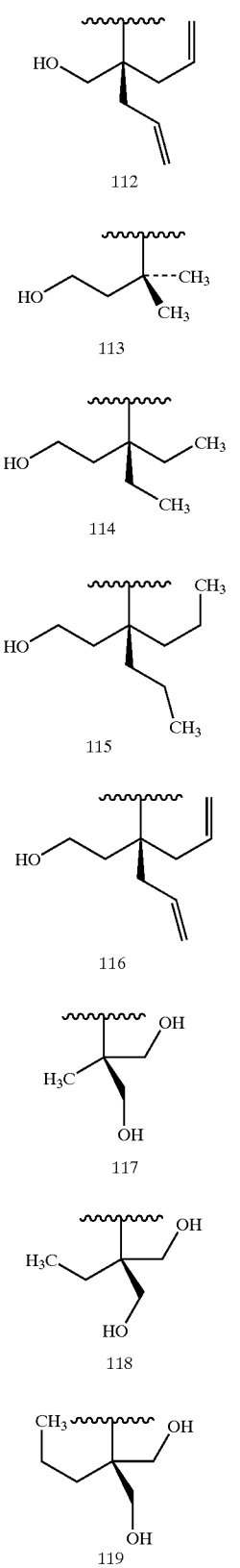
TABLE 4f-continued
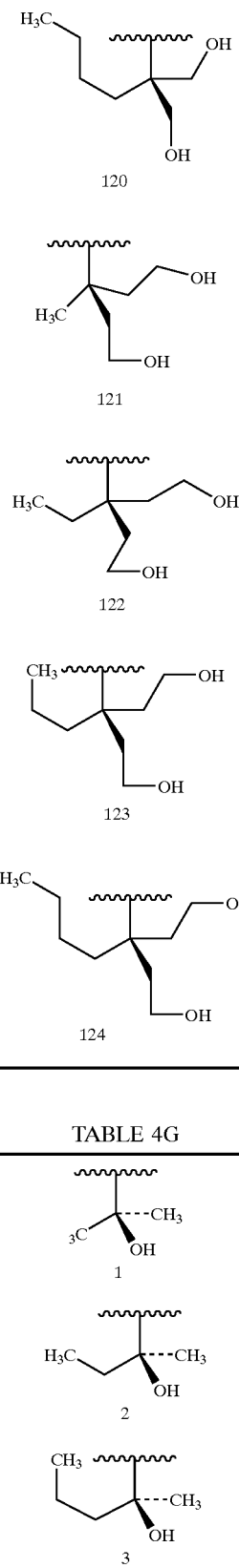
TABLE 4G
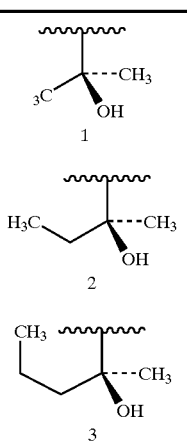

TABLE 4G-continued

TABLE 4G-continued

TABLE 4G-continued
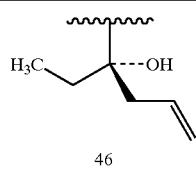
46
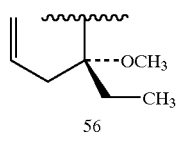
47
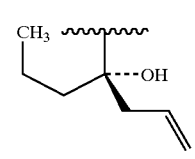
48
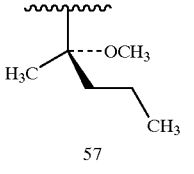
49
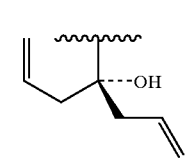
50
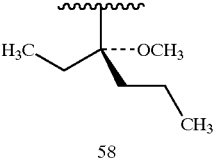
51
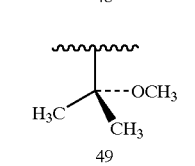
52
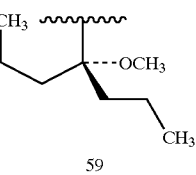
53
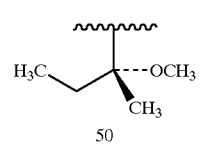
54
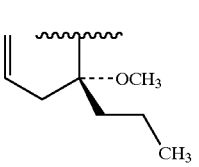
55
TABLE 4G-continued
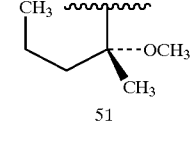
56
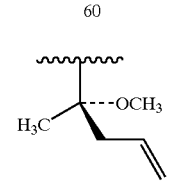
57
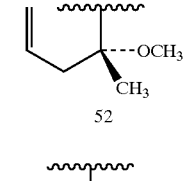
58
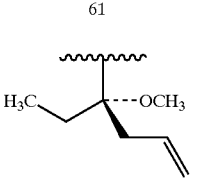
59
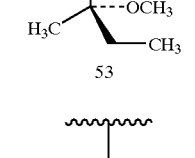
60
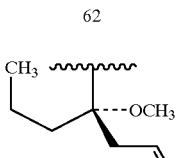
61
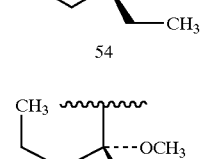
62
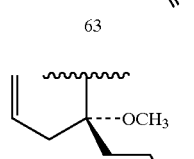
63
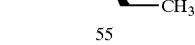
64

TABLE 4G-continued
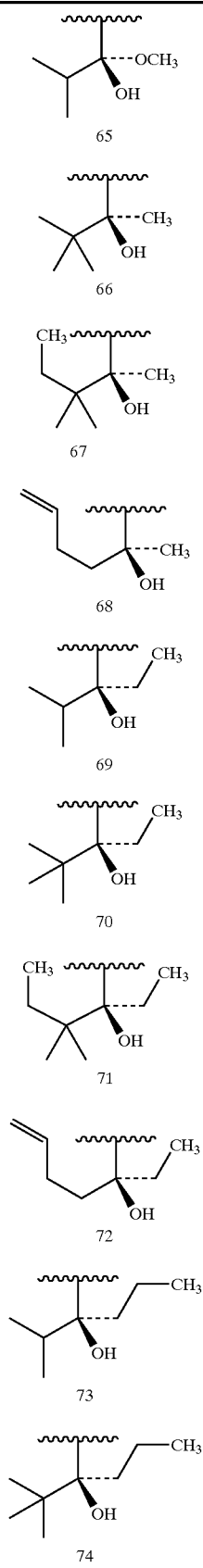
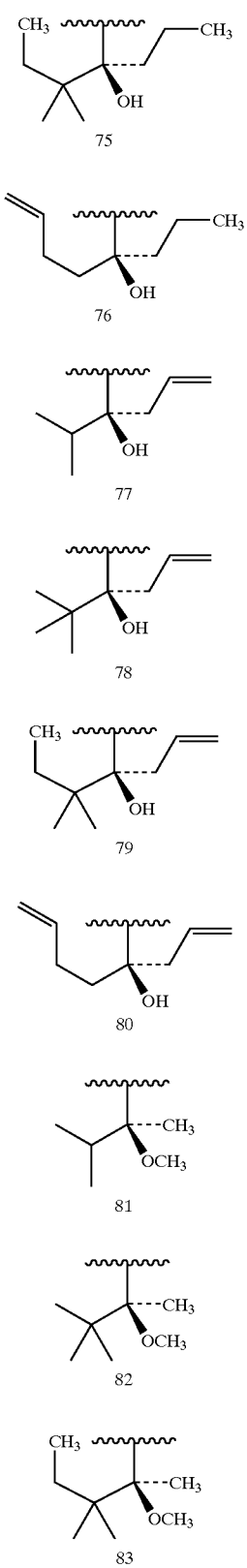

TABLE 4G-continued
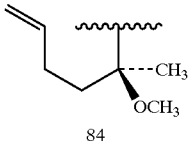
84
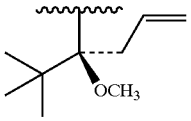
85
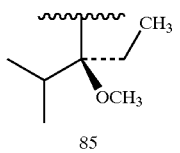
86
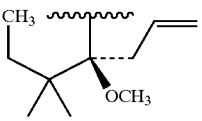
87
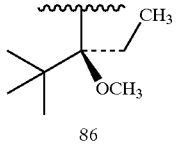
88
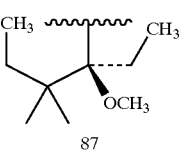
89
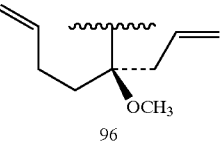
90
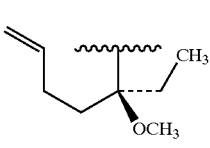
91
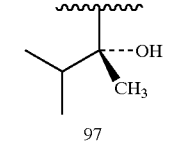
92
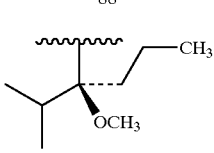
93
TABLE 4G-continued
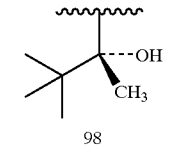
94
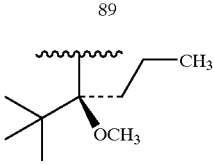
95
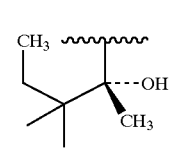
96
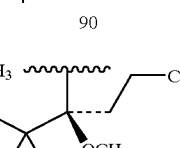
97
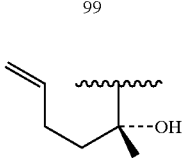
98
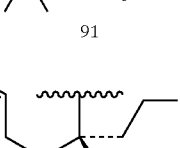
99
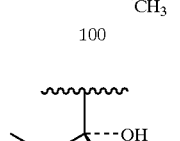
100
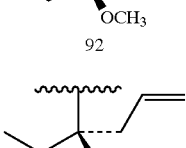
101
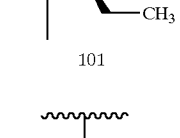
102

TABLE 4G-continued
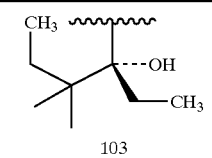
103
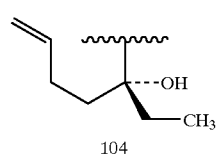
104
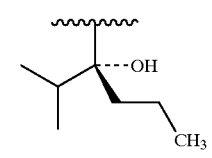
105
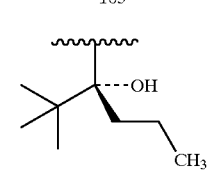
106
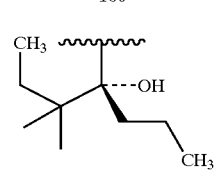
107
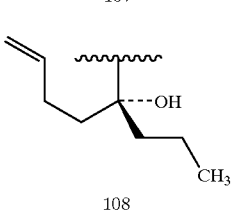
108
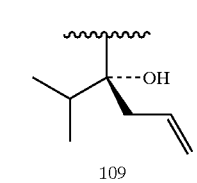
109
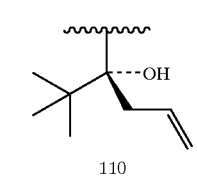
110
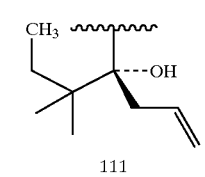
111
TABLE 4G-continued
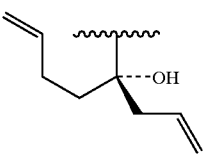
112
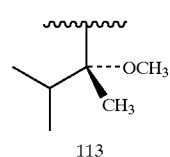
113
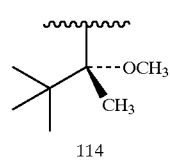
114
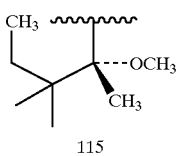
115
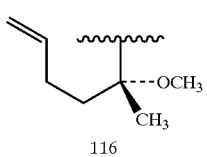
116
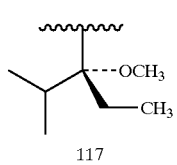
117
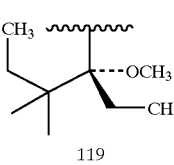
119
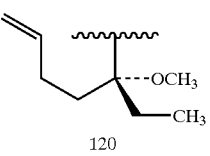
120
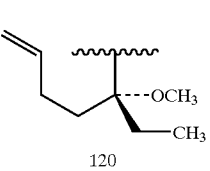
120

TABLE 4G-continued

TABLE 4G-continued
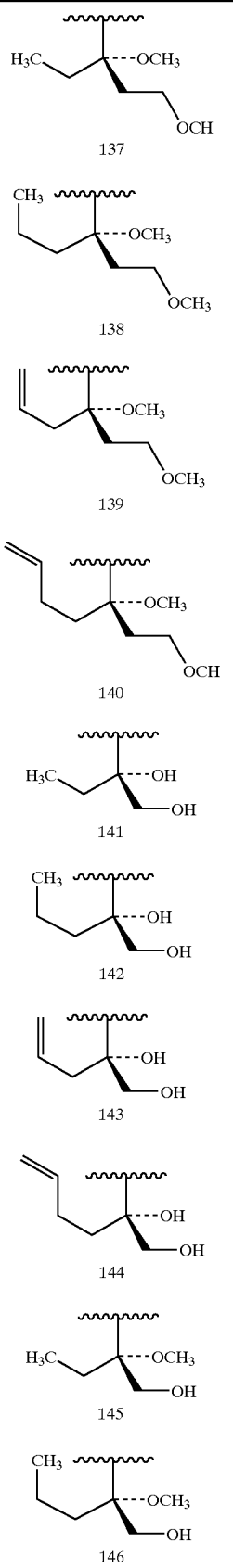
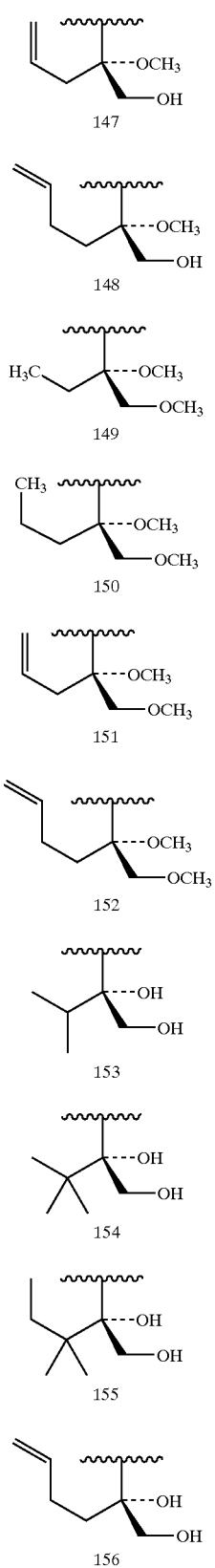

TABLE 4G-continued
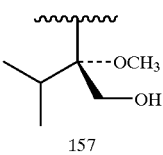
157
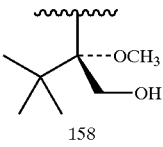
158
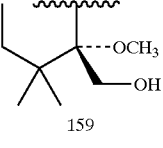
159
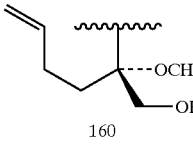
160
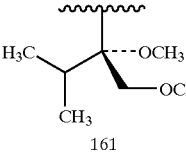
161
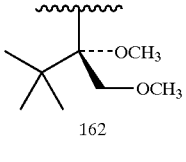
162
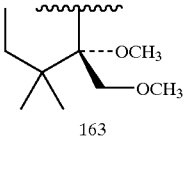
163
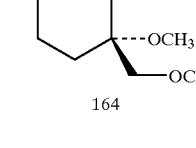
164
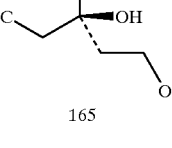
165
TABLE 4G-continued
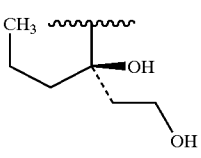
166
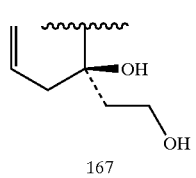
167
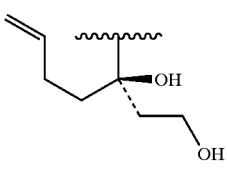
168
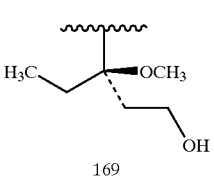
169
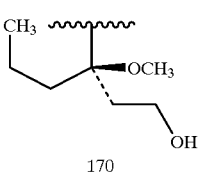
170
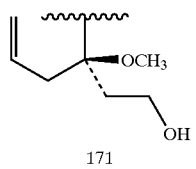
171
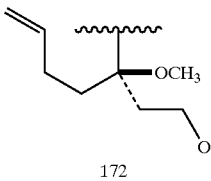
172
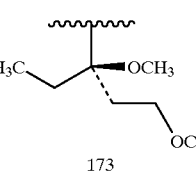
173

TABLE 4G-continued
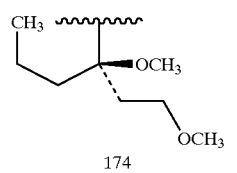
174
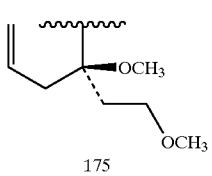
175
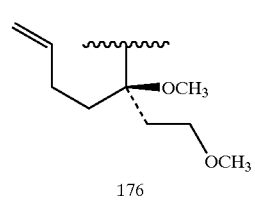
176
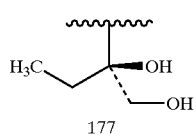
177
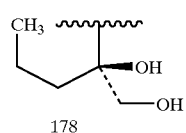
178
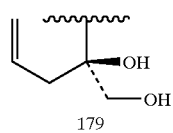
179
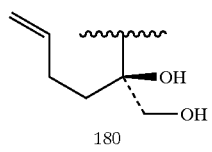
180
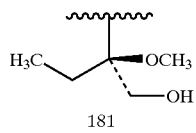
181
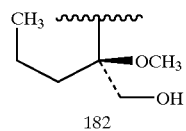
182
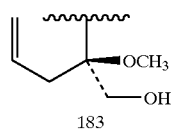
183
TABLE 4G-continued
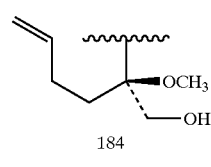
184
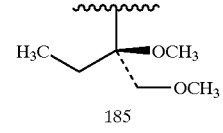
185
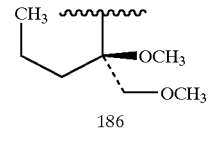
186
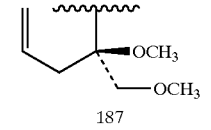
187
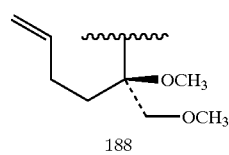
188
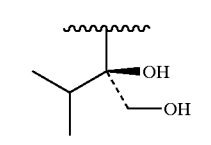
189
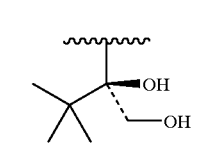
190
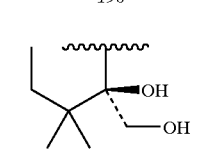
191
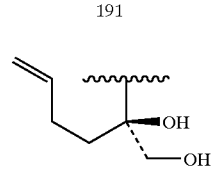
192
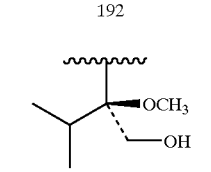
193

TABLE 4G-continued
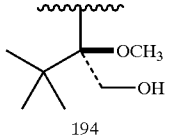
194
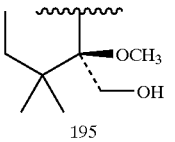
195
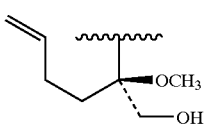
196
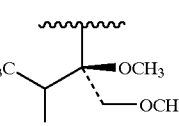
197
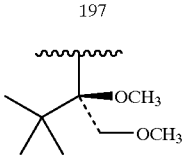
198
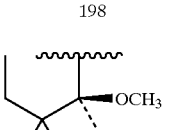
199
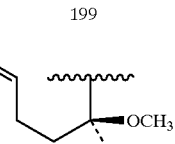
200
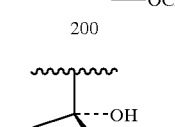
201
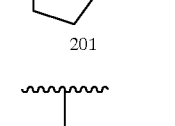
202
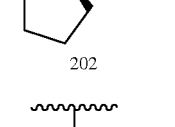
203
TABLE 4G-continued
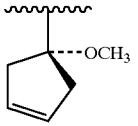
204
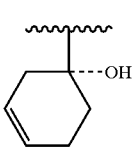
205
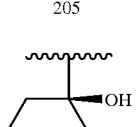
206
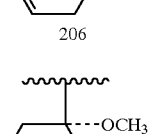
207
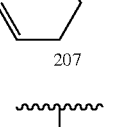
208
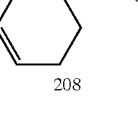
209
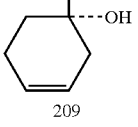
210
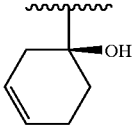
211
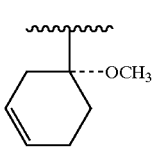
212

TABLE 4G-continued
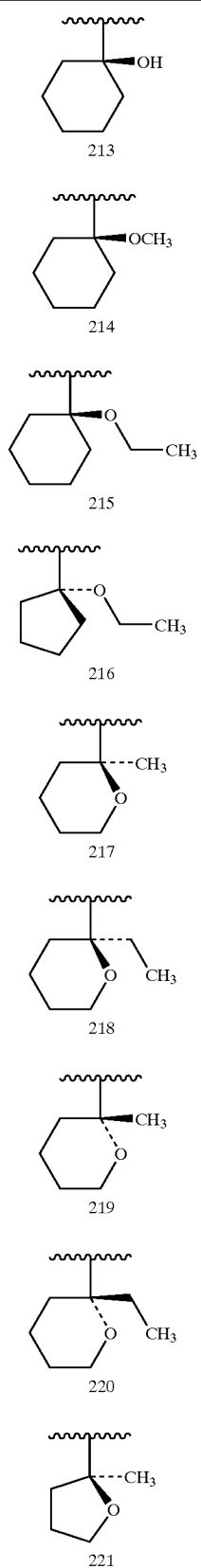
TABLE 4G-continued
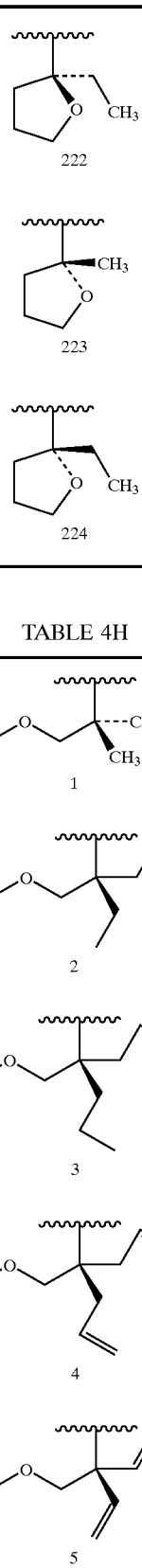
TABLE 4H

TABLE 4H-continued

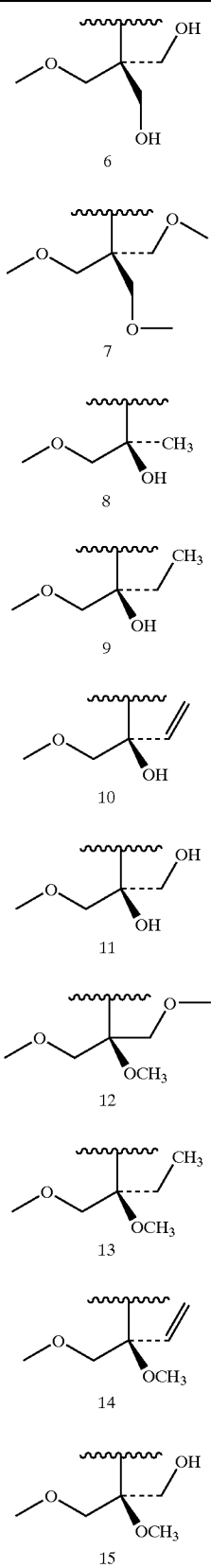

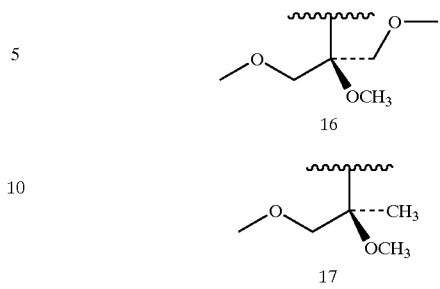

TABLE 5

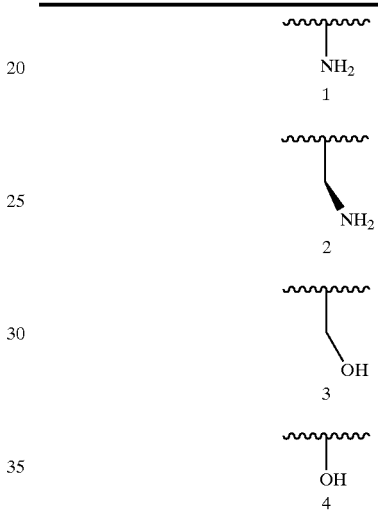

The ability of the compounds of the invention to inhibit neuraminidase in vitro can be determined according to the method described below.

Neuraminidase Inhibition Assay:

Influenza virus A/N1/PR/8/34 was grown in the allantoic cavity of fertilized eggs and purified by sucrose density gradient centrifugation (Laver, W. G. (1969) in "Fundamental Techniques in Virology" (K. Habel and N. P. Salzman, eds.) pp. 92–86, Academic Press, New York). Influenza virus A/N2/Tokyo/3/67 was obtained from the tissue culture supernatents of virus grown on MDCK cells. Neuraminidase from B/Memphis/3/89 virus was prepared by digestion of the virus with TPCK-trypsin followed by centrifugation and then purification of the neuraminidase catalytic fragment using sucrose density gradient centrifugation and dialysis as described previously (Air, G. M., Laver, W. G., Luo, M., Stray, S. J., Legrone, G., and Webster, R. G. (1990) *Virology* 177, 578–587).

The neuraminidase inhibition assays used the neuraminidase enzymatic activity associated with the A/N1/PR/8/34 or A/N2/Tokyo/3/67 whole virus, or the B/Memphis/3/89 catalytic head fragment. The whole virus or catalytic fragment was diluted appropriately with 20 mM N-ethylmorpholine, 10 mM calcium choride, pH 7.5 buffer on the day of the experiment. Neuraminidase inhibition assays were conducted in 20 mM N-ethylmorpholine, 10 mM calcium choride, pH 7.5 buffer with 5% DMSO. Reaction mixtures included neuraminidase, inhibitor (test compound) and 20–30 μM 4-methylumbelliferyl sialic acid substrate in a total volume of 200 μL and were contained in white 96-well U-shaped plates. Typically, five to eight concentrations of inhibitor were used for each Ki value measurement. The reactions were initiated by the addition of enzyme and allowed to proceed for 30–60 minutes at room temperature. The fluorescence for each well of the plate was measured once each minute during the reaction period by a Fluoroskan II plate reader (ICN Biomedical) equipped with excitation and emission filters of 355 +/−35 nm and 460+/−25 nm, respectively. The plate reader was under the control of DeltaSoft II software (Biometallics) and a Macintosh computer. If the compound exhibited linear reaction velocities during the reaction period, then the reaction velocities for the dose-response study were fit to equation 1 using a nonlinear regression program (Kaleidagraph) to determine the overall Ki value (Segel, I. H. (1975) in Enzyme Kinetics, pp. 105–106, Wiley-Interscience, New York).

$$(1-V_i/V_o)=[1]/\{[1]+K_i(1+[S]/K_m)\} \qquad \text{eqn 1}$$

In equation 1, Vi and Vo represent inhibited and uninhibited reaction velocities, respectively, and Km=16–40 μM depending on the neuraminidase strain tested. For those compounds exhibiting slow-binding inhibition (Morrison, J. F. (1982) *Trends Biochem. Sci.* 7, 102–105), a second experiment was performed in a manner identical to the first except that neuraminidase and inhibitor were preincubated in the absence of substrate for 2 hours at room temperature prior to initiating the reactions with substrate. Data analysis for the resulting linear velocities was conducted as described above.

Equation 2 was used to measure Ki values in the sub-nanomolar range (Morrison, J. F. And Stone, S. R. (1985) *Comments Mol. Cell Biophys.* 2, 347–368).

$$V=A\{sqrt\{(K_i'+I_t-E_t)^2+4K_i'E_t\}-(K_i'+I_t-E_t)] \qquad \text{eqn. 2}$$

In equation 2, V=velocity; A=αkcat[S]/2(Km+[S]); α is a factor to convert fluorescence units to molar concentrations; Ki'=Ki(1+[S]/Km); It=total inhibitor concentration and Et=total active concentration of neuraminidase.

The compounds of the invention inhibit influenza A neuraminidase and influenza B neuraminidase with $K_i$ values between about 24 micromolar and about 0.77 micromolar.

The ability of the compounds of the invention to inhibit plaque formation in cell culture can be determined by the method described below.

Cell Culture Plaque Formation Inhibition Assay

Cell Cultures: MDCK cells obtained from the American Type Culture Collection were grown in Dulbecco's Modified Eagle Medium (DMEM) high glucose (GibcoBRL) supplemented with 10% fetal calf serum (JRH Biosciences), 40 mM HEPES buffer (GibcoBRL) and antibiotics (GibcoBRL). Cells were routinely cultured in flasks or roller bottles at 37° C. and 5% $CO_2$. At confluence cells were reduced to a density of 500,000 cells in a ml using trypsin/EDTA (GibcoBRL) treatment of the monolayer followed by cell centrifugation, resuspension, and dilution into growth media. Cells were planted at a volume to surface area ratio of 1 ml over 1 $cm^2$ of growth surface.

Plaque Assay Protocol: On MDCK cell confluent 6 well plates growth media was removed and the cells were overlaid with 1.5 ml of assay media (DMEM with 1% fetal calf serum, 40 mM HEPES buffer and antibiotics) containing pre-mixed virus (influenza A/Tokyo/3/67 [H2N2]) (40–100 plaque forming units) and 2× concentration test compound. The plates were placed on a rocker and incubated for 2 hours at room temperature. During the virus adsorption period agar overlay media was prepared. In a microwave oven 2× agarose (final concentration of 0.6% agarose) in overlay media (DMEM with 40 mM HEPES buffer) was melted and then placed in a 48° C. water bath for temperature equilibration. After the virus adsorption period was completed 1.5 ml agar over media was added and mixed with the 1.5 ml virus and test compound containing media per well.

Cultures were incubated at 35° C. for the period required for plaque development, usually several days. Plaques were fixed with 3.7% formalin in PBS for 20 minutes followed by removal of the agar overlay and staining with 0.1% crystal violet in distilled water for 15 minutes. Plaques were counted and EC 50 concentration determined from multiple concentrations of the tested compound using regression analysis.

Viral Stocks: Stocks were prepared in MDCK confluent roller bottles incubated at 37° C. in DMEM supplemented with 1% FCS, 40 mM HEPES buffer, and antibiotics. Bottles were inoculated with a multiplicity of infection of approximately 0.1 plaque forming unit for each cell. Roller bottles were harvested after the cytopathic effect of the virus was observed to be complete. Stocks were prepared from the supernatant resulting from the low speed centrifugation of the media and cell lysate. Stocks were titered and stored at −80° C.

The compounds of the invention can be tested for in vivo antiviral activity using the method described below.

In Vivo Antiviral Efficacy Method

Female BALB/c mice were placed under anesthesia (sevoflurane) and inoculated intranasally (IN) with 0.1 ml of influenza A VR-95 (Puerto Rico PR8-34) at 10—2 (diluted from frozen stock). This viral concentration consistently produced disease in mice within 5 days of inoculation. Animals were treated 4 h. pre-infection and 4 h. post-infection, and periodically thereafter, with one of the following therapies: no treatment; test compound (100, 25, 6.25,1.39 mg/kg/day BID, PO); or vehicle (sterile water BID, PO). A group of ten animals (designated as control) was inoculated with 0.9% saline. Percent survival was determined. On day five, lungs were harvested, weighed and assigned scores of 0, 1, 2, 3 or 4 based on percentage consolidation (0; 10–20; 25–50; 50–75; 75–100%, respectively). In addition, each lung pair was image analyzed to determine objective lung consolidation percentages.

The compounds of the present invention can be used in the form of salts derived from inorganic or organic acids. These salts include but are not limited to the following: acetate, trifluoroacetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, hydrobromic acid, sulfuric acid and phosphoric acid and such organic acids as oxalic acid, maleic acid, succinic acid and citric acid. Other salts include salts with alkali metals or alkaline earth metals, such as sodium, potassium, lithium, calcium or magnesium or with ammonium or $N(R^{})_4^+$ salts (where $R^{}$ is loweralkyl).

In addition, salts of the compounds of this invention with one of the naturally occurring amino acids are also contemplated.

Preferred salts of the compounds of the invention include hydrochloride, methanesulfonate, sulfonate, phosphonate and isethionate.

The compounds of the Formula Ia, Ib, IIa, IIb, IIIa, IIIb, IVa, IVb, Va, Vb, VIa, VIb, VIIa, VIIb, VIIIa, VIIIb, IXa, IXb, Xa, Xb, XIa, XIb, XIIa, XIIb, XIIIa, XIIIb, XIVa, XIVb, XVa or XVb of this invention can have a substituent which is an acid group (for example, $—CO_2H$, $—SO_3H$, $—SO_2H$, $—PO_3H_2$, $—PO_2H$). Compounds of the Formula Ia, Ib, IIa, IIb, IIIa, IIIb, IVa, IVb, Va, Vb, VIa, VIb, VIIa, VIIb, VIIIa, VIIIb, IXa, IXb, Xa, Xb, XIa, XIb, XIIa, XIIb, XIIIa, XIIIb, XIVa, XIVb, XVa or XVb of this invention having a substituent which is an ester of such an acidic group are also encompassed by this invention. Such esters may serve as prodrugs. The prodrugs of this invention are metabolized in vivo to provide the above-mentioned acidic substituent of the parental compound of Formula Ia, Ib, Ia, IIb, IIIa, IIIb, IVa, IVb, Va, Vb, VIa, VIb, VIIa, VIIb, VIIIa, VIIIb, IXa, IXb, Xa, Xb, XIa, XIb, XIIa, XIIb, XIIIa, XIIIb, XIVa, XIVb, XVa or XVb. Prodrugs may also serve to increase the solubility of these substances and/or absorption from the gastrointestinal tract. These prodrugs may also serve to increase solubility for intravenous administration of the compounds. Prodrugs may also serve to increase the hydrophobicity of the compounds. Prodrugs may also serve to increase the oral bioavailability of the compounds by increasing absorption and/or decreasing first-pass metabolism. Prodrugs may also serve to increase tissue penetration of the compounds, thereby leading to increased activity in infected tissues and/or reduced rate of clearance.

Such esters contemplated by this invention include:

alkyl esters, especially loweralkyl esters, including, but not limited to, ethyl, n-propyl, isopropyl, n-butyl, sec-butyl, isobutyl, t-butyl, n-pentyl esters and the like;

alkoxyalkyl esters, especially, loweralkoxyloweralkyl esters, including, but not limited to, methoxymethyl, 1-ethoxyethyl, 2-methoxyethyl, isopropoxymethyl, t-butoxymethyl esters and the like;

alkoxyalkoxyalkyl esters, especially, alkoxyalkoxy-substituted loweralkyl esters, including, but not limited to, 2-methoxyethoxymethyl esters and the like;

aryloxyalkyl esters, especially, aryloxy-substituted loweralkyl esters, including, but not limited to, phenoxymethyl esters and the like, wherein the aryl group is unsubstituted or substituted as previously defined herein;

haloalkoxyalkyl esters, especially, haloalkoxy-substituted loweralkyl esters, including, but not limited to, 2,2,2-trichloroethoxymethyl esters and the like;

alkoxycarbonylalkyl esters, especially, loweralkoxycarbonyl-substituted loweralkyl esters, including, but not limited to, methoxycarbonylmethyl esters and the like;

cyanoalkyl esters, especially, cyano-substituted loweralkyl esters, including, but not limited to, cyanomethyl, 2-cyanoethyl esters and the like;

thioalkoxymethyl esters, especially, lowerthioalkoxy-substituted methyl esters, including, but not limited to, methylthiomethyl, ethylthiomethyl esters and the like;

alkylsulfonylalkyl esters, especially, loweralkylsulfonyl-substituted loweralkyl esters, including, but not limited to, 2-methanesulfonylethyl esters and the like;

arylsulfonylalkyl esters, especially, arylsulfonyl-substituted loweralkyl esters, including, but not limited to, 2-benzenesulfonylethyl and 2-toluenesulfonylethyl esters and the like;

acyloxyalkyl esters, especially, loweralkylacyloxy-substituted loweralkyl esters, including, but not limited to, formyloxymethyl, acetoxymethyl, pivaloyloxymethyl, acetoxyethyl, pivaloyloxyethyl esters and the like;

cycloalkylcarbonyloxyalkyl esters including, but not limited to, cyclopentanecarbonyloxymethyl, cyclohexanecarbonyloxymethyl, cyclopentanecarbonyloxyethyl, cyclohexanecarbonyloxyethyl esters and the like;

arylcarbonyloxyalkyl esters including, but not limited to, benzoyloxymethyl esters and the like;

(alkoxycarbonyloxy)alkyl esters, especially, (loweralkoxycarbonyloxy)-substituted loweralkyl esters, including, but not limited to, methoxycarbonyloxymethyl, ethoxycarbonyloxymethyl, 1-(methoxycarbonyloxy)ethyl, 2-(ethoxycarbonyloxy)ethyl esters and the like;

(cycloalkyloxycarbonyloxy)alkyl esters, especially, (cycloalkyloxycarbonyloxy)-substituted loweralkyl esters, including, but not limited to, cyclohexyloxycarbonyloxymethyl, cyclopentyloxycarbonyloxyethyl, cyclohexyloxycarbonyloxypropyl esters and the like;

oxodioxolenylmethyl esters including, but not limited to, (5-phenyl-2-oxo-1,3-dioxolen-4-yl)methyl, [5-(4-methylphenyl)-2-oxo-1,3-dioxolen-4-yl]methyl, (5-(4-methoxyphenyl)-2-oxo-1,3-dioxolen-4-yl)methyl, [5-(4-fluorophenyl)-2-oxo-1,3-dioxolen4-yl]methyl, [5-(4-chlorophenyl)-2-oxo-1,3-dioxolen-4-yl]methyl, (2-oxo-1,3-dioxolen-4-yl)methyl, (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl, (5-butyl-2-oxo-1,3-dioxolen-4-yl)methyl esters and the like;

phthalidyl esters wherein the phenyl ring of the phthalidyl group is unsubstituted or substituted as defined previously herein, including, but not limited to, phthalidyl, dimethylphthalidyl, dimethoxyphthalidyl esters and the like;

aryl esters including, but not limited to, phenyl, naphthyl, indanyl esters and the like;

arylalkyl esters, especially, aryl-substitued loweralkyl esters, including, but not limited to, benzyl, phenethyl, 3-phenylpropyl, naphthylmethyl esters and the like, wherein the aryl part of the arylalkyl group is unsubstituted or substituted as previously defined herein;

dialkylaminoalkyl esters, especially dialkylamino-substituted loweralkyl esters, including, but not limited to, 2-(N,N-dimethylamino)ethyl, 2-(N,N-diethylamino)ethyl ester and the like (heterocyclic)alkyl esters, especially, heterocyclic-substituted loweralkyl esters wherein the heterocycle is a nitrogen-containing heterocycle, including, but not limited to, (heterocyclic)methyl esters and the like, wherein the heterocyclic part of the (heterocyclic)alkyl group is unsubstituted or substituted as previously defined herein; and carboxyalkyl esters, especially, carboxy-substituted loweralkyl esters, including, but not limited to carboxymethyl esters and the like;

and the like.

Preferred prodrug esters of acid-containing compounds of the Formula Ia, Ib, IIa, IIb, IIIa, IIIb, IVa, IVb, Va, Vb, VIa, VIb, VIIa, VIIb, VIIIa, VIIIb, IXa, IXb, Xa, Xb, XIa, XIb, XIIa, XIIb, XIIIa, XIIIb, XIVa, XIVb, XVa or XVb are loweralkyl esters, including, but not limited to, ethyl, n-propyl, isopropyl, n-butyl, sec-butyl, isobutyl, t-butyl, n-pentyl esters, 3-pentyl esters, cycloalkyl esters, cycloalkylalkyl esters and benzyl esters wherein the phenyl ring is unsubstituted or substituted as previously defined herein.

Methods for the preparation of prodrug esters of compounds of the Formula Ia, Ib, IIa, IIb, IIIa, IIIb, IVa, IVb, Va, Vb, VIa, VIb, VIIa, VIIb, VIIIa, VIIIb, IXa, IXb, Xa, Xb, XIa, XIb, XIIa, XIIb, XIIIa, XIIIb, XIVa, XIVb, XVa or XVb are well-known in the art and include:

reacting the acid with the corresponding halide (for example, chloride or acyl chloride) and a base (for example, triethylamine, DBU, N,N-dimethylaminopyridine and the like) in an inert solvent (for example, DMF, acetonitrile, N-methylpyrrolidone and the like);

reacting an activated derivative of the acid (for example, an acid chloride, sulfonyl chloride, monochlorophosphonate and the like) with the corresponding alcohol or alkoxide salt; and the like.

Other examples of prodrugs of the present invention include amides derived from the substituent which is an acid group.

Such amides contemplated by this invention include:

simple amides, such as —C(O)NH$_2$ and the like;

alkylamino amides, especially, loweralkylamino amides, including, but not limited to, methylamino, ethylamino, n-propylamino, isopropylamino amides and the like;

cylcoalkylamino amides, including, but not limited to, cylopropylamino, cylcobutylamino, cyclopentylamino, cyclohexylamino amides and the like;

acylamino amides, including, but not limited to acetylamino, propionylamino, butanoylamino amides and the like;

cylcoalkylcarbonylamino amides, including, but not limited to, cyclopropylcarbonylamino, cyclobutylcarbonylamino amides and the like;

alkoxycarbonylalkylamino amides, including, but not limited to, ethoxycarbonylmethylamino, t-butyloxycarbonylmethylamino and the like;

aminoacylamino amides, including, but not limited to, aminoacetylamino amides and the like;

dialkylaminoacylamino amides, including, but not limited to, dimethylaminoacetylamino, diethylaminoacetylamino amides and the like;

(heterocyclic)acylamino amides, including, but not limited to, piperidin-1-ylacetylamino amides and the like;

amides derived from single naturally occuring L-amino acids (or from acid-protected L-amino acids, for example, esters of such amino acids and the like) or from dipeptides comprising two naturally occuring L-amino acids wherein each of the two amino acids is the same or is different (or from acid-protected dipeptides, for example, esters of such dipeptides and the like);

and the like.

Methods for preparation of prodrug amides of compounds of the invention are well-known in the art and include reacting the acid with the appropriate amine in the presence of an amide bond or peptide bond-forming coupling reagent or reacting an activated derivative of the acid with the appropriate amine and the like.

Other examples of prodrugs of the present invention include esters of hydroxyl-substituted compounds of Formula Ia, Ib, IIa, IIb, IIIa, IIIb, IVa, IVb, Va, Vb, VIa, VIb, VIIa, VIIb, VIIIa, VIIIb, IXa, IXb, Xa, Xb, XIa, XIb, XIIa, XIIb, XIIIa, XIIIb, XIVa, XIVb, XVa or XVb which have been acylated with a blocked or unblocked amino acid residue, a phosphate function, a hemisuccinate residue, an acyl residue of the formula $R^{100}C(O)$— or $R^{100}C(S)$— wherein $R^{100}$ is hydrogen, lower alkyl, haloalkyl, alkoxy, thioalkoxy, alkoxyalkyl, thioalkoxyalkyl or haloalkoxy, or an acyl residue of the formula $R^a$—$C(R^b)(R^d)$—$C(O)$— or $R^a$—$C(R^b)(R^d)$—$C(S)$— wherein $R^b$ and $R^d$ are independently selected from hydrogen or lower alkyl and $R^a$ is —$N(R^e)(R^f)$, $OR^e$ or —$SR^e$ wherein $R^e$ and $R^f$ are independently selected from hydrogen, lower alkyl and haloalkyl, or an amino-acyl residue having the formula $R^{100}NH(CH_2)_2NHCH_2C(O)$— or $R^{101}NH(CH_2)_2OCH_2C(O)$— wherein $R^{101}$ is hydrogen, lower alkyl, (aryl)alkyl, (cycloalkyl)alkyl, acyl, benzoyl or an ax-amino acyl group. The amino acid esters of particular interest are of glycine and lysine; however, other amino acid residues can also be used, including any of the naturally occuring amino acids and also including those wherein the amino acyl group is —$C(O)CH_2NR^{102}R^{103}$ wherein $R^{102}$ and $R^{103}$ are independently selected from hydrogen and lower alkyl, or the group —$NR^{102}R^{103}$, where $R^{102}$ and $R^{103}$, taken together, forms a nitrogen containing heterocyclic ring.

Other prodrugs include a hydroxyl-substituted compound of Formula Ia, Ib, IIa, IIb, IIIa, IIIb, IVa, IVb, Va, Vb, VIa, VIb, VIIa, VIIb, VIIIa, VIIIb, IXa, IXb, Xa, Xb, XIa, XIb, XIIa, XIIb, XIIIa, XIIIb, XIVa, XIVb, XVa or XVb wherein the hydroxyl group is functionalized with a substituent of the formula —$CH(R^{104})OC(O)R^{105}$ or —$CH(R^{104})OC(S)R^{105}$ wherein $R^{105}$ is lower alkyl, haloalkyl, alkoxy, thioalkoxy or haloalkoxy and $R^{104}$ is hydrogen, lower alkyl, haloalkyl, alkoxycarbonyl, aminocarbonyl, alkylaminocarbonyl or dialkylaminocarbonyl. Such prodrugs can be prepared according to the procedure of Schreiber (*Tetrahedron Lett.* 1983, 24, 2363) by ozonolysis of the corresponding methallyl ether in methanol followed by treatment with acetic anhydride.

The preparation of esters of hydroxyl-substituted compounds of formula Formula Ia, Ib, IIa, IIb, IIIa, IIIb, IVa, IVb, Va, Vb, VIa, VIb, VIIa, VIIb, VIIIa, VIIb, IXa, IXb, Xa, Xb, XIa, XIb, XIIa, XIIb, XIIIa, XIIIb, XIVa, XIVb, XVa or XVb is carried out by reacting a hydroxyl-substituted compound of formula Formula Ia, Ib, IIa, IIb, IIIa, IIIb, IVa, IVb, Va, Vb, VIa, VIb, VIIa, VIIb, VIIIa, VIIIb, IXa, IXb, Xa, Xb, XIa, XIb, XIIa, XIIb, XIIIa, XIIIb, XIVa, XIVb, XVa or XVb, with an activated amino acyl, phosphoryl, hemisuccinyl or acyl derivative.

Prodrugs of hydroxyl-substituted-compounds of the invention can also be prepared by alkylation of the hydroxyl substituted compound of formula Formula Ia, Ib, IIa, IIb, IIa, IIIb, IVa, IVb, Va, Vb, VIa, VIb, VIIa, VIIb, VIIIa, VIIIb, IXa, IXb, Xa, Xb, XIa, XIb, XIIa, XIIb, XIIIa, XIIIb, XIVa, XIVb, XVa or XVb, with (halo)alkyl esters, transacetalization with bis-(alkanoyl)acetals or condensation of the hydroxyl group with an activated aldehyde followed by acylation of the intermediate hemiacetal.

In preparing prodrugs it often is necessary to protect other reactive functional groups, in order to prevent unwanted side reactions. After protection of the reactive groups the desired group can be functionalized. The resulting functionalized product is then deprotected, to remove the protecting groups that were added to prevent unwanted side reactions. This will provide the desired prodrug. Suitable reaction conditions for preparing protecting groups are well known in the art. One source for reaction conditions is found in T. H. Greene and P. G. M. Wuts, *Protective Groups in Organic Synthesis,* 2nd edition, John Wiley & Sons, New York (1991).

This invention also encompasses compounds of the Formula Ia, Ib, IIa, IIb, IIIa, IIIb, IVa, IVb, Va, Vb, VIa, VIb, VIIa, VIIb, VIIIa, VIIb, IXa, IXb, Xa, Xb, XIa, XIb, XIIa, XIIb, XIIa, XIIIb, XIVa, XIVb, XVa or XVb which are esters or prodrugs and which are also salts. For example, a compound of the invention can be an ester of a carboxylic acid and also an acid addition salt of an amine or nitrogen-containing substituent in the same compound.

The compounds of the present invention are useful for inhibiting neuraminidase from disease-causing microorganisms which comprise a neuraminidase. The compounds of the invention are useful (in humans, other mammals and fowl) for treating or preventing diseases caused by microorganisms which comprise a neuraminidase The compounds of the present invention are useful for inhibiting influenza A virus neuraminidase and influenza B virus neuraminidase, in vitro or in vivo (especially in mammals and, in particular, in humans). The compounds of the present invention are also useful for the inhibition of influenza viruses, orthomyxoviruses, and paramyxoviruses in vivo, especially the inhibition of influenza A viruses and influenza B viruses in humans and other mammals. The compounds of the present invention are also useful for the treatment of infections caused by influenza viruses, orthomyxoviruses, and paramyxoviruses in vivo, especially the human diseases caused by influenza A and influenza B viruses. The compounds of the present invention are also useful for the prophylaxis of infections caused by influenza viruses, orthomyxoviruses, and paramyxoviruses in vivo in humans and other mammals, especially the prophylaxis of influenza A and influenza B viral infections; and, in particular, the prophylaxis of influenza A and influenza B viral infections in human subjects who are at high risk of developing other respiratory diseases concurrent with or as a consequence of influenza virus infections, or who suffer from chronic respiratory illness, such as asthma, emphysema, or cystic fibrosis.

Total daily dose administered to a human or other mammal host in single or divided doses may be in amounts, for example, from 0.001 to 300 mg/kg body weight daily and more usually 0.1 to 10 mg/kg body weight daily. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

Administration of a compound of this invention will begin before or at the time of infection or after the appearance of established symptoms and/or the confirmation of infection.

The compounds of the present invention may be administered orally, parenterally, sublingually, intranasally, by intrapulmonary administration, by inhalation or insufflation as a solution, suspension or dry powder (for example, in a spray), or rectally, in dosage unit formulations containing conventional nontoxic pharmaceutically acceptable carriers, adjuvants, and vehicles as desired. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic.

Methods to form liposomes are known in the art. See, for example, Prescott, Ed., *Methods in Cell Biology,* Volume XIV, Academic Press, New York, N.Y. (1976), p. 33 et seq.

While the compounds of the invention can be administered as the sole active pharmaceutical agent, they can also be used in combination with one or more anti-infective agents and/or other agents used to treat other acute or chronic respiratory ailments. Other agents to be administered in combination with a compound of the present invention include: an influenza vaccine; other influenza inhibitors such as, for example, amantadine, rimantadine, ribavirin, and the like; another influenza neuraminidase inhibitor, such as, for example, zanamivir or GS 4104 and the like; agents used to treat respiratory bacterial infections and bronchitis, such as, for example, erythromycin, clarithromycin, azithromycin and the like; and agents used to treat asthma, such as, for example, zileuton, albuterol (salbutamol), salmeterol, formoterol, ipratropium bromide, inhaled steroids and the like, or anti-inflammatory agents for treating asthma such as, for example, beclomethasone dipropionate, fluticasone propionate, budesonide, triamcinolone acetonide, flunisolide, cromolyn, zafirlukast, montelukast used in combination with a compound of the present invention.

When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:
1. A compound of the formula:

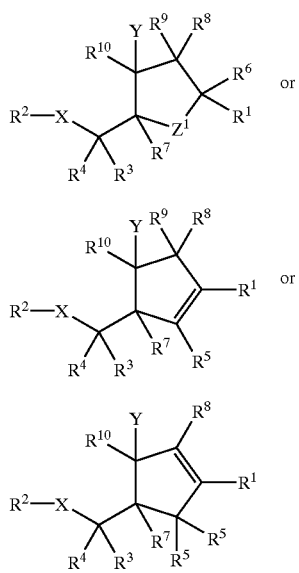

or a pharmaceutically acceptable salt or ester thereof, wherein
$R^1$ is selected from the group consisting of
(a) —$CO_2H$, (b) —$CH_2CO_2H$, (c) —$SO_3H$, (d) —$CH_2SO_3H$, (e) —$SO_2H$, (f) —$CH_2SO_2H$, (g) —$PO_3H_2$, (h) —$CH_2PO_3H_2$, (i) —$PO_2H$, (j) —$CH_2PO_2H$, (k) tetrazolyl, (l) —$CH_2$-tetrazolyl, (m) —C(=O)—NH—S(O)$_2$—$R^{11}$, (n) —$CH_2$C(=O)—NH—S(O)$_2$—$R^{11}$, (o) —$SO_2$N(T—$R^{11}$)$R^{12}$ and (p) —$CH_2SO_2$N(T—$R^{11}$)$R^{12}$
wherein T is selected from the group consisting of (i) a bond, (ii) —C(=O)—, (iii) —C(=O)O—, (iv) —C(=O)S—, (v) —C(=O)NR$^{36}$—, (vi) —C(=S)O—, (vii) —C(=S)S—, and (viii) —C(=S)NR$^{36}$—,
$R^{11}$ is selected from the group consisting of
(i) $C_1$–$C_{12}$ alkyl, (ii) $C_2$–$C_{12}$ alkenyl, (iii) cycloalkyl, (iv) (cycloalkyl)alkyl, (v) (cycloalkyl)alkenyl, (vi) cycloalkenyl, (vii) (cycloalkenyl)alkyl, (viii) (cycloalkenyl)alkenyl, (ix) aryl, (x) (aryl)alkyl, (xi) (aryl)alkenyl, (xii) heterocyclic, (xiii) (heterocyclic)alkyl and (xiv) (heterocyclic)alkenyl; and
$R^{12}$ and $R^{36}$ are independently selected from the group consisting of
(i) hydrogen, (ii) $C_1$–$C_{12}$ alkyl, (iii) $C_2$–$C_{12}$ alkenyl, (iv) cycloalkyl, (v) (cycloalkyl)alkyl, (vi) (cycloalkyl)alkenyl, (vii) cycloalkenyl, (viii) (cycloalkenyl)alkyl, (ix) (cycloalkenyl)alkenyl, (x) aryl, (xi) (aryl)alkyl, (xii) (aryl)alkenyl, (xiii) heterocyclic, (xiv) (heterocyclic)alkyl and (xv) (heterocyclic)alkenyl;
X is selected from the group consisting of
(a) —C(=O)—N(R*)—, (b) —N(R*)—C(=O)—, (c) —C(=S)—N(R*)—, (d) —N(R*)—C(=S)—, (e) —N(R*)—SO$_2$—, and (f) —SO$_2$—N(R*)—
wherein R* is hydrogen, $C_1$–$C_3$ loweralkyl or cyclopropyl;
$R^2$ is selected from the group consisting of
(a) hydrogen, (b) $C_1$–$C_6$ alkyl, (c) $C_2$–$C_6$ alkenyl, (d) $C_3$–$C_6$ cycloalkyl, (e) $C_5$–$C_6$ cycloalkenyl, (f) halo $C_1$–$C_6$ alkyl and (g) halo $C_2$–$C_6$ alkenyl; or
$R^2$—X— is

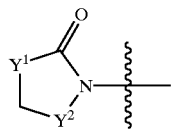

wherein $Y^1$ is —$CH_2$—, —O—, —S— or —NH— and
$Y^1$ is —C(=O)— or —C(R$^{aa}$)(R$^{bb}$)—
wherein $R^{aa}$ and $R^{bb}$ are indepedently selected from the group consisting of
hydrogen, $C_1$–$C_3$ loweralkyl, hydroxymethyl, 1-hydroxyethyl, 2-hydroxyethyl, aminomethyl, 1-aminoethyl, 2-aminoethyl, thiolmethyl, 1-thiolethyl, 2-thiolethyl, methoxymethyl, N-methylaminomethyl and methylthiomethyl;
$Z^1$ is —O—, —S—, or C(R$^5$)$_2$;
$R^3$ and $R^4$ are independently selected from the group consisting of (a) hydrogen, (b) cycloalkyl, (c) cycloalkenyl, (d) heterocyclic, (e) aryl and (f) —Z—R$^{14}$
wherein Z is
(i) —C(R$^{37a}$)(R$^{37b}$)—, (ii) —C(R$^{47}$)=C(R$^{48}$)—, (iii) —C≡C—, (iv) —C(=O)—, (v) —C(=S)—, (vi) —C(=NR$^{15}$)—, (vii) —C(R$^{37a}$)(OR$^{37c}$)—, (viii) —C(R$^{37a}$)(SR$^{37c}$)—, (ix) —C(R$^{37a}$)(N(R$^{37b}$)(R$^{37c}$))—, (x) —C(R$^{37a}$)(R$^{37b}$)—O—, (xi) —C(R$^{37a}$)(R$^{37b}$)—N(R$^{37c}$)—, (xii) —C(R$^{37a}$)(R$^{37b}$)—N(O)(R$^{37c}$)—, (xiii) —C(R$^{37a}$)(R$^{37b}$)—N(OH)—, (xiv) —C(R$^{37a}$)(R$^{37b}$)—S—, (xv) —C(R$^{37a}$)R$^{37b}$)—S(O)—, (xvi) —C(R$^{37a}$)(R$^{37b}$)—S(O)$_2$—, (xvii) —C(R$^{37a}$)(R$^{37b}$)—C(=O)—, (xviii) —C(R$^{37a}$)(R$^{37b}$)—C(=S)—, (xix) —C(R$^{37a}$)(R$^{37b}$)—C(=NR$^{15}$)—, (xx) —C(R$^{37a}$)(OR$^{37c}$)—C(=O)—, (xxi) —C(R$^{37a}$)(SR$^{37c}$)—C(=O)—, (xxii) —C(R$^{37a}$)(OR$^{37c}$)—C(=S)—, (xxiii) —C(R$^{37a}$)(SR$^{37c}$)—C(=S)—, (xxiv) —C(=O)—C(R$^{37a}$)(OR$^{37c}$)—, (xxv) —C(=O)—C(R$^{37a}$)(SR$^{37c}$)—, (xxvi) —C(=S)—C(R$^{37a}$)(OR$^{37c}$)—, (xxvii) —C(=S)—C(R$^{37a}$)(SR$^{37c}$)—, (xxviii) —C(R$^{37a}$)(OR$^{37c}$)—C(R$^{37a}$)(OR$^{37c}$)—, (xxix) —C(R$^{37a}$)

$(SR^{37c})$—$C(R^{37a})(OR^{37c})$—, (xxx) —$C(R^{37a})$ $(OR^{37c})$—$C(R^{37a})(SR^{37c})$—, (xxxi) —$C(R^{37a})$ $(SR^{37c})$—$C(R^{37a})(SR^{37c})$—, (xxxii) —$C(=O)$— $C(=O)$—, (xxxiii) —$C(=S)$—$C(=S)$—, (xxxiv) —$C(=O)$—$O$—, (xxxv) —$C(=O)$—$S$—, (xxxvi) —$C(=S)$—$O$—, (xxxvii) —$C(=S)$— $S$—, (xxxviii) —$C(=O)$—$N(R^{37a})$—, (xxxix) —$C(=S)$—$N(R^{37a})$—, (xl) —$C(R^{37a})(R^{37b})$—$C$ $(=O)$—$N(R^{37a})$—, (xli) —$C(R^{37a})(R^{37b})$—$C$ $(=S)$—$N(R^{37a})$—, (xlii) —$C(R^{37a})(R^{37b})$—$C$ $(=O)$—$O$—, (xliii)—$C(R^{37a})(R^{37b})$—$C(=O)$— $S$—, (xliv) —$C(R^{37a})(R^{37b})$—$C(=S)$—$O$—, (xlv) —$C(R^{37a})(R^{37b})$—$C(=S)$—$S$—, (xlvi) —$C(R^{37a})(R^{37b})$—$N(R^{37b})$—$C(=O)$—, (xlvii) —$C(R^{37a})(R^{37b})$—$N(R^{37b})$—$C(=S)$—, (xlviii)—$C(R^{37a})(R^{37b})$—$O$—$C(=O)$—, (xlix) —$C(R^{37a})(R^{37b})$—$S$—$C(=O)$—, (l) —$C(R^{37a})$ $(R^{37b})$—$O$—$C(=S)$—, (li) —$C(R^{37a})(R^{37b})$— $S$—$C(=S)$—, (lii) —$C(R^{37a})(R^{37b})$—$N(R^{37b})$— $C(=O)$—$N(R^{37a})$—, (liii) —$C(R^{37a})(R^{37b})$—$N$ $(R^{37b})$—$C(=S)$—$N(R^{37a})$—, (liv) —$C(R^{37a})$ $(R^{37b})$—$N(R^{37b})$—$C(=O)$—$O$—, (lv) —$C(R^{37a})$ $(R^{37b})$—$N(R^{37b})$—$C(=O)$—$S$—, (lvi) —$C(R^{37a})$ $(R^{37b})$—$N(R^{37b})$—$C(=S)$—$O$—, (lvii) —$C(R^{37a})(R^{37b})$—$N(R^{37b})$—$C(=S)$—$S$—, (lviii) —$C(R^{37a})(R^{37b})$—$O$—$C(=O)$—$N$ $(R^{37a})$—, (lix) —$C(R^{37a})(R^{37b})$—$S$—$C(=O)$—$N$ $(R^{37a})$—, (lx) —$C(R^{37a})(R^{37b})$—$O$—$C(=S)$—$N$ $(R^{37a})$—, (lxi) —$C(R^{37a})(R^{37b})$—$S$—$C(=S)$—$N$ $(R^{37a})$—, (lxii) —$C(R^{37a})(R^{37b})$—$O$—$C(=O)$— $O$—, (lxiii) —$C(R^{37a})(R^{37b})$—$S$—$C(=O)$—, (lxiv) —$C(R^{37a})(R^{37b})$—$O$—$C(=O)$—$S$—, (lxv) —$C(R^{37a})(R^{37b})$—$S$—$C(=O)$—$S$—, (lxvi) —$C(R^{37a})(R^{37b})$—$O$—$C(=S)$—$O$—, (lxvii) —$C(R^{37a})(R^{37b})$—$S$—$C(=S)$—$O$—, (lxviii) —$C(R^{37a})(R^{37b})$—$O$—$C(=S)$—$S$—, (lxix) —$C(R^{37a})(R^{37b})$—$S$—$C(=S)$—$S$— or (lxx) —$C(R^{37a})(R^{37b})$—$C(R^{37a})(OR^{37c})$—;

$R^{14}$ is (i) hydrogen, (ii) $C_1$–$C_{12}$ alkyl, (iii) haloalkyl, (iv) hydroxyalkyl, (v) thiol-substituted alkyl, (vi) $R^{37c}$O-substituted alkyl, (vii) $R^{37c}$S-substituted alkyl, (viii) aminoalkyl, (ix) ($R^{37c}$)NH-substituted alkyl, (x) $(R^{37a})(R^{37c})$N-susbstituted alkyl, (xi) $R^{37a}$O—(O=)—C-substituted alkyl, (xii) $R^{37a}$S—(O=)—C-substituted alkyl, (xiii) $R^{37a}$O—(S=)C-substituted alkyl, (xiv) $R^{37a}$S—(S=)C-substituted alkyl, (xv) $(R^{37a}O)_2$—P(=O)-substituted alkyl, (xvi) cyanoalkyl, (xvii) $C_2$–$C_{12}$ alkenyl, (xviii) haloalkenyl, (xix) $C_2$–$C_{12}$ alkynyl, (xx) cycloalkyl, (xxi) (cycloalkyl)alkyl, (xxii) (cycloalkyl)alkenyl, (xxiii) (cycloalkyl)alkynyl, (xxiv) cycloalkenyl, (xxv) (cycloalkenyl)alkyl, (xxvi) (cycloalkenyl)alkenyl, (xxvii) (cycloalkenyl)alkynyl, (xxviii) aryl, (xxix) (aryl) alkyl, (xxx) (aryl)alkenyl, (xxxi) (aryl)alkynyl, (xxxii) heterocyclic, (xxxiii) (heterocyclic)alkyl, (xxxiv) (heterocyclic)alkenyl or (xxxv) (heterocyclic)alkynyl, with the proviso that $R^{14}$ is other than hydrogen when Z is —$C(R^{37a})(R^{37b})$— $N(R^{37b})$—$C(=O)$—$O$—, —$C(R^{37a})(R^{37b})$—$N$ $(R^{37b})$—$C(=S)$—$O$—, —$C(R^{37a})(R^{37b})$—$N$ $(R^{37b})$—$C(=O)$—$S$—, —$C(R^{37a})(R^{37b})$—$N$ $(R^{37b})$—$C(=S)$—$S$—, —$C(R^{37a})(R^{37b})$—$O$—$C$ $(=O)$—$O$—, —$C(R^{37a})(R^{37b})$—$O$—$C(=S)$— $O$—, —13 $C(R^{37a})(R^{37b})$—$S$—$C(=O)$—$O$—, —$C(R^{37a})(R^{37b})$—$S$—$C(=S)$—$O$—, —$C(R^{37a})$ $(R^{37b})$—$O$—$C(=O)$—$S$—, —$C(R^{37a})(R^{37b})$— $O$—$C(=S)$—$S$—, —$C(R^{37a})(R^{37})$—$S$—$C$ $(=O)$—$S$— or —$C(R^{37a})(R^{37b})$—$S$—$C(=S)$— $S$—;

$R^{37a}$, $R^{37b}$, $R^{47}$, and $R^{48}$ at each occurrence are independently selected from the group consisting of (i) hydrogen, (ii) $C_1$–$C_{12}$ alkyl, (iii) haloalkyl, (iv) hydroxyalkyl, (v) alkoxyalkyl, (vi) $C_2$–$C_{12}$ alkenyl, (vii) haloalkenyl, (viii) $C_2$–$C_{12}$ alkynyl, (ix) cycloalkyl, (x) (cycloalkyl)alkyl, (xi) (cycloalkyl)alkenyl, (xii) (cycloalkyl)alkynyl, (xiii) cycloalkenyl, (xiv) (cycloalkenyl)alkyl, (xv) (cycloalkenyl)alkenyl, (xvi) (cycloalkenyl) alkynyl, (xvii) aryl, (xviii) (aryl)alkyl, (xix) (aryl) alkenyl, (xx) (aryl)alkynyl, (xxi) heterocyclic, (xxii) (heterocyclic)alkyl, (xxiii) (heterocyclic) alkenyl and (xxiv) (heterocyclic)alkynyl; and $R^{37c}$ at each occurrence is independently selected from the group consisting of (i) hydrogen, (ii) $C_1$–$C_{12}$ alkyl, (iii) haloalkyl, (iv) $C_2$–$C_{12}$ alkenyl, (v) haloalkenyl, (vi) $C_2$–$C_{12}$ alkynyl, (vii) cycloalkyl, (viii) (cycloalkyl)alkyl, (ix) (cycloalkyl)alkenyl, (x) (cycloalkyl)alkynyl, (xi) cycloalkenyl, (xii) (cycloalkenyl)alkyl, (xiii) (cycloalkenyl)alkyl, (xiv) (cycloalkenyl) alkynyl, (xv) aryl, (xvi) (aryl)alkyl, (xvii) (aryl) alkenyl, (xviii) (aryl)alkynyl, (xix) heterocyclic, (xx) (heterocyclic)alkyl, (xxi) (heterocyclic) alkenyl, (xxii) (heterocyclic)alkynyl, (xxiii) —$C(=O)$—$R$ , (xxiv) —$C(=S)$—$R^{14}$, (xxv) —$S(O)_2$—$R^{14}$ and (xxvi) hydroxyalkyl; or when Z is —$C(R^{37a})(R^{37b})$—$N(R^{37c})$—, then $N(R^{37c})$ and $R^{14}$ when taken together are an azido group; or when Z is —$C(R^{37a})(R^{37b})$—$N(O)(R^3c)$—, then $N(O)$ $(R^{37c})$ and $R^{14}$ when taken together are an N-oxidized 3–7 membered heterocyclic ring having at least one N-oxidized ring nitrogen atom; or when Z is —$C(R^{37a})(R^{37b})$—, —$C(R^{37a})(OR^{37c})$, —$C(R^{37a})(SR^{37c})$— or —$C(R^{37a})(N(R^{37b})(R^{37c}))$—, then $R^{37a}$, $R^{14}$ and the carbon atom to which they are bonded when taken together form a cyclopentyl, cyclopentenyl, cyclohexyl or cyclohexenyl ring or when $OR^{37c}$ or $SR^{37c}$ or $N(R^{37})$ and $R^{14}$ and the carbon atom to which they are bonded when taken together form a heterocyclic ring containing an O, S or N atom, respectively, and having from 4 to 8 ring atoms; and R is selected from the group consisting of (i) hydrogen, (ii) hydroxy, (iii) amino, (iv) $C_1$–$C_{12}$ alkyl, (v) haloalkyl, (vi) $C_2$–$C_{12}$ alkenyl, (vii) haloalkenyl, (viii) cycloalkyl, (ix) (cycloalkyl) alkyl, (x) (cycloalkyl)alkenyl, (xi) cycloalkenyl, (xii) (cycloalkenyl)alkyl, (xiii) (cycloalkenyl) alkenyl, (xiv) aryl, (xv) (aryl)alkyl, (xvi) (aryl) alkenyl, (xvii) heterocyclic, (xviii) (heterocyclic) alkyl and (xix) (heterocyciic)alkenyl; or $R^3$ and $R^4$ taken together, with the atom to which they are attached, form a carbocyclic or heterocyclic ring having from 3 to 8 ring atoms;

$R^5$ at each occurrence is independently selected from the group consisting of (a) hydrogen, (b) —$CH(R^{38})_2$, (c) —$(CH_2)_r$—$O$—$R^{40}$, (d) $C_2$–$C_4$ alkynyl, (e) cyclopropyl, (f) cyclobutyl, (g) —$C(=Q^1)$—$R^{17}$, and (h) —$(CH_2)_r$—$N(R^{19})_2$ wherein r is 0, 1 or 2;

with the proviso that when one $R^5$ is —$O$—$R^{40}$ or —$N(R^{19})_2$, then the other $R^5$ is other than —$O$—$R^{40}$ or —$N(R^{19})_2$;

wherein $Q^1$ is O, S, or $N(R^{18})$;

$R^{17}$ and $R^{18}$ are independently selected, at each occurrence, from the group consisting of hydrogen, methyl, and ethyl;

$R^{19}$, $R^{38}$, and $R^{40}$ are independently selected, at each occurrence, from the group consisting of (i) hydrogen, (ii) $C_1$–$C_{12}$ alkyl, (iii) haloalkyl, (iv) $C_2$–$C_{12}$ alkenyl, (v) haloalkenyl, (vi) cycloalkyl, (vii) (cycloalkyl)alkyl, (viii) (cycloalkyl)alkenyl, (ix) cycloalkenyl, (x) (cycloalkenyl)alkyl, (xi) (cycloalkenyl)alkenyl, (xii) aryl, (xiii) (aryl)alkyl, (xiv) (aryl)alkenyl, (xv) heterocyclic, (xvi) (heterocyclic)alkyl and (xvii) (heterocyclic)alkenyl; or one $R_{19}$ is an N-protecting group; or the two $R^5$ groups taken together with the carbon atom to which they are bonded, form a carbocyclic or heterocyclic ring having from 3 to 6 ring atoms;

Y is selected from the group consisting of (a) $C_1$–$C_5$ alkyl, (b) $C_1$–$C_5$ haloalkyl, (c) $C_2$–$C_5$ alkenyl, (d) $C_2$–$C_5$ haloalkenyl, (e) $C_2$–$C_5$ alkynyl, (f) $C_3$–$C_5$ cycloalkyl, (g) $C_3$–$C_5$ cycloalkyl-$C_1$-to-$C_3$-alkyl, (h) $C_5$ cycloalkenyl, (i) $C_5$ cycloalkenyl-$C_1$-to-$C_3$-alkyl, (j) $C_5$ cycloalkenyl-$C_2$-to-$C_3$-alkenyl, (k) —$(CHR^{39})_n OR^{20}$, (l) —$CH(OR^{20})$—$CH_2(OR^{20})$, (m) —$(CHR^{39})_n SR^{21}$, (n) phenyl, (o) halo-substituted phenyl, (p) —$(CHR^{39})_n C(=Q^3)R^{22}$, (q) —$(CHR^{39})_n N(=Q^3)$, (r) —$N(O)=CHCH_3$, (s) —$(CHR^{39})_n N(CH_3)R^{24}$ and (t) a heterocyclic ring having from 3 to 6 ring atoms; wherein n is 0, 1, or 2; $Q^2$ is O, S, $NR^{25}$, or $CHR^{26}$; and $Q^3$ is $NR^{41}$, or $CHR^{42}$;

with the proviso that compounds are excluded wherein Z is —$C(R^{37a})(R^{37b})$—, —$C(R^{37a})(OR^{37c})$—$C(R^{37a})(OR^{37c})$—, —$C(R^{37a})(SR^{37c})$—$C(R^{37a})(OR^{37c})$, —$C(R^{37a})(OR^{37c})$—$C(R^{37a})(SR^{37c})$—, or —$C(R^{37a})(SR^{37c})$—$C(R^{37a})(SR^{37c})$—;

$R^{14}$ is hydroxyalkyl, thiol-substituted alkyl, $R^{37c}$O-substituted alkyl, $R^{37c}$S-substituted alkyl, (viii) aminoalkyl, $(R^{37c})$NH-substituted alkyl, $(R^{37a})(R^{37c})$ N-susbstituted alkyl, $R^{37a}$O—(O=)C-substituted alkyl, $R^{37a}$S—(O=)C-substituted alkyl, $R^{37a}$O—(S=)C-substituted alkyl, or $R^{37a}$S—(S=)C-substituted alkyl; and Y is —$(CHR^{39})_n OR^{20}$, —$CH(OR^{20})$—$CH_2(OR^{20})$, —$(CHR^{39})_n SR^{21}$, —$(CHR^{39})_n C(=Q^2)R^{22}$, —$(CHR^{39})_n N(=Q^3)$, —$N(O)=CHCH_3$, or —$(CHR^{39})_n N(CH_3)R^{24}$;

$R^{20}$ at each occurrence is independently (i) methyl, (ii) ethyl, (iii) n-propyl, (iv) isopropyl, (v) $C_1$–$C_3$ haloalkyl, (vi) vinyl, (vii) propenyl, (viii) isopropenyl, (ix) allyl, (x) $C_2$–$C_3$ haloalkenyl, (xi) amino, (xii) —$NHCH_3$, (xiii) —$N(CH_3)_2$, (xiv) —$NHCH_2CH_3$, (xv) —$N(CH_3)(CH_2CH_3)$, (xvi) —$N(CH_2CH_3)_2$ or (xvii) —$N(=CH_2)$;

$R^{21}$ is (i) hydrogen, (ii) methyl, (iii) ethyl, (iv) n-propyl, (v) isopropyl, (vi) $C_1$–$C_3$ haloalkyl, (vii) vinyl, (viii) propenyl, (ix) isopropenyl, (x) allyl or (xi) $C_2$–$C_3$ haloalkenyl;

$R^{22}$ is (i) hydrogen, (ii) methyl, (iii) ethyl, (iv) n-propyl, (v) isopropyl, (vi) hydroxy, (vii) thiol, (viii) methoxy, (ix) ethoxy, (x) n-propoxy,(xi) isopropoxy, (xii) cyclopropyloxy, (xiii) methylthio, (xiv) ethylthio, (xv) n-propylthio, (xvi) isopropylthio, (xvii) cyclopropylthio, (xviii) vinyl, (xix) propenyl, (xx) isopropenyl, (xxi) allyl, (xxii) —$N(R^{28a})(R^{28b})$, (xxiii) —$CH_2 R^{29}$, (xxiv) aminomethyl, (xxv) hydroxymethyl, (xxvi) thiolmethyl, (xxvii) —$NHNH_2$, (xxviii) —$N(CH_3)NH_2$ or (xxix) —$NHNH(CH_3)$;

$R^{39}$ is hydrogen or methyl;

$R^{41}$ and $R^{42}$ are independently hydrogen, methyl, or ethyl;

$R^{24}$ is selected from the group consisting of (i) hydrogen, (ii) $C_1$–$C_4$ alkyl, (iii) $C_2$–$C_4$ alkenyl, (iv) $C_2$–$C_4$ alkynyl, (v) cyclopropyl, (vi) —$C(=Q^4)$—$R^{30}$, (v) —$OR^{31}$ and (vi) —$N(R^{32})_2$, wherein $Q^4$ is O, S, or $N(R^{33})$;

$R^{25}$ is hydroxy, methyl, ethyl, amino, —CN, or —$NO_2$;

$R^{26}$ group is hydrogen, methyl or ethyl;

$R^{28a}$ is hydrogen, hydroxy, methyl, ethyl, amino, —$NHCH_3$, —$N(CH_3)_2$, methoxy, ethoxy, or —CN;

$R^{28b}$ is hydrogen, methyl or ethyl;

or $R^{28a}$, $R^{28b}$ and the nitrogen to which they are bonded taken together represent azetidinyl;

$R^{29}$ group is hydrogen, hydroxy, thiol, methyl, ethyl, amino, methoxy, ethoxy, methylthio, ethylthio, methylamino or ethylamino;

$R^{30}$ group is hydrogen, methyl, ethyl, —$OR^{34}$, —$SR^{34}$, —$N(R^{35})_2$, —NHOH, —$NHNH_2$, —$N(CH_3)NH_2$, or —$N(CH_2CH_3)NH_2$;

$R^{31}$ and $R^{32}$ substituents, at each occurrence, are independently hydrogen, methyl or ethyl;

$R^{33}$ group is hydrogen, hydroxy, methyl, ethyl, amino, —CN, or —$NO_2$;

$R^{34}$ group is methyl or ethyl;

$R^{35}$ group is independently hydrogen, methyl or ethyl;

with the proviso that when $Q^2$ is $CHR^{26}$ then $R^{22}$ is selected from the group consisting of hydrogen, —$CH_3$, —$C_2H_5$, —$C_3H_7$, —$OCH_3$, —$SCH_3$, —O—$C_2H_5$, and —S—$C_2H_5$;

$R^6$ and $R^7$ are independently selected from the group consisting of (a) hydrogen, (b) $C_1$–$C_{12}$ alkyl, (c) $C_2$–$C_{12}$ alkenyl, (d) cycloalkyl, (e) (cycloalkyl)alkyl, (f) (cycloalkyl) alkenyl, (g) cycloalkenyl, (h) (cycloalkenyl)alkyl, (i) (cycloalkenyl)alkenyl, (j) aryl, (k) (aryl)alkyl, (l) (aryl)alkenyl, (m) heterocyclic, (n) (heterocyclic) alkyl, (o) (heterocyclic)alkenyl, (p) —$OR^{37a}$ and (q) —$N(R^{37a})_2$; and $R^8$, $R^9$, and $R^{10}$ are independently selected from the group consisting of (a) hydrogen, (b) $C_1$–$C_6$ alkyl, (c) $C_2$–$C_6$ alkenyl, (d) $C_3$–$C_6$ cycloalkyl, (e) $C_3$–$C_6$ cycloalkenyl, and (f) fluorine, with the proviso that the total number of atoms, other than hydrogen, in each of $R^8$, $R^9$, and $R^{10}$, is 6 atoms or less.

2. The compound according to claim 1 of the formula:

Ia

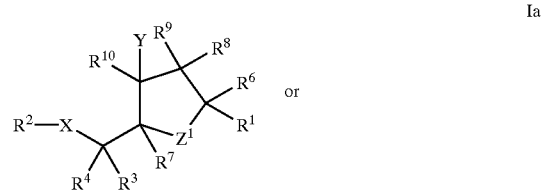

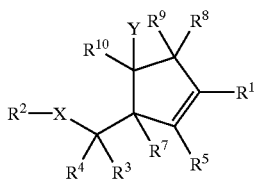
IIa or a pharmaceutically acceptable salt or ester thereof, wherein $R^1$, $R^2$, $R^3$, $R^4$, $R^5$, $R^6$, $R^7$, $R^8$, $R^9$, $R^{10}$, X, Y and $Z^1$ are as defined therein.

3. The compound according to claim 1 having the relative stereochemistry of the formula:

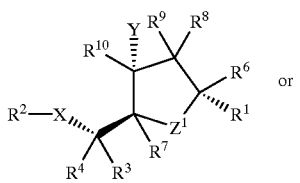
IVa

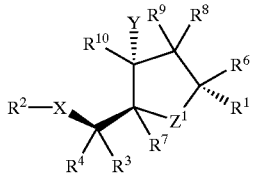
Va

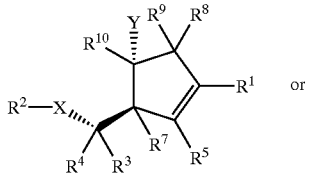
VIIIa

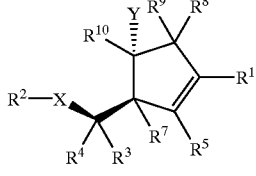
IXa or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein and wherein $R^3$ and $R^4$ are not the same.

4. The enantiomerically enriched compound according to claim 1 having the absolute stereochemistry of the formula:

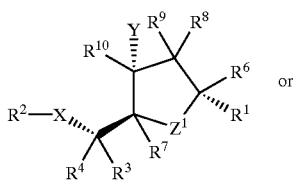
Xa

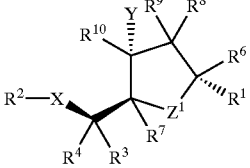
XIa

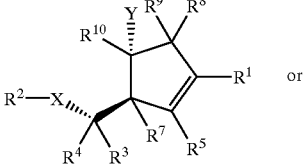
XIVa or

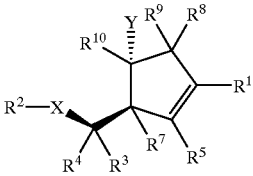
XVa or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein and wherein $R^3$ and $R^4$ are not the same.

5. The compound according to claim 1 wherein —X—$R^2$ is $R^2$—C(=O)—NH—, $R^2$—NH—C(=O)—, $R^2$—NH—$SO_2$— or $R^2$—$SO_2$—NH— wherein $R^2$ is $C_1$–$C_3$ loweralkyl, halo $C_1$–$C_3$ loweralkyl, $C_2$–$C_3$ alkenyl or halo $C_2$–$C_3$ alkenyl or —X—R is

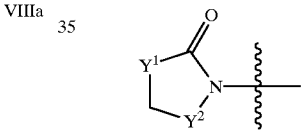

wherein $Y^1$ is —$CH_2$—, —O—, —S— or —NH— and $Y^2$ is —C(=O)— or —C($R^{aa}$)($R^{bb}$)— wherein $R^{aa}$ and $R^{bb}$ are independently selected from the group consisting of hydrogen, $C_1$–$C_3$ loweralkyl, hydroxymethyl, 1-hydroxyethyl, 2-hydroxyethyl, aminomethyl, 1-aminoethyl, 2-aminoethyl, thiolmethyl, 1-thiolethyl, 2-thiolethyl, methoxymethyl, N-methylaminomethyl and methylthiomethyl;

$R^3$ and $R^4$ are independently selected from hydrogen, heterocyclic and —Z—$R^{14}$ wherein Z and $R^{14}$ are defined therein and wherein one of $R^3$ and $R^4$ is other than hydrogen;

$Z^1$ is —O—, —S— or —CH($R^5$)— wherein $R^5$ is hydrogen, loweralkyl, —$(CH_2)_r$$OR^4$ or —$(CH_2)_r$N$(R^{19})_2$ wherein r and $R^{19}$ and $R^{40}$ are defined as above; or $R^5$ is hydrogen, loweralkyl, —$(CH_2)_r$$OR^{40}$ or —$(CH_2)_r$N$(R^{19})_2$ wherein r and $R^{19}$ and $R^{40}$ are defined as above;

$R^6$ and $R^7$ are independently hydrogen or loweralkyl;

$R^8$ and $R^9$ are independently hydrogen, fluoro or loweralkyl;

$R^{10}$ is hydrogen, fluoro or loweralkyl; and

Y is $C_2$–$C_5$ alkenyl, $C_2$–$C_5$ haloalkenyl, —C(=$Q^2$)$R^{22}$, —N(=$Q^3$), —N(O)=CHCH$_3$, —N(CH$_3$)R$^{24}$ or a heterocyclic ring having from 3 to 6 ring atoms, wherein R$^{22}$, R$^{24}$, Q$^2$ and Q$^3$ are defined as therein;
or a pharmaceutically acceptable salt or ester thereof.

6. The compound according to claim 5 having the relative stereochemistry of the formula:

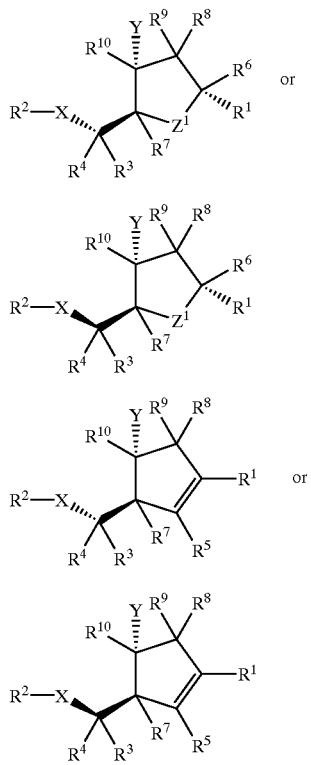

or a pharmaceutically acceptable salt or ester thereof, wherein R$^1$, R$^2$, R$^3$, R$^4$, R$^5$, R$^6$, R$^7$, R$^{10}$, X, Y and Z$^1$ are as defined therein and wherein R$^3$ and R$^4$ are not the same.

7. The enantiomerically enriched compound according to claim 5 having the absolute stereochemistry of the formula:

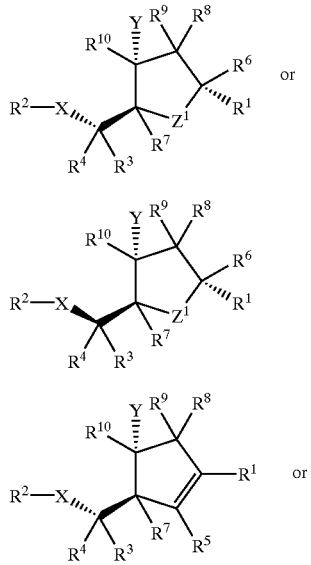

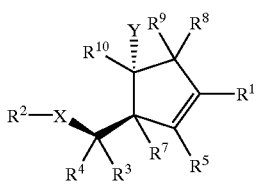

or a pharmaceutically acceptable salt or ester thereof, wherein R$^1$, R$^2$, R$^3$, R$^4$, R$^5$, R$^6$, R$^7$, R$^{10}$, X, Y and Z$^1$ are as defined therein and wherein R$^3$ and R$^4$ are not the same.

8. The compound according to claim 1 wherein —X—R$^2$ is R$^2$—C(=O)—NH—, R$^2$—NH—C(=O)—, R$^2$—NH—SO$_2$— or R$^2$—SO$_2$—NH— wherein R$^2$ is C$_1$-C$_3$ loweralkyl, halo C$_1$-C$_3$ loweralkyl, C$_2$-C$_3$ alkenyl or halo C$_2$-C$_3$ alkenyl or —X—R$^2$ is

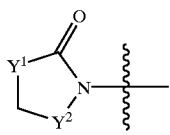

wherein Y$^1$ is —CH$_2$— and Y$^2$ is —C(=O)— or —C(R$^{aa}$)(R$^{bb}$)— wherein R$^{aa}$ and R$^{bb}$ are independently selected from the group consisting of hydrogen, C$_1$-C$_3$ loweralkyl, hydroxymethyl, 1-hydroxyethyl and 2-hydroxyethyl;

R$^3$ and R$^4$ are independently selected from hydrogen, heterocyclic and —Z—R$^{14}$ wherein Z and R$^{14}$ are defined therein and wherein one of R$^3$ and R$^4$ is other than hydrogen;

Z$^1$ is —O—, —S— or —CH(R$^5$)— wherein R$^5$ is hydrogen, loweralkyl, —(CH$_2$)$_r$OR$^{40}$ or —(CH$_2$)$_r$N(R$^{19}$)$_2$ wherein r and R$^{19}$ and R$^{40}$ are defined as above; or R$^5$ is hydrogen, loweralkyl, —(CH$_2$)$_r$OR$^{40}$ or —(CH$_2$)$_r$N(R$^{19}$)2 wherein r and R$^{19}$ and R$^{40}$ are defined as above;

R$^6$ and R$^7$ are independently hydrogen or loweralkyl;

R$^8$ and R$^9$ are independently hydrogen or loweralkyl;

R$^{10}$ is hydrogen or loweralkyl; and

Y is C$_2$-C$_5$ alkenyl, C$_2$-C$_5$ haloalkenyl, —C(=Q$^2$)R$^{22}$, —N(=Q$^3$), —N(O)=CHCH$_3$.

9. The compound according to claim 8 having the relative stereochemistry of the formula:

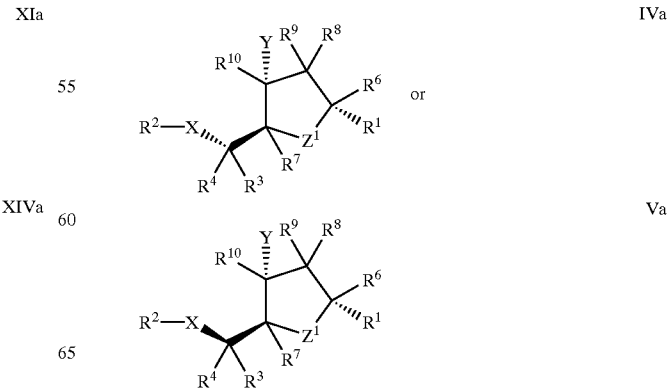

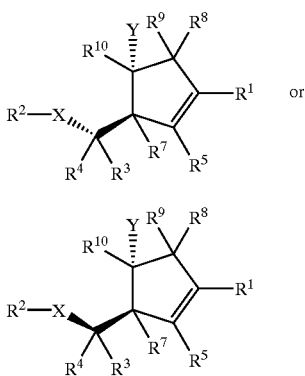

or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein and wherein $R^3$ and $R^4$ are not the same.

10. The enantiomerically enriched compound according to claim 8 having the absolute stereochemistry of the formula:

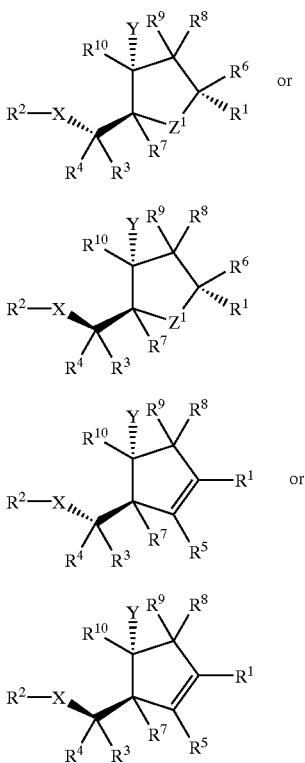

or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein and wherein $R^3$ and $R^4$ are not the same.

11. The compound according to claim 1 wherein —X—$R^2$ is $R^2$—C(=O)—NH—, $R^2$—NH—C(=O)—, $R^2$—NH—SO$_2$— or $R^2$—SO$_2$—NH— wherein $R^2$ is $C_1$–$C_3$ loweralkyl, halo $C_1$–$C_3$ loweralkyl, $C_2$–$C_3$ alkenyl or halo $C_1$–$C_3$ alkenyl or —X—$R^2$ is

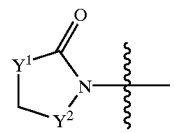

wherein $Y^1$ is —CH$_2$— and $Y^2$ is —C(=O)— or —C($R^{aa}$)($R^{bb}$)— wherein $R^{aa}$ and $R^{bb}$ are independently selected from the group consisting of hydrogen, $C_1$–$C_3$ loweralkyl, hydroxymethyl, 1-hydroxyethyl and 2-hydroxyethyl;

$R^3$ and $R^4$ are independently selected from hydrogen, heterocyclic and —Z—$R^{14}$ wherein Z and $R^{14}$ are defined therein and wherein one of $R^3$ and $R^4$ is other than hydrogen;

$Z^1$ is —O—, —S— or —CH($R^5$)— wherein $R^5$ is hydrogen, loweralkyl, —(CH$_2$)$_r$OR$^{40}$ or —(CH$_2$)$_r$N($R^{19}$)$_2$ wherein r and $R^{19}$ and $R^{40}$ are defined as above; or $R^5$ is hydrogen, loweralkyl, —(CH$_2$)$_r$OR$^{40}$ or —(CH$_2$)$_r$N($R^{19}$)$_2$ wherein r and $R^{19}$ and $R^{40}$ are defined as above;

$R^6$ and $R^7$ are independently hydrogen or loweralkyl;

$R^8$ and $R^9$ are independently hydrogen or loweralkyl;

$R^{10}$ is hydrogen or loweralkyl; and

Y is $C_2$–$C_5$ alkenyl, $C_2$–$C_5$ haloalkenyl or a heterocyclic ring having 5 ring atoms and also containing one or two double bonds; or a pharmaceutically acceptable salt or ester thereof.

12. The compound according to claim 11 having the relative stereochemistry of the formula:

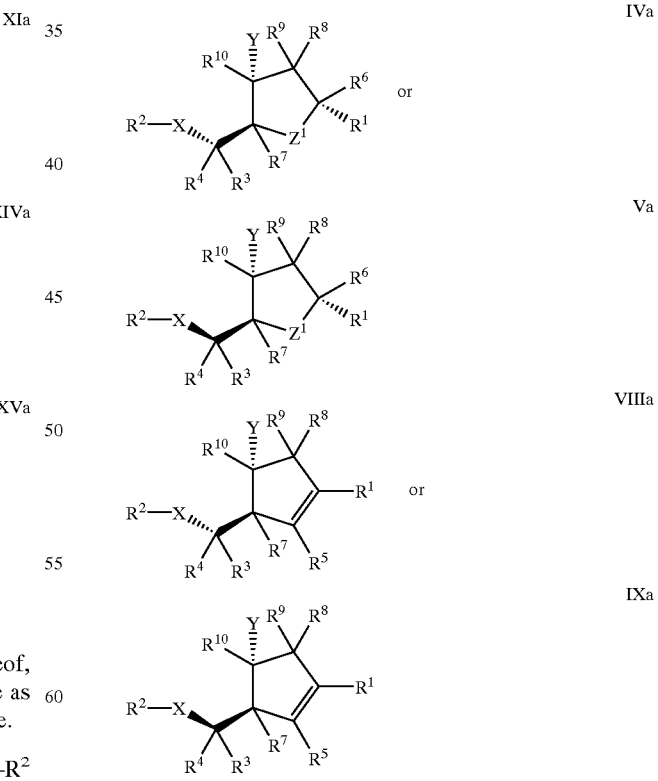

or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein and wherein $R^3$ and $R^4$ are not the same.

13. The enantiomerically enriched compound according to claim 11 having the absolute stereochemistry of the formula:

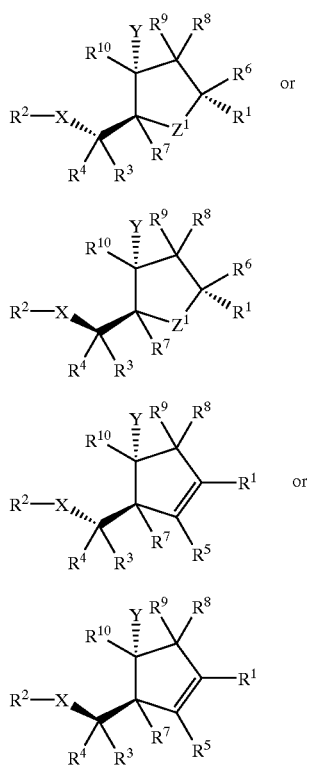

Xa

XIa

XIVa

XVa or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein and wherein $R^3$ and $R^4$ are not the same.

14. The compound according to claim 1 wherein $R^1$ is —$CO_2H$; —X—$R^2$ is $R^2$—C(=O)—NH—, $R^2$—NH—C(=O)—, $R^2$—NH—$SO_2$— or $R^2$—$SO_2$—NH— wherein $R^2$ is $C_1$-$C_3$ loweralkyl or halo-$C_1$-$C_3$ loweralkyl;

$R^3$ and $R^4$ are independently selected from hydrogen, heterocyclic and —Z—$R^{14}$ wherein Z and $R^{14}$ are defined therein;

$Z^1$ is —O—, —S—, —$CH_2$—,

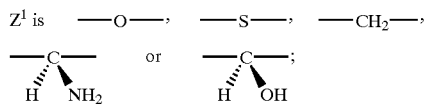

or $R^5$ is hydrogen;

$R^6$ and $R^7$ are independently hydrogen or loweralkyl;

$R^8$ and $R^9$ are hydrogen independently hydrogen or loweralkyl;

$R^{10}$ is hydrogen or loweralkyl; and

Y is $C_2$-$C_5$ alkenyl, $C_2$14 $C_5$ haloalkenyl or a heterocyclic ring having 5 ring atoms and also containing one or two double bonds;

or a pharmaceutically acceptable salt or ester thereof.

15. The compound according to claim 14 having the relative stereochemistry of the formula:

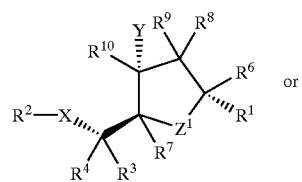

IVa

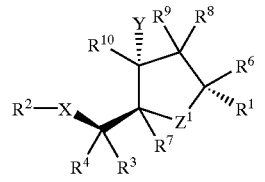

Va

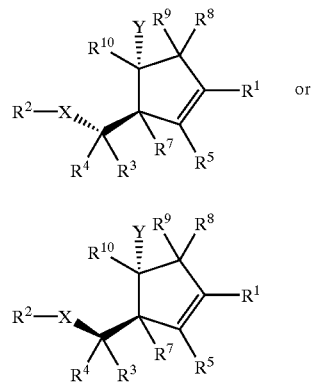

VIIIa

IXa or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein and wherein $R^3$ and $R^4$ are not the same.

16. The enantiomerically enriched compound according to claim 14 having the absolute stereochemistry of the formula:

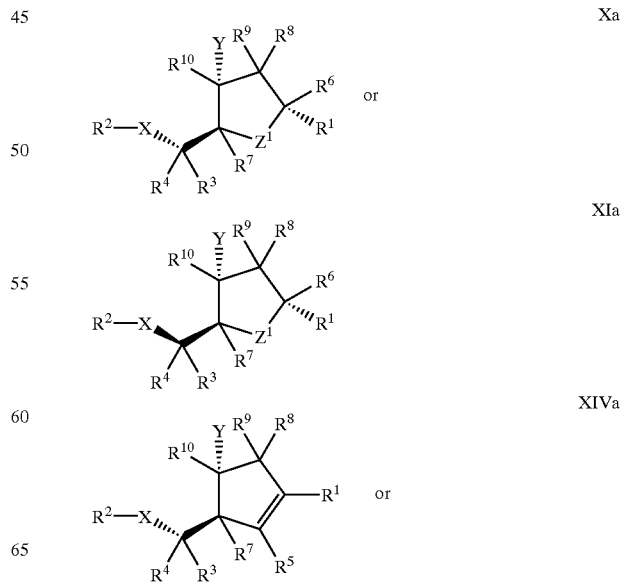

Xa

XIa

XIVa

XVa

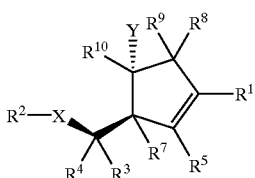

or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein and wherein $R^3$ and $R^4$ are not the same.

17. The compound according to claim 1 wherein $R^1$ is —$CO_2H$;

—X—$R^2$ is $R^2$—C(=O)—NH—, $R^2$—NH—C(=O)—, $R^2$—NH—$SO_2$— or $R^2$—$SO_2$—NH— wherein $R^2$ is $C_1$–$C_3$ loweralkyl or halo-$C_1$–$C_3$ loweralkyl;

$R^4$ is hydrogen or loweralkyl and $R^3$ is heterocyclic or —Z—$R^{14}$ wherein Z and $R^{14}$ are defined as therein;

$Z^1$ is —O—, —S—, —$CH_2$—, $$-\underset{\underset{NH_2}{|}}{\overset{\overset{H}{|}}{C}}- \quad \text{or} \quad -\underset{\underset{OH}{|}}{\overset{\overset{H}{|}}{C}}-;$$

or $R^5$ is hydrogen;

$R^6$ and $R^7$ are hydrogen;

$R^8$ and $R^9$ are hydrogen;

$R^{10}$ is hydrogen; and

Y is $C_2$–$C_5$ alkenyl, $C_2$–$C_5$ haloalkenyl or a heterocyclic ring having 5 ring atoms and also containing one or two double bonds;

or a pharmaceutically acceptable salt or ester thereof.

18. The compound according to claim 17 having the relative stereochemistry of the formula:

IVa

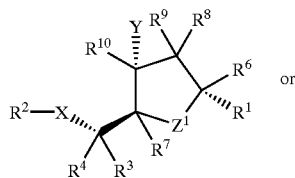

Va

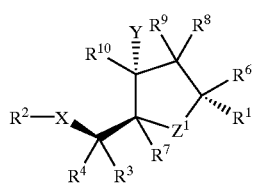

XIIIa

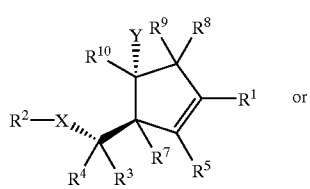

IXa

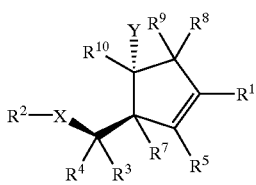

or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein and wherein $R^3$ and $R^4$ are not the same.

19. The enantiomerically enriched compound according to claim 17 having the absolute stereochemistry of the formula:

Xa

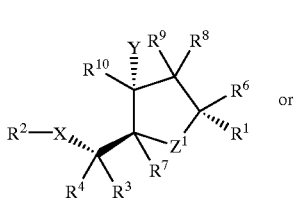

or

XIa

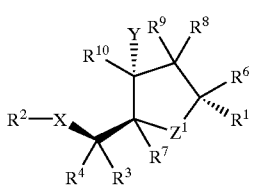

XIVa

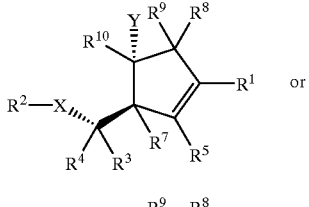

or

XVa

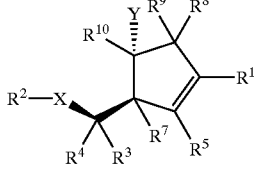

or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein and wherein $R^3$ and $R^4$ are not the same.

20. The compound according to claim 1 wherein $R^1$ is —$CO_2H$;

—X—$R^2$ is $R^2$—C(=O)—NH—, $R^2$—NH—C(=O)—, $R^2$—NH—$SO_2$— or $R^2$—$SO_2$—NH— wherein $R^2$ is $C_1$–$C_3$ loweralkyl or halo $C_1$–$C_3$ loweralkyl;

$R^4$ is hydrogen or loweralkyl and $R^3$ is (a) heterocyclic, (b) cycloalkyl, (c) —C(=O)—$R^{14}$, (d) —C($R^{37a}$)(O$R^{37c}$)—$R^{14}$ or (e) —C($R^{37a}$)($R^{37b}$)—N(O)($R^{37c}$)$R^{14}$ wherein $R^{14}$ is (i) alkyl, (ii) cycloalkyl, (iii) cycloalkylalkyl, (iv) alkenyl, (v) haloalkyl, (vi) haloalkenyl, (vii) aryl, (viii) arylalkyl, (ix) heterocyclic, (x) (heterocyclic)alkyl, (xi) hydroxyalkyl, (xii) alkoxyalkyl, (xiii) cyanoalkyl, (xiv) ($R^{37a}$O)—

(O=)C-substituted alkyl or (xv) $(R^{37a}O)_2$—P (=O)-substituted alkyl; $R^{37a}$ and $R^{37b}$ are independently selected from the group consisting of (i) hydrogen, (ii) loweralkyl and (iii) loweralkenyl; and $R^{37c}$ is (i) hydrogen, (ii) loweralkyl or (iii) loweralkenyl;

$Z^1$ is —O—, —S—, —CH$_2$—,

—C(H)(NH$_2$)— or —C(H)(OH)—;

or $R^5$ is hydrogen;
$R^6$ and $R^7$ are hydrogen;
$R^8$ and $R^9$ are hydrogen;
$R^{10}$ is hydrogen; and
Y is $C_2$–$C_5$ alkenyl, $C_2$–$C_5$ haloalkenyl or a heterocyclic ring having 5 ring atoms and also containing one or two double bonds;

or a pharmaceutically acceptable salt or ester thereof.

21. The compound according to claim 20 having the relative stereochemistry of the formula:

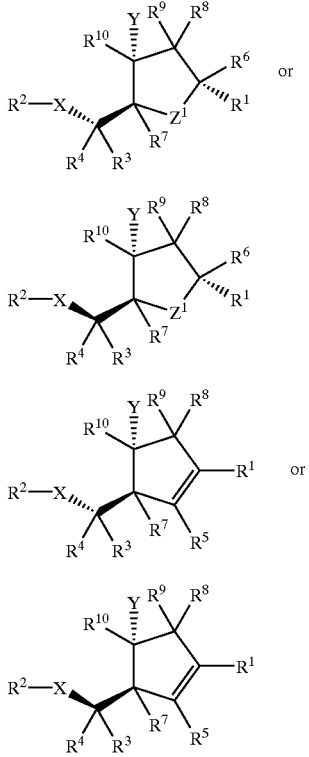

or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein and wherein $R^3$ and $R^4$ are not the same.

22. The enantiomerically enriched compound according to claim 20 having the absolute stereochemistry of the formula:

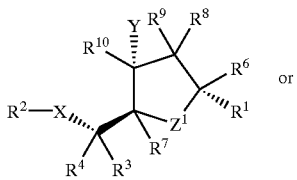

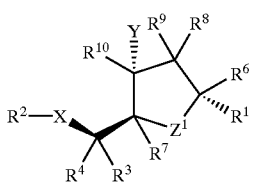

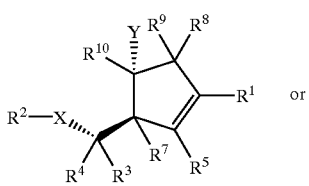

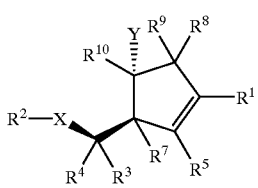

or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein and wherein $R^3$ and $R^4$ are not the same.

23. The compound according to claim 1 wherein $R^1$ is —CO$_2$H;

—X—$R^2$ is $R^2$—C(=O)—NH—, $R^2$—NH—C(=O)—, $R^2$—NH—SO$_2$— or $R^2$—SO$_2$—NH— wherein $R^2$ is $C_1$–$C_3$ loweralkyl or halo $C_1$–$C_3$ loweralkyl;

$R^4$ is hydrogen and $R^3$ is (a) heterocyclic, (b) alkyl or (c) —C($R^{37a}$)(O$R^{37c}$)— $R^{14}$ wherein $R^{14}$ is (i) alkyl, (ii) cycloalkyl, (iii) cycloalkylalkyl, (iv) alkenyl, (v) haloalkyl, (vi) haloalkenyl, (vii) aryl, (viii) arylalkyl, (ix) heterocyclic, (x) (heterocyclic)alkyl, (xi) hydroxyalkyl, (xii) alkoxyalkyl, (xiii) cyanoalkyl, (xiv) $(R^{37a}O)$—(O=)C-substituted alkyl or (xv) $(R^{37a}O)_2$—P (=O)-substituted alkyl; $R^{37a}$ and $R^{37b}$ are independently selected from the group consisting of (i) hydrogen, (ii) loweralkyl and (iii) loweralkenyl; and $R^{37c}$ is (i) hydrogen, (ii) $C_1$–$C_3$ loweralkyl or (iii) allyl;

$Z^1$ is —O—, —S—, —CH$_2$—,

—C(H)(NH$_2$)— or —C(H)(OH)—;

or $R^5$ is hydrogen;
$R^6$ and $R^7$ are hydrogen;
$R^8$ and $R^9$ are hydrogen;
$R^{10}$ is hydrogen; and Y is $C_2$–$C_5$ alkenyl, $C_2$–$C_5$ haloalkenyl or a heterocyclic ring having 5 ring atoms and also containing one or two double bonds;

or a pharmaceutically acceptable salt or ester thereof.

24. The compound according to claim 23 having the relative stereochemistry of the formula:

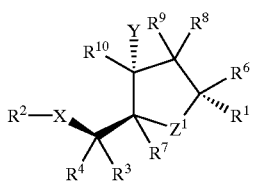
IVa

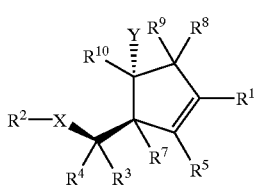
Va

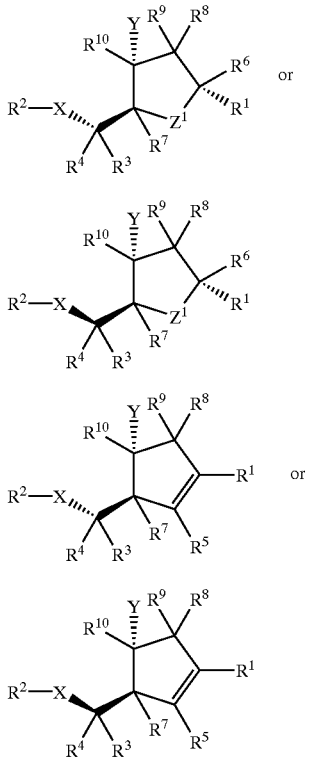
VIIIa

IXa or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein.

25. The enantiomerically enriched compound according to claim 23 having the absolute stereochemistry of the formula:

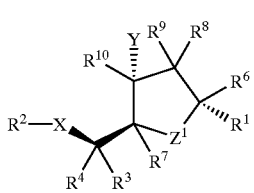
Xa

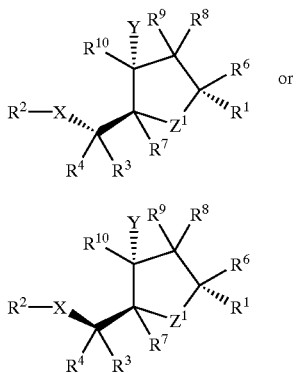
XIa

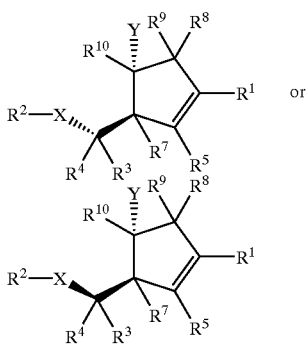
XIVa

XVa or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein.

26. The compound according to claim 1 wherein $R^1$ is —$CO_2H$;
—X—$R^2$ is $R^2$—C(=O)—NH— or $R^2$—$SO_2$—NH— wherein $R^2$ is $C_1$–$C_3$ loweralkyl or halo $C_1$–$C_3$ loweralkyl;
$R^4$ is hydrogen and $R^3$ is (a) heterocyclic or (b)

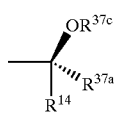

wherein $R^{14}$ is
(i) loweralkyl, (ii) loweralkenyl, (iii) hydroxy-substituted loweralkyl or (iv) alkoxy-substituted loweralkyl;
$R^{37a}$ is (i) hydrogen, (ii) loweralkyl or (iii) loweralkenyl; and
$R^{37c}$ is hydrogen, (ii) $C_1$–$C_3$ loweralkyl or (iii) allyl;
$Z^1$ is —O—, —S—, —$CH_2$—,

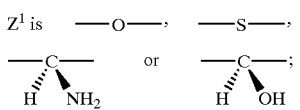

or $R^5$ is hydrogen;
$R^6$ and $R^7$ are hydrogen;
$R^8$ and $R^9$ are hydrogen;
$R^{10}$ is hydrogen; and
Y is $C_2$–$C_5$ alkenyl, $C_2$–$C_5$ haloalkenyl or a heterocyclic ring having 5 ring atoms and also containing one or two double bonds;
or a pharmaceutically acceptable salt or ester thereof.

27. The compound according to claim 26 having the relative stereochemistry of the formula:

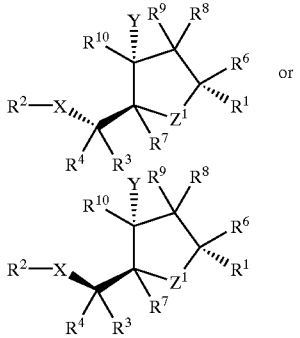
IVa

Va

-continued

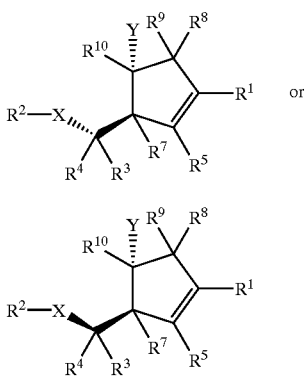
VIIIa

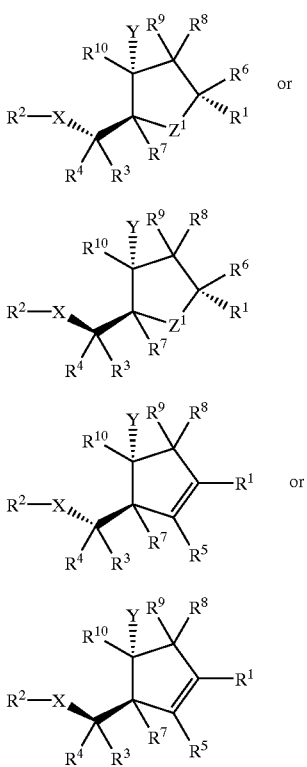
IXa

Xa

XIa

XIVa

XVa or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein.

29. The compound according to claim 1 wherein $R^1$ is —CO$_2$H;

—X—$R^2$ is $R^2$—C(=O)—NH— or $R^2$—SO$_2$—NH— wherein $R^2$ is $C_1$–$C_3$ loweralkyl or halo $C_1$–$C_3$ loweralkyl;

$R^4$ is hydrogen and $R^3$ is

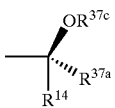

wherein $R^{14}$ is loweralkyl, loweralkenyl or alkoxy-substituted loweralkyl;
$R^{37a}$ is loweralkyl or loweralkenyl; and
$R^{37c}$ is hydrogen, $C_1$–$C_3$ loweralkyl or allyl;
$Z^1$ is —O—, —S—, —CH$_2$—, $Z^1$ is —O—, —S—, —CH$_2$—, $$\begin{array}{c}-\underset{\underset{NH_2}{|}}{\overset{\overset{H}{|}}{C}}- \end{array}$$ or $$\begin{array}{c}-\underset{\underset{OH}{|}}{\overset{\overset{H}{|}}{C}}-; \end{array}$$

or $R^5$ is hydrogen;
$R^6$ and $R^7$ are hydrogen;
$R^8$ and $R^9$ are hydrogen;
$R^{10}$ is hydrogen; and
Y is $C_2$–$C_5$ alkenyl, $C_2$–$C_5$ haloalkenyl or a heterocyclic ring having 5 ring atoms and also containing one or two double bonds;
or a pharmaceutically acceptable salt or ester thereof.

30. The compound according to claim 29 having the relative stereochemistry of the formula:

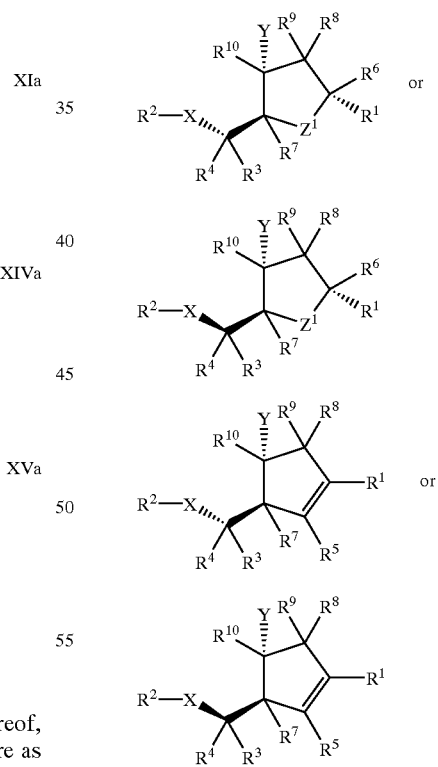
IVa

Va

VIIIa

IXa or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein.

31. The enantiomerically enriched compound according to claim 29 having the absolute stereochemistry of the formula:

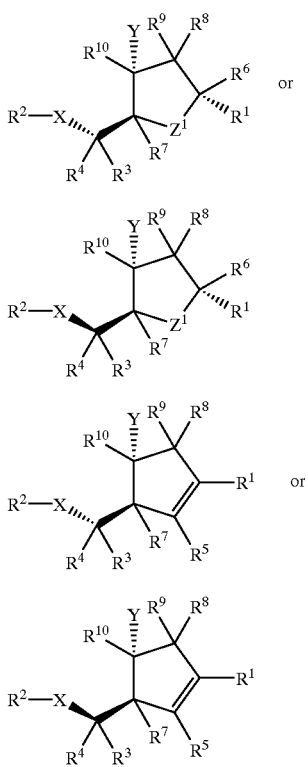

Xa

XIa

XIVa

XVa or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein.

32. The compound according to claim 1 wherein $R^1$ is —$CO_2H$;
—X—$R^2$ is $R^2$—C(=O)—NH— or $R^2$—$SO_2$—NH— wherein $R^2$ is $C_1$–$C_3$ loweralkyl or halo $C_1$–$C_3$ loweralkyl;
$R^4$ is hydrogen and $R^3$ is

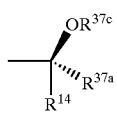

wherein $R^{14}$ is loweralkyl, loweralkenyl or alkoxy-substituted loweralkyl;
$R^{37a}$ is loweralkyl or loweralkenyl; and
$R^{37c}$ is hydrogen, $C_1$–$C_3$ loweralkyl or allyl;
$Z^1$ is —$CH_2$—, $Z^1$ is —$CH_2$—,

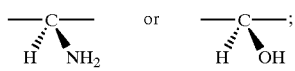

or $R^5$ is hydrogen;
$R^5$ is hydrogen;
$R^6$ and $R^7$ are hydrogen;
$R^8$ and $R^9$ are hydrogen;
$R^{10}$ is hydrogen; and
Y is $C_2$–$C_5$ alkenyl;
or a pharmaceutically acceptable salt or ester thereof.

33. The compound according to claim 32 having the relative stereochemistry of the formula:

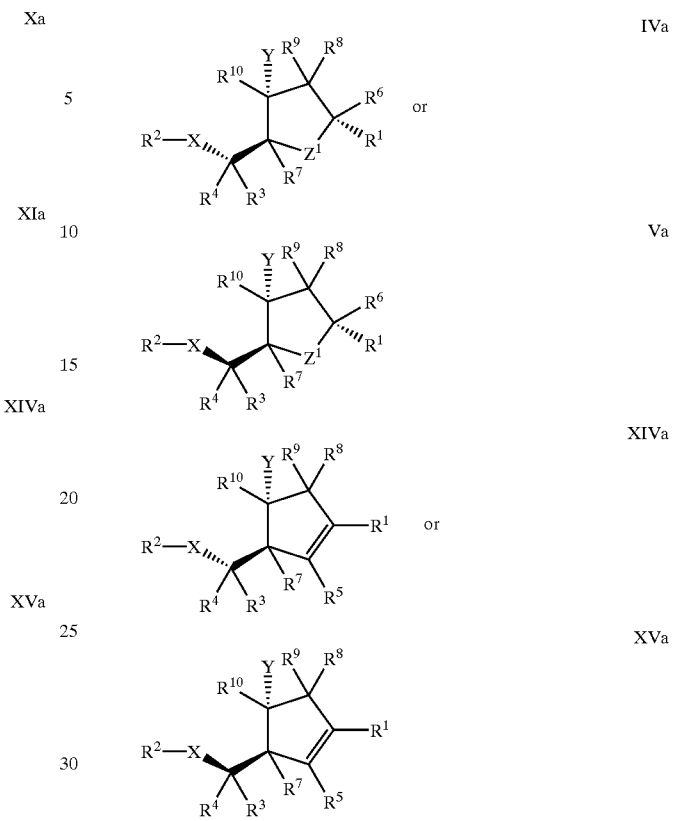

IVa

Va

XIVa

XVa or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein.

34. The enantiomerically enriched compound according to claim 32 having the absolute stereochemistry of the formula:

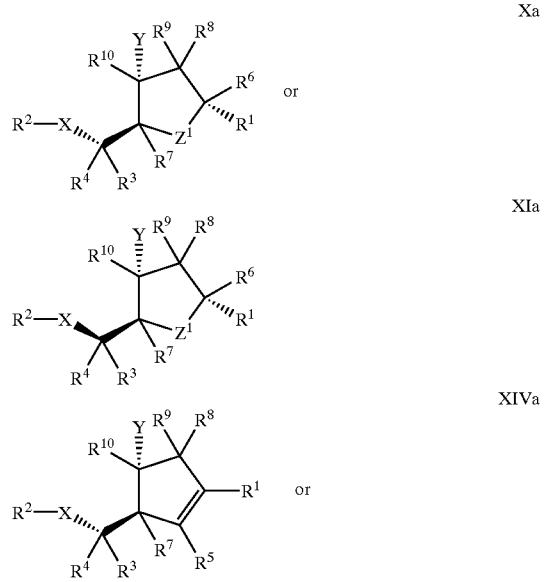

Xa

XIa

XIVa

-continued

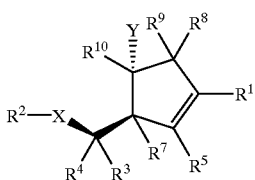
XVa or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein.

35. A compound of the formula:

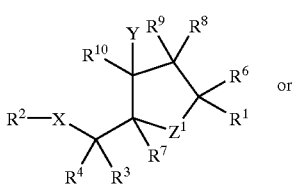
Ib or

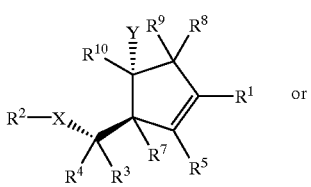
IIb or

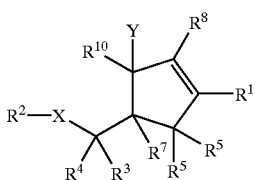
IIIb or a pharmaceutically acceptable salt or ester thereof, wherein $R^1$, $R^2$, $R^3$, $R^4$, $R^5$, $R^6$, $R^7$, $R^{10}$, X and $Z^1$ are as defined in claim 1 and wherein Y is $C_2$–$C_5$ alkenyl, $C_2$–$C_5$ haloalkenyl, or a heterocyclic ring having 5 ring atoms and also containing one or two double bonds and wherein $R^3$ is —Z—$R^{14}$ wherein Z is (i) —C($R^{37a}$)($R^{37b}$)—, (ii) —C($R^{37a}$)(O$R^{37c}$)—, (iii) —C($R^{37a}$)(S$R^{37c}$)—, (iv) —C($R^{37a}$)(N($R^{37b}$)($R^{37c}$))—, (v) —C($R^{37a}$)($R^{37b}$)—O—, (vi) —C($R^{37a}$)($R^{37b}$)—N($R^{37c}$)—, (vii) —C($R^{37a}$)($R^{37b}$)—N(O)($R^{37c}$)—, (Viii) —C($R^{37a}$)($R^{37b}$)—N(OH)—, (ix) —C($R^{37a}$)($R^{37b}$)—S—, (x) —C($R^{37a}$)($R^{37b}$)—S(O)—, (xi) —C($R^{37a}$)($R^{37b}$)—S(O)$_2$—, (vii) —C($R^{37a}$)($R^{37b}$)—C(=O)—, (xiii) —C($R^{37a}$)($R^{37b}$)—C(=S)—, (xiv) —C($R^{37a}$)($R^{37b}$)—C(=N$R^{15}$)—, (xv) —C($R^{37a}$)(O$R^{37c}$)—C(=O)—, (xvi) —C($R^{37a}$)(S$R^{37c}$)—C(=O)—, (xvii) —C($R^{37a}$)(O$R^{37c}$)—C(=S)—, (xviii)—C($R^{37a}$)(S$R^{37c}$)—C(=S)—, (xix) —C($R^{37b}$)(o$r^{37c}$)—, (xx) —C($R^{37a}$)(S$R^{37c}$)—C($R^{37a}$)(O$R^{37c}$)—, (xxi) —C($R^{37a}$)(O$R^{37c}$)—C($R^{37a}$)(S$R^{37c}$)—, (xii) —C($R^{37a}$)(S$R^{37c}$)—C($R^{37a}$)(S$R^{37c}$)—, (xiii) —C($R^{37a}$)($R^{37b}$)—C(=O)—N($R^{37a}$)—, (xxiv) —C($R^{37a}$)($R^{37b}$)—C(=S)—N($R^{37a}$)—, (xxv) —C($R^{37a}$)($R^{37b}$)—C(=O)—O—, (xxvi) —C($R^{37a}$)($R^{37b}$)—C(=O)—S—, (xxvii) —C($R^{37a}$)($R^{37b}$)—C(=S)—O—, (xxviii) —C($R^{37a}$)($R^{37b}$)—C(=S)—S—, (xxix) —C($R^{37a}$)($R^{37}b$ )—N($R^{37}b$ )—C(=O)—, (xxx) —C($R^{37a}$)($R^{37b}$)—N($R^{37b}$)—C(=S)—, (xxxi) —C($R^{37a}$)($R^{37b}$)—O—C(=O)—, (xxxii) —C($R^{37a}$)($R^{37b}$)—S—C(=O)—, (xxxiii) —C($R^{37a}$)($R^{37b}$)—O—C(=S)—, (xxxiv) —C($R^{37a}$)($R^{37b}$)—S—C(=S)—, (xxxv) —C($R^{37a}$)($R^{37b}$)—N($R^{37b}$)—C(=O)—N($R^{37b}$)—, (xxxvi) —C($R^{37a}$)($R^{37b}$)—N($R^{37b}$)—C(=S)—N($R^{37a}$)—, (xxxvii) —C($R^{37a}$)($R^{37b}$)—N($R^{37b}$)—C(=O)—O—, (xxxviii) —C($R^{37a}$)($R^{37b}$)—N($R^{37b}$)—C(=O)—S—, (xxxix) —C($R^{37a}$)($R^{37b}$)—N($R^{37b}$)—C(=S)—O—, (xl) —C($R^{37a}$)($R^{37b}$)—N($R^{37b}$)—C(=S)—S—, (xli) —C($R^{37a}$)($R^{37b}$)—O—C(=O)—N($R^{37a}$)—, (xlii) —C($R^{37a}$)($R^{37b}$)—S—C(=O)—N($R^{37a}$)—, (xliii) —C($R^{37a}$)($R^{37b}$)—O—C(=S)—N($R^{37a}$)—, (xliv) —C($R^{37a}$)($R^{37b}$)—S—C(=S)—N($R^{37a}$)—, (xlv) —C($R^{37a}$)($R^{37b}$)—O—C(=O)—O—, (xlvi) —C($R^{37a}$)($R^{37b}$)—S—C(=O)—O—, (xlvii) —C($R^{37a}$)($R^{37b}$)—O—C(=O)—S—, (xlviii) —C($R^{37a}$)($R^{37b}$)—S—C(=O)—S—, (xlix) —C($R^{37a}$)($R^{37b}$)—O—C(=S)—O—, (l) —C($R^{37a}$)($R^{37b}$)—S—C(=S)—O—, (li) —C($R^{37a}$)($R^{37b}$)—O—C(=S)—S—, (lii) —C($R^{37a}$)($R^{37b}$)—S—C(=S)—S— or (liii) —C($R^{37a}$)($R^{37b}$)—C($R^{37a}$)(O$R^{37c}$)— wherein $R^{37a}$, $R^{37b}$, $R^{37c}$ and $R^{14}$ are as defined in claim 1 with the proviso that $R^{37a}$ when bonded to the first carbon atom in the Z group is other than hydrogen and with the proviso that $R^{37b}$ when bonded to the first carbon atom in the Z group is other than hydrogen and with the proviso that $R^{14}$ is other than hydrogen when Z is —C($R^{37a}$)($R^{37b}$)—, —C($R^{37a}$)(O$R^{37c}$)—, —C($R^{37a}$)(S$R^{37c}$)— or —C($R^{37a}$)(N($R^{37b}$)($R^{37c}$))—; or a pharmaceutically acceptable salt or ester thereof.

36. The compound according to claim 35 of the formula:

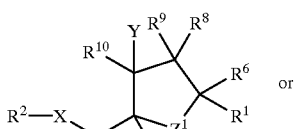
Ib or

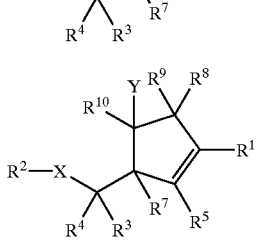
IIb wherein $R^1$, $R^2$, $R^3$, $R^4$, $R^5$, $R^6$, $R^7$, $R^{10}$, X, Y and $Z^1$ are as defined therein.

37. The compound according to claim 35 having the relative stereochemistry of the formula:

IVb

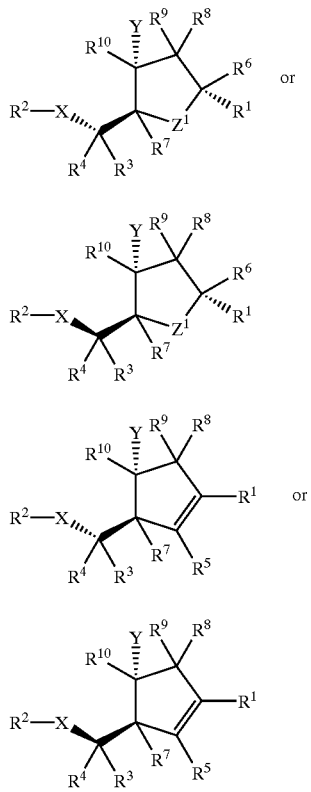

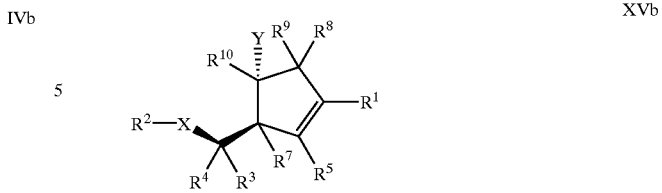

Vb or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein and wherein $R^3$ and $R^4$ are not the same.

39. The compound according to claim 35 wherein —X—$R^2$ is $R^2$—C(=O)—NH—, $R^2$—NH—C(=O)—, $R^2$—NH—$SO_2$— or $R^2$—$SO_2$—NH— wherein $R^2$ is $C_1$–$C_3$ loweralkyl, halo $C_1$–$C_3$ loweralkyl, $C_2$–$C_3$ alkenyl or halo $C_2$–$C_3$ alkenyl or —X—$R^2$ is

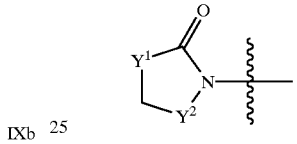

wherein $Y^1$ is —$CH_2$—, —O—, —S— or —NH— and $Y^2$ is —C(=O)— or —C($R^{aa}$)($R^{bb}$)— wherein $R^{aa}$ and $R^{bb}$ are independently selected from the group consisting of hydrogen, $C_1$–$C_3$ loweralkyl, hydroxymethyl, 1-hydroxyethyl, 2-hydroxyethyl, aminomethyl, 1-aminoethyl, 2-aminoethyl, thiolmethyl, 1-thiolethyl, 2-thiolethyl, methoxymethyl, N-methylaminomethyl and methylthiomethyl;

$R^4$ is hydrogen or loweralkyl and $R^3$ is defined as therein and wherein one of $R^3$ and $R^4$ is other than hydrogen;

$Z^1$ is —O—, —S— or —CH($R^5$)— wherein $R^5$ is hydrogen, loweralkyl, —($CH_2$)$_r$$OR^{40}$ or —($CH_2$)$_r$N($R^{19}$)$_2$ wherein r and $R^{19}$ and $R^{40}$ are defined as above; or $R^5$ is hydrogen, loweralkyl, —($CH_2$)$_r$$OR^{40}$ or —($CH_2$)$_r$N($R^{19}$)$_2$ wherein r and $R^{19}$ and $R^{40}$ are defined as above;

$R^6$ and $R^7$ are independently hydrogen or loweralkyl;

$R^8$ and $R^9$ are independently hydrogen, fluoro or loweralkyl;

$R^{10}$ is hydrogen, fluoro or loweralkyl; and

Y is —$C_5$ alkenyl, $C_2$–$C_5$ haloalkenyl or a heterocyclic ring having 5 ring atoms and also containing one or two double bonds; or a pharmaceutically acceptable salt or ester thereof.

40. The compound according to claim 39 having the relative stereochemistry of the formula:

or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein and wherein $R^3$ and $R^4$ are not the same.

38. The enantiomerically enriched compound according to claim 35 having the absolute stereochemistry of the formula:

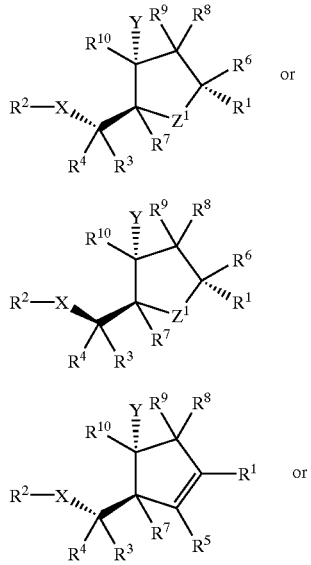

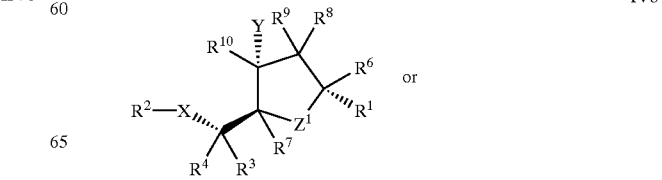

IVb

-continued

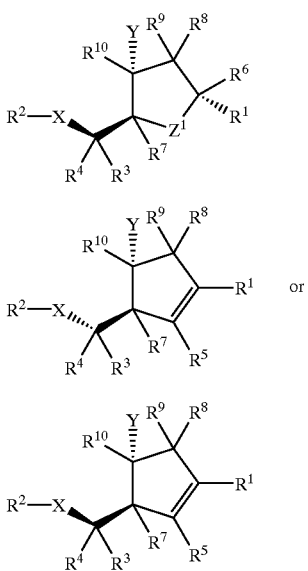

VIIIb

IXb or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein and wherein $R^3$ and $R^4$ are not the same.

41. The enantiomerically enriched compound according to claim 39 having the absolute stereochemistry of the formula:

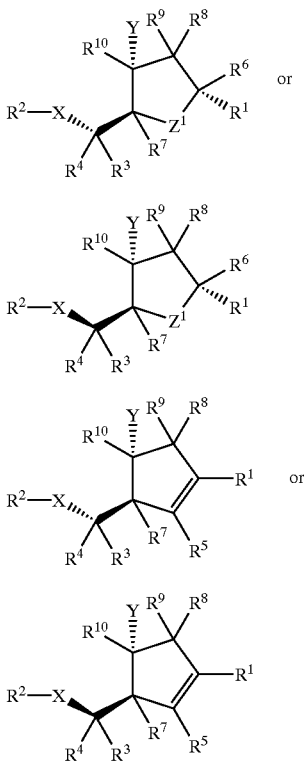

Xb

XIb

XIVb

XVb or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein and wherein $R^3$ and $R^4$ are not the same.

42. The compound according to claim 35 wherein —X—$R^2$ is $R^2$—C(=O)—NH—, $R^2$—NH—C(=O)—, $R^2$—NH—$SO_2$— or $R^2$—$SO_2$—NH— wherein $R^2$ is $C_1$–$C_3$ loweralkyl, halo $C_1$–$C_3$ loweralkyl, $C_2$–$C_3$ alkenyl or halo $C_2$–$C_3$ alkenyl or —X—$R^2$ is

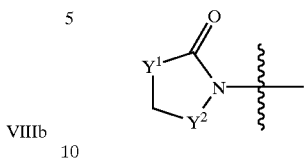

wherein $Y^1$ is —$CH_2$— and $Y^2$ is —C(=O)— or —C($R^{aa}$)($R^{bb}$)— wherein $R^{aa}$ and $R^{bb}$ are independently selected from the group consisting of hydrogen, $C_1$–$C_3$ loweralkyl, hydroxymethyl, 1-hydroxyethyl and 2-hydroxyethyl;

$R^4$ is hydrogen or loweralkyl and $R^3$ is defined as therein and wherein one of $R^3$ and $R^4$ is other than hydrogen;

$Z^1$ is —O—, —S— or —CH($R^5$)— wherein $R^5$ is hydrogen, loweralkyl, —$(CH_2)_rOR^{40}$ or —$(CH_2)_rN(R^{19})_2$ wherein r and $R^{19}$ and $R^{40}$ are defined as above; or $R^5$ is hydrogen, loweralkyl, —$(CH_2)_rOR^{40}$ or —$(CH_2)_rN(R^{19})_2$ wherein r and $R^{19}$ and $R^{40}$ are defined as above;

$R^6$ and $R^7$ are independently hydrogen or loweralkyl;

$R^8$ and $R^9$ are independently hydrogen or loweralkyl;

$R^{10}$ is hydrogen or loweralkyl; and

Y is $C_2$–$C_5$ alkenyl, $C_2$$C_5$ haloalkenyl or a heterocyclic ring having 5 ring atoms and also containing one or two double bonds; or a pharmaceutically acceptable salt or ester thereof.

43. The compound according to claim 42 having the relative stereochemistry of the formula:

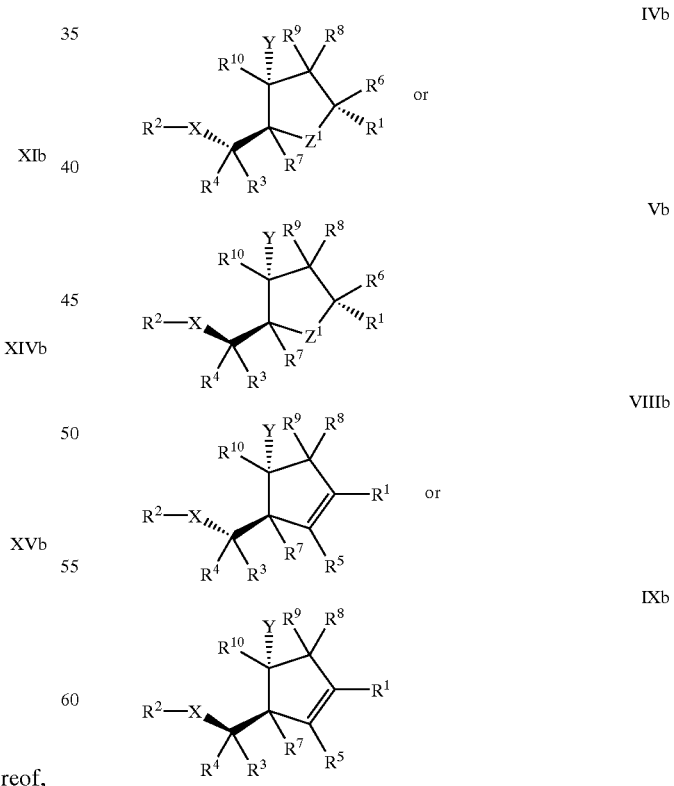

IVb

Vb

VIIIb

IXb or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein and wherein $R^3$ and $R^4$ are not the same.

44. The enantiomerically enriched compound according to claim 42 having the absolute stereochemistry of the formula:

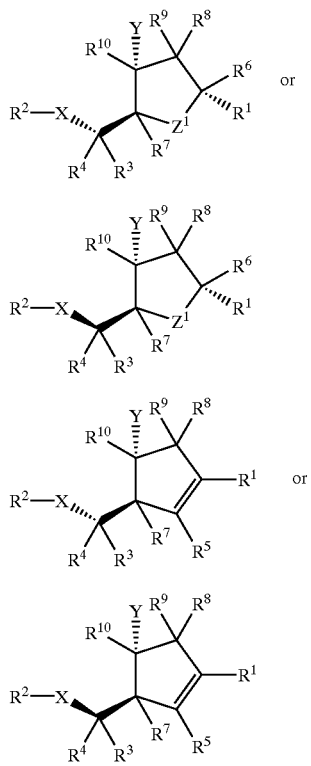

or a pharmaceutically acceptable salt or ester thereof, wherein $R^1$, $R^2$, $R^3$, $R^4$, $R^5$, $R^6$, $R^7$, $R^{10}$, X, Y and $Z^3$ are as defined therein and wherein $R^3$ and $R^4$ are not the same.

45. The compound according to claim 35 wherein —X—$R^2$ is $R^2$—C(=O)—NH—, $R^2$—NH—C(=O)—, $R^2$—NH—$SO_2$— or $R^2$—$SO_2$—NH— wherein $R^2$ is $C_1$–$C_3$ loweralkyl, halo $C_1$–$C_3$ loweralkyl, $C_2$–$C_3$ alkenyl or halo $C_1$–$C_3$ alkenyl or —X—$R^2$ is

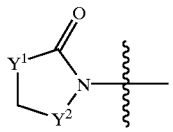

wherein $Y^1$ is —$CH_2$— and $Y^2$ is —C(=O)— or —C($R^{aa}$)($R^{bb}$)— wherein $R^{aa}$ and $R^{bb}$ are independently selected from the group consisting of hydrogen, $C_1$–$C_3$ loweralkyl, hydroxymethyl, 1-hydroxyethyl and 2-hydroxyethyl;

$R^4$ is hydrogen or loweralkyl and $R^3$ is defined as therein and wherein one of $R^3$ and $R^4$ is other than hydrogen;

$Z^1$ is —O—, —S— or —CH($R^5$)— wherein $R^5$ is hydrogen, loweralkyl, —$(CH_2)_rOR^{40}$ or —$(CH_2)_rN(R^{19})_2$ wherein r and $R^{19}$ and $R^{40}$ are defined as above; or $R^5$ is hydrogen, loweralkyl, —$(CH_2)_rOR^{40}$ or —$(CH_2)_rN(R^{19})_2$ wherein r and $R^{19}$ and $R^{40}$ are defined as above;

$R^6$ and $R^7$ are independently hydrogen or loweralkyl;

$R^8$ and $R^9$ are independently hydrogen or loweralkyl;

$R^{10}$ is hydrogen or loweralkyl; and

Y is $C_2$–$C_5$ alkenyl, $C_2$–$C_5$ haloalkenyl or a heterocyclic ring having 5 ring atoms and also containing one or two double bonds; or a pharmaceutically acceptable salt or ester thereof.

46. The compound according to claim 45 having the relative stereochemistry of the formula:

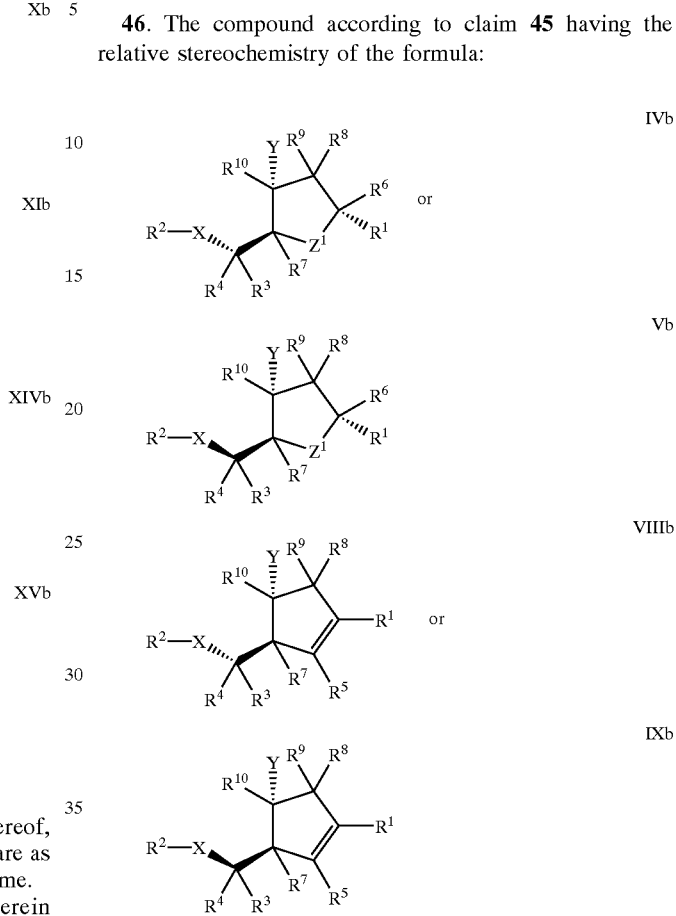

or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein and wherein $R^3$ and $R^4$ are not the same.

47. The enantiomerically enriched compound according to claim 45 having the absolute stereochemistry of the formula:

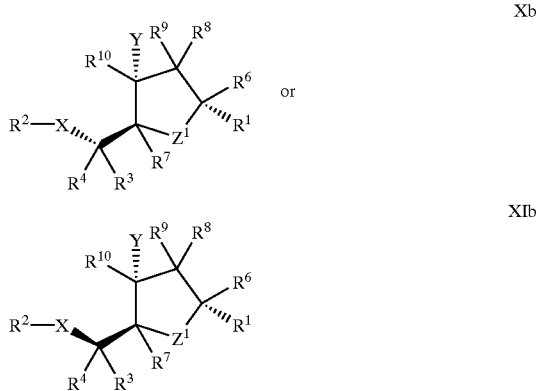

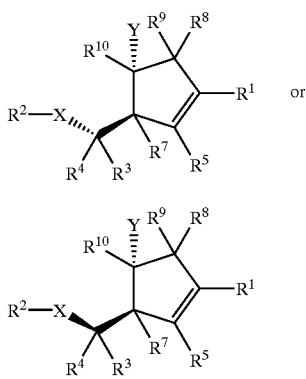

XIVb

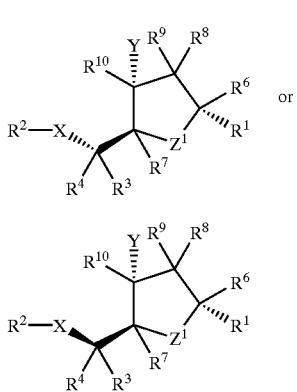

XVb or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein and wherein $R^3$ and $R^4$ are not the same.

48. The compound according to claim 35 wherein $R^1$ is —$CO_2H$; —X—$R^2$ is $R^2$—C(=O)—NH—, $R^2$—NH—C(=O)—, $R^2$—NH—$SO_2$— or $R^2$—$SO_2$—NH— wherein $R^2$ is $C_1$–$C_3$ loweralkyl or halo-$C_1$–$C_3$ loweralkyl;

$R^4$ is hydrogen or loweralkyl and $R^3$ is defined as therein and wherein one of $R^3$ and $R^4$ is other than hydrogen;

$Z^1$ is —O—, —S—, —$CH_2$—,

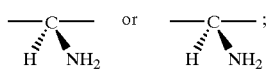

or $R^5$ is hydrogen;

$R^6$ and $R^7$ are independently hydrogen or loweralkyl;

$R^8$ and $R^9$ are hydrogen independently hydrogen or loweralkyl;

$R^{10}$ is hydrogen or loweralkyl; and

Y is $C_2$–$C_5$ alkenyl, $C_2$–$C_5$ haloalkenyl or a heterocyclic ring having 5 ring atoms and also containing one or two double bonds; or a pharmaceutically acceptable salt or ester thereof.

49. The compound according to claim 48 having the relative stereochemistry of the formula:

IVb

Vb

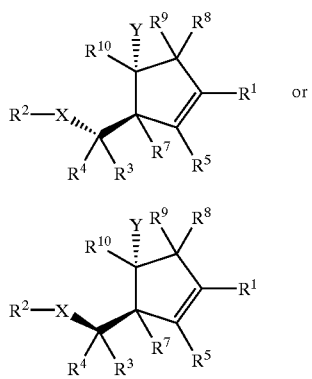

VIIIb

IXb or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein and wherein $R^3$ and $R^4$ are not the same.

50. The enantiomerically enriched compound according to claim 48 having the absolute stereochemistry of the formula:

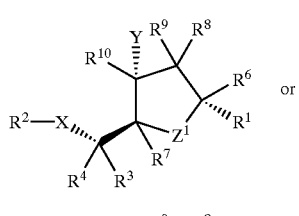

Xb

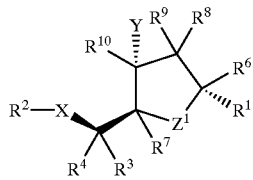

XIb

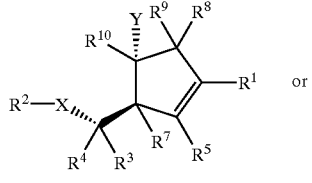

XIVb

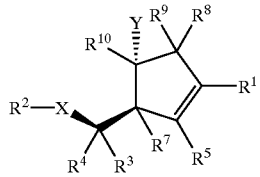

XVb or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein and wherein $R^3$ and $R^4$ are not the same.

51. The compound according to claim 35 wherein wherein $R^1$ is —$CO_2H$;

—X—$R^2$ is $R^2$—C(=O)—NH—, $R^2$—NH—C(=O)—, $R^2$—NH—$SO_2$— or $R^2$—$SO_2$—NH— wherein $R^2$ is $C_1$–$C_3$ loweralkyl or halo-$C_1$–$C_3$ loweralkyl;

$R^4$ is hydrogen or loweralkyl and $R^3$ is defined as therein and wherein one of $R^3$ and $R^4$ is other than hydrogen;

$Z^1$ is 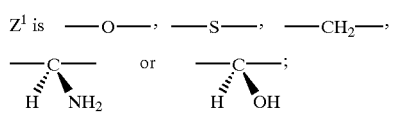

or $R^5$ is hydrogen;

$R^6$ and $R^7$ are hydrogen;

$R^8$ and $R^9$ are hydrogen;

$R^{10}$ is hydrogen; and

Y is $C_2$–$C_5$ alkenyl, $C_2$–$C_5$ haloalkenyl or a heterocyclic ring having 5 ring atoms and also containing one or two double bonds; or a pharmaceutically acceptable salt or ester thereof.

52. The compound according to claim 51 having the relative stereochemistry of the formula:

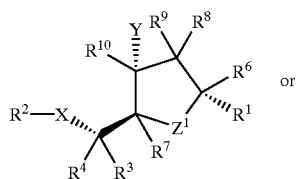 IVb

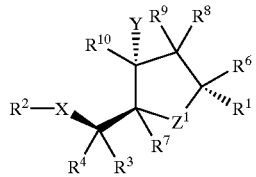 Vb

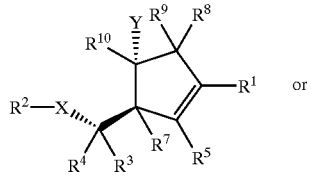 VIIIb

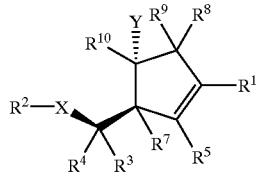 IXb or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein and wherein $R^3$ and $R^4$ are not the same.

53. The enantiomerically enriched compound according to claim 51 having the absolute stereochemistry of the formula:

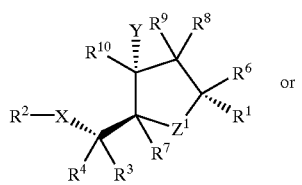 Xb

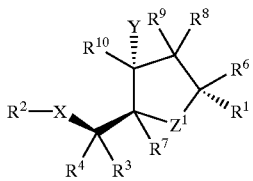 XIb

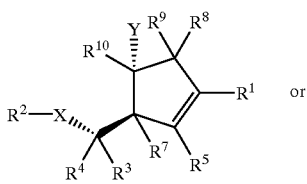 XIVb or

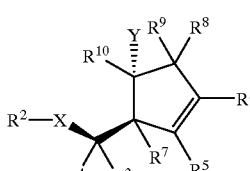 XVb or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein and wherein $R^3$ and $R^4$ are not the same.

54. The compound according to claim 35 wherein $R^1$ is —$CO_2H$;

—X—$R^2$ is $R^2$—C(=O)—NH—, $R^2$—NH—C(=O)—, $R^2$—NH—$SO_2$— or $R^2$—$SO_2$—NH— wherein $R^2$ is $C_1$–$C_3$ loweralkyl or halo $C_1$–$C_3$ loweralkyl;

$R^4$ is hydrogen or loweralkyl and $R^3$ is —C($R^{37a}$)(O$R^{37c}$)—$R^{14}$ or —C($R^{37a}$)($R^{37b}$)—N(O)($R^{37c}$)$R^{14}$ wherein $R^{14}$ is (i) alkyl, (ii) cycloalkyl, (iii) cycloalkylalkyl, (iv) alkenyl, (v) haloalkyl, (vi) haloalkenyl, (vii) aryl, (viii) arylalkyl, (ix) heterocyclic, (x)(heterocyclic)alkyl, (xi) hydroxyalkyl, (xii) alkoxyalkyl, (xiii) cyanoalkyl, (xiv)($R^{37a}$O)—(O=)C-substituted alkyl or (xv)($R^{37a}$O)$_2$—P(=O)-substituted alkyl;

$R^{37a}$ and $R^{37b}$ are independently selected from the group consisting of (i) loweralkyl and (ii) loweralkenyl; and $R^{37c}$ is (i) hydrogen, (ii) loweralkyl or (iii) loweralkenyl;

$Z^1$ is —O—, —S—, —$CH_2$—,

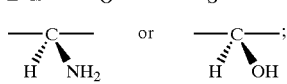

or $R^5$ is hydrogen;

$R^6$ and $R^7$ are hydrogen;

$R^8$ and $R^9$ are hydrogen;

$R^{10}$ is hydrogen; and

Y is $C_2$–$C_5$ alkenyl, $C_2$–$C_5$ haloalkenyl or a heterocyclic ring having 5 ring atoms and also containing one or two double bonds; or a pharmaceutically acceptable salt or ester thereof.

55. The compound according to claim 54 having the relative stereochemistry of the formula:

IVb

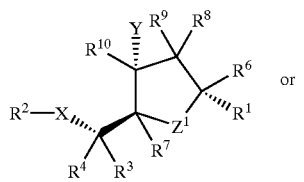

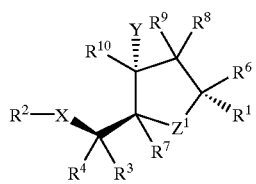

VIIIb

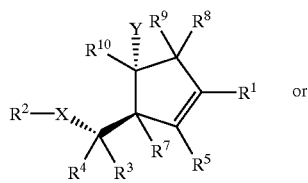  or

IXb

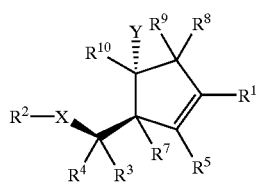

or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein and wherein $R^3$ and $R^4$ are not the same.

56. The enantiomerically enriched compound according to claim 54 having the absolute stereochemistry of the formula:

Xb

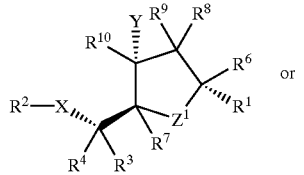  or

XIb

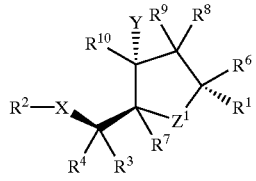

XIVb

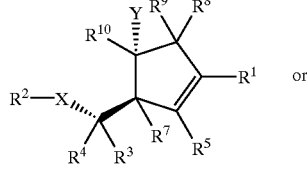  or

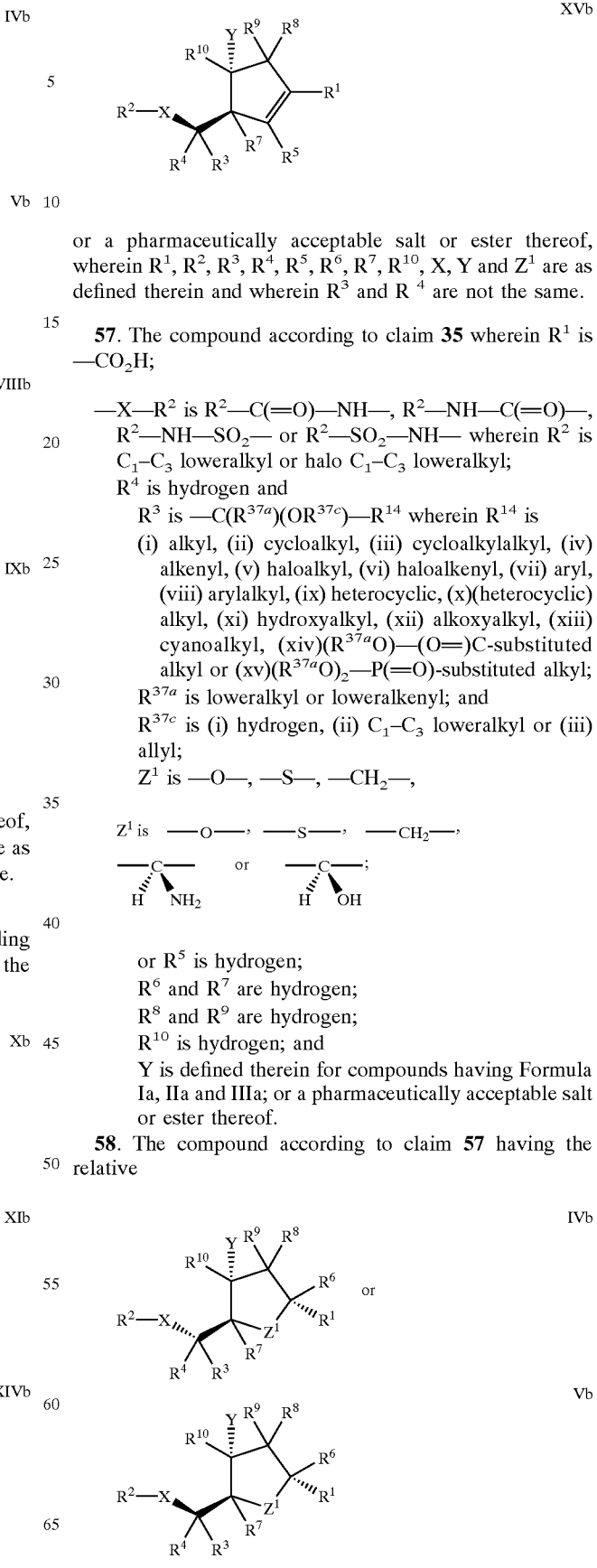

or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein and wherein $R^3$ and $R^4$ are not the same.

57. The compound according to claim 35 wherein $R^1$ is —$CO_2H$;

—X—$R^2$ is $R^2$—C(=O)—NH—, $R^2$—NH—C(=O)—, $R^2$—NH—$SO_2$— or $R^2$—$SO_2$—NH— wherein $R^2$ is $C_1$–$C_3$ loweralkyl or halo $C_1$–$C_3$ loweralkyl;

$R^4$ is hydrogen and $R^3$ is —C($R^{37a}$)(O$R^{37c}$)—$R^{14}$ wherein $R^{14}$ is (i) alkyl, (ii) cycloalkyl, (iii) cycloalkylalkyl, (iv) alkenyl, (v) haloalkyl, (vi) haloalkenyl, (vii) aryl, (viii) arylalkyl, (ix) heterocyclic, (x)(heterocyclic) alkyl, (xi) hydroxyalkyl, (xii) alkoxyalkyl, (xiii) cyanoalkyl, (xiv)($R^{37a}$O)—(O=)C-substituted alkyl or (xv)($R^{37a}$O)$_2$—P(=O)-substituted alkyl;

$R^{37a}$ is loweralkyl or loweralkenyl; and $R^{37c}$ is (i) hydrogen, (ii) $C_1$–$C_3$ loweralkyl or (iii) allyl;

$Z^1$ is —O—, —S—, —$CH_2$—, or $R^5$ is hydrogen;

$R^6$ and $R^7$ are hydrogen;

$R^8$ and $R^9$ are hydrogen;

$R^{10}$ is hydrogen; and

Y is defined therein for compounds having Formula Ia, IIa and IIIa; or a pharmaceutically acceptable salt or ester thereof.

58. The compound according to claim 57 having the relative

-continued

VIIIb

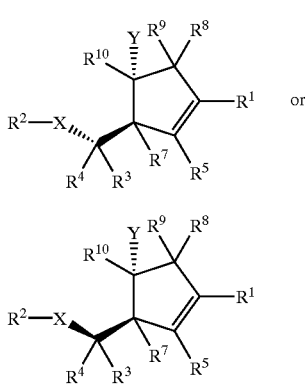

IXb

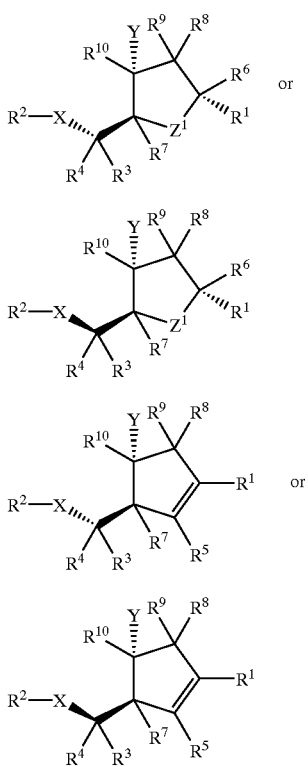

or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein.

59. The enantiomerically enriched compound according to claim 57 having the absolute stereochemistry of the formula:

Xb

XIb

XIVb

XVb or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein.

60. The compound according to claim 35 wherein $R^1$ is —$CO_2H$;

—X—$R^2$ is $R^2$—C(=O)—NH— or $R^2$—$SO_2$—NH— wherein $R^2$ is $C_1$–$C_3$ loweralkyl or halo $C_1$–$C_3$ loweralkyl;

$R^4$ is hydrogen and $R^3$ is

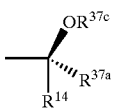

wherein $R^{14}$ is (i) loweralkyl, (ii) loweralkenyl, (iii) hydroxy-substituted loweralkyl or (iv) alkoxy-substituted loweralkyl;
$R^{37a}$ is loweralkyl or loweralkenyl; and
$R^{37c}$ is (i) hydrogen, (ii) $C_1$–$C_3$ loweralkyl or (iii) allyl;
$Z^1$ is —O—, —S—, —$CH_2$—, $Z^1$ is —O—, —S—, —$CH_2$—, or $R^5$ is hydrogen;
$R^6$ and $R^7$ are hydrogen;
$R^8$ and $R^9$ are hydrogen;
$R^{10}$ is hydrogen; and
Y is defined therein for compounds having Formula Ia, IIa and IIIa; or a pharmaceutically acceptable salt or ester thereof.

61. The compound according to claim 60 having the relative stereochemistry of the formula:

IVb

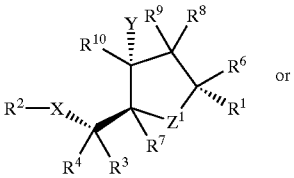

Vb

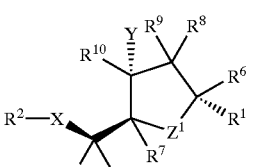

VIIIb

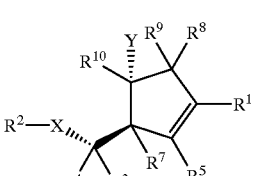

IXb

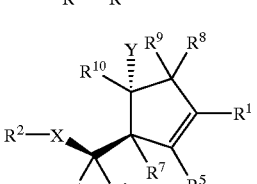

or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein.

62. The enantiomerically enriched compound according to claim 60 having the absolute stereochemistry of the formula:

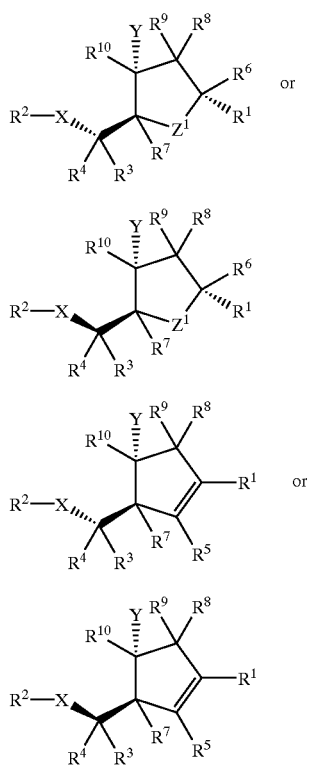

Xb

XIb

XIVb

XVb or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein.

63. The compound according to claim 35 wherein $R^1$ is —$CO_2H$;
—X—$R^2$ is $R^2$—C(=O)—NH— or $R^2$—$SO_2$—NH— wherein $R^2$ is $C_1$–$C_3$ loweralkyl or halo $C_1$–$C_3$ loweralkyl;
$R^4$ is hydrogen and
$R^3$ is

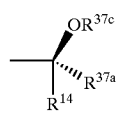

wherein $R^{14}$ is loweralkyl, loweralkenyl or alkoxy-substituted loweralkyl;
$R^{37a}$ is loweralkyl or loweralkenyl; and
$R^{37c}$ is (i) hydrogen, (ii) $C_1$–$C_3$ loweralkyl or (iii) allyl;

$Z^1$ is —O—, —S—, —$CH_2$—,

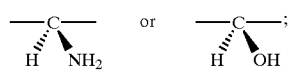

or $R^5$ is hydrogen;
$R^6$ and $R^7$ are hydrogen;
$R^8$ and $R^9$ are hydrogen;
$R^{10}$ is hydrogen; and
Y is $C_2$–$C_5$ alkenyl, $C_2$–$C_5$ haloalkenyl or a heterocyclic ring having 5 ring atoms and also containing one or two double bonds; or a pharmaceutically acceptable salt or ester thereof.

64. The compound according to claim 63 having the relative stereochemistry of the formula:

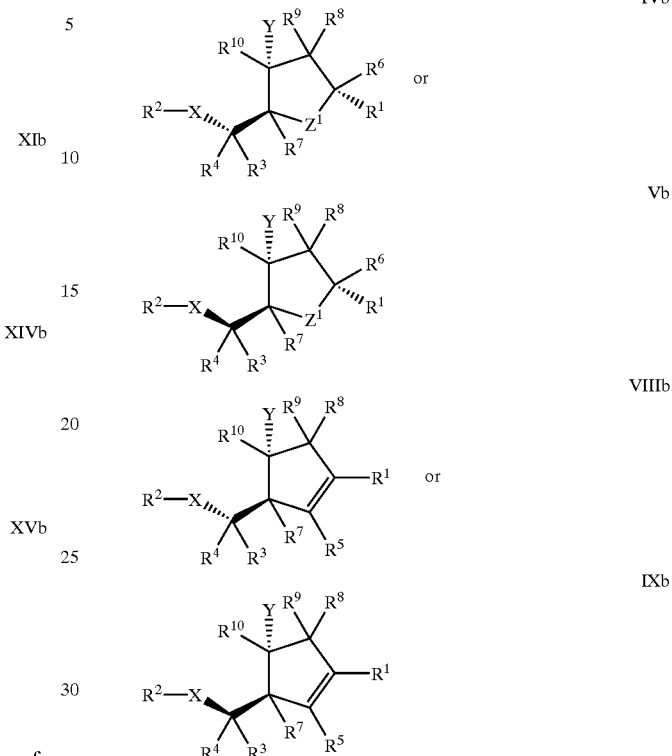

IVb

Vb

VIIIb

IXb or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein.

65. The enantiomerically enriched compound according to claim 63 having the absolute stereochemistry of the formula:

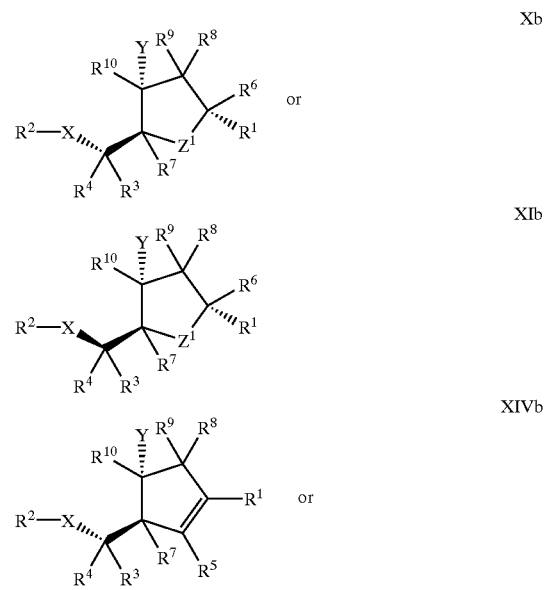

Xb

XIb

XIVb

-continued

XVb
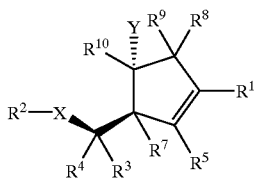

or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein.

66. The compound according to claim 35 wherein $R^1$ is —$CO_2H$;

—X—$R^2$ is $R^2$—C(=O)—NH— or $R^2$—$SO_2$—NH— wherein $R^2$ is $C_1$–$C_3$ loweralkyl or halo $C_1$–$C_3$ loweralkyl;
$R^4$ is hydrogen and
$R^3$ is

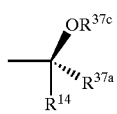

wherein $R^{14}$ is loweralkyl or loweralkenyl;
$R^{37a}$ is loweralkyl or loweralkenyl; and
$R^{37c}$ is (i) hydrogen, (ii) $C_1$–$C_3$ loweralkyl or (iii) allyl;

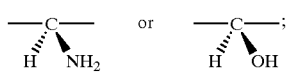

$Z^1$ is —$CH_2$—,
or $R^5$ is hydrogen;
$R^5$ is hydrogen;
$R^6$ and $R^7$ are hydrogen;
$R^8$ and $R^9$ are hydrogen;
$R^{10}$ is hydrogen; and
Y is —$NH_2$ or —NH—C(=NH)—$NH_2$; or a pharmaceutically acceptable salt or ester thereof.

67. The compound according to claim 66 having the relative stereochemistry of the formula:

IVb
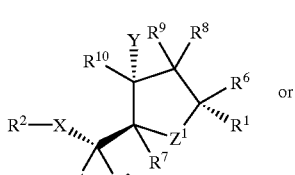

Vb
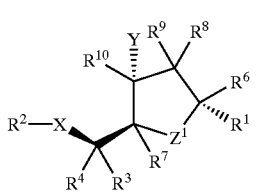

VIIIb
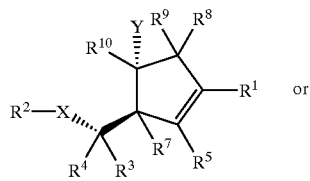

IXb
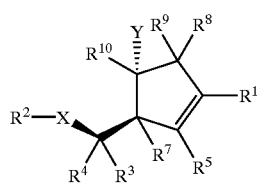

or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein.

68. The enantiomerically enriched compound according to claim 66 having the absolute stereochemistry of the formula:

Xb
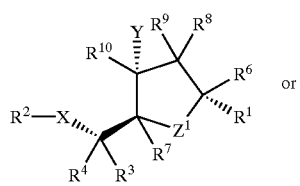

XIb
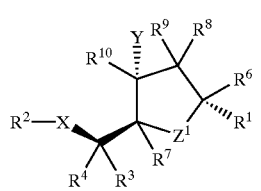

XIVb
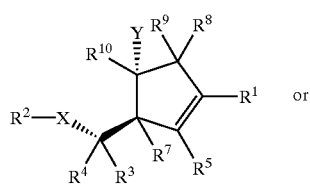

XVb
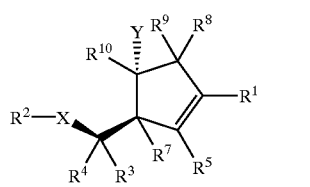

or a pharmaceutically acceptable salt or ester thereof, wherein $R^1$, $R^2$, $R^3$, $R^4$, $R^5$, $R^6$, $R^7$, $R^{10}$, X, Y and $Z^1$ are as defined therein.

69. A pharmaceutical composition comprising a pharmaceutical carrier and a therapeutically effective amount of a compound of claim 1.

70. A pharmaceutical composition comprising a pharmaceutical carrier and a therapeutically effective amount of a compound of claim 35.

71. A pharmaceutical composition comprising a pharmaceutical carrier and a therapeutically effective amount of a compound of claim 34.

72. A pharmaceutical composition comprising a pharmaceutical carrier and a therapeutically effective amount of a compound of claim 68.

73. A method for inhibiting neuraminidase from a disease-causing microorganism comprising administering to a human or other mammal in need thereof, a therapeutically effective amount of a compound of claim 1.

74. The method of claim 73 wherein the disease-causing microorganism is a virus.

75. The method of claim 74 wherein the virus is influenza virus.

76. A method for treating a disease caused by a microorganism which has a neuraminidase, comprising administering to a human or other mammal in need thereof, a therapeutically effective amount of a compound of claim 1.

77. The method of claim 76 wherein the disease-causing microorganism is a virus.

78. The method of claim 77 wherein the virus is influenza virus.

79. A method for preventing a disease caused by a microorganism which has a neuraminidase, comprising administering to a human or other mammal in need thereof, a therapeutically effective amount of a compound of claim 1.

80. The method of claim 79 wherein the disease-causing microorganism is a virus.

81. The method of claim 80 wherein the virus is influenza virus.

82. A method for inhibiting neuraminidase from a disease-causing microorganism comprising administering to a human or other mammal in need thereof, a therapeutically effective amount of a compound of claim 35.

83. The method of claim 82 wherein the disease-causing microorganism is a virus.

84. The method of claim 83 wherein the virus is influenza virus.

85. A method for treating a disease caused by a microorganism which has a neuraminidase, comprising administering to a human or other mammal in need thereof, a therapeutically effective amount of a compound of claim 35.

86. The method of claim 85 wherein the disease-causing microorganism is a virus.

87. The method of claim 86 wherein the virus is influenza virus.

88. A method for preventing a disease caused by a microorganism which has a neuraminidase, comprising administering to a human or other mammal in need thereof, a therapeutically effective amount of a compound of claim 35.

89. The method of claim 88 wherein the disease-causing microorganism is a virus.

90. The method of claim 89 wherein the virus is influenza virus.

91. A method for inhibiting neuraminidase from a disease-causing microorganism comprising administering to a human or other mammal in need thereof, a therapeutically effective amount of a compound of claim 34.

92. The method of claim 91 wherein the disease-causing microorganism is a virus.

93. The method of claim 92 wherein the virus is influenza virus.

94. A method for treating a disease caused by a microorganism which has a neuraminidase, comprising administering to a human or other mammal in need thereof, a therapeutically effective amount of a compound of claim 34.

95. The method of claim 94 wherein the disease-causing microorganism is a virus.

96. The method of claim 95 wherein the virus is influenza virus.

97. A method for preventing a disease caused by a microorganism which has a neuraminidase, comprising administering to a human or other mammal in need thereof, a therapeutically effective amount of a compound of claim 34.

98. The method of claim 97 wherein the disease-causing microorganism is a virus.

99. The method of claim 98 wherein the virus is influenza virus.

100. A method for inhibiting neuraminidase from a disease-causing microorganism comprising administering to a human or other mammal in need thereof, a therapeutically effective amount of a compound of claim 68.

101. The method of claim 100 wherein the disease-causing microorganism is a virus.

102. The method of claim 101 wherein the virus is influenza virus.

103. A method for treating a disease caused by a microorganism which has a neuraminidase, comprising administering to a human or other mammal in need thereof, a therapeutically effective amount of a compound of claim 68.

104. The method of claim 103 wherein the disease-causing microorganism is a virus.

105. The method of claim 104 wherein the virus is influenza virus.

106. A method for preventing a disease caused by a microorganism which has a neuraminidase, comprising administering to a human or other mammal in need thereof, a therapeutically effective amount of a compound of claim 68.

107. The method of claim 106 wherein the disease-causing microorganism is a virus.

108. The method of claim 105 wherein the virus is influenza virus.

or a heterocyclic ring having 5 ring atoms and also containing one or two double bonds, wherein $R^{22}$, $Q^2$ and $Q^3$ are defined as therein;

or a pharmaceutically acceptable salt or ester thereof.

109. The compound according to claim 35 wherein $R^1$ is —$CO_2H$;

—X—$R^2$ is $R^2$—C(=O)—NH— or $R^2$—$SO_2$—NH— wherein $R^2$ is $C_1$–$C_3$ loweralkyl or halo $C_1$–$C_3$ loweralkyl;

$R^4$ is hydrogen and $R^3$ is

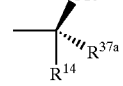

wherein $R^{14}$ is loweralkyl, loweralkenyl or haloalkyl;

$R^{37a}$ is loweralkyl or loweralkenyl; and $R^{37c}$ is (i) hydrogen, (ii) $C_1$–$C_3$ loweralkyl or (iii) allyl;

$Z^1$ is —O—, —S—, —$CH_2$—,

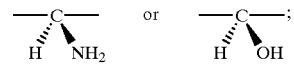

or $R^5$ is hydrogen;

$R^6$ and $R^7$ are hydrogen;

$R^8$ and $R^9$ are hydrogen;

R$^{10}$ is hydrogen; and

Y is —NHR$^{24}$ wherein R$^{24}$ is hydrogen or —C(=Q$^4$)—R$^{30}$ wherein Q$^4$ is O, S or N(R$^{33}$) wherein R$^{33}$ is hydrogen, hydroxy, methyl, ethyl, amino, —CN or —NO$_2$ and R$^{30}$ is —N(R$^{35}$)$_2$, —NHOH, —NHNH$_2$, —N(CH$_3$)NH$_2$ or —N(CH$_2$CH$_3$)NH$_2$ wherein each R$^{35}$ is independently hydrogen, methyl or ethyl; or a pharmaceutically acceptable salt thereof.

110. (±)-(1S,2S,3R,4R)-2-(N-methyl-N-t-butyloxycarbonylamino)-3-acetamidomethyl-4-methoxycarbonyl-cyclopentane-1-carboxylic acid, (±)-(1S,2S, 3R,4R)-2-N-methyl-3-acetamidomethyl-4-methoxycarbonyl-cyclopentanecarboxylic acid, (±)-(1S,2S,3R,4R)-2-(N-methyl-N-benzyloxycarbonylamino)-3-acetamidomethyl-4-methoxycarbonyl-cyclopentanecarboxylic acid, (±)-(1S,2S,3R,4R)-2-(t-butyloxycarbonylamino)-3-(acetamidomethyl)-4-(methoxycarbonyl)-cyclopentane-1-carboxylic acid, (±)-(1S,2S,3R,4R)-2-amino-3-(acetamidomethyl)-4-(methoxycarbonyl)-cyclopentane-1-carboxylic acid Hydrochloride, (±)-(1S,2S,3R,4R)-3-acetamidomethyl-2-(N-t-butoxycarbonylamino)methyl-4-methoxycarbonyl-cyclopentane-1-carboxylic acid, (±)-(1S,2S,3R,4R)-2-aminomethyl-3-acetamidomethyl-4-methoxycarbonyl-cyclopentane-1-carboxylic acid Hydrochloride, (±)-(1S,2S,3R,4R)-2-N-t-butoxycarbonylamino-3-(acetamidomethyl)-4-carbamoyl-cyclopentane-1-carboxylic acid, (±)-(1S,2S,3R,4R)-2,3-acetamidomethyl-4-methoxycarbonylcyclopentane-1-carboxylic acid, (±)-(1S,2S,3R,4R)-2-N-t-butoxycarbonylamino-3-(acetamidomethyl)-4-N-methylcarboxamido-cyclopentane-1-carboxylic acid, (±)-(1S,2S,3R,4R)-3-acetamidomethyl-2,4-diamino-cyclopentane-1-carboxylic acid Hydrochloride, (±)-(1R,2R,4R,1'S)4-(1'-Acetamido-3'-ethyl)pentyl-3-methoxycarbonyl-cyclopentane-1-carboxylic acid, (1R,3R,4R,1'S)-3-hydroxymethyl-4-(1'-Acetamido-3'-ethyl)pentyl-cyclopentane-1-carboxylic acid, (1R,3R,4R,1'S)-3-formyl-4-(1'-Acetamido-3'-ethyl)pentyl-cyclopentane-1-carboxylic acid, (1R,3R,4R,1'S)-3-(imidazol-2-yl)-4-(1-Acetamido-3-ethyl)pentyl-cyclopentane-1-carboxylic acid, (1R, 3R,4R,1'S)-3-(oxazol-5-yl)-4-(1'-Acetamido-3'-ethyl)pentyl-cyclopentane-1-carboxylic acid, (1R,3R,4R,1'S)-3-(N,N-dimethylcarbamoyl)-4-(1'-Acetamido-3'-ethyl)pentyl-cyclopentane-1-carboxylic acid, (1R,3R,4R,1'S)-3-propionyl-4-(1'-Acetamido-3'-ethyl)pentyl-cyclopentane-1-carboxylic acid, (±)-(2R,3R,5R,1'S)-2-(1'-Acetamido-3'-Methyl)butyl-3-methoxycarbonyl-tetrahydrofuran-5-carboxylic acid, (±)-(2R,3S,5R,1'S)-2-(1'-Acetamido-3'-Methyl)butyl-3-(imidazol-4-yl)-tetrahydrofuran-5-carboxylic acid, (1S,3R,4S,1'S)-3-(1'-Acetamido-3'-ethyl)pentyl-4-vinyl-cyclopentane-1-carboxylic acid, (±)-(1R,3R,4R,1'S)-3-N-methylcarbamoyl-4-(1'-Acetamido-3'-ethyl)pentyl-cyclopentane-1-carboxylic acid, (1R,3R,4R,1'S)-3-(imidazol-4-yl)-4-(1'-Acetamido-3'-Methyl)butyl-cyclopentane-1-carboxylic acid, (3R,4R,1'S)4-(imidazol-2-yl)-3-(1'-Acetamido-3'-ethyl)pentyl-cyclopent-1-ene-1-carboxylic acid, (1S,2S,3R,4R,1'R,2'S)-3-(1'-Acetamido-2'-methoxy-2'-Methyl)pentyl-4-amino-2-hydroxycyclopentan-1-carboxylic acid, (1S,2S,3R,4R,1'R,2'S)-3-(1'-Acetamido-2'-methoxy-2'-Methyl)pentyl-4-((amino-imino)methyl)amino-2-hydroxycyclopentan-1-carboxylic acid, (1R,3R,4R,1'R,2'S)-3-(1'-Acetamido-2'-methoxy-2'-Methyl)pentyl-4-amino-cyclopentan-1-carboxylic acid, (1S,2S,3R,4R,1'R,2'S)-3-(1'-Acetamido-2'-methoxy-2'-Methyl)pentyl-4-((amino-imino)methyl)aminocyclopentan-1-carboxylic acid, (3R,4R,1'R,2'S)-3-(1'-Acetamido-2'-methoxy-2'-Methyl)pentyl-4-aminocyclopent-1-ene-1-carboxylic acid, or (3R,4R,1'R,2'S)-3-(1'-Acetamido-2'-methoxy-2'-Methyl)pentyl4-((amino-imino)methyl)aminocyclopent-1-ene-1-carboxylic acid, or a pharmaceutically acceptable salt thereof.

* * * * *

UNITED STATES PATENT AND TRADEMARK OFFICE
CERTIFICATE OF CORRECTION

PATENT NO.    : 6,518,305 B1
DATED         : February 11, 2003
INVENTOR(S)   : Clarence J. Maring et al.

It is certified that error appears in the above-identified patent and that said Letters Patent is hereby corrected as shown below:

<u>Column 264,</u>
Line 48, replace after ",-N(O)= CHCH3," with -- or a heterocyclic ring having 5 ring atoms and also containing one or two double bonds, wherein $R^{22}$, $Q^2$ and $Q^3$ are defined as therein; or a pharmaceutically acceptable salt or ester thereof. --.

<u>Column 274,</u>
Line 38, delete "$Z^1$ is -0-,S-,-CH$_2$-,"

<u>Column 276,</u>
Line 12, delete "$Z^1$ is -O-,-S-, CH$_2$-,"

<u>Column 285,</u>
Line 37, replace "$Z^3$" with -- $Z^1$ --.

<u>Column 287,</u>
Line 35, replace " 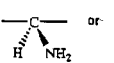 or 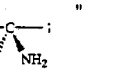 ; " with -- 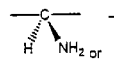 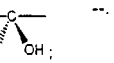 --.

<u>Column 290,</u>
Line 50, delete "$Z^1$ is -O-, -S-, CH$_2$-,".

<u>Column 292,</u>
Line 33, delete "$Z^1$ is -O-, -S-,CH$_2$-,".
Line 33, after the word "relative", insert the phrase -- stereochemistry of the formula: --.

<u>Column 294,</u>
Line 15, delete "$Z^1$ is -O-, -S-, CH$_2$-,".

<u>Column 300,</u>
Line 36, delete the phrase "or a heterocyclic ring having 5 ring atoms and also containing one or two double bonds, wherein $R^{22}$, $Q^2$ and $Q^3$ are defined as therein.".

<u>Column 301,</u>
Lines 42, 44 and 46 replace "(1'-Acetamido-3'-ethyl)" with -- (1'-acetamido-3'-ethyl) --.

UNITED STATES PATENT AND TRADEMARK OFFICE
CERTIFICATE OF CORRECTION

PATENT NO.    : 6,518,305 B1
DATED         : February 11, 2003
INVENTOR(S)   : Clarence J. Maring et al.

It is certified that error appears in the above-identified patent and that said Letters Patent is hereby corrected as shown below:

Column 302,
Line 1, replace "(1-Acetamido-3-ethyl)" with -- (1-acetamido-3-ethyl) --.
Line 3, replace "(1R, 3R, 4R,1'S)-3-(oxazol-5-yl)-4-(1'-Acetamido-3'-ethyl)" with -- (1R,3R,4R,1'S)-3-(oxazol-5-yl)-4-(1'-acetamido-3'-ethyl) --.
Lines 5 and 9, replace "(1'-Acetamido-3'-ethyl)" with -- (1'acetamido-3'-ethyl) --.
Lines 11 and 14, replace "(1'-Acetamido-3'-Methyl)" with
-- (1'-acetamido-3'-methyl) --.
Line 16, replace "(1'-Acetamido-3'-ethyl)" with -- (1'-acetamido-3'-ethyl) --.
Line 18, replace "(1'-Acetamido-3'-ethyl)" with -- (1'-acetamido-3'-ethyll) --.
Line 21, replace "(1'-Acetamido-3'-Methyl)" with -- (1'-acetamido-3'-methyl) --.
Line 24, replace "(1'-Acetamido-3'-ethyl)" with -- (1'-acetamido-3'-ethyl) --.
Lines 26, 30 and 33, replace "(1'-Acetamido-2'-methoxy-2'-Methyl)" with
-- (1'-acetamido-2'-methoxy-2'-methyl) --.
Lines 36 and 40, replace "(1'-Acetamido-2'-methoxy-2'-Methyl)" with
-- (1'-acetamido-2'-methoxy-2'-methyl) --.
Line 42, "(1'-Acetamido-2'-methoxy-2-Methyl)" with
-- (1'-acetamido-2'-methoxy-2-methyl) --.

Signed and Sealed this

Twelfth Day of August, 2003

JAMES E. ROGAN
*Director of the United States Patent and Trademark Office*